US012730102B2

(12) United States Patent
Potyrailo et al.

(10) Patent No.: US 12,730,102 B2
(45) Date of Patent: Sep. 8, 2026

(54) LOCOMOTIVE SENSOR SYSTEM FOR MONITORING ENGINE AND LUBRICANT HEALTH

(71) Applicant: Transportation IP Holdings, LLC, Norwalk, CT (US)

(72) Inventors: Radislav Alexandrovich Potyrailo, Niskayuna, NY (US); Igor Tokarev, Niskayuna, NY (US); Najeeb M. Kuzhiyil, McKinney, TX (US); Pradheepram Ottikkutti, Lawrence Park, PA (US)

(73) Assignee: Transportation IP Holdings, LLC, Norwalk, CT (US)

( * ) Notice: Subject to any disclaimer, the term of this patent is extended or adjusted under 35 U.S.C. 154(b) by 0 days.

(21) Appl. No.: 18/796,160

(22) Filed: Aug. 6, 2024

(65) Prior Publication Data

US 2025/0035608 A1 Jan. 30, 2025

Related U.S. Application Data

(63) Continuation-in-part of application No. 16/251,897, filed on Jan. 18, 2019, now abandoned, which is a continuation-in-part of application No. 16/146,322, filed on Sep. 28, 2018, now Pat. No. 10,996,210, and a continuation-in-part of application No. 15/884,889, filed on Jan. 31, 2018, now abandoned, and a (Continued)

(51) Int. Cl.
*G01N 33/28* (2006.01)
*F01M 11/10* (2006.01)
*G01N 27/60* (2006.01)

(52) U.S. Cl.
CPC ......... *G01N 33/2888* (2013.01); *F01M 11/10* (2013.01); *G01N 27/60* (2013.01); *F01M 2011/1406* (2013.01)

(58) Field of Classification Search
CPC ..... G01N 27/60; G01N 33/2888; F01M 11/10
See application file for complete search history.

(56) References Cited

U.S. PATENT DOCUMENTS

2004/0093931 A1* 5/2004 Carlstrom .......... G01N 33/2876 73/53.05
2009/0216471 A1* 8/2009 Akiyama .......... G01N 33/2876 702/65
2017/0355374 A1* 12/2017 Glugla ............ B60W 30/18136

OTHER PUBLICATIONS

Simon S. Wang, "Road tests of oil condition sensor and sensing technique," Delphi Research Laboratories, Sep. 17, 2000 (Year: 2000).*

* cited by examiner

*Primary Examiner* — Kevin A Lathers
(74) *Attorney, Agent, or Firm* — K&L Gates LLP

(57) ABSTRACT

A locomotive sensor system includes a sensor configured to be in contact with lubricant within an engine of a locomotive. The sensor includes a sensing region circuit that is configured to generate stimuli at different times during an operational life of the engine. The system also includes one or more processors configured to receive signals from the sensor. The signals are representative of responses of the lubricant to the stimuli. The one or more processors are configured to analyze the responses and determine a characteristic of the lubricant that represents one or more of a total base number (TBN) or a total acid number (TAN) of the lubricant. The are configured to determine an unhealthy state of one or more of the engine or the lubricant based on the characteristic of the lubricant that is determined.

18 Claims, 100 Drawing Sheets

Related U.S. Application Data continuation-in-part of application No. 15/418,820, filed on Jan. 30, 2017, now Pat. No. 10,539,524, and a continuation-in-part of application No. 15/365,127, filed on Nov. 30, 2016, now Pat. No. 10,260,388, and a continuation-in-part of application No. 15/285,415, filed on Oct. 4, 2016, now Pat. No. 10,254,220, and a continuation-in-part of application No. 15/271,692, filed on Sep. 21, 2016, now abandoned, and a continuation-in-part of application No. 15/270,442, filed on Sep. 20, 2016, now Pat. No. 10,368,146, and a continuation-in-part of application No. 15/187,934, filed on Jun. 21, 2016, now Pat. No. 10,261,036, and a continuation-in-part of application No. 15/060,193, filed on Mar. 3, 2016, now Pat. No. 10,746,680, said application No. 15/365,127 is a continuation-in-part of application No. 14/866,320, filed on Sep. 25, 2015, now Pat. No. 10,018,613, said application No. 15/060,193 is a continuation-in-part of application No. 14/866,320, filed on Sep. 25, 2015, now Pat. No. 10,018,613, said application No. 15/418,820 is a continuation-in-part of application No. 14/866,320, filed on Sep. 25, 2015, now Pat. No. 10,018,613, which is a continuation-in-part of application No. 14/421,245, filed on Feb. 12, 2015, now Pat. No. 9,746,452, said application No. 15/884,889 is a continuation-in-part of application No. 14/585,690, filed on Dec. 30, 2014, now Pat. No. 10,914,698, said application No. 14/866,320 is a continuation-in-part of application No. 14/585,690, filed on Dec. 30, 2014, now Pat. No. 10,914,698, which is a continuation-in-part of application No. 14/532,168, filed on Nov. 4, 2014, now Pat. No. 9,536,122, and a continuation-in-part of application No. 14/031,965, filed on Sep. 19, 2013, now Pat. No. 8,990,025, and a continuation-in-part of application No. 14/031,951, filed on Sep. 19, 2013, now Pat. No. 9,037,418, and a continuation-in-part of application No. 13/838,884, filed on Mar. 15, 2013, now Pat. No. 9,389,296, and a continuation-in-part of application No. 13/729,800, filed on Dec. 28, 2012, now Pat. No. 9,097,639, and a continuation-in-part of application No. 13/729,851, filed on Dec. 28, 2012, now Pat. No. 9,261,474, and a continuation-in-part of application No. 13/630,587, filed on Sep. 28, 2012, now Pat. No. 9,658,178, and a continuation-in-part of application No. 13/630,939, filed on Sep. 28, 2012, now Pat. No. 9,389,260, and a continuation-in-part of application No. 13/630,954, filed on Sep. 28, 2012, now Pat. No. 9,147,144, and a continuation-in-part of application No. 13/630,739, filed on Sep. 28, 2012, now Pat. No. 9,176,083, and a continuation-in-part of application No. 13/558,499, filed on Jul. 26, 2012, now Pat. No. 9,195,925, and a continuation-in-part of application No. 13/538,570, filed on Jun. 29, 2012, now Pat. No. 9,538,657, and a continuation-in-part of application No. 13/484,674, filed on May 31, 2012, now Pat. No. 9,052,263, and a continuation-in-part of application No. 13/331,003, filed on Dec. 20, 2011, now Pat. No. 9,045,973, and a continuation-in-part of application No. 12/977,568, filed on Dec. 23, 2010, now abandoned, and a continuation-in-part of application No. 12/827,623, filed on Jun. 30, 2010, now Pat. No. 8,936,191, and a continuation-in-part of application No. 12/824,436, filed on Jun. 28, 2010, now abandoned, said application No. 13/484,674 is a continuation-in-part of application No. 12/424,016, filed on Apr. 15, 2009, now Pat. No. 8,364,419, said application No. 14/585,690 is a continuation-in-part of application No. 12/325,653, filed on Dec. 1, 2008, now abandoned, and a continuation-in-part of application No. 11/560,476, filed on Nov. 16, 2006, now Pat. No. 9,589,686.

(60) Provisional application No. 62/612,855, filed on Jan. 2, 2018, provisional application No. 62/459,806, filed on Feb. 16, 2017, provisional application No. 61/987,853, filed on May 2, 2014.

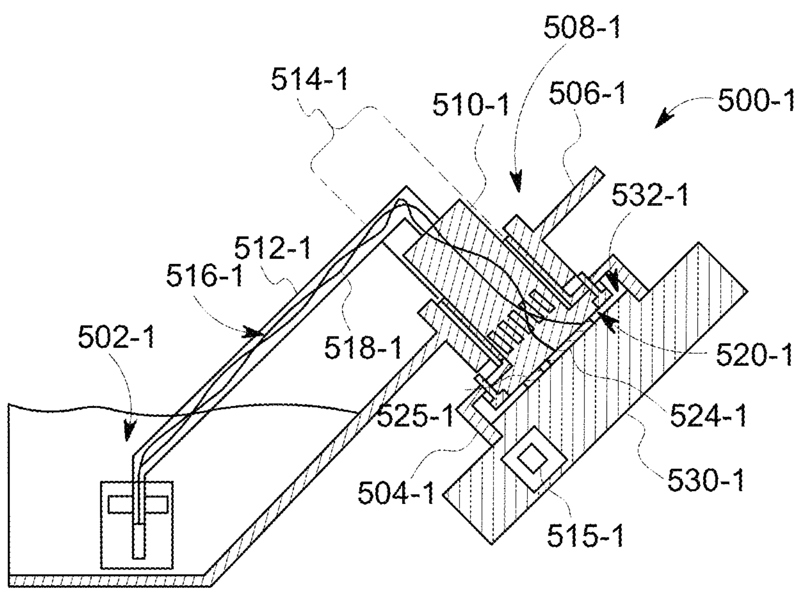
FIG. 60
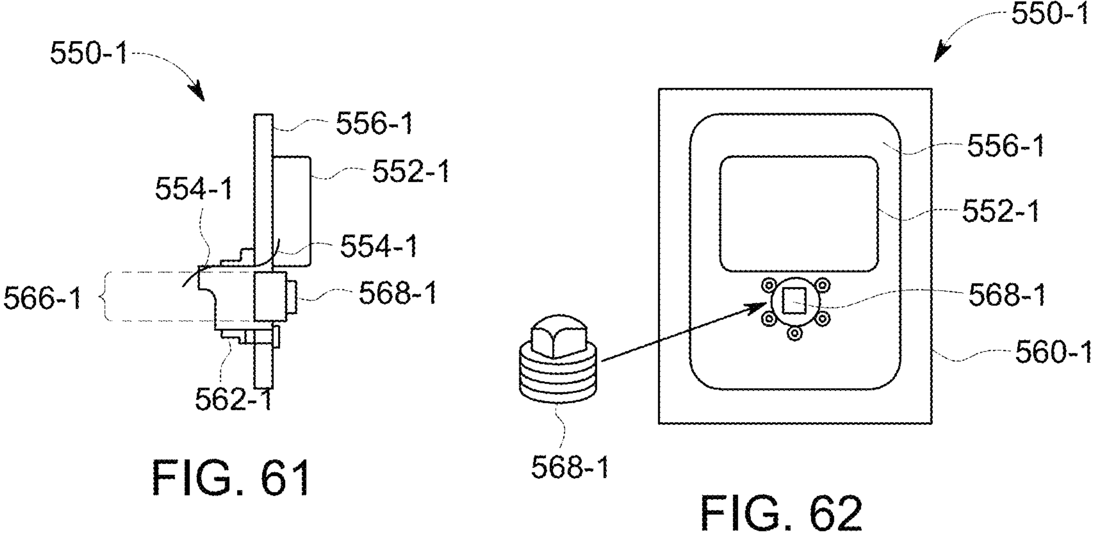
FIG. 61
FIG. 62

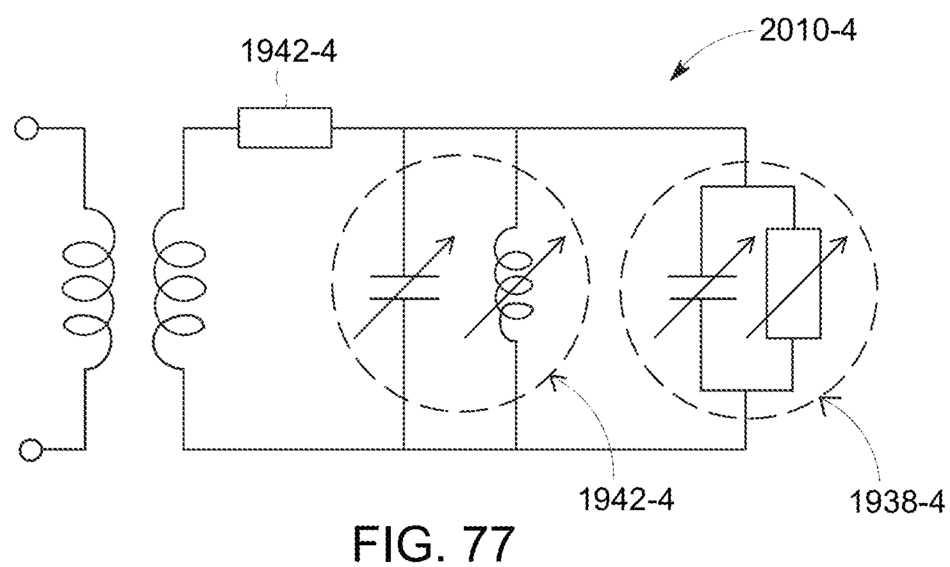
FIG. 77
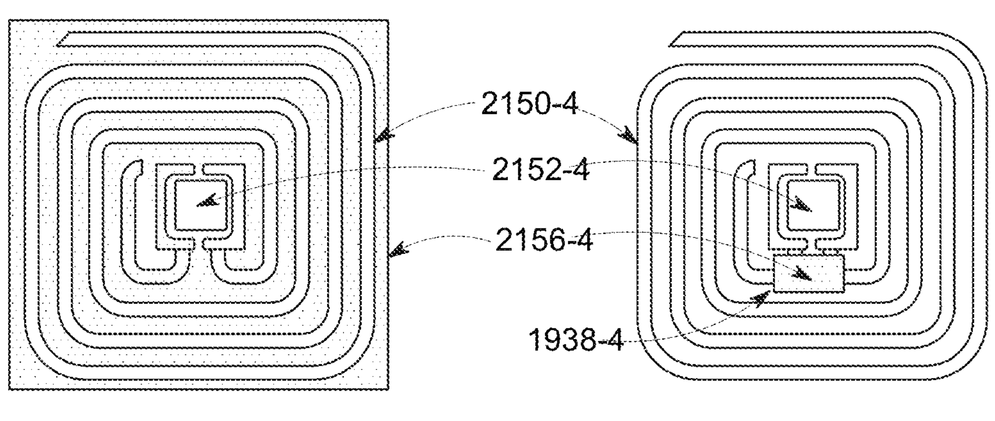
FIG. 78
FIG. 79
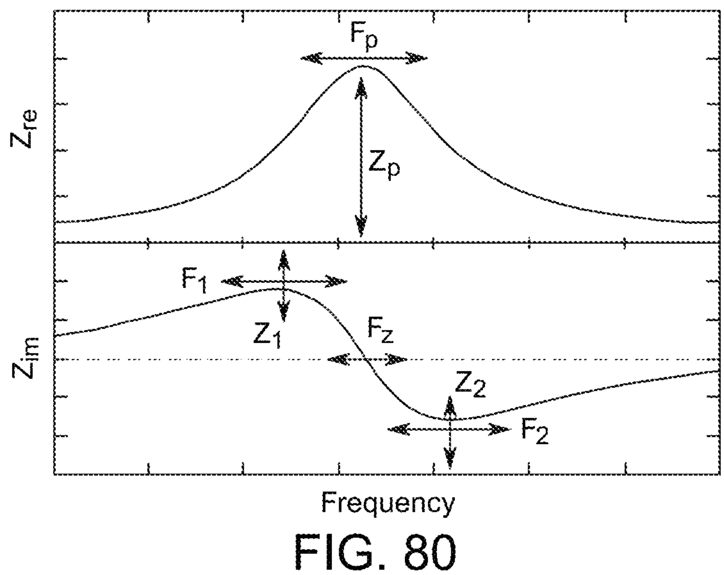
FIG. 80

LOCOMOTIVE SENSOR SYSTEM FOR MONITORING ENGINE AND LUBRICANT HEALTH

CROSS-REFERENCE TO RELATED APPLICATIONS

This application is a continuation of U.S. patent application Ser. No. 16/251,897, filed Jan. 18, 2019, which is a continuation-in-part of U.S. patent application Ser. No. 15/884,889, filed Jan. 31, 2018, U.S. patent application Ser. No. 15/187,934, filed Jun. 21, 2016 (now U.S. Pat. No. 10,261,036, issued on 16 Apr. 2019), U.S. patent application Ser. No. 15/271,692, filed Sep. 21, 2016, U.S. Patent Application No. 15/060,193, filed Mar. 3, 2016 (now U.S. Pat. No. 10,746,680, issued on Aug. 18, 2020), U.S. patent application Ser. No. 15/270,442, filed Sep. 20, 2016 (now U.S. Pat. No. 10,368,146, issued on Jul. 30, 2019), U.S. patent application Ser. No. 15/285,415, filed Oct. 4, 2016 (now U.S. Pat. No. 10,254,220, issued on Apr. 9, 2019), U.S. patent application Ser. No. 15/418,820, filed Jan. 30, 2017 (now U.S. Pat. No. 10,539,524, issued on Jan. 21, 2020), U.S. patent application Ser. No. 15/365,127, filed Nov. 30, 2016 (now U.S. Pat. No. 10,260,388, issued on Apr. 16, 2019), U.S. patent application Ser. No. 16/146,322, filed Sep. 28, 2018, and U.S. patent application Ser. No. 16/251,897, filed Jan. 18, 2019.

U.S. patent application Ser. No. 15/884,889 claims priority to U.S. Provisional Application No. 62/459,806, filed on 16 Feb. 2017, and is a continuation-in-part of U.S. patent application Ser. No. 14/585,690, which was filed on 30 Dec. 2014.

U.S. patent application Ser. No. 14/585,690 claims priority to U.S. Provisional Patent Application No. 61/987,853 filed on 2 May 2014, and is a continuation-in-part of the following applications: U.S. patent application Ser. No. 11/560,476, filed on 16 Nov. 2006 (now U.S. Pat. No. 9,589,686, issued on 7 Mar. 2017); U.S. patent application Ser. No. 12/325,653, filed on 1 Dec. 2008; U.S. patent application Ser. No. 12/824,436, filed on 28 Jun. 2010; U.S. patent application Ser. No. 12/827,623, filed on 30 Jun. 2010 (now U.S. Pat. No. 8,936,191, issued on 20 Jan. 2015); U.S. patent application Ser. No. 12/977,568, filed on 23 Dec. 2010; U.S. patent application Ser. No. 13/331,003, filed on 20 Dec. 2011 (now U.S. Pat. No. 9,045,973, issued 2 Jun. 2015); U.S. patent application Ser. No. 13/484,674, filed on 31 May 2012 (now U.S. Pat. No. 9,052,263, which issued on 9 Jun. 2015, which is a continuation-in-part of U.S. patent application Ser. No. 12/424,016, filed on 15 Apr. 2009 (now U.S. Pat. No. 8,364,419, issued on 29 Jan. 2013); U.S. patent application Ser. No. 13/538,570, filed on 29 Jun. 2012 (now U.S. Pat. No. 9,538,657, issued on 3 Jan. 2017); U.S. patent application Ser. No. 13/558,499, filed on 26 Jul. 2012 (now U.S. Pat. No. 9,195,925, issued on 24 Nov. 2015); U.S. patent application Ser. No. 13/630,939 (now U.S. Pat. No. 9,389,260, issued on 12 Jul. 2016), Ser. No. 13/630,954 (now U.S. Pat. No. 9,147,144, issued on 29 Sep. 2015), Ser. No. 13/630,587 (now U.S. Pat. No. 9,658,178, issued on 23 May 2017), and Ser. No. 13/630,739 (now U.S. Pat. No. 9,176,083, issued on 3 Nov. 2015), all filed on 28 Sep. 2012; U.S. patent application Ser. No. 13/729,800 (now U.S. Pat. No. 9,097,639, issued on 4 Aug. 2015) and Ser. No. 13/729,851 (now U.S. Pat. No. 9,261,474, issued on 16 Feb. 2016), both filed on 28 Dec. 2012; U.S. patent application Ser. No. 13/838,884, filed on 15 Mar. 2013 (now U.S. Pat. No. 9,389,296, issued on 12 Jul. 2016); U.S. patent application Ser. No. 14/031,951 (now U.S. Pat. No. 9,037,418, issued on 19 May 2015) and Ser. No. 14/031,965 (now U.S. Pat. No. 8,990,025, issued on 24 Mar. 2015), both filed on 19 Sep. 2013; and U.S. patent application Ser. No. 14/532,168, filed on 4 Nov. 2014 (now U.S. Pat. No. 9,536,122, issued on 3 Jan. 2017).

Each of U.S. patent application Ser. No. 15/060,193, U.S. patent application Ser. No. 15/365,127 and U.S. patent application Ser. No. 15/418,820 is a continuation-in-part of U.S. patent application Ser. No. 14/866,320, filed 25 Sep. 2015 (now U.S. Pat. No. 10,018,613, issued on 10 Jul. 2018), which is a continuation-in-part of U.S. patent application Ser. No. 14/585,690 and is a continuation-in-part of U.S. patent application Ser. No. 14/421,245, filed on 12 Feb. 2015 (now U.S. Pat. No. 9,746,452, issued on 29 Aug. 2017), which claims the benefit of U.S. Provisional Patent Application No. 61/692,230, filed on 22 Aug. 2012.

U.S. patent application Ser. No. 16/146,322 claims priority to U.S. Provisional Application No. 62/612,855, filed 2 Jan. 2018.

The entirety of each of the aforementioned patent applications and patents is incorporated herein by reference.

FIELD

One or more embodiments are disclosed that relate to systems and methods for sensing lubricant health and/or lubricant consumption in engines.

BACKGROUND

Many industrial machines include equipment or assemblies (e.g., engines) that use lubricants (e.g., oil) to operate. It is desirable to monitor a condition of the lubricant to ensure that the lubricant is replaced or replenished before severe and permanent damage is sustained by the machine. In addition to lubricants, machines may use other industrial fluid such as fuels, hydraulic media, drive fluids, power steering fluids, power brake fluids, drilling fluids, oils, insulating fluids, heat transfer fluids, or the like. Such fluids allow efficient and safe operation of machinery in transportation, industrial, locomotive, marine, automotive, construction, medical, and other applications.

The quality of a lubricant may deteriorate over time due to the introduction of contaminants and/or aging of the lubricant. Generally, lubricants contain additives that provide increased resilience. Such additives also break down in service over time. As the additives deplete, acidic components such as by-products from the degradation of the additive and/or the lubricant due to aging, may be introduced into the lubricant. In case of engine oil, combustion products that ingress into the oil sump introduce acidic components into the oil. The acidic components can reduce the effectiveness and performance of the lubricant. In order to neutralize acidic components, engine oils are formulated with basic (alkaline) additives. The quantity of alkaline additives remaining in the engine oil (Total Base Number or TBN) is a measure of its health.

Current technique employed for determining the quality of engine oils is to collect oil samples every fifteen to thirty days and to analyze in a chemical laboratory. The process of collection of oil samples, their storage and transport to a chemical laboratory for analysis may add relatively large variability in measured results in initially identical oil samples. The typical lead time for results is another fifteen to thirty days. This process is inefficient to provide timely information on the condition of the oil and hence on the health of the engine and also to provide real time information on oil consumption rate. Use of this fast response, real-time oil quality/health monitoring eliminates possible mistakes or mishaps caused by mishandled or mislabeled oil samples, oil sample bottles lost in transit, analysis reports that are incorrectly numbered or mislabeled, the normal 15 to 30 days required to complete the oil analysis (being too long), and resulting in engine failure and road failure of the vehicle if the quality of the oil (used) is very close to an end-of-life limit, etc.

BRIEF DESCRIPTION

In one embodiment, a system includes a sensor configured to be in contact with oil within an engine of a vehicle system. The sensor includes a sensing region circuit that is configured to generate stimuli at different times during an operational life of the engine. The system also includes one or more processors configured to receive signals from the sensor. The signals are representative of responses of the oil to the stimuli. The one or more processors are configured to analyze the responses and determine a characteristic of the oil that represents one or more of a total base number (TBN) or a total acid number (TAN) of the oil. The one or more processors are configured to determine an unhealthy state of one or more of the engine or the oil based on the characteristic of the oil that is determined.

In one embodiment, a method includes placing a sensor in contact with oil within an engine of a vehicle system, generating stimuli at a sensing region circuit of the sensor during an operational life of the engine, receiving signals from the sensor, the signals representative of responses of the oil to the stimuli, analyzing the responses to determine a characteristic of the oil that represents one or more of a total base number (TBN) or a total acid number (TAN) of the oil, and determining an unhealthy state of one or more of the engine or the oil based on the characteristic TBN and/or TAN of the oil that is determined.

In one embodiment, a system includes a sensor configured to be in contact with lubricating oil within a rotating equipment of a system. The sensor is configured to generate detectable stimuli at different times during an operational life of the rotating equipment. The system also includes one or more processors configured to receive signals from the sensor. The signals are representative of responses of the oil to the stimuli. The one or more processors are configured to analyze the responses and determine a characteristic of the oil that represents one or more of a total base number (TBN) or a total acid number (TAN) of the oil. The one or more processors are configured to determine an unhealthy state of one or more of the engine or the oil based on the characteristic of the oil that is determined.

In one embodiment, a method includes placing a sensor in contact with oil within an engine of a vehicle system, generating stimuli at a sensing region circuit of the sensor during an operational life of the engine, receiving signals from the sensor, the signals representative of responses of the oil to the stimuli, analyzing the responses to determine a characteristic of the oil that represents one or more of a total base number (TBN) or a total acid number (TAN) of the oil, and determining health state of one or more of the engine or the oil based on the characteristic of the oil that is determined.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 60 is a cross-section of a wireless device utilizing the sensor of FIG. 54 in accordance with an embodiment;

FIG. 61 is a cross-section of a portion of a wireless device formed in accordance with an embodiment;

FIG. 62 is a front view of the wireless device of FIG. 61;

FIG. 77 illustrates another sensor circuit;

FIG. 78 illustrates an embodiment of the sensor circuit in an adapted RFID tag;

FIG. 79 illustrates an additional embodiment of the sensor circuit in an adapted RFID tag;

FIG. 80 depicts a graph of measured resonant impedance parameters of an embodiment of the resonant sensor, in accordance with embodiments of the present technique;

DETAILED DESCRIPTION

Figure 1:
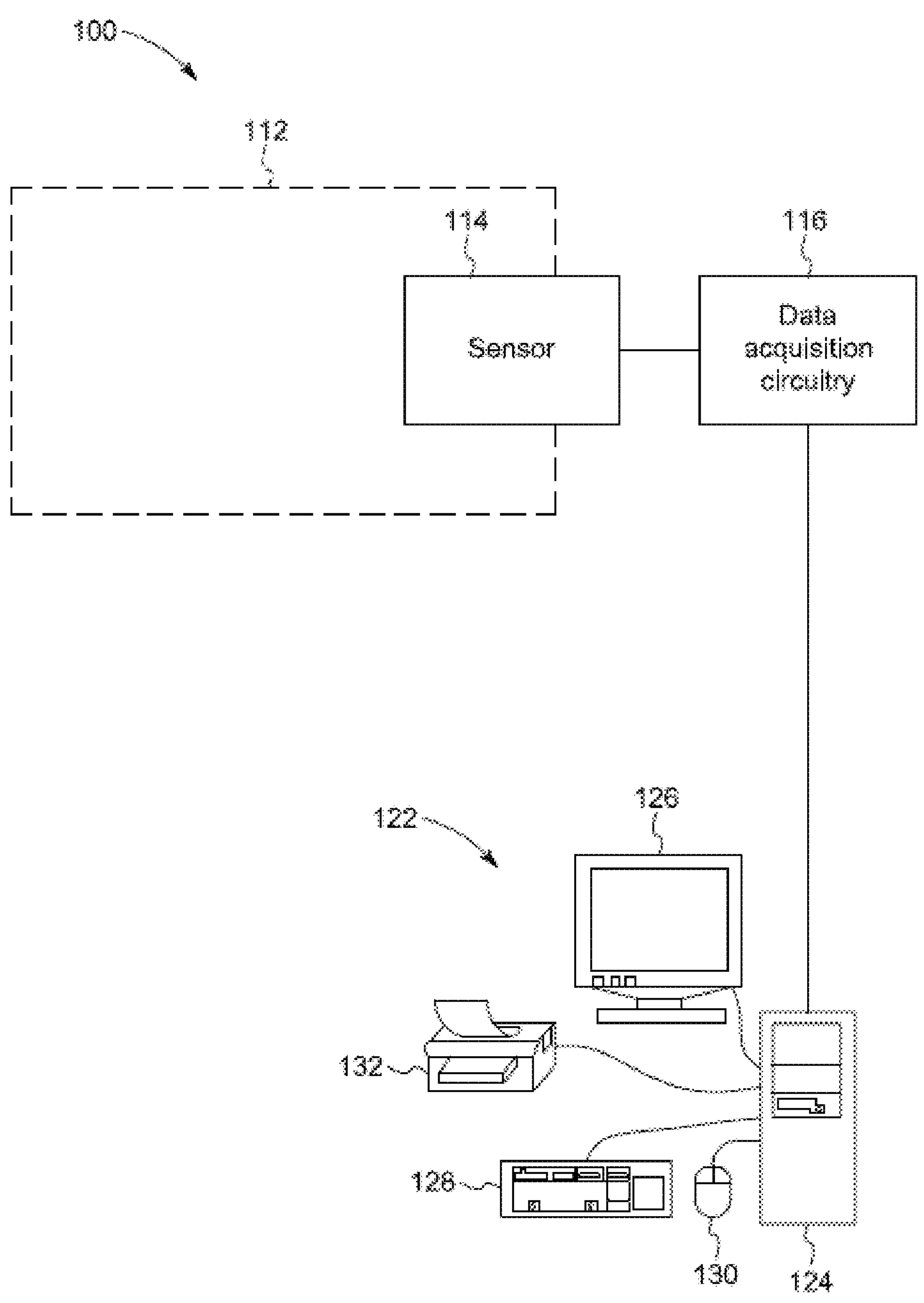
FIG. 1 illustrates one embodiment of a sensing system.

Unless defined otherwise, technical and scientific terms used herein have the same meaning as is commonly understood by one of ordinary skill in the art to which this specification belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean one, some, or all the listed items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect. Furthermore, the terms "circuit", "circuitry", and "controller" may include either a single component or a plurality of components, which are either active and/or passive and are connected or otherwise coupled together to provide the described function. Also, the term "operatively coupled" as used herein includes wired coupling, wireless coupling, electrical coupling, magnetic coupling, radio communication, software-based communication, or combinations thereof.

The term "fluids" can include liquids, gases, vapors, and solids and their combinations forming multiphase compositions. Non-limiting examples of multiphase compositions include emulsions such as oil/water emulsions, food emulsions such as salad dressings oil-in-water emulsions, colloids such as solutions that have particles distributed throughout the solution, food colloids, food colloids such as ice scream, jam, mayonnaise, solid foams such as bread, cake. Fluid can also include a food product that has been gone through mechanical re-forming. Alternatively, a fluid may not include a solid. Fluid can also include industrial, non-industrial, and/or naturally occurring fluids. Fluids may include naturally occurring fluids such as air, hydrocarbons, water, oils, body fluids, biological fluids, and the like that occur in natural living and non-living systems.

The term "industrial fluid" as used herein includes fluids that typically may be used on an industrial site or structure. In one example, the industrial fluid is at least one of a lubricant, a fuel, a hydraulic media, a drive fluid, a power steering fluid, a solvent, a power brake fluid, a drilling fluid, an oil, an insulating fluid, a heat transfer fluid, compressed air, ambient air, water, a naturally occurring fluid, or a synthetic fluid. In one example, the industrial fluid is a lubricating oil with known type and level of additives designed for exposure to multiple environmental conditions and with different wear protection and different particles-deposit control.

The term "multivariable sensor" as used herein refers to a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof. The multivariable sensor has a sensing region that is in operational contact with a fluid. The multivariable sensor may be in an operational contact with a fluid where the sensing region is bare or coated with a protective layer or with a sensing film.

The terms "transducer" and "sensor" as used herein refer to electronic devices such as LCR resonator intended for sensing. "Transducer" is a device before it is calibrated for a sensing application. "Sensor" is a device typically after it is calibrated for the sensing application. The sensor has a fluid-sensing region with an electrode. The fluid sensing region with the electrode may be alternatively referred to as a sensor probe. The sensing region may be placed in operational contact with a fluid of interest.

The electrical field may be applied by a sensor probe. The sensor probe may be in direct or indirect electrical contact with the industrial fluid. A sensing region may be either bare or coated with a protective dielectric layer or a sensing layer. In each of the disclosed cases, the sensing region may be considered to be in operational contact with a fluid. One example of indirect electrical contact with the fluid may be when a sensor probe is coated with a dielectric protective coating and when the electric field that may be generated by the sensor probe interacts with the fluid after penetrating through the dielectric protective coating. A suitable dielectric protective coating may be conformally applied to the sensor probe.

Embodiments described herein include various systems, assemblies, devices, apparatuses, and methods that may be used in a connection with obtaining one or more measurements of a machine. The measurement(s) may be representative or indicative of an operative condition of the machine. The operative condition of the machine may refer to an operative condition of the machine as a whole or an operative condition of a component (e.g., element, assembly, or sub-system) of the machine. The operative condition can relate to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

Internal combustion engine oils can be made with additives to neutralize acidic combustion products that get into the oil. In modern internal combustion engines with medium to high rates of exhaust gas recirculation (EGR), more acidic combustion products are likely to enter engine oil. These products can rapidly deplete the total base number (TBN) of the oil. One or more embodiments of the inventive subject matter described herein repeatedly measure (such as by continuously measuring) the total base number of engine oil using a sensor to detect and measure abnormal rate of oil consumption in the engine. These measurements can be used for engine prognostics and engine protection.

One or more embodiments of the oil sensor described herein measures the TBN of the oil in a real-time basis and sends data representative of the measurements to a prognosis device. The prognosis device compares a rate of TBN depletion with a previously determined or calibrated depletion rate. The predetermined rate may be selected from several different predetermined rates, with the different predetermined rates being associated with different engine operating conditions (e.g., idle, low/medium/full power, operating within a tunnel, operating at different altitudes, etc.), different ages of the engine, and/or different ambient conditions. The predetermined rate that is used to compare to the measured depletion rate is selected from the different predetermined rate by matching the operating conditions in which the engine is or has been operating with the operating conditions associated with one or more of the predetermined rates.

When the rate of TBN depletion is higher (e.g., faster) than normal or outside of a set range (as determined from or based on the predetermined rate), the engine may be identified as needing inspection for excessive engine wear, fuel system wear, specification and quality of lube oil being used, and/or lubricating oil system functionality. For example, decreases or depletion of TBN may indicate that the engine needs inspection, repair, and/or maintenance. TBN is depleted from lubricating oil when the oil comes into contact with acidic products of the combustion process of the engine (e.g., which can arise from high wear of the engine cylinders, liners, and/or piston rings). Changes in the TBN value (e.g., below a designated threshold, decreasing at rates that are faster than a designated rate, and/or having second derivatives that change faster than designated second derivatives) can indicate a need for repair, inspection, and/or maintenance of the lubricant and/or engine. Repair, inspection, and/or maintenance of the engine may be automatically implemented responsive to determining that the TBN depletion rate is faster than desired.

Similarly, an increase in total acid number (TAN) of the oil may be measured (e.g., in real time) using the sensor, and data representative of the measurements can be used to determine engine wear, fuel system wear, and/or lube oil system prognostics. TAN is a measurement of an amount of acid content in oil. A similar approach to comparing normal and abnormal rates of increase of TAN in the oil and to flag engines for inspection may be used. For example, increases in TAN (e.g., above a designated threshold, at rates that are faster than a designated rate, and/or having second derivatives that are faster than designated second derivatives) may indicate that the engine needs inspection, repair, and/or maintenance. TAN increases in the oil when the oil comes into contact with acidic products of the combustion process of the engine (e.g., which can arise from high wear of the engine cylinders, liners, and/or piston rings).

In addition or instead of the rate of depletion of TBN or an increase of TAN, a first derivative or a higher derivative of the rate of depletion of TBN or an increase of TAN can be used. The TBN and/or TAN of engine lubricating oil can be continuously monitored and measured values recorded periodically and frequently (e.g., every hour) as dictated by the specific application and/or duty cycle of the engine. Using a self-learning or a machine-learning algorithm, behavior of the oil for each engine will be mapped. For each engine, individual TBN and/or TAN readings, the rates of change, and/or the rate of change of rate of change (e.g., the first and second derivatives of the rate of change) of TBN and/or TAN can be determined. The systems and methods determine whether the values are within the normal or healthy values by comparing the measured values with established normal values and ranges. Responsive to the amounts of TBN or TAN, the rates of TBN or TAN depletion, and/or the second derivatives of depletion rates are outside the healthy-engine range, one or more responsive actions can be automatically implemented to check the engine and the relevant engine components. At least one technical effect of the subject matter described herein includes the ability to replace or replenish lubricant in a machine due to the measured TBN and/or TAN prior to damage to the machine occurring.

FIG. 1 illustrates one embodiment of a sensing system 100. The sensing system 100 examines a fluid in contact with the sensing system 100. This fluid may be engine oil. The system 100 may include a fluid reservoir 112 for holding the fluid and one or more sensors 114 at least partially disposed in, on, or within the fluid reservoir 112. Alternatively, the sensor 114 may be set in a flow path of the fluid outside of the reservoir 112, such as coupled to in-line connectors in fluid communication with the fluid reservoir that define a flow path. In one embodiment, the sensor 114 may provide continuous monitoring of the fluid within the reservoir or flow path. The sensor 114 optionally can be referred to herein as a sensing unit.

Suitable fluids may include hydrocarbon fuels and lubricants. Suitable lubricants may include engine oil, gear oil, hydraulic fluid, lubricating oils, synthetic based lubricants, lubricating fluids, greases, silicones, and the like. Suitable fuels may include gasoline, diesel fuel, jet fuel or kerosene, bio-fuels, petrodiesel-biodiesel fuel blends, natural gas (liquid or compressed), and fuel oils. Still other fluids may be insulating oils in transformers, solvents, or mixtures of solvents. Still other fluids may be included with correspondingly appropriate sensor parameters, such as water, air, engine exhaust, biologic fluids, and organic and/or vegetable oils. The fluid may be a liquid, or may be in a gaseous phase. Further contemplated are multiphase compositions. The fluids may be disposed in and/or used in an operating machine, such as a movable vehicle or a wind turbine.

Nonlimiting examples of design of the sensor 114 include various sensor designs. Depending on the measured parameter of oil and the concentration level of the measured parameter, an oil sensor can be a capacitor sensor, a resistor sensor, a non-resonant impedance sensor, a resonant impedance sensor, an electro-mechanical resonator sensor (e.g., tuning fork, cantilever sensor, acoustic device sensor), a thermal sensor, an optical sensor, an acoustic sensor, a photoacoustic sensor, a near-infrared sensor, a ultraviolet sensor, an infrared sensor, a visible light sensor, fiber-optic sensor, and reflection sensor, a multivariable sensor, or a single-output sensor. The sensor may generate electrical or optical stimuli to the measured oil.

In one embodiment, the sensor 114 may detect characteristics or properties of the fluid via a resonant impedance spectral response. One or more of the inductor-capacitor-resistor resonant circuits (LCR resonators) may measure the resonant impedance spectral response. As opposed to simple impedance measurements, the disclosed embodiments probe the sample with at least one resonant electrical circuit. The resonant impedance spectrum of the sensor 114 in proximity to the fluid varies based on sample composition and/or components and/or temperature. The measured resonant impedance values Z' (which may be the real part of resonant impedance, Zre) and Z" (which may be the imaginary part of resonant impedance, Zim) reflect the response of the fluid (for example, the portion of the fluid in proximity to the sensor) to a stimulus of the electric field of the resonant electrical circuit.

The electrical field may be applied by the sensor 114 via electrodes. The electrodes may be in direct or indirect electrical contact with the sample. For example, a sensor 114 may be a combination of a sensing region and associated circuits. The sensing region may be either bare or coated with a protective dielectric layer or a sensing layer. In each of the disclosed cases, the sensing region may be in operational contact with a fluid. In such embodiments, the sensor circuits may not contact the fluid directly. An example of indirect electrical contact with the sample may be when a sensing electrode structure is coated with a dielectric protective coating and when the electric field that may be generated between the electrodes interacts with the fluid after penetrating through the dielectric protective coating. A suitable dielectric protective coating may be conformally applied to the electrode.

Suitable sensors may include single use or multi-use sensors. A suitable multi-use resonant sensor may be a re-usable sensor that may be used during the lifetime of a system in which it may be incorporated into. In one embodiment, the resonant sensor may be a single use sensor that may be used during all or part of a reaction or process. For example, the resonant sensor may include one or more pairs of electrodes and one or more tuning elements, e.g., a resistor, a capacitor, an inductor, a resonator, impedance transformer, or combinations of two or more thereof to form an inductor-capacitor-resistor (LCR) resonant circuit operated at one or more resonant frequencies. In certain embodiments, different resonant circuits of a plurality of resonant circuits of a resonant sensor may be configured to resonate at different frequencies. Different frequencies may be selected to be across the dispersion profile of the measured fluid composition. The dispersion profile may depend on the dielectric properties of the fluid composition on the probing frequency. Various components of the fluid have different dispersion profiles. When measured at multiple resonance frequencies, concentrations of different components of the fluid may be determined.

Data from the resonant sensor 114 may be acquired via data acquisition circuitry 116, which may be associated with the sensor or which may be associated with a control system, such as a controller or workstation 122 including data processing circuitry, where additional processing and analysis may be performed. The controller or workstation may include one or more wireless or wired components, and may also communicate with the other components of the system. Suitable communication models include wireless or wired. At least one suitable wireless model includes radio frequency devices, such as radio frequency identification (RFID) wireless communications. Other wireless communication modalities may be used based on application specific parameters. For example, where there may be electromagnetic field (EMF) interference, certain modalities may work where others may not. The data acquisition circuitry optionally can be disposed within the sensor 114. Other suitable locations may include disposition being within the workstation. Further, the workstation can be replaced with a control system of the whole process where the resonant sensor and its data acquisition circuitry may be connected to the control system of process.

The data acquisition circuitry may be in the form of a sensor reader, which may be configured to communicate wirelessly or wired with the fluid reservoir and/or the workstation. For example, the sensor reader may be a battery-operated device and/or may be powered using energy available from the main control system or by using harvesting of energy from ambient sources (light, vibration, heat, or electromagnetic energy).

Additionally, the data acquisition circuitry may receive data from one or more resonant sensors 114 (e.g., multiple sensors formed in an array or multiple sensors positioned at different locations in or around the fluid reservoir). The data may be stored in short or long-term memory storage devices, such as archiving communication systems, which may be located within or remote from the system and/or reconstructed and displayed for an operator, such as at the operator workstation. The sensors may be positioned on or in fuel or fluid reservoirs, associated piping components, connectors, flow-through components, and any other relevant process components. The data acquisition circuitry may include one or more processors for analyzing the data received from the sensor 114. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed in the hardware of the one or more processors.

In addition to displaying the data, the operator workstation may control the above-described operations and functions of the system. The operator workstation may include one or more processor-based components, such as general purpose or application-specific computers 124. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation or by associated components of the system. Alternatively, the programs and routines may be stored on a computer accessible storage and/or memory remote from the operator workstation but accessible by network and/or communication interfaces present on the computer. The computer may also comprise various input/output (I/O) interfaces, as well as various network or communication interfaces. The various I/O interfaces may allow communication with user interface devices, such as a display 126, keyboard 128, electronic mouse 130, and printer 132, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

The sensor 114 may include a plurality of resonant circuits that may be configured to probe the fluid in the fluid reservoir with a plurality of frequencies. The fluid reservoir may be a reservoir bound by the engineered fluid-impermeable walls or by naturally formed fluid-impermeable walls or by the distance of the electromagnetic energy emitted from the sensor region to probe the fluid. Further, the different frequencies may be used to probe a fluid sample at different depths. In certain embodiments, an integrated circuit memory chip may be galvanically coupled to the resonant sensor. The integrated circuit memory chip may contain different types of information. Non-limiting examples of such information in the memory of the integrated circuit chip include calibration coefficients for the sensor, sensor lot number, production date, and/or end-user information. In another embodiment, the resonant sensor may comprise an interdigital structure that has a fluid-sensing region.

In certain embodiments, when an integrated circuit memory chip may be galvanically coupled to the resonant sensor, readings of the sensor response may be performed with a sensor reader that contains circuitry operable to read the analog portion of the sensor. The analog portion of the sensor may include resonant impedance. The digital portion of the sensor may include information from the integrated circuit memory chip.

Figure 2:
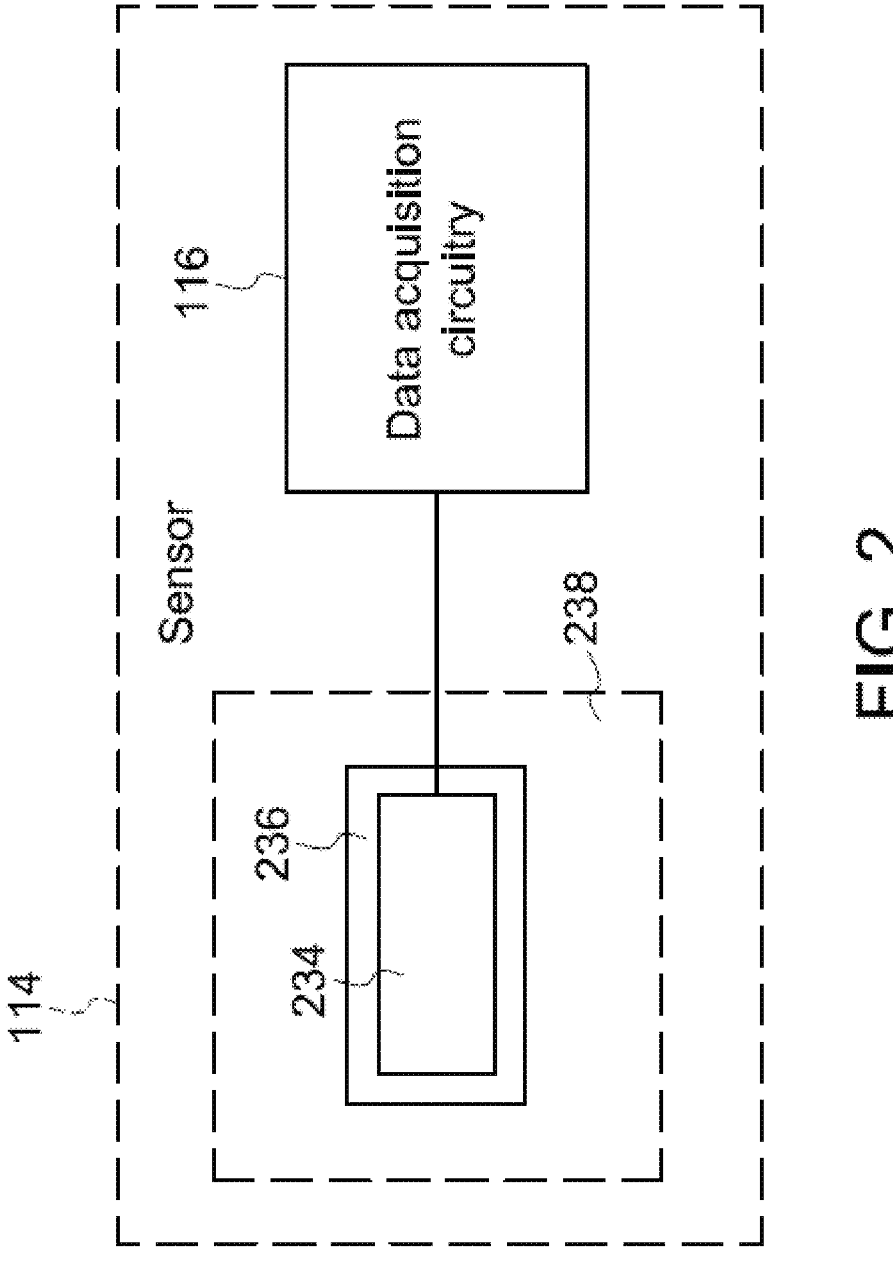
FIG. 2 illustrates a non-limiting example of a design of the resonant sensor shown in FIG. 1.

FIG. 2 illustrates a non-limiting example of a design of the resonant sensor 114. A sensing electrode structure 234 of the sensor may be connected to the tuning circuits and the data acquisition circuitry 116. The sensing electrode structure 234 can be bare and in direct contact with the fluid. Alternatively, the sensing electrode structure can be coated with a protective or sensing coating 236. The sensing electrode structure, without or with the protective or sensing coating, forms a sensing region 238. The coating may be applied conformably, and may be a dielectric material. The sensing electrode structure, without or with the protective coating that forms the sensing region, may operationally contact a fluid. The fluid contains the analyte or contaminant(s). The sensing electrode structure may be either without (bare) or with a protective coating.

A bare sensing electrode structure may generate an electric field between the electrodes that interacts directly with the fluid. A dielectric protective coated sensing electrode structure may generate an electric field that is between the electrodes that interacts with the fluid after penetrating through the dielectric protective coating. In one embodiment, the coating may be applied onto electrodes to form a conformal protective layer having the same thickness over all electrode surfaces and between electrodes on the substrate. Where a coating has been applied onto electrodes to form a protective layer, it may have a generally constant or variable final thickness over the substrate and sensor electrodes on the substrate. In another embodiment, a substrate simultaneously serves as a protective layer when the electrodes are separated from the fluid by the substrate. In this scenario, a substrate has electrodes on one side that do not directly contact the fluid, and the other side of the substrate does not have electrodes that face the fluid. Detection of the fluid may be performed when the electric field from the electrodes penetrates the substrate and into the fluid. Suitable examples of such substrate materials may include ceramic, aluminum oxide, zirconium oxide, and others. The coating changes as the concentration of contaminants in the lubricant bind to, coupled with, diffuse into, etc., the coating. As the concentration of contaminants in or on the coating changes, the frequencies at which the circuit in the sensor resonates changes. The change in resonance of the circuit can be used to identify and/or measure the level or amount of contaminants in the lubricant. Alternatively, no coating may be used, and the frequencies at which the resonant circuit of the sensor resonates may change based on the concentration of contaminants in the electric field between the electrodes. Alternatively, no coating may be used, and Fp, Zp and other responses from the sensor may change based on the concentration of contaminants in the electric field between the electrodes.

Figure 3:
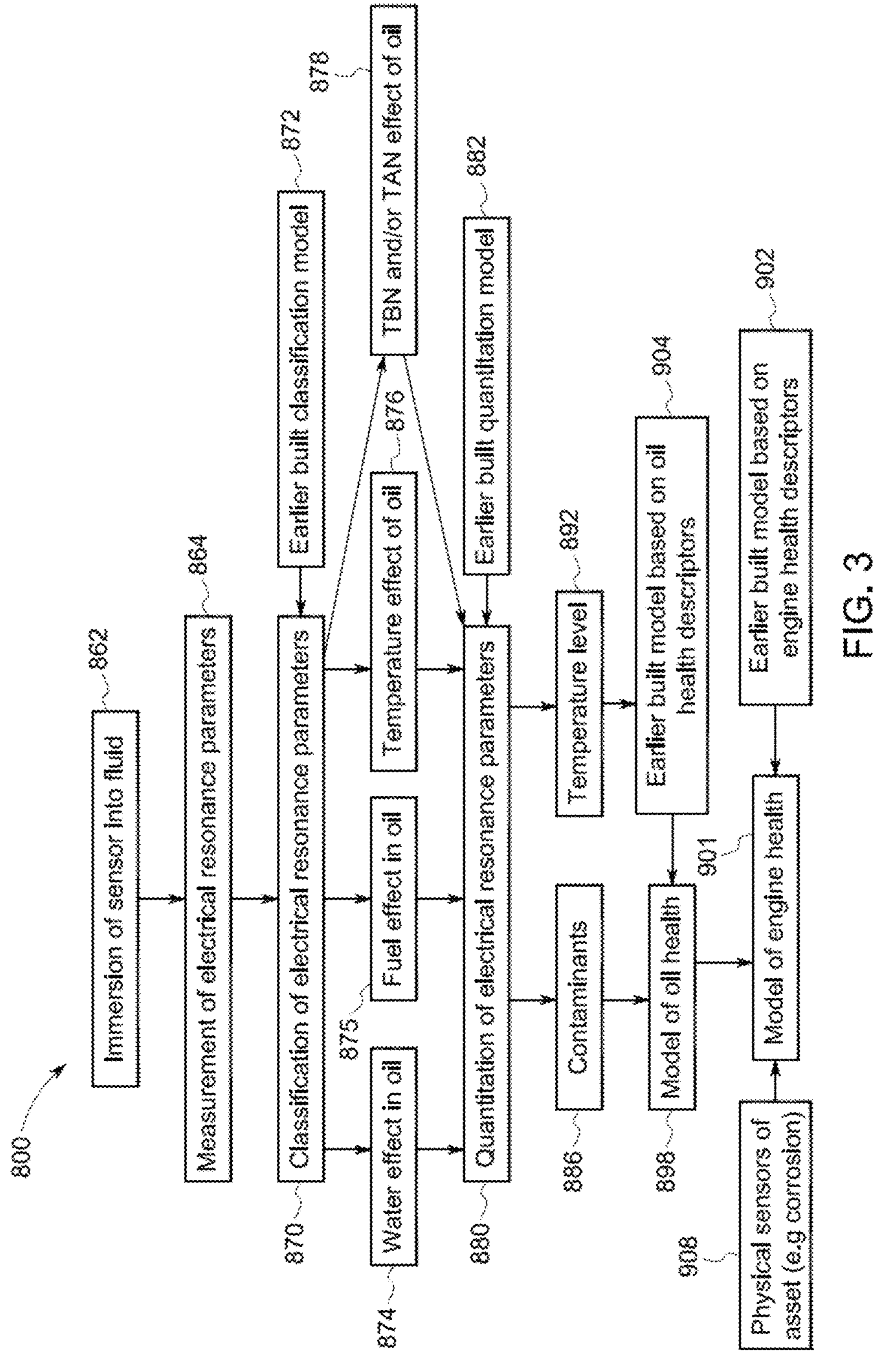
FIG. 3 illustrates a flowchart of one embodiment of a method for monitoring lubricant (e.g., oil) health.

FIG. 3 illustrates a flowchart of one embodiment of a method 800 for monitoring lubricant (e.g., oil) health. At 862, the sensor is at least partially immersed into an oil. At 864, measurement of electrical resonance parameters of the resonance spectra at several resonances of the sensor is performed. For quantitation of contamination of engine oil by water, fuel leaks, and levels of TBN and/or TAN with a sensor, the sensor may be placed into operational contact with the fluid at 862. In a specific embodiment, the resonant impedance spectra $\check{Z}(f)=Z_{re}(f)+jZ_{im}(f)$ of a sensor may be determined at 864. For example, the parameters from the measured $\check{Z}(f)$ spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_Z$ of $Z_{im}(f)$, may be calculated. In another embodiment, the electrical resonance parameters may include capacitance parameters of the sensor in operational contact with the fluid, instead or in addition to impedance parameters.

At 870, the electrical resonance parameters are classified. This may be done using a determined classification model at 872 to assess, for example, one or more of water effects (e.g., at 874), fuel effects (e.g., at 875), temperature effects (e.g., at 876), and/or TBN and/or TAN effects (e.g., at 878). At 880, quantitation of the electrical resonance parameters may be performed using a predetermined, earlier saved quantitation model (e.g., at 882). At 886, a determination of components in the oil, such as water, fuel, soot, wear metal particles (e.g., at 890), as well as the temperature (e.g., at 892), prediction of the oil health (e.g., at 898) and the engine health (e.g., at 901). Optionally, the amount of TBN and/or TAN may be determined at 886. This may be done by using one or more of determined engine health descriptors (e.g., at 902) and oil health descriptors (e.g., at 904), as well as inputs from any additional sensors (e.g., at 908). Suitable additional sensors may include those sensing corrosion, temperature, pressure, system (engine) load, system location (e.g., by GPS signal), equipment age calculator, pH, and the like.

For example, in one embodiment, a sensor system may be an electrical resonator that may be excited with a wired or wireless excitation and where a resonance spectrum may be collected and analyzed to extract at least four parameters that may be further processed upon auto scaling or mean centering of the parameters and to quantitatively determine properties of the oil. The properties of the oil that are determined via analyzing the resonance impedance spectrum may include the concentration of water, acid, and/or fuel in engine oil, and the properties may be used to predict the remaining life of the engine oil and/or the remaining life of the engine in which the oil is disposed. The spectral parameters of the resonance spectrum such as $F_p$, $Z_p$, $F_z$, $F_1$, $F_2$, $Z_1$, and $Z_2$ or the whole resonance spectrum with a single or multiple resonators can be used for data processing.

The classification model 872 may be built using the predicted contributions of the spectral parameters for an uncontaminated fluid and for fluid contamination using previously determined component effects and their corresponding spectral parameters. Based on previously or empirically determined effects of components on a particular fluid, the resonance parameters, both real and imaginary, may be changed and/or affected in a quantifiable manner if specific components of interest are present. Further, based on the measured parameters, a concentration of a particular component may also be predicted, and multi-component models may be generated. The disclosed techniques may be used to sense a suitable fluid and to build a component and environmental effect model.

Measurements of the resonant impedance of sensors may be performed with a network analyzer (Agilent) or a precision impedance analyzer (Agilent), under computer control using LabVIEW. Collected resonant impedance data may be analyzed using KaleidaGraph (Synergy Software, Reading, Pa.) and PLS Toolbox (Eigenvector Research, Inc., Manson, Wash.) operated with Matlab (The Mathworks Inc., Natick, Mass.). In another embodiment, measurements of the resonant impedance of sensors may be performed with a mini network analyzer or an integrated circuit impedance analyzer.

By using multivariate analysis of calculated parameters of $\check{Z}(f)$ spectra, classification of analyte may be performed. Suitable analysis techniques for multivariate analysis of spectral data from the multivariable sensors may include Principal Components Analysis (PCA), Independent Component Analysis (ICA), Linear Discriminant Analysis (LDA), and Flexible Discriminant Analysis (FDA). PCA may be used to discriminate between different vapors using the peptide-based sensing material.

By using multivariate analysis, also calculations of non-resonant impedance spectra or optical spectra may be performed.

The one or more processors are configured to analyze the resonant spectral response and determine properties of the fluid. For example, in one embodiment, the one or more processors may be configured to determine a concentration of potassium hydroxide or other basic components in order to determine the TBN of the oil. As another example, the one or more processors may be configured to determine a concentration of acids in order to determine the TAN of the oil.

In one embodiment, measurements of the sensor installed in an asset are correlated to TAN/TBN in the following manner. First, the sensor is calibrated to different levels of TAN and/or TBN. For such calibration, the sensor is exposed to samples related to known levels of TAN and/or TBN. Such sensor exposure allows the sensor to produce responses that are different to different known levels of TAN and/or TBN. As described above, a known quantity of potassium hydroxide can be placed into oil that is examined by the sensor to measure the TBN of the oil. A known quantity of an acid that is placed into oil (e.g., one or more naphthenic acids, such as carboxylic acid) can be examined by the sensor to measure the TAN of the oil.

The response of the sensor may have peaks at frequencies associated with the presence of TAN in the sample and/or associated with the presence of TBN in the sample. The size or magnitude of the peaks, and/or the frequencies at which the peaks occur, can indicate different concentrations of TAN and/or TBN in the sample. The calibration is complete when a correlation between the different known levels of TAN and/or TBN and the corresponding responses from the sensor is established. Such correlation is known as a calibration function. This calibration function unambiguously relates a measured sensor response to a particular level of TAN and/or TBN. Next, the calibrated sensor is now installed in an asset and every time the sensor measures a response, the sensor (or computing assembly) consults with the calibration function on the correspondence of the measured sensor response to the exact value of TAN and/or TBN.

The multivariable sensor described herein can refer to a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a real and imaginary parts of impedance of a sensing region in an operational contact with oil. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

In other embodiments, a single (or univariate) response signal can be used to monitor TBN or TAN. This response signal can originate from a sensor. This response signal can comprise a change in a capacitance, a change in a resistance, a change in an inductance, or any change correlated to TBN or TAN. A separate other sensor can be used in combination with a TBN or TAN univariate response sensor to correct for environmental effects not correlated with TBN or TAN. Nonlimiting examples of such environmental effects include ambient temperature, humidity, pressure, and other known effects.

Multivariate analysis includes a mathematical procedure that is used to analyze more than one variable from the sensor response and to provide the information about the type of at least one environmental parameter from the measured sensor parameters and/or to provide quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

Alternative or complementary to multivariate analysis, machine learning can be used. Machine learning includes mathematical procedures that automate creation of analytical models. These analytical models may predict future outcomes of TBN or TAN change or change of another parameter or other parameters of interest and change of the engine or another access using collected data. Machine learning is the approach to build and implement predictive algorithms to achieve these goals. Non-limiting examples of machine learning tools may include classification, regression, dimensionality reduction, preprocessing, model selection, clustering, decision tree learning, association rule learning, artificial neural networks, support vector machines, bayesian networks, genetic algorithms, and others.

Spectral parameters include measurable variables of the sensor response. The sensor response is the impedance spectrum of the LCR sensor. In another embodiment, the sensor response is the impedance spectrum of the non-resonant impedance sensor. In yet another embodiment, the sensor response is the optical spectrum in infrared, near-infrared, visible or ultraviolet range of spectrum. In addition to measuring the impedance spectrum in the form of Z-parameters, S-parameters, and other parameters, the impedance spectrum (for example, both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Spectral parameters calculated from the impedance spectra may also be called features or descriptors. The appropriate selection of features is performed from all potential features that can be calculated from spectra.

Sensing materials and sensing films include, but are not limited to, materials deposited onto a transducer's electronics circuit components, such as LCR circuit components to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other techniques.

One or more embodiments of the sensing systems described herein may measure the amount or concentration of basic (alkaline) and/or acidic components in engine oil and, based on the measurements, determine the corresponding TBN and/or TAN of the oil. The data acquisition circuitry may direct the sensor to measure the TBN and/or TAN repeatedly (e.g., on a continuous basis). The measured values of TBN and/or TAN may be periodically recorded by the computer 124 onto one or more memories. The frequency at which the TBN and/or TAN is determined and/or recorded may be based on the application (e.g., use) of the engine and/or the duty cycle of the engine. For example, the TBN and/or TAN of engines used for higher loads (e.g., engines operating to propel heavy vehicles) and/or used more often (e.g., over a wide range of engine operating conditions) may be measured or recorded more often than for engines used for lighter loads (e.g., lighter vehicles) and/or engines used less often (e.g., engines having fewer cycles).

The in-cylinder health of the engine can be monitored by measuring the amount of TBN and/or TAN in the oil that lubricates the engine. Normal lube oil consumption in the engine or a normal rate of oil consumption (e.g., within designated or predetermined limits) can indicate a healthy engine and healthy combustion within the engine. But, excess oil consumption or an excessive rate of oil consumption (e.g., outside of the designated or predetermined limits) can indicate an unhealthy engine and/or unhealthy combustion within the engine. Monitoring the TAN and/or TBN in the oil over time can allow for the engine to be proactively inspected or serviced before additional cylinder wear and/or seizing of cylinders within the engine. This can save the engine from major or significant repairs or catastrophic failure, and can reduce the life cycle cost of the engine. Monitoring the TBN and/or TAN changes can provide insight into the reliability and/or durability of the engine. The "unhealthy" state of a component such as an engine can be identified or determined responsive to an increase or decrease in the TBN or TAN, as appropriate and as described herein, relative to one or more previous measurements and/or by comparing the TBN or TAN measurement to one or more thresholds.

Although FIG. 3 illustrates a flowchart of one embodiment of a method 800 for monitoring lubricant (e.g., oil) health where at 864, measurement of electrical resonance parameters of the resonance spectra at several resonances of the sensor is performed, other sensors known in the art may be used at steps 864, 870, and 880, and other steps.

As described herein, the method 400 can involve tracking the rate of change in TBN and/or TAN in the oil of an engine. Changes in the TBN and/or TAN can be correlated to oil consumption based on sensor calibrations. If the TBN and/or TAN indicates that the oil consumption in the engine exceeds an allowable upper limit for a healthy engine, then the method 800 can involve servicing, inspecting, and/or repairing the engine. By examining the rates of change in the TBN and/or TAN (e.g., by using [d(TBN)/dt] and/or [d(TAN)/dt]), the method can be a self-learning method that accounts for engine-to-engine variability and that examines each engine as a separate or unique entity with its own inherent variations and/or tolerances. Optionally, tracking changes in TBN and/or TAN in one or more engines can be used to facilitate future engine designs.

Figure 4:
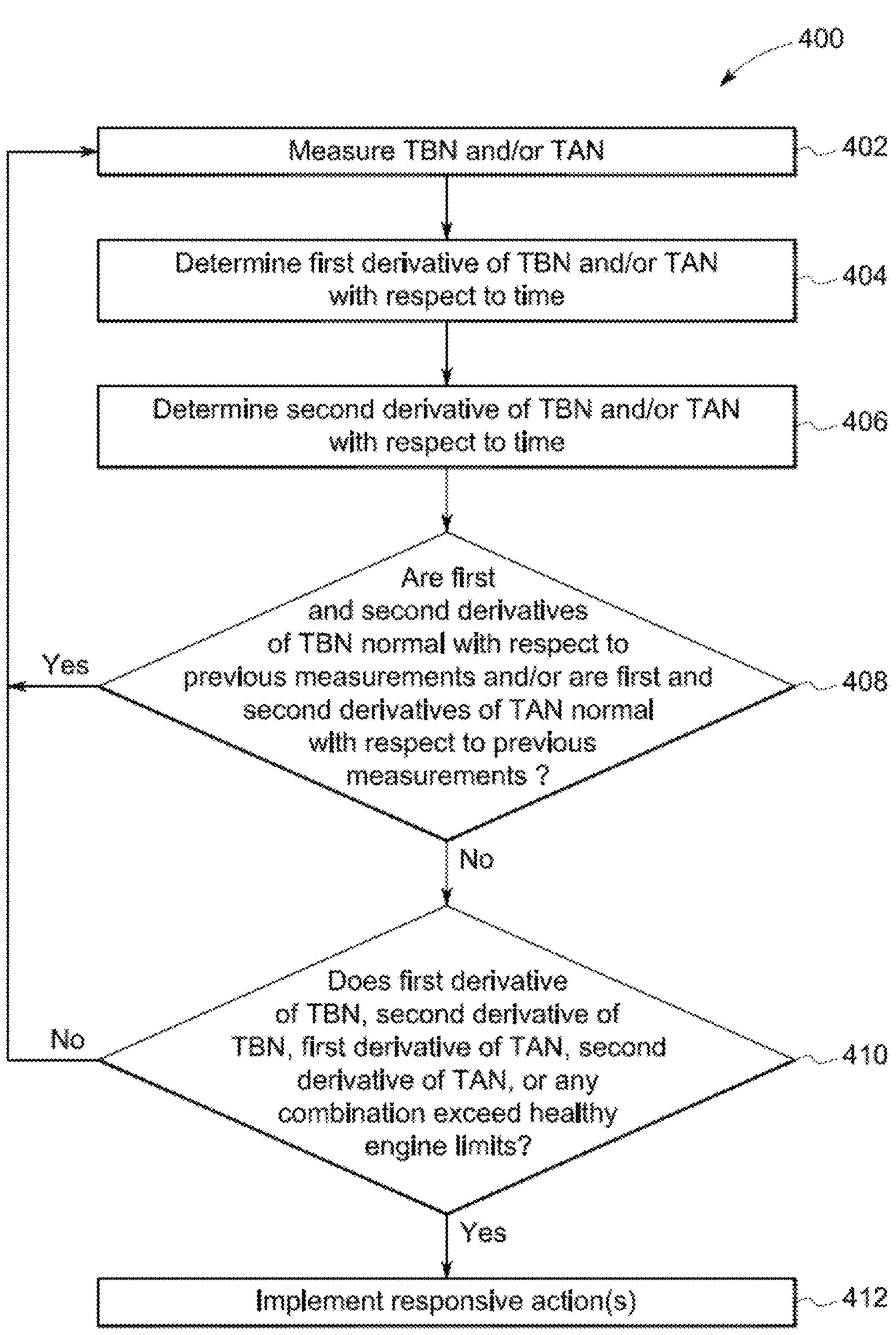
FIG. 4 illustrates a flowchart of one embodiment of a method for monitoring lubricant (e.g., oil) health.

FIG. 4 illustrates a flowchart of one embodiment of a method 400 for monitoring lubricant (e.g., oil) health. The in-cylinder health of the engine can be monitored by measuring the amount of TBN and/or TAN in the oil that lubricates the engine. Normal lube oil consumption in the engine or a normal rate of oil consumption (e.g., within designated or predetermined limits) can indicate a healthy engine and healthy combustion within the engine. But, excess oil consumption or an excessive rate of oil consumption (e.g., outside of the designated or predetermined limits) can indicate an unhealthy engine and/or unhealthy combustion within the engine. Monitoring the TAN and/or TBN in the oil over time can allow for the engine to be proactively inspected or serviced before additional cylinder wear and/or seizing of cylinders within the engine. This can save the engine from major or significant repairs or catastrophic failure, and can reduce the life cycle cost of the engine. Monitoring the TBN and/or TAN changes can provide insight into the reliability and/or durability of the engine.

As described herein, the method 400 can involve tracking the rate of change in TBN and/or TAN in the oil of an engine. Changes in the TBN and/or TAN can be correlated to oil consumption based on sensor calibrations. If the TBN and/or TAN indicates that the oil consumption in the engine exceeds an allowable upper limit for a healthy engine, then the method 800 can involve servicing, inspecting, and/or repairing the engine. By examining the rates of change in the TBN and/or TAN (e.g., by using [d(TBN)/dt] and/or [d(TAN)/dt]), the method can be a self-learning method that accounts for engine-to-engine variability and that examines each engine as a separate or unique entity with its own inherent variations and/or tolerances. Optionally, tracking changes in TBN and/or TAN in one or more engines can be used to facilitate future engine designs.

At 402, TBN and/or TAN of oil in an engine is measured. One or more embodiments of the sensor described herein is at least partially immersed into the oil. Electrical resonance parameters of the resonance spectra at several resonances of the sensor is measured. For quantitation of contamination of engine oil by water, fuel leaks, and levels of TBN and/or TAN with a sensor, the sensor may be placed into operational contact with the fluid. In a specific embodiment, the resonant impedance spectra $\check{Z}(f)=Z_{re}(f)+jZ_{im}(f)$ of a sensor may be determined. For example, the parameters from the measured $\check{Z}(f)$ spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_Z$ of $Z_{im}(f)$, may be calculated. In another embodiment, the electrical resonance parameters may include capacitance parameters of the sensor in operational contact with the fluid, instead or in addition to impedance parameters. The measurements of TBN and/or TAN may be repeated multiple times in order to monitor for changes in TBN and/or TAN, as described herein.

Figure 5:
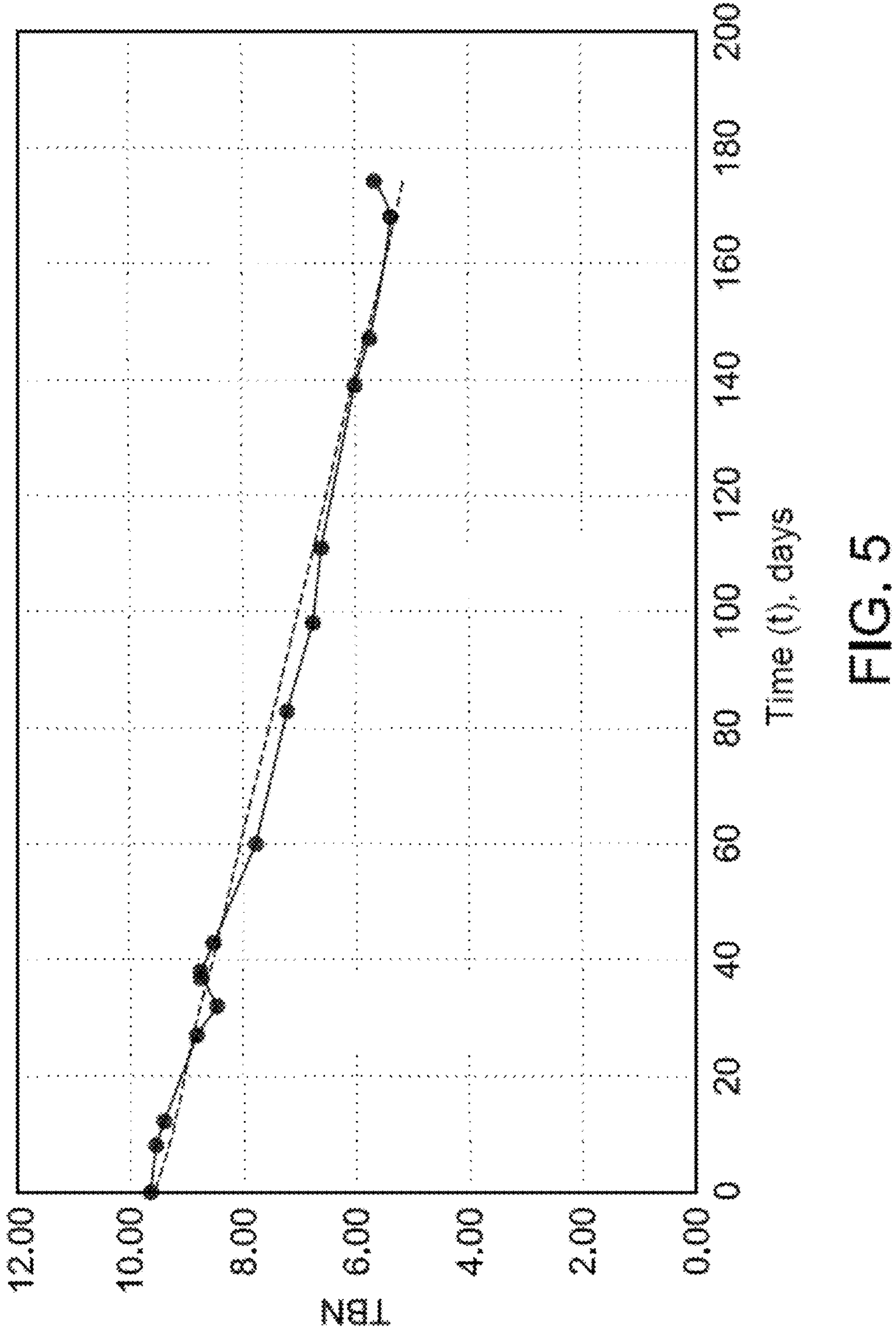
FIG. 5 illustrates measurements of TBN according to one example.
Figure 6:
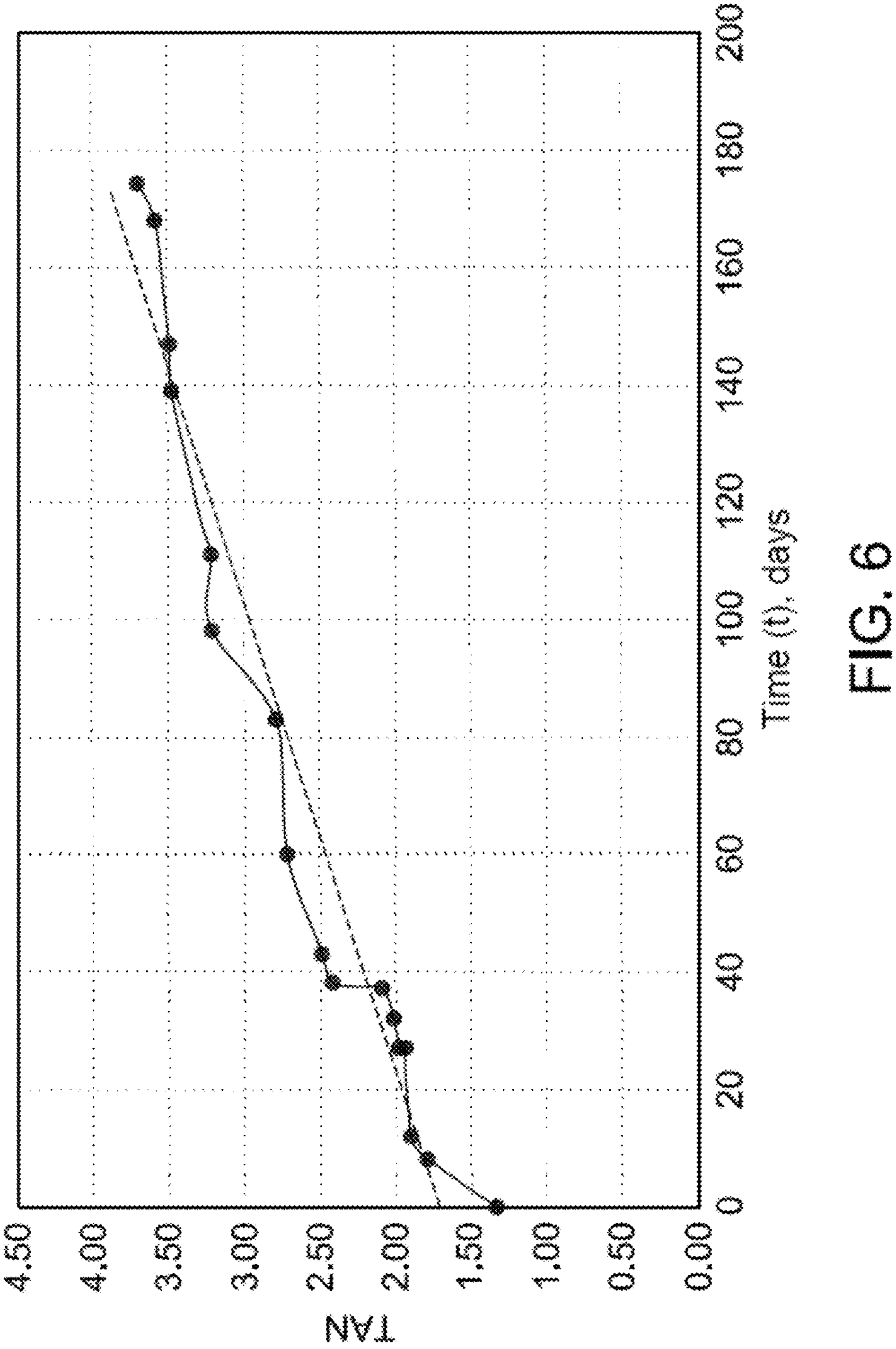
FIG. 6 illustrates measurements of TAN according to one example.

With continued reference to the flowchart of the method 400 shown in FIG. 4, FIGS. 5 and 6 illustrate measurements of TBN and TAN, respectively, according to one example. The TBN and TAN measurements are shown alongside horizontal axes indicative of time or number of measurements, and are shown alongside vertical axes indicative of the TBN and/or TAN measured in the oil. As shown in FIGS. 5 and 6, the TBN measurements may decrease over time while the TAN measurements may increase over time.

At 404 in the flowchart of the method 400, the first derivative of TBN and/or the first derivative of TAN with respect to time are determined. For example, the data acquisition circuitry 116 and/or the processor(s) of the computer 124 can calculate the change in TBN with respect to time (e.g., [d(TBN)/dt]) and/or the change in TAN with respect to time (e.g., [d(TAN)/dt]).

Figure 7:
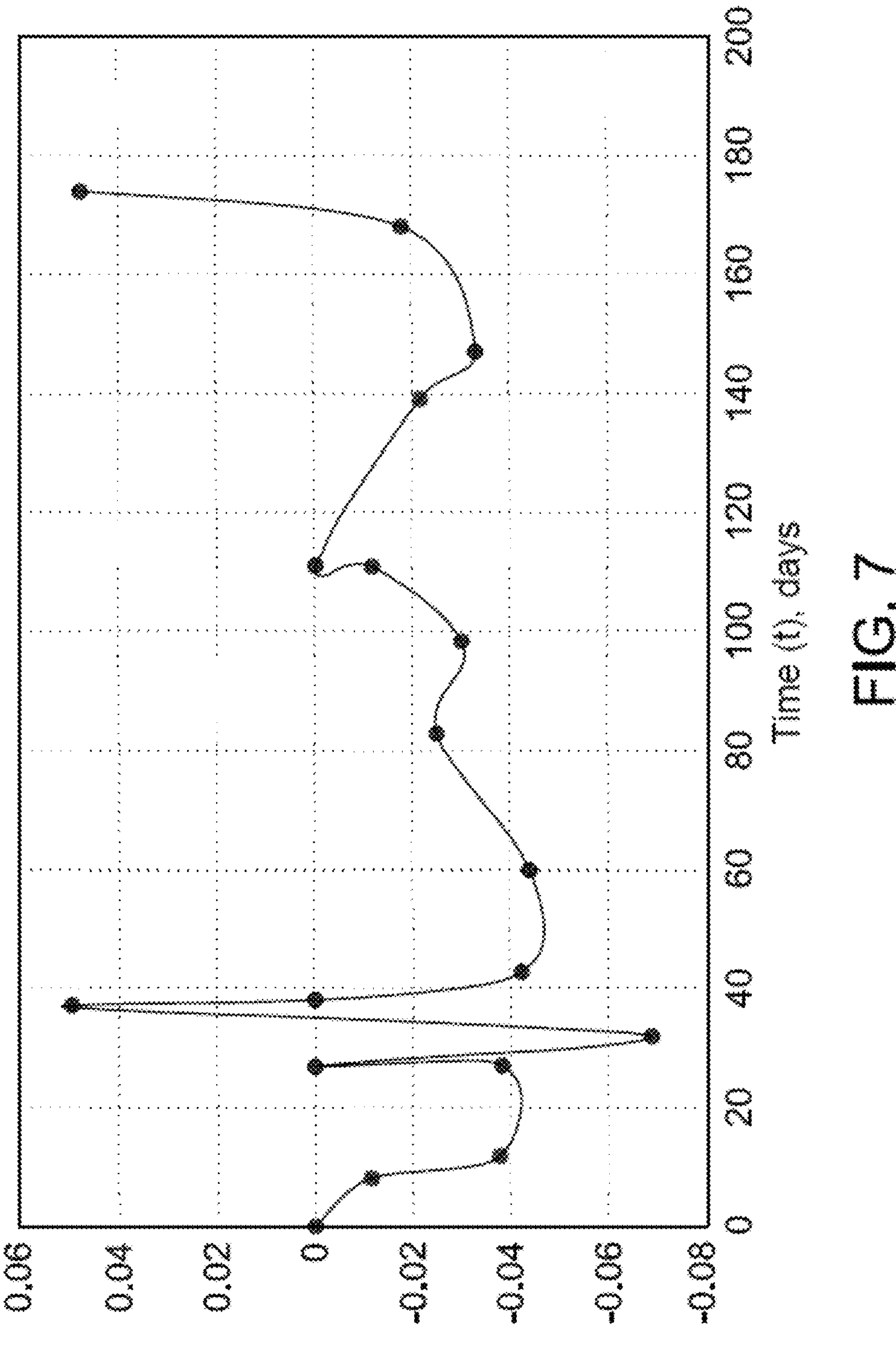
FIG. 7 illustrates a first derivative of TBN with respect to time according to one example.
Figure 8:
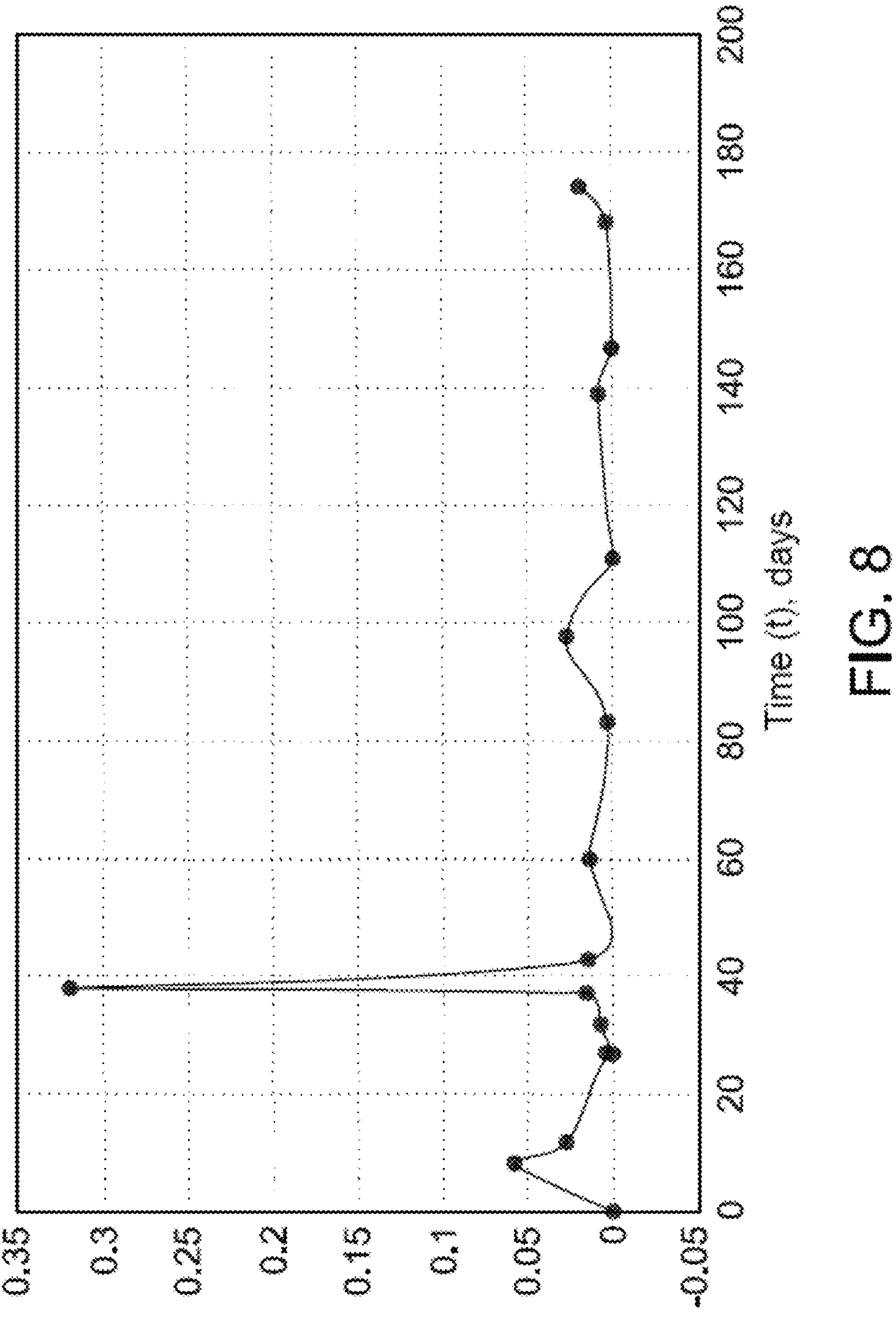
FIG. 8 illustrates a first derivative of TAN with respect to time according to one example.

With continued reference to the flowchart of the method 400 shown in FIG. 4, FIGS. 7 and 8 illustrate first derivatives of TBN and TAN, respectively, with respect to time according to one example. The first derivatives of TBN and TAN are shown alongside horizontal axes indicative of time or number of measurements, and are shown alongside vertical axes indicative of the rates of change in the TBN and/or TAN. As shown in FIG. 7, the first derivative of TBN includes several peaks and valleys that indicate significant changes in the TBN measurements with respect to time. In contrast, the first derivative of TAN is relatively flat with a single large peak, which indicates that the TAN in the oil does not significantly change with respect to time except for the time at or near forty along the horizontal axis.

At 406 in the flowchart of the method 400, the second derivative of TBN and/or the second derivative of TAN with respect to time are determined. For example, the data acquisition circuitry 116 and/or the processor(s) of the computer 124 can calculate the second derivative of TBN with respect to time (e.g., [$d^2$(TBN)/$dt^2$]) and/or the change in TAN with respect to time (e.g., [$d^2$(TAN)/$dt^2$]).

Figure 9:
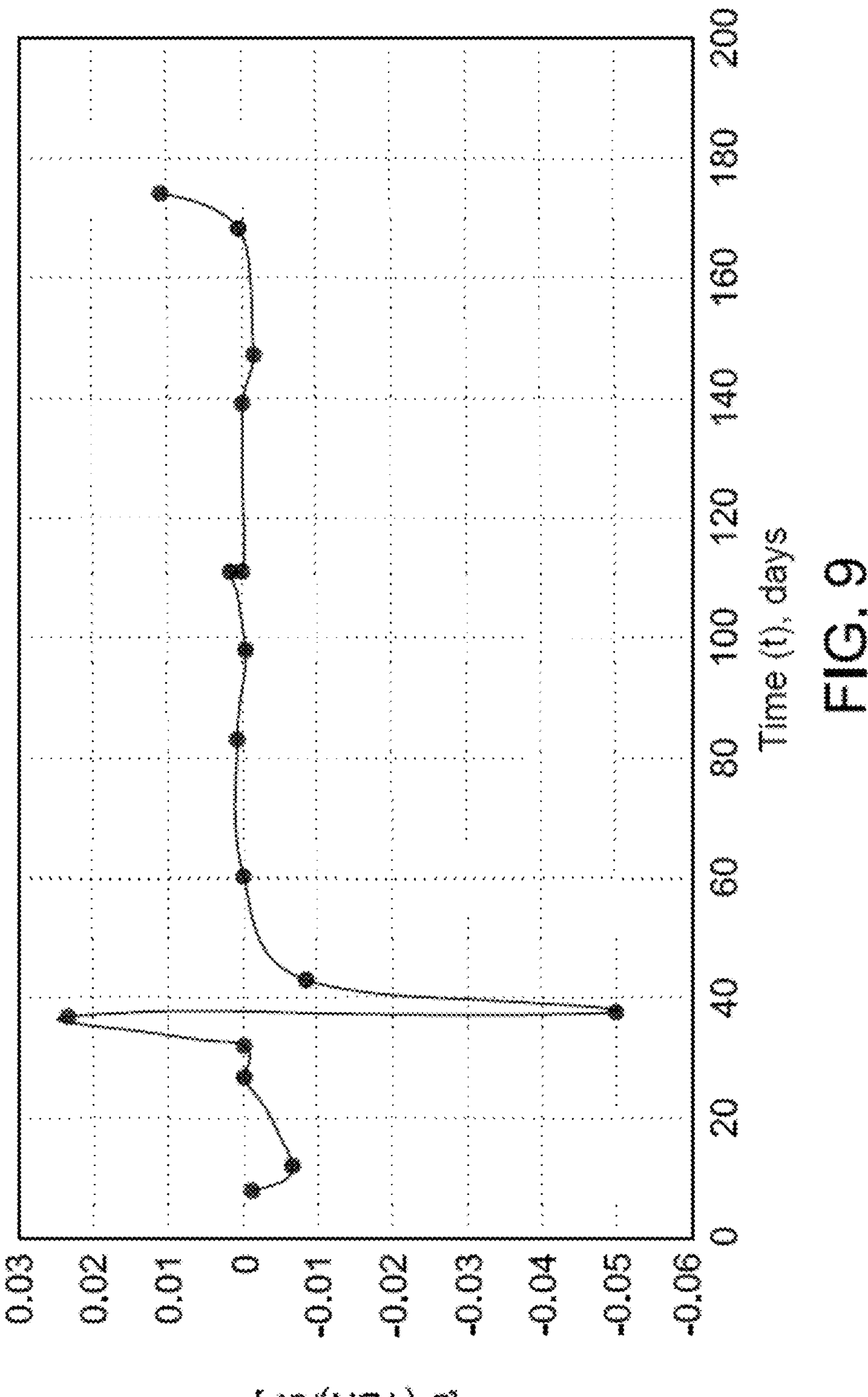
FIG. 9 illustrates a second derivative of TBN with respect to time according to one example.
Figure 10:
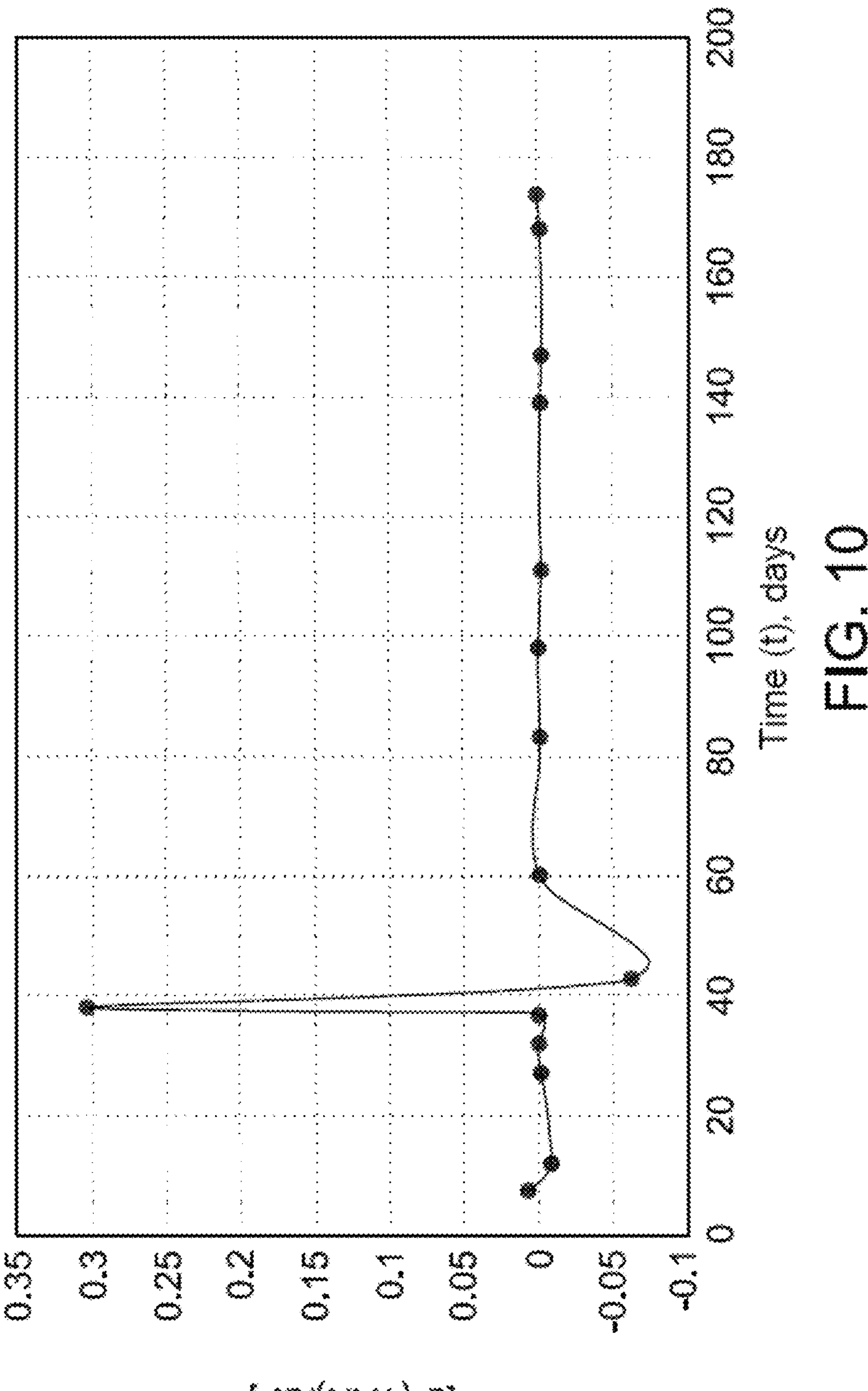
FIG. 10 illustrates a second derivative of TAN with respect to time according to one example.

With continued reference to the flowchart of the method 400 shown in FIG. 4, FIGS. 9 and 10 illustrate second derivatives of TBN and TAN, respectively, with respect to time according to one example. The second derivatives of TBN and TAN are shown alongside horizontal axes indicative of time or number of measurements, and are shown alongside vertical axes indicative of the second derivatives of TBN and/or TAN.

At 408 in the flowchart of the method 400, a determination is made as to whether the first and/or second derivatives of TBN and/or the first and/or second derivatives of TAN are normal. This determination may be performed by the acquisition circuitry 116 and/or processor(s) of the computer 124 comparing the first and/or second derivatives of TBN and/or the first and/or second derivatives of TAN to one or more predetermined or previously designated limits.

Figure 11:
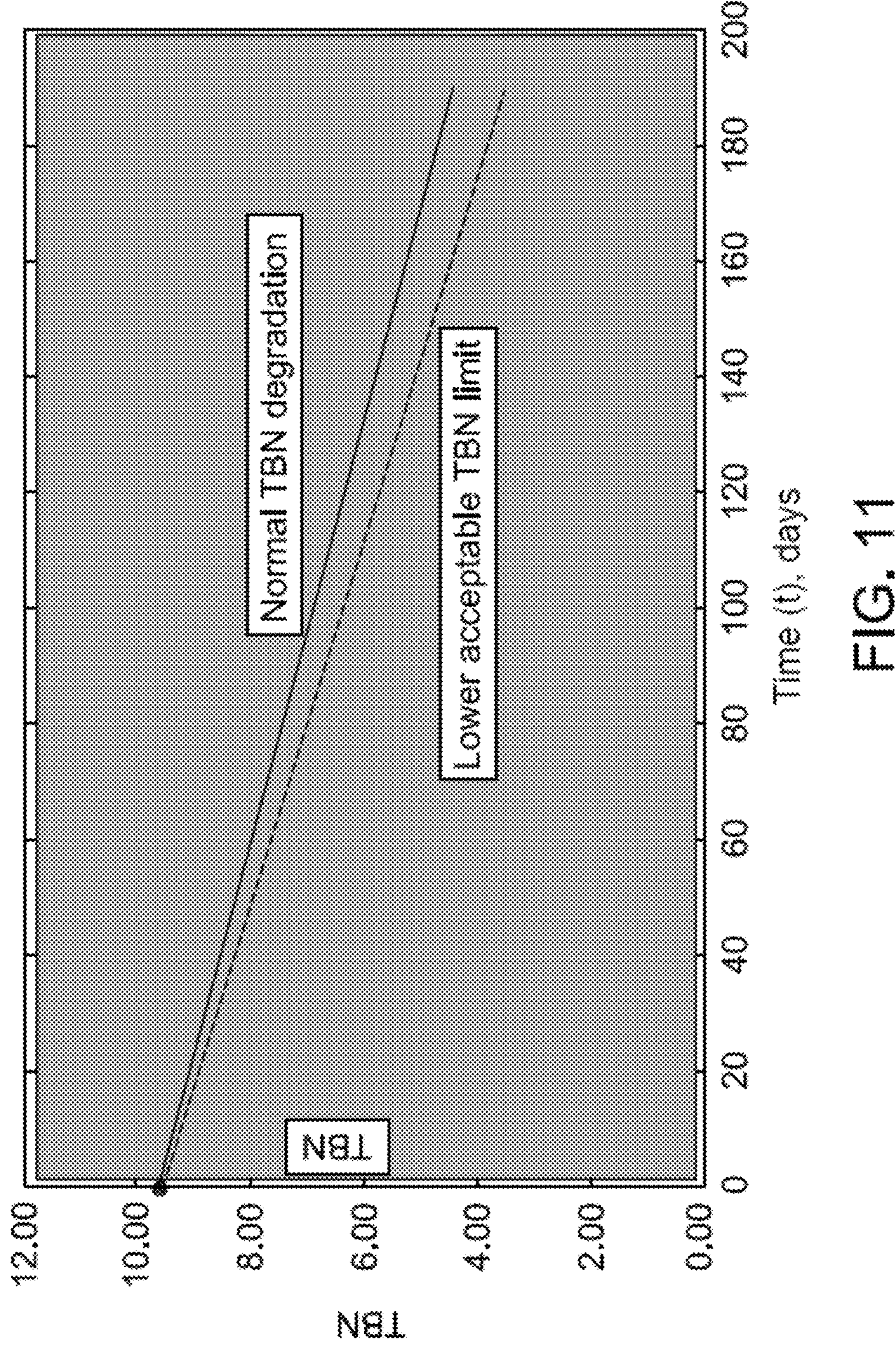
FIG. 11 illustrates examples of normal and acceptable limits of TBN measurements.

With continued reference to the flowchart of the method 400 shown in FIG. 4, FIG. 11 illustrates examples of predetermined or previously designated limits of TBN measurements. As shown in FIG. 11, TBN can normally degrade over time without indicating the need for repair, inspection, or maintenance of the engine. The limit on how the TBN can degrade over time is indicated by the "Normal TBN Degradation" line shown in FIG. 11, which is shown alongside a horizontal axis indicative of time or number of measurements and is shown alongside a vertical axis indicative of TBN measurements. Measurements of TBN that are above the normal TBN degradation limit or line indicate that the TBN in the oil is still within acceptable limits, and do not indicate a need to inspect, repair, or maintain the engine. A "Lower Acceptable TBN Limit" in FIG. 11 indicates a lower limit on the TBN measurements that indicates an unhealthy oil or engine. For example, TBN measurements that fall below this limit may indicate the need to repair, inspect, or maintain the engine, or to remove the engine from service.

Figure 12:
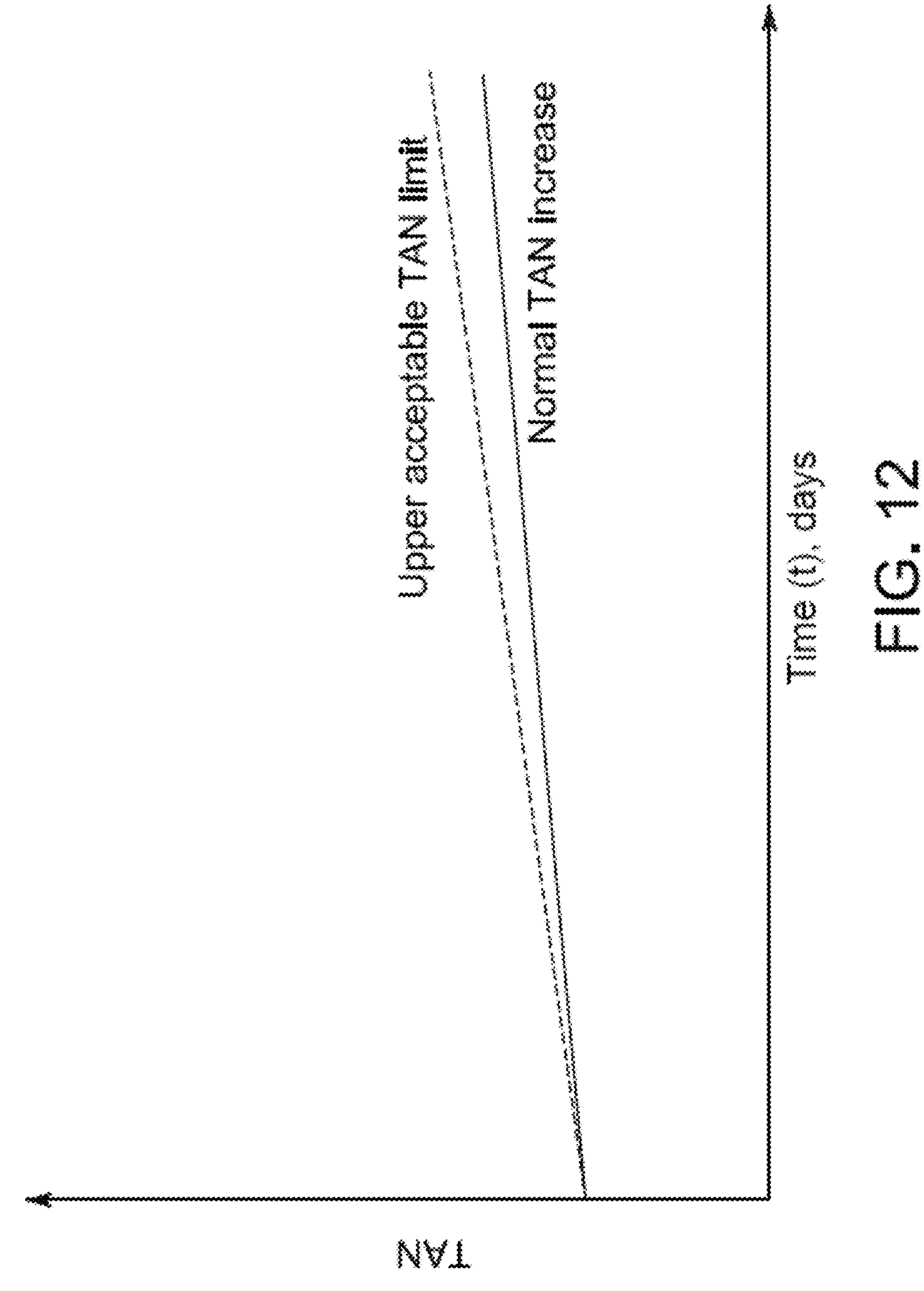
FIG. 12 illustrates examples of normal and acceptable limits of TAN measurements.

FIG. 12 illustrates examples of predetermined or previously designated limits of TAN measurements. As shown in FIG. 12, TAN can normally increase over time without indicating the need for repair, inspection, or maintenance of the engine. The limit on how the TAN can increase over time is indicated by the "Normal TAN Increase" line shown in FIG. 12, which is shown alongside a horizontal axis indicative of time or number of measurements and is shown alongside a vertical axis indicative of TAN measurements. Measurements of TAN that are below the normal TAN increase limit or line indicate that the TAN in the oil is still within acceptable limits, and do not indicate a need to inspect, repair, or maintain the engine. An "Upper Acceptable TAN Limit" in FIG. 12 indicates an upper limit on the TAN measurements that indicates an unhealthy oil or engine. For example, TAN measurements that fall above this limit may indicate the need to repair, inspect, or maintain the engine, or to remove the engine from service.

Figure 13:
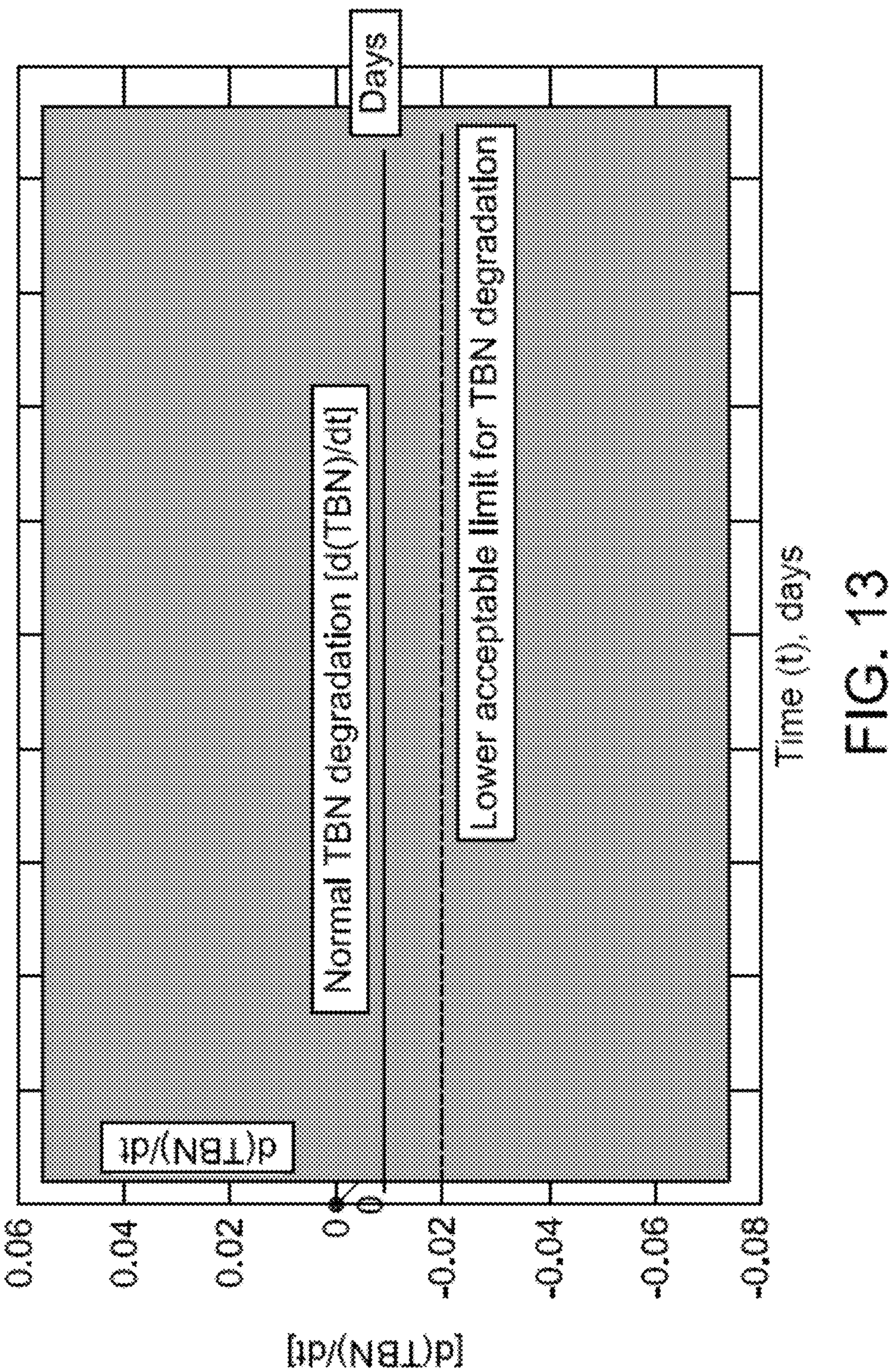
FIG. 13 illustrates examples of normal and acceptable limits of the first derivative of TBN.

With respect to the determination that is made at 408 in the flowchart of the method 400 shown in FIG. 4, FIG. 13 illustrates examples of predetermined or previously designated limits of the first derivative of TBN. As shown in FIG. 13, a normal limit on the first derivative of TBN ("Normal TBN Degradation [d(TBN)/dt]" in FIG. 13) indicates a lower limit on the first derivative of TBN. First derivatives of TBN that are at or above this limit can be indicative of healthy oil or a healthy engine, and are not indicative of a need to repair, inspect, or maintain the engine, or to remove the engine from service, in one embodiment. Another, lower limit on the first derivative of TBN ("Lower Acceptable Limit for TBN Degradation" in FIG. 13) is described below.

Figure 14:
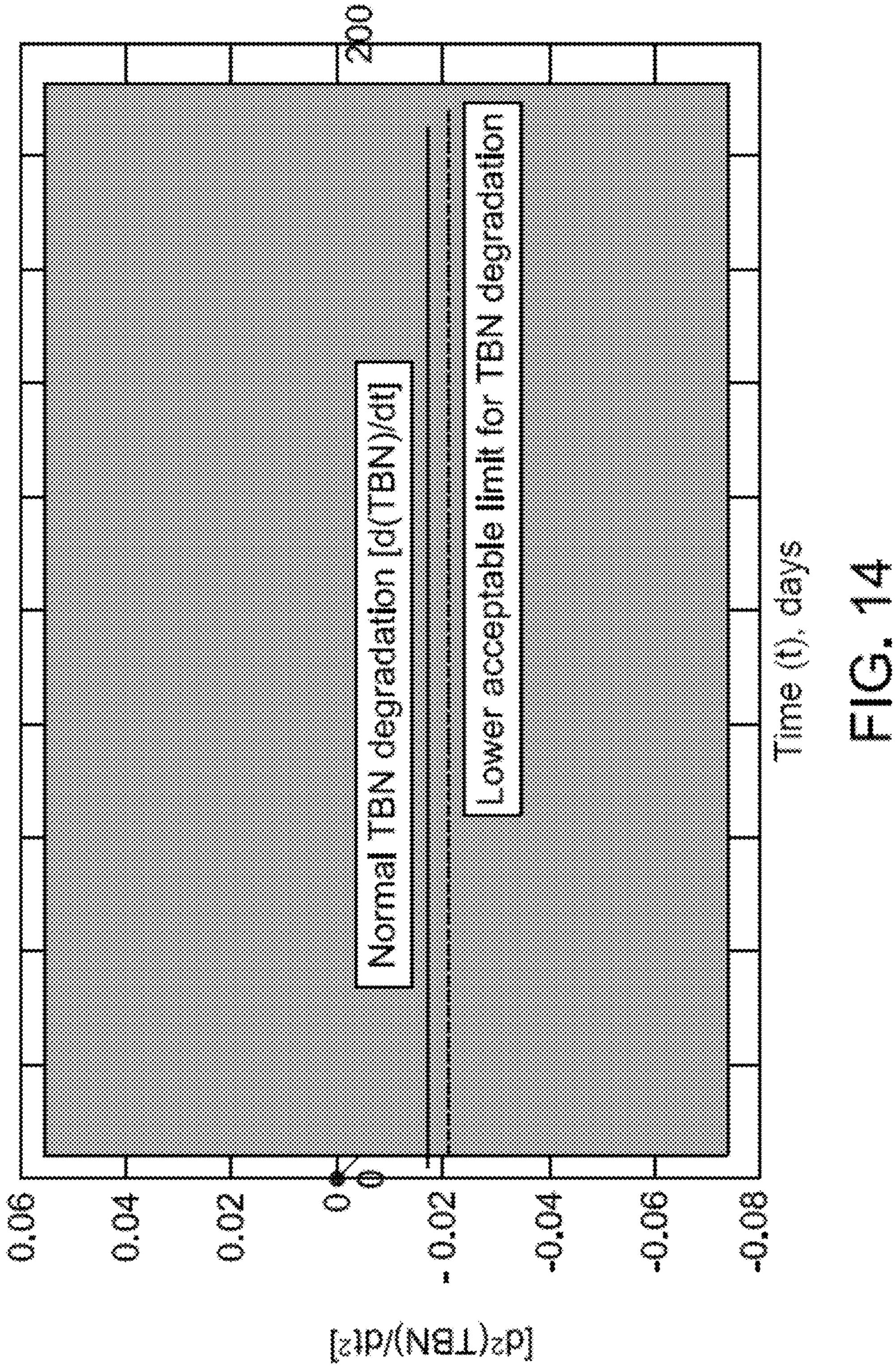
FIG. 14 illustrates examples of normal and acceptable limits of the second derivative of TBN.

FIG. 14 illustrates examples of predetermined or previously designated limits of the second derivative of TBN. As shown in FIG. 14, a normal limit on the second derivative of TBN ("Normal TBN Degradation [d(TBN)/dt]" in FIG. 14) indicates a lower limit on the second derivative of TBN. Second derivatives of TBN that are at or above this limit can be indicative of healthy oil or a healthy engine, and are not indicative of a need to repair, inspect, or maintain the engine, or to remove the engine from service, in one embodiment. Another, lower limit on the second derivative of TBN ("Lower Acceptable Limit for TBN Degradation" in FIG. 14) is described below.

Figure 15:
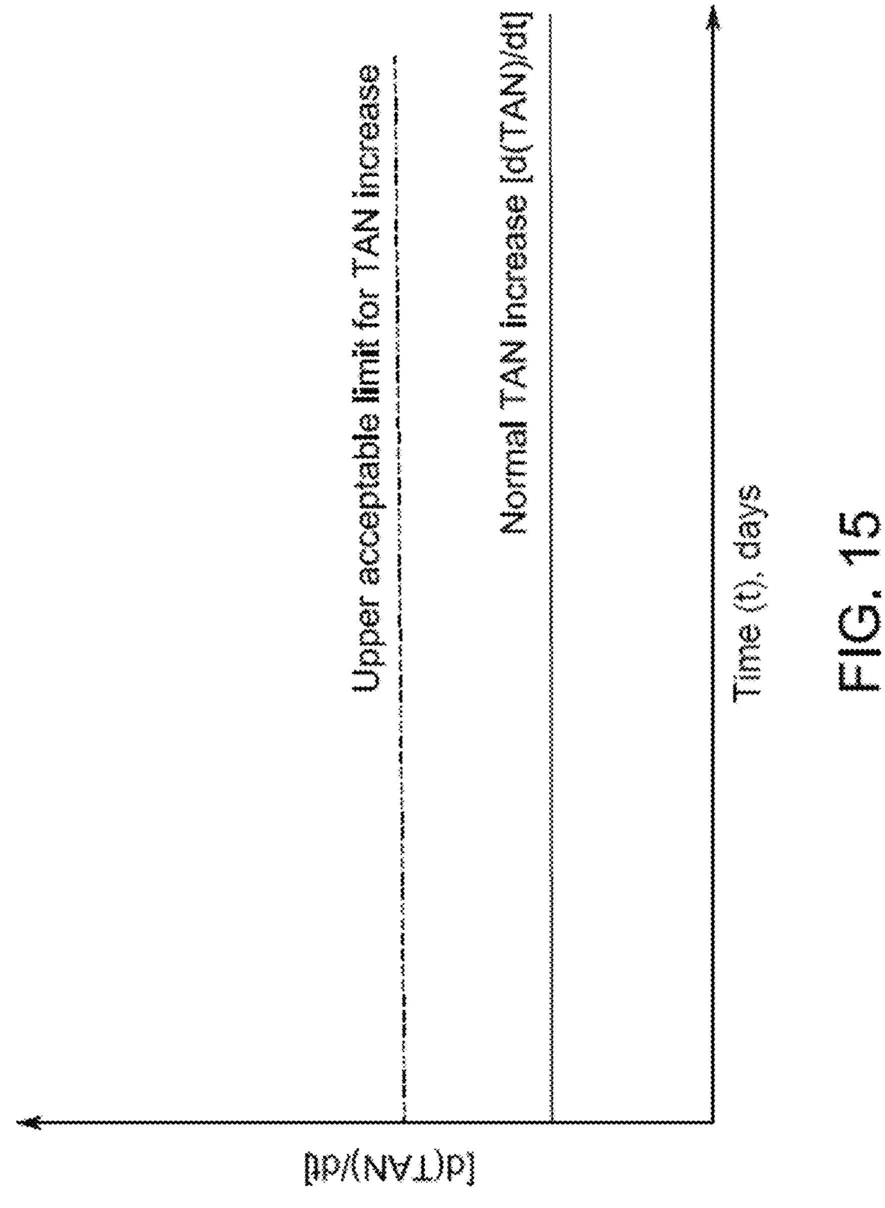
FIG. 15 illustrates examples of normal and acceptable limits of the first derivative of TAN.

FIG. 15 illustrates examples of predetermined or previously designated limits of the first derivative of TAN. As shown in FIG. 15, a normal limit on the first derivative of TAN ("Normal TAN Increase [d(TAN)/dt]" in FIG. 15) indicates an upper limit on the first derivative of TAN. First derivatives of TAN that are at or below this limit can be indicative of healthy oil or a healthy engine, and are not indicative of a need to repair, inspect, or maintain the engine, or to remove the engine from service, in one embodiment. Another, greater limit on the first derivative of TAN ("Upper Acceptable Limit for TAN Increase" in FIG. 15) is described below.

Figure 16:
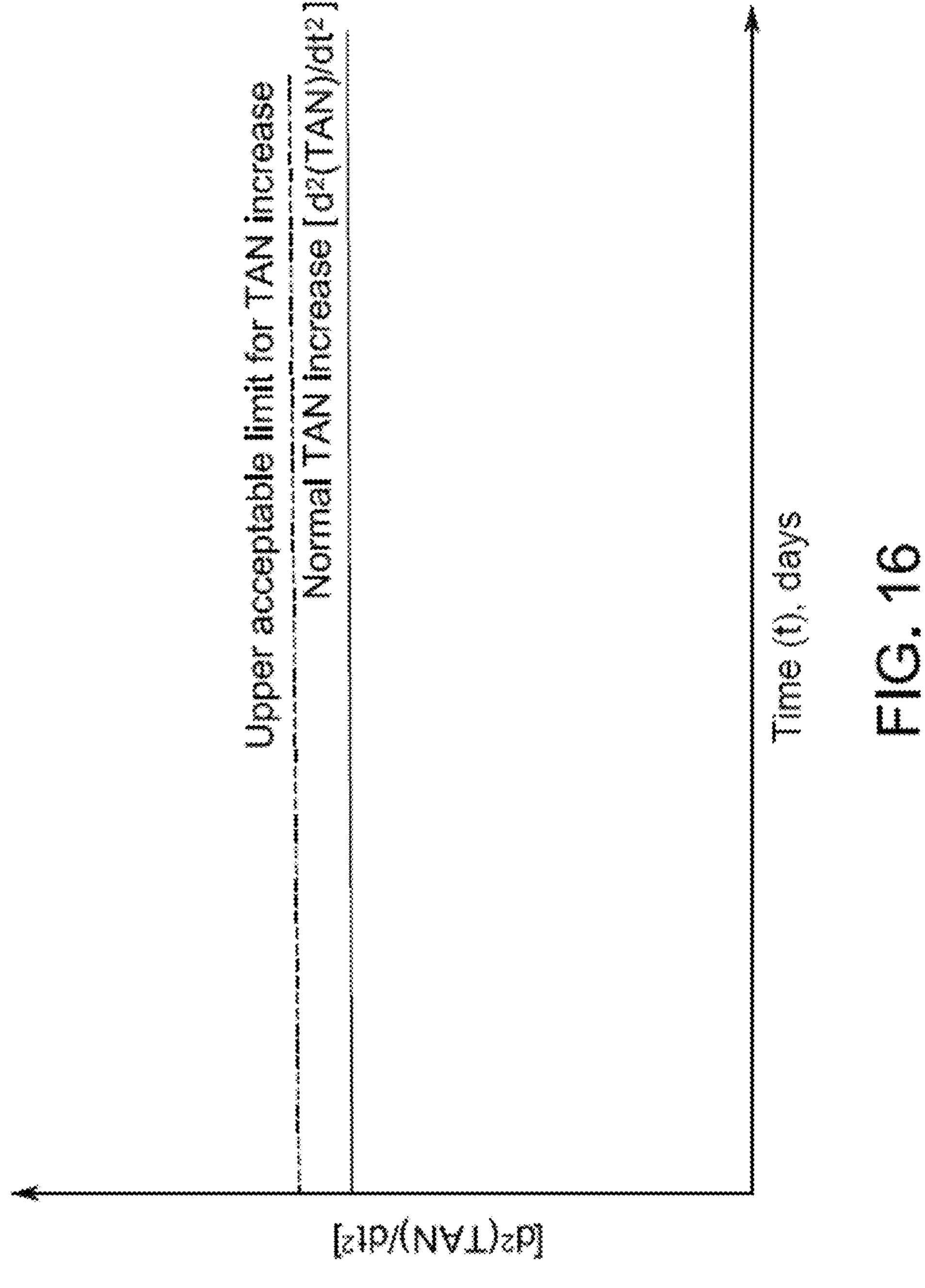
FIG. 16 illustrates examples of normal and acceptable limits of the second derivative of TAN.

FIG. 16 illustrates examples of predetermined or previously designated limits of the second derivative of TAN. As shown in FIG. 16, a normal limit on the second derivative of TAN ("Normal TAN Increase [$d^2$(TBN)/$dt^2$]" in FIG. 16) indicates an upper limit on the second derivative of TAN. Second derivatives of TAN that are at or below this limit can be indicative of healthy oil or a healthy engine, and are not indicative of a need to repair, inspect, or maintain the engine, or to remove the engine from service, in one embodiment. Another, greater limit on the second derivative of TAN ("Upper Acceptable Limit for TAN Increase" in FIG. 16) is described below.

With respect to the determination made at 408 in the method 400, if (a) the first derivative of TBN is greater than the associated normal limit (the upper of the two limits on the first derivative of TBN), (b) the first derivative of TAN is smaller than the associated normal limit (the lower of the two limits on the first derivative of TAN), (c) the second derivative of TBN is greater than the associated normal limit (the upper of the two limits on the second derivative of TBN), and (d) the second derivative of TAN is smaller than the associated normal limit (the lower of the two limits on the second derivative of TAN), then the first and second derivatives may indicate that the TBN and/or TAN of the oil are not outside of designated or predetermined (e.g., normal) limits. Optionally, the determination at 408 may determine whether a combination of two or more (but not all) of these first and/or second derivatives are above (e.g., for TBN) or below (e.g., for TAN) the associated normal limits described above. This can mean that the engine is not in need of repair, inspection, or maintenance, and that the engine can continue to operate. As a result, flow of the method 400 can return toward 402. Optionally, the method 400 can terminate.

But, if (a) the first derivative of TBN is smaller than the associated normal limit (the upper of the two limits on the first derivative of TBN), (b) the first derivative of TAN is greater than the associated normal limit (the lower of the two limits on the first derivative of TAN), (c) the second derivative of TBN is smaller than the associated normal limit (the upper of the two limits on the second derivative of TBN), and (d) the second derivative of TAN is greater than the associated normal limit (the lower of the two limits on the second derivative of TAN), then the first and second derivatives may indicate that the TBN and/or TAN of the oil are outside of designated or predetermined (e.g., normal) limits. Optionally, the determination at 408 may determine whether a combination of two or more of these first and/or second derivatives are below (e.g., for TBN) or above (e.g., for TAN) the associated normal limits described above. This can mean that the engine is in need of repair, inspection, or maintenance, and that the engine can no longer continue to safely operate. As a result, flow of the method 400 can proceed toward 410.

At 410, a determination is made as to whether the first and/or second derivatives of TBN and/or the first and/or second derivatives of TAN exceed healthy engine limits. This determination may be performed by the acquisition circuitry 116 and/or processor(s) of the computer 124 comparing the first and/or second derivatives of TBN and/or the first and/or second derivatives of TAN to one or more predetermined or previously designated limits. These limits (which differ from the normal limits used to make the determination at 408) can be referred to as acceptable limits.

For example, if (a) the first derivative of TBN is smaller than the associated acceptable limit (the lower of the two limits on the first derivative of TBN), (b) the first derivative of TAN is greater than the associated acceptable limit (the upper of the two limits on the first derivative of TAN), (c) the second derivative of TBN is smaller than the associated acceptable limit (the lower of the two limits on the second derivative of TBN), and (d) the second derivative of TAN is greater than the associated acceptable limit (the upper of the two limits on the second derivative of TAN), then the first and second derivatives may indicate that the TBN and/or TAN of the oil are outside of designated or predetermined (e.g., acceptable) limits. Optionally, the determination at 410 may determine whether a combination of two or more (but not all) of these first and/or second derivatives are below (e.g., for TBN) or above (e.g., for TAN) the associated acceptable limits. This can mean that the engine is in need of repair, inspection, or maintenance, and that the engine cannot continue to operate. As a result, flow of the method 400 can proceed toward 412.

But, if (a) the first derivative of TBN is not smaller than the associated acceptable limit, (b) the first derivative of TAN is not greater than the associated acceptable limit, (c) the second derivative of TBN is not smaller than the associated acceptable limit, and (d) the second derivative of TAN is not greater than the associated acceptable limit, then the first and second derivatives may indicate that the TBN and/or TAN of the oil are within the designated or predetermined (e.g., acceptable) limits. Optionally, the determination at 410 may determine whether a combination of two or more (but not all) of these first and/or second derivatives are not below (e.g., for TBN) or not above (e.g., for TAN) the associated acceptable limits. This can mean that the engine is not in need of repair, inspection, or maintenance, and that the engine can continue to operate. As a result, flow of the method 400 can return toward 402 or optionally terminate.

At 412, one or more responsive actions are implemented. These actions can include automatically stopping operation of the engine. For example, the computer 124 can generate a deactivation signal or instruct a vehicle controller to generate the deactivation signal that is communicated to fuel injectors of the engine and that directs the fuel injectors to stop providing fuel to the engine. As another example, the deactivation signal can otherwise control the engine, such as by decreasing (but not stopping) the supply of fuel to the engine from the fuel injectors. As another example, a control signal may be communicated to a facility to instruct the facility to inspect the engine and/or the oil, and potentially repair the engine or replace the oil.

Operation of the method 400 can be performed during operation of the engine to allow for monitoring and inspection of the health of the oil in the engine during operation of the engine. Instead of periodically collecting samples from the engine at times separated by many days (e.g., collecting samples every fifteen days), the sensor systems and methods described herein may collect measurements of characteristics of the oil on a much more frequent basis (e.g., once every second) or may continuously measure the characteristics of the oil. This can allow for very small changes in the health of the oil to be discovered immediately or very soon after the change occurs. This can allow for the engine to be repaired and/or the oil to be replaced or replenished before significant (e.g., catastrophic) damage to the engine occurs.

In one embodiment, a system includes a sensor configured to be in contact with oil within an engine of a vehicle system. The sensor includes a sensing region circuit that is configured to generate stimuli at different times during an operational life of the engine. The system also includes one or more processors configured to receive signals from the sensor. The signals are representative of responses of the oil to the stimuli. The one or more processors are configured to analyze the responses and determine a characteristic of the oil that represents one or more of a total base number (TBN) or a total acid number (TAN) of the oil. The one or more processors are configured to determine an unhealthy state of one or more of the engine or the oil based on the characteristic of the oil that is determined.

In one example, the sensor is one or more of an electrical sensor or an optical sensor.

In one example, the stimuli are one or more of electrical stimuli or optical stimuli.

In one example, the sensor is configured to continually generate the signals to the one or more processors such that the one or more processors are configured to continually monitor the one or more of the engine or the oil.

In one example, the one or more processors are configured to determine a rate of change in the TBN of the oil as the characteristic between a first time and a second time.

In one example, the one or more processors are configured to determine the unhealthy state of the one or more of the engine or the oil by comparing the rate of change in the TBN of the oil with a designated rate of change.

In one example, the one or more processors are configured to determine the unhealthy state of the one or more of the engine or the oil responsive to the rate of change in the TBN of the oil decreasing at a rate that is faster than the designated rate of change.

In one example, the one or more processors are configured to determine a rate of change in the TAN of the oil as the characteristic.

In one example, the one or more processors are configured to determine the unhealthy state of the one or more of the engine or the oil by comparing the rate of change in the TAN of the oil with a designated rate of change.

In one example, the one or more processors are configured to determine the unhealthy state of the one or more of the engine or the oil responsive to the rate of change in the TAN of the oil increasing at a rate that is faster than the designated rate of change.

In one example, the one or more processors are configured to determine a second derivative of the TBN of the oil as the characteristic.

In one example, the one or more processors are configured to determine the unhealthy state of the one or more of the engine or the oil by comparing the second derivative of the TBN of the oil with a predetermined second derivative.

In one example, the one or more processors are configured to determine the unhealthy state of the one or more of the engine or the oil responsive to the second derivative of the TBN of the oil changing at a rate that is faster than the designated second derivative.

In one example, the one or more processors are configured to determine a second derivative of the TAN of the oil as the characteristic.

In one example, the one or more processors are configured to determine the unhealthy state of the one or more of the engine or the oil by comparing the second derivative of the TAN of the oil with a designated second derivative.

In one example, the one or more processors are configured to determine the unhealthy state of the one or more of the engine or the oil responsive to the second derivative of the TAN of the oil changing at a rate that is faster than the designated second derivative.

In one example, the one or more processors are configured to determine the TBN of the oil as the characteristic.

In one example, the one or more processors are configured to determine the unhealthy state of the one or more of the engine or the oil by comparing the TBN of the oil with a designated TBN.

In one example, the one or more processors are configured to determine the unhealthy state of the one or more of the engine or the oil responsive to the TBN of the oil being smaller than the designated TBN.

In one example, the one or more processors are configured to determine the level of TAN of the oil as the characteristic.

In one example, the one or more processors are configured to determine the unhealthy state of the one or more of the engine or the oil by comparing the TAN of the oil with a designated TAN.

In one example, the one or more processors are configured to deactivate the engine responsive to determining the unhealthy state of the one or more of the engine or the oil based on the characteristic TBN and/or TAN of the oil that is determined.

In one example, the sensor includes a resonant circuit coupled with electrodes that are configured to generate an electric field between the electrodes as the stimuli with at least part of the lubricant disposed between the electrodes and within the electric field. At least one of the electrodes can include a dielectric coating. Alternatively, no coating is used. The resonant circuit can be configured to resonate at different frequencies responsive to generation of the electric field based on changes in the dielectric coating brought about by changes in one or more basic compounds or acidic compounds in the lubricant. Alternatively, the resonant circuit can resonate at different frequencies responsive to generation of the electric field based on changes in the concentration of basic compounds and/or acidic compounds in the lubricant in the electric field. The signals that are output from the sensor to the one or more processors can represent one or more of the frequencies at which the resonant circuit resonates. The one or more processors can be configured to compare the one or more frequencies at which the resonant circuit resonates with one or more designated frequencies associated with different TBN or TAN of the lubricant to determine the one or more of the TBN or the TAN of the lubricant.

In one embodiment, a method includes placing a sensor in contact with oil within an engine of a vehicle system, generating stimuli at a sensing region circuit of the sensor during an operational life of the engine, receiving signals from the sensor, the signals representative of responses of the oil to the stimuli, analyzing the responses to determine a characteristic of the oil that represents one or more of a total base number (TBN) or a total acid number (TAN) of the oil, and determining an unhealthy state of one or more of the engine or the oil based on the characteristic TBN and/or TAN of the oil that is determined.

In one example, the sensor is one or more of an electrical sensor or an optical sensor.

In one example, the signals are one or more of electrical signals or optical signals.

In one example, the stimuli are one or more of electrical stimuli or optical stimuli.

In one example, the responses are one or more of electrical responses or optical responses.

In one example, the signals are continually received from the sensor to continually monitor the one or more of the engine or the oil.

In one example, the characteristic that is determined is a rate of change in the TBN of the oil.

In one example, the unhealthy state of the one or more of the engine or the oil is determined by comparing the rate of change in the TBN of the oil with a designated rate of change.

In one example, the unhealthy state of the one or more of the engine or the oil is determined responsive to the rate of change in the TBN of the oil decreasing at a rate that is faster than the designated rate of change.

In one example, the characteristic that is determined is a rate of change in the TAN of the oil.

In one example, the unhealthy state of the one or more of the engine or the oil is determined by comparing the rate of change in the TAN of the oil with a designated rate of change.

In one example, the unhealthy state of the one or more of the engine or the oil is determined responsive to the rate of change in the TAN of the oil changing at a rate that is faster than the designated rate of change.

In one example, the characteristic is a second derivative of the TBN of the oil.

In one example, the unhealthy state of the one or more of the engine or the oil is determined by comparing the second derivative of the TBN of the oil with a designated second derivative.

In one example, the unhealthy state of the one or more of the engine or the oil is determined responsive to the second derivative of the TBN of the oil changing at a rate that is faster than the designated second derivative.

In one example, the characteristic is a second derivative of the TAN of the oil.

In one example, the unhealthy state of the one or more of the engine or the oil is determined by comparing the second derivative of the TAN of the oil with a designated second derivative.

In one example, the unhealthy state of the one or more of the engine or the oil is determined responsive to the second derivative of the TAN of the oil changing at a rate that is faster than the designated second derivative.

In one example, the characteristic is the TBN of the oil.

In one example, the unhealthy state of the one or more of the engine or the oil is determined by comparing the TBN of the oil with a designated TBN.

In one example, the unhealthy state of the one or more of the engine or the oil is determined responsive to the TBN of the oil being smaller than the designated TBN.

In one example, the characteristic is the TAN of the oil.

In one example, the unhealthy state of the one or more of the engine or the oil is determined by comparing the TAN of the oil with a designated TAN.

In one example, the method also includes deactivating the engine responsive to determining the unhealthy state of the one or more of the engine or the oil based on the characteristic TBN and/or TAN of the oil that is determined.

In one embodiment, a system includes a sensor configured to be in contact with lubricating oil within a rotating equipment of a system. The sensor is configured to generate detectable stimuli at different times during an operational life of the rotating equipment. The system also includes one or more processors configured to receive signals from the sensor. The signals are representative of responses of the oil to the stimuli. The one or more processors are configured to analyze the responses and determine a characteristic of the oil that represents one or more of a total base number (TBN) or a total acid number (TAN) of the oil. The one or more processors are configured to determine an unhealthy state of one or more of the engine or the oil based on the characteristic of the oil that is determined.

In one example, the sensor is an electrical, resonant, non-resonant, optical, and/or mechanical sensor.

In one example, the stimuli are electrical or optical stimuli.

In one embodiment, a method includes placing a sensor in contact with oil within an engine of a vehicle system, generating stimuli at a sensing region circuit of the sensor during an operational life of the engine, receiving signals from the sensor, the signals representative of responses of the oil to the stimuli, analyzing the responses to determine a characteristic of the oil that represents one or more of a total base number (TBN) or a total acid number (TAN) of the oil, and determining health state of one or more of the engine or the oil based on the characteristic of the oil that is determined.

In one example, the sensor is an electrical, resonant, non-resonant, optical, and/or mechanical sensor.

In one example, the stimuli are electrical or optical stimuli.

In one embodiment, a method includes generating stimuli at a sensing region circuit of a sensor that is in contact with oil associated with an engine system, receiving signals from the sensor, the signals representative of responses of the oil to the stimuli, analyzing the responses to determine a characteristic of the oil that represents one or more of a total base number (TBN) or a total acid number (TAN) of the oil, performing a comparison of the characteristic of the oil that is determined to one or more designated corresponding characteristic thresholds that are indicative of oil conditions, and controlling the engine system based at least in part on the comparison. The engine system can be controlled in a variety of different manners based on results of the comparison. For example, for some TBN measurements, TAN measurements, changes in TBN or TAN measurements, etc., the engine system can be controlled by restricting a power output of the engine system. For other TBN measurements, TAN measurements, changes in TBN or TAN measurements, etc., the engine system can be controlled by automatically shutting off or deactivating the engine system. For other TBN measurements, TAN measurements, changes in TBN or TAN measurements, etc., the engine system can be controlled by automatically restricting how rapidly changes in the power output of the engine system can occur.

In one or more embodiments, sensor probe may be coated with a sensing material that is responsive to one or more fluid components of interest. When the sensor probe is in operational contact with the oil, dissolved gases in oil also interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material.

The sensor probe may detect characteristics of the fluid via a resonant impedance spectral response. One or more of the LCR resonators may measure the resonant impedance spectral response. As opposed to simple impedance measurements, the disclosed embodiments probe the sample with at least one resonant electrical circuit. The resonant impedance spectrum of the sensor probe in proximity to the sample (the sensor in operational contact with the fluid) varies based on sample composition and/or components and/or temperature. The measured resonant impedance values Z' (which may be the real part of resonant impedance, Zre) and Z" (which may be the imaginary part of resonant impedance, Zim) reflect the response of the fluid (for example, the portion of the fluid in proximity to the sensor) to a stimulus of the electric field of a resonant electrical circuit.

As will be described in detail hereinafter, various embodiments of an exemplary sensing system for monitoring an industrial fluid are disclosed. Specifically, a sensing system includes a sensor probe disposed in a housing. The sensor probe disposed in the housing, has preserved sensor sensitivity and selectivity compared to a sensor probe disposed outside the housing. In other words, if the sensor probe is disposed in the housing, the sensor sensitivity and selectivity are not compromised. The specific design parameters of the housing and sensor probe packaging in the housing allows the sensor probe to provide sensitive, selective, and stable response. The housing wall thickness may be in the range from about 0.1 millimeter to about 10 millimeters.

Figure 17:
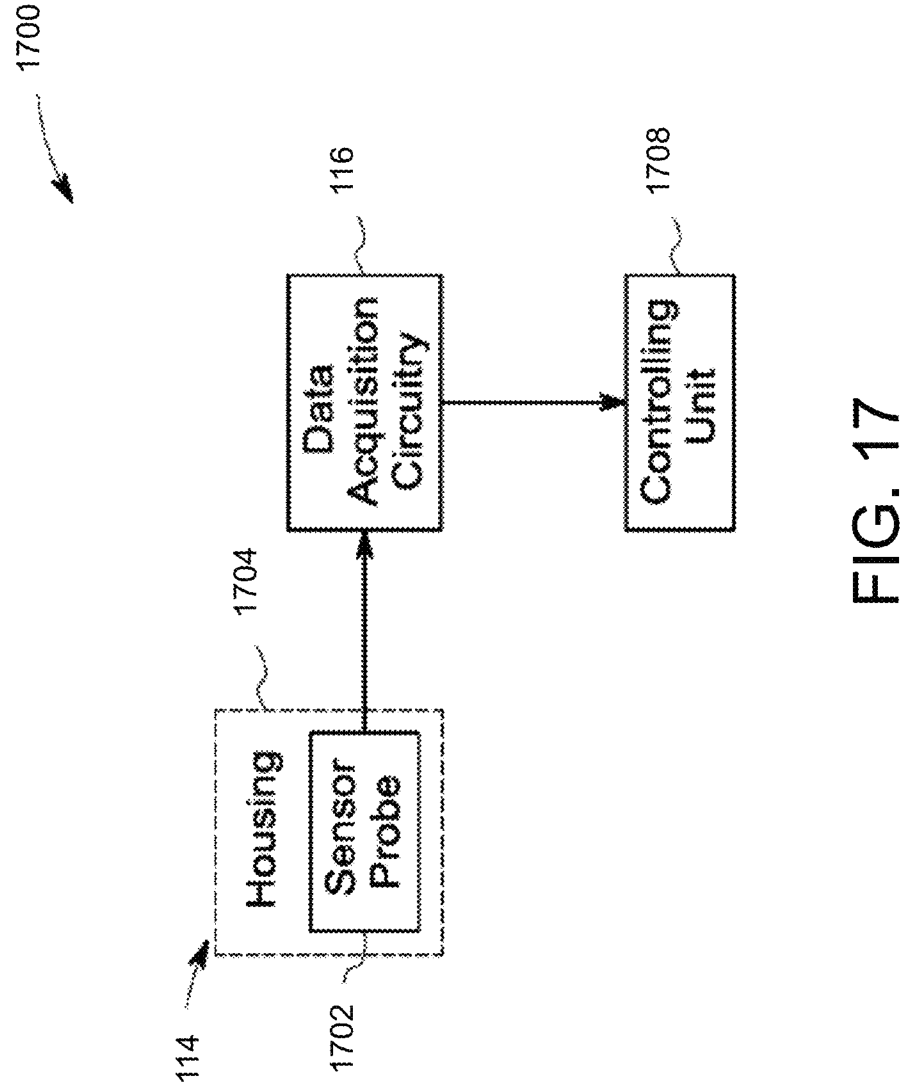
FIG. 17 is a block diagram of a sensing system in accordance with one or more embodiments.

Turning now to the drawings and by way of example in FIG. 17, a block diagram of a sensing system 12500 in accordance with one or more embodiments is presented. The sensing system 12500 can represent the sensing system 100 shown in FIG. 1 or one or more other sensing systems described herein. The sensing system 12500 includes the sensor probe 12502, a housing 12504, the data acquisition circuitry (DAC) 116, and a controlling unit 12508. The controlling unit 12508 can represent the controller 122 shown in FIG. 1. The sensor probe 12502 is disposed at least partially in the housing 12504. The sensor probe 12502 can include a multivariable LCR resonator as described herein, in one non-limiting example.

In one embodiment, the housing 12504 is configured to provide a radio frequency shielding for the sensor probe 12502. In another embodiment, the housing 12504 is also configured to withstand temperature of at least two hundred fifty degrees Celsius. In yet another embodiment, the housing 12504 is configured to hermetically seal the sensor probe 12502. The sensor probe 12502 and the housing 12504 together form the sensing unit 114.

In one embodiment, the sensor probe 12502 is in operational contact with an industrial fluid. The sensor probe 12502 may be configured to measure data such as a resonance impedance spectrum corresponding to the industrial fluid. In another embodiment, the data may be any parameter associated with properties such as complex permittivity of the industrial fluid.

Furthermore, the data may be acquired by the DAC 116. The DAC 116 is coupled to the controlling unit 12508. The data acquired by the DAC 116 may be further processed by the controlling unit 12508 to identify occurrence of any anomaly in the industrial fluid. In particular, composition/properties of the industrial fluid may be determined by processing of the data acquired in the DAC 116. In one embodiment, the level of water in the industrial fluid may be determined.

The controlling unit 12508 includes one or more processors. The processor is configured to perform the functions of the controlling unit 12508. As used herein, the term "processor" refers not only to integrated circuits included in a computer, but also refers to a controller, a microcontroller, a microcomputer, a programmable logic controller (PLC), an application specific integrated circuit, application-specific processors, digital signal processors (DSPs), Application Specific Integrated Circuits (ASICs), Field Programmable Gate Arrays (FPGAs), and/or any other programmable circuits.

Furthermore, the system 12500 may include a memory device to store the data acquired using the sensor probe 12502 or to store any data after being processed by the controlling unit 12508. The memory device(s) may generally include memory element(s) including, but are not limited to, computer readable medium (e.g., random access memory (RAM)), computer readable non-volatile medium (e.g., a flash memory), one or more hard disk drives, a floppy disk, a compact disc-read only memory (CD-ROM), compact disk-read/write (CD-R/W) drives, a magneto-optical disk (MOD), a digital versatile disc (DVD), flash drives, optical drives, solid-state storage devices, and/or other suitable memory elements.

Figure 18:
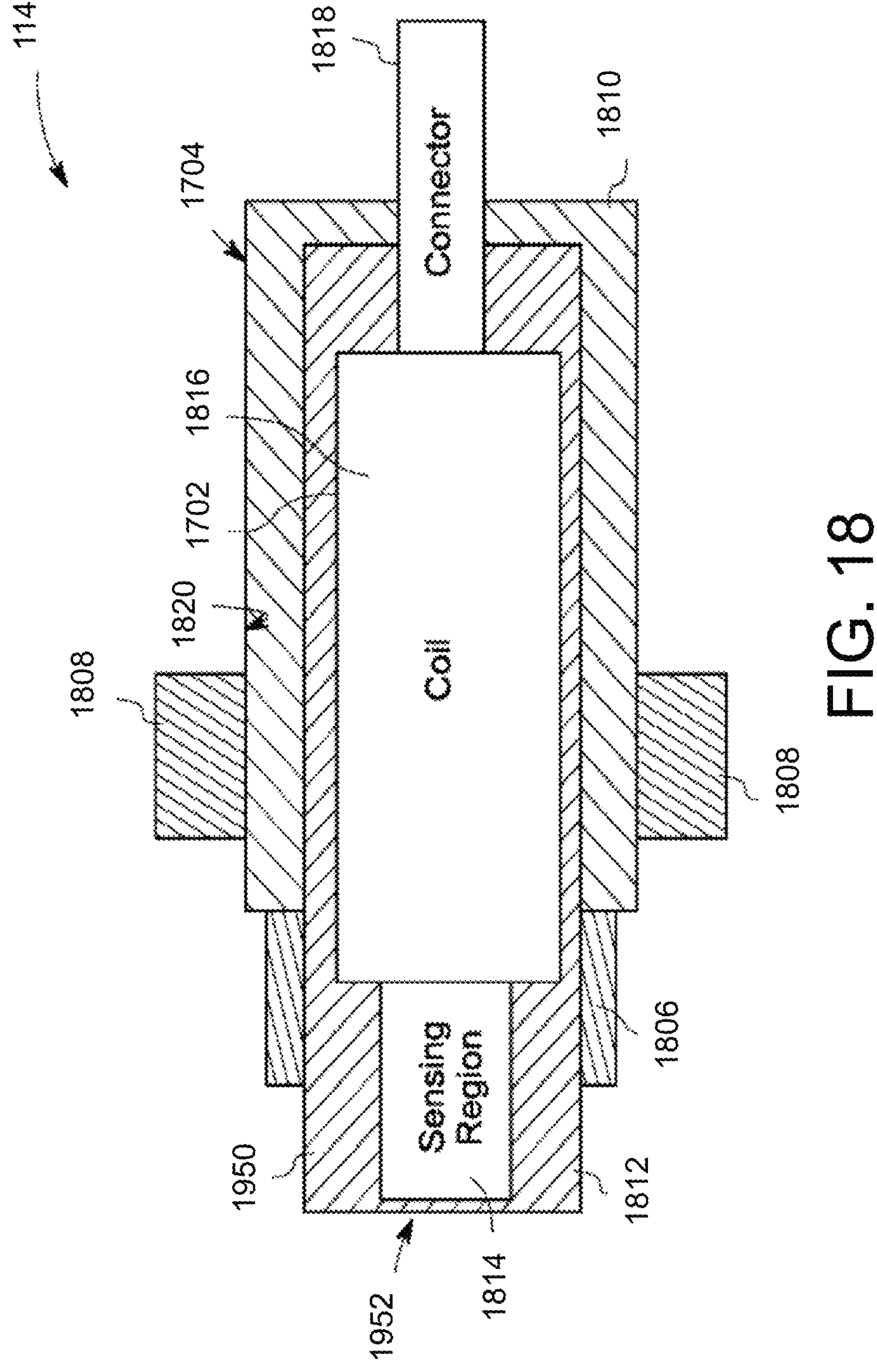
FIG. 18 is a diagrammatical representation of one embodiment of the sensing unit of FIG. 1 or FIG. 17.

Referring now to FIG. 18, a diagrammatical representation of one embodiment of the sensing unit 114 is presented. In the illustrated embodiment, a portion of the sensor probe 12502 is disposed in the housing 12504 is depicted.

The housing 12504 includes a thread portion 12906, a flange portion 12908, and a body portion 12910. In one embodiment, the housing 12504 is a tubular structure, where either ends of the housing 12504 are open. If the housing 12504 is a tubular structure, then the thread portion 12906, the flange portion 12908, and the body portion 12910 may have different diameters. In one specific embodiment, the flange portion 12908 may have a larger diameter compared to the thread portion 12906 and the body portion 12910. In such an embodiment, the thread portion 12906 has a smallest diameter. The housing 12504 is made of at least one of metal, stainless steel, aluminum, metal alloys, metal-ceramic composites, and metal dielectric composites.

The sensor probe 12502 includes a substrate 12912, a sensing region 12914, a coil 12916, and a connector 12918. The substrate 12912 is made of at least one of a ceramic material, a composite material, an inorganic material, and a polymeric material.

Figure 19:
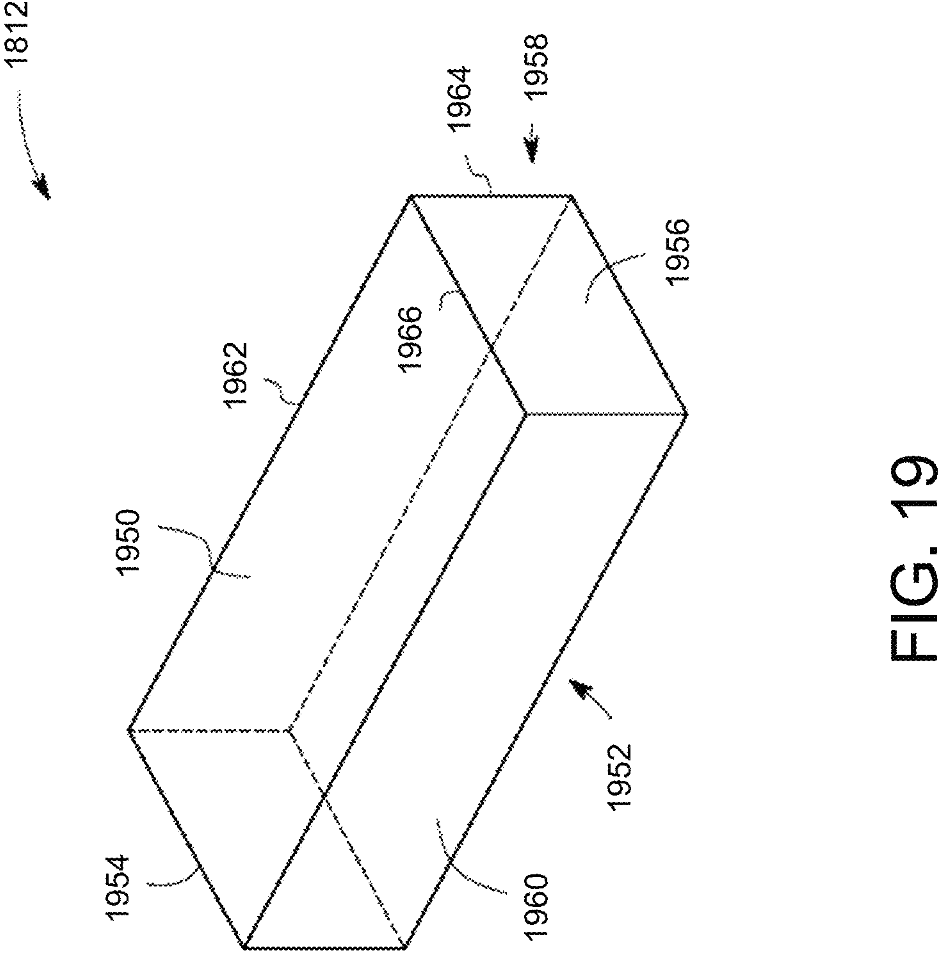
FIG. 19 is a perspective view of a substrate in accordance with the embodiment of FIG. 18.

Referring now to FIG. 19, a perspective view of the substrate 12912 in accordance with an exemplary embodiment is presented. The substrate 12912 has a shape of a rectangular cuboid. In particular, the substrate 12912 includes a first face 1950, a second face 1952 opposite to the first face 1950, a third face 1954 perpendicular to the first face 1950 and the second face 1952, a fourth face 1956 opposite to the third face 1954. Further, the substrate 12912 includes a fifth face 1958 perpendicular to the first face 1950, the second face 1952, the third face 1954, and the fourth face 1956, and a sixth face 1960 opposite to the fifth face 1958. Furthermore, the substrate 12912 has a length 1962, a depth 1964, and a breadth 1966. In one non-limiting embodiment, dimensions of the substrate 12912 may range from about 0.1 mm×0.1 mm to about one hundred mm by one hundred mm.

The substrate 12912 may have different shapes such as a rectangular shape, a circular shape, and the like. In one embodiment, the area of the substrate 12912 that is in operational contact with the industrial fluid may be in the range of about 0.01 mm2 to about 1000 mm2.

Referring back to FIG. 18 in combination with FIG. 19, only the first face 1950 of the substrate 12912 is depicted. The sensing region 12914, the coil 12916, and the connector 12918 are disposed on the substrate 12912. Specifically, the sensing region 12914 and the coil 12916 are disposed on the first face 1950 of the substrate 12912. The coil 12916 is an inductor coil for the sensing region 12914. The connector 12918 is disposed on the second face 1952 of the substrate 12912.

Furthermore, the sensing region 12914 is galvanically coupled to the coil 12916. In particular, the sensing region 12914 can be directly coupled to the coil 12916. In one embodiment, a combination of the coil 12916 and the sensing region 12914 forms an LCR resonator. In one embodiment, the sensing region 12914 includes an inter-digital electrode. Reference numeral 12920 is representative of an inner surface of the housing 12504. The sensor probe 12502 is disposed at a predetermined distance apart from the inner surface 12920 of the housing 12504. In one non-limiting embodiment, the predetermined distances may range from about 1 mm to about 20 mm. Furthermore, the sensor probe is packaged to have minimal effects due to thermal shocks, mechanical shocks, and electrical shocks.

Further, the housing 12504 is configured to direct flow of the industrial fluid to the sensing region 12914 such that the sensing region 12914 is in operational contact with the industrial fluid. In the illustrated embodiment, the substrate 12912 and a portion of the sensing region 12914 protrude outwards from the housing 12504. In particular, the substrate 12912 and the portion of the sensing region 12914 extend outwards from the thread portion 12906 of the housing 12504. Further, the connector 12918 extends outward from the housing 12504. Specifically, the connector 12918 extends outward from the body portion 12910 of the housing 12504.

In one embodiment, length of the housing 12504 may be in a range from about one mm to about one hundred mm. Further, cross-sectional area of the housing 12504 may be in a range from about one mm2 to about one thousand mm2. The housing 12504 may have different cross sections such as a rectangular cross section, a circular cross section, and the like.

Figure 20:
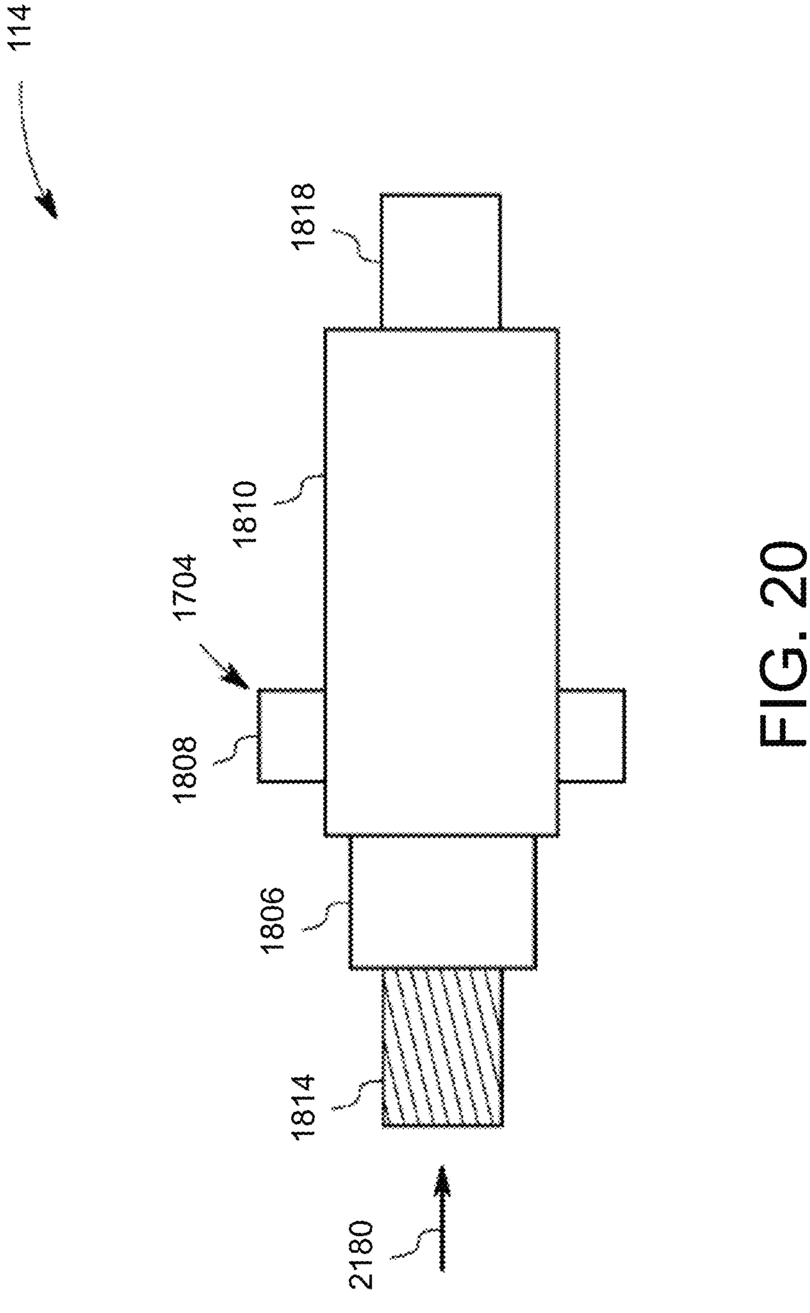
FIG. 20 is a top view of the sensing unit in accordance with the embodiment of FIG. 17.

FIG. 20 is a top view of the sensing unit 114 in accordance with one embodiment. The sensing region 12914, the housing 12504, and connector 12918 are depicted. The housing 12504 includes the thread portion 12906, the flange portion 12908, and the body portion 12910. The sensing region 12914 and the connector 12918 extend outwards from either ends of the housing 12504.

Figure 21:
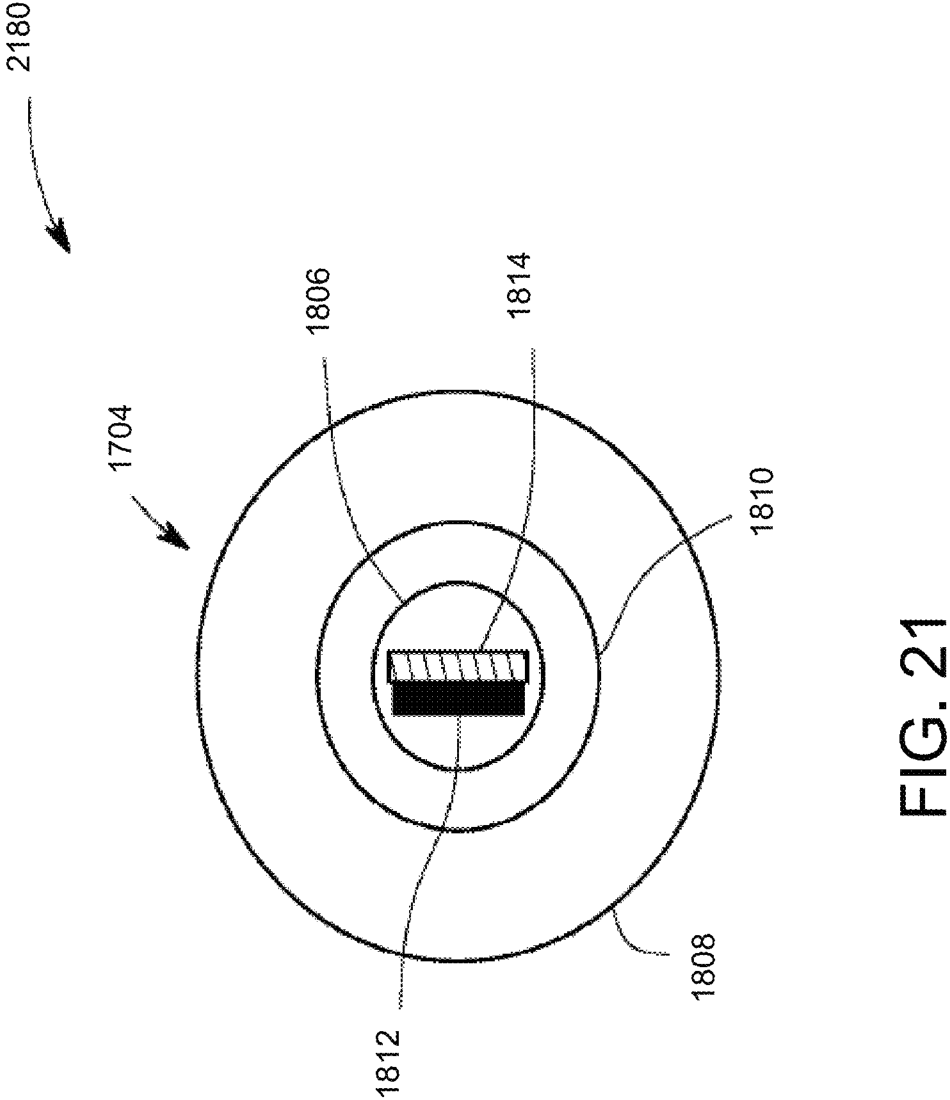
FIG. 21 is a side view of the sensing unit in accordance with the embodiment of FIG. 20.

FIG. 21 is a side view 2180 of the sensing unit 114 of FIG. 20 in accordance with one embodiment. In the illustrated embodiment, a portion of the sensing unit 114 having the sensing region 12914 and the housing 12504, is presented. The sensing region 12914 is disposed on the substrate 12912. An outer periphery of the thread portion 12906, the flange portion 12908, and the body portion 12910 are shown.

Figure 22:
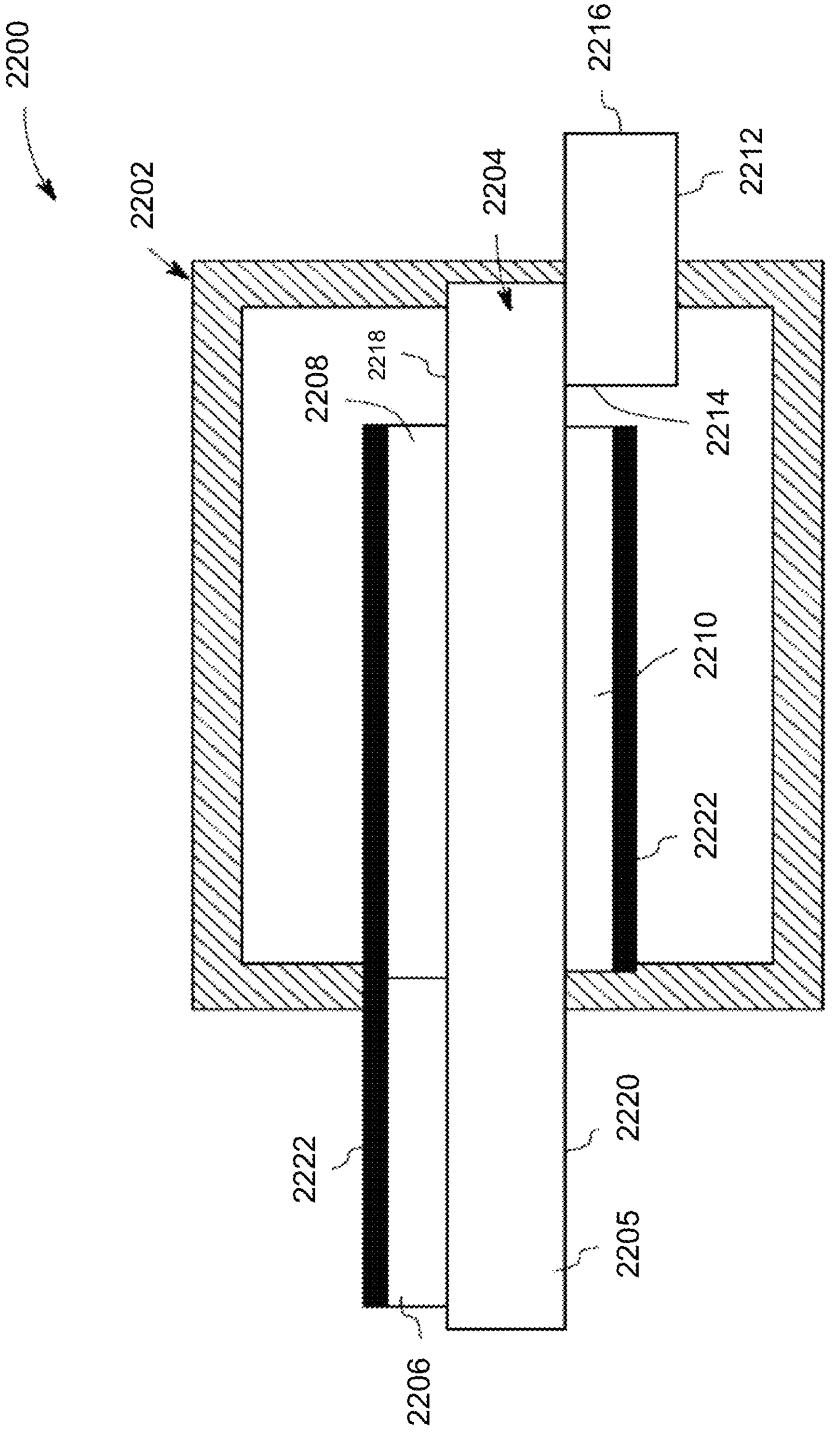
FIG. 22 is a diagrammatical representation of a sensing unit in accordance with another example embodiment.

FIG. 22 is a diagrammatical representation of a sensing unit 2200 in accordance with another exemplary embodiment. The sensing unit 2200 includes a housing 2202 and a sensor probe 2204. The sensor probe 2204 is disposed at least partially in the housing 2202. The sensor probe 2204 includes a substrate 2205, a sensing region 2206, a first coil 2208, a second coil 2210, and a connector 2212. The sensing region 2206 and the first coil 2208 are disposed on a first face 2218 (similar to the first face 1950 of FIG. 19) of the substrate 2205. The second coil 2210 and the connector 2212 are disposed on a second face 2220 (similar to the second face 1952 of FIG. 19) of the substrate 2205.

The first coil 2208 and the sensing region 2206 are galvanically coupled to each other. Further, the second coil 2210 is inductively coupled to the first coil 2208 and the sensing region 2206. The sensor probe 2204 is configured to provide an impedance match between the first coil 2208 and the second coil 2210. In one embodiment, the second coil 2210 is an inductive pick up coil. Furthermore, the second coil 2210 is non-galvanically coupled to the first coil 2208 and the sensing region 2206. The second coil 2210 is configured to acquire a response from the first coil 2208 and the sensing region 2206. In one embodiment, the response from the first coil 2208 and the sensing region 2206 may be similar. In another embodiment, the response from the first coil 2208 and the sensing region 2206 may be different. In one specific embodiment, the response from the first coil 2208 may be a function of the response from the sensing region 2206.

The connector 2212 is galvanically coupled to the second coil 2210. The connector 2212 has a first end 2214 and a second end 2216. The first end 2214 of the connector 2212 is coupled to the second coil 2210. Further, the second end 2216 of the connector 2212 is configured to deliver an output signal of the sensor probe 2204. The output signal of the sensor probe 2204 is provided to the data acquisition circuitry such as the DAC 116. The sensor probe 2204 further includes a dielectric material layer 2222 disposed on at least one of the sensing region 2206, the first coil 2208, and the second coil 2210. Furthermore, the housing 2202 is configured to provide an environmental sealing for the first coil 2208 and the second coil 2210.

Figure 23:
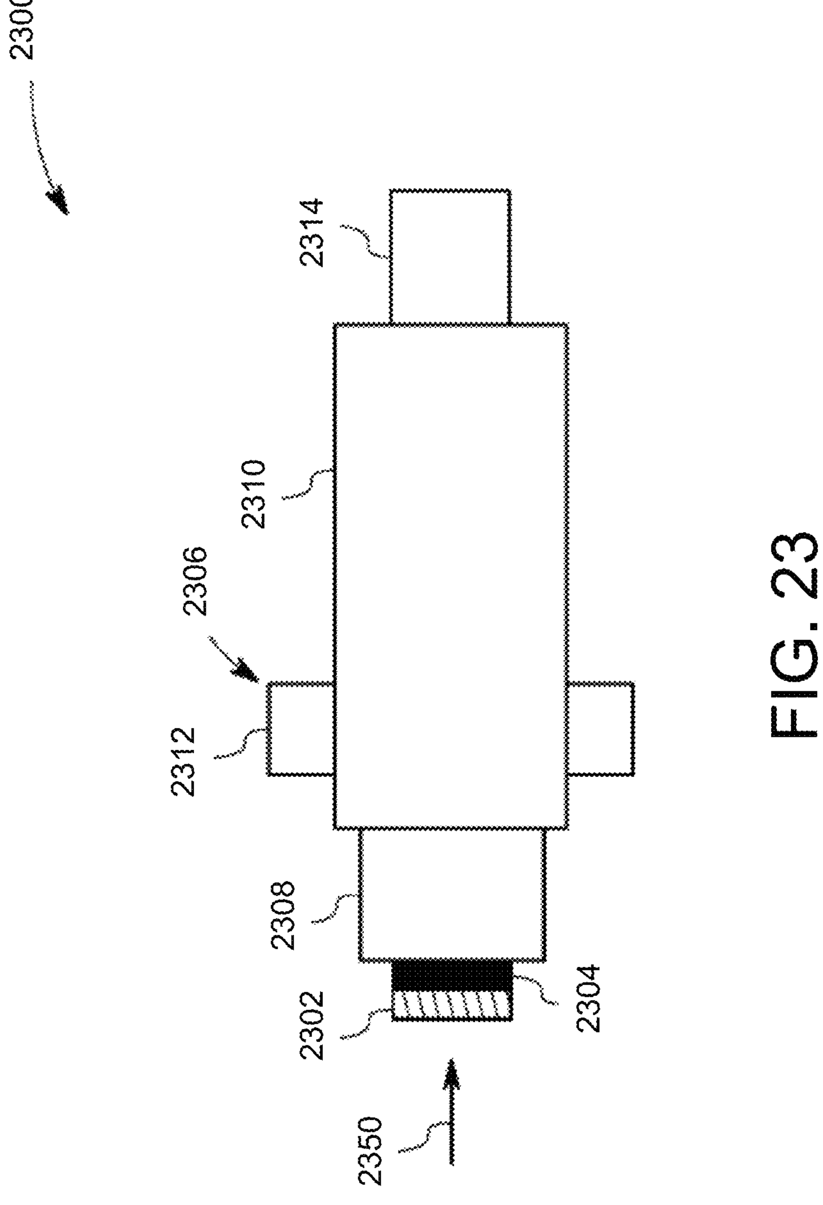
FIG. 23 is a top view of another embodiment of a sensing unit in accordance with another embodiment.

FIG. 23 is a diagrammatical representation of a top view of another embodiment of a sensing unit 2300. In the illustrated embodiment, a portion of the sensing unit 2300 includes a sensing region 2302, a substrate 2304, a housing 2306, and a connector 2314 is depicted. The sensing region 2302 is disposed on the substrate 2304. In particular, the sensing region 2302 is disposed on a face (similar to the third face 1954 of FIG. 19) of the substrate 2304. The housing 2306 includes a thread portion 2308, a flange portion 2312, and a body portion 2310.

Figure 24:
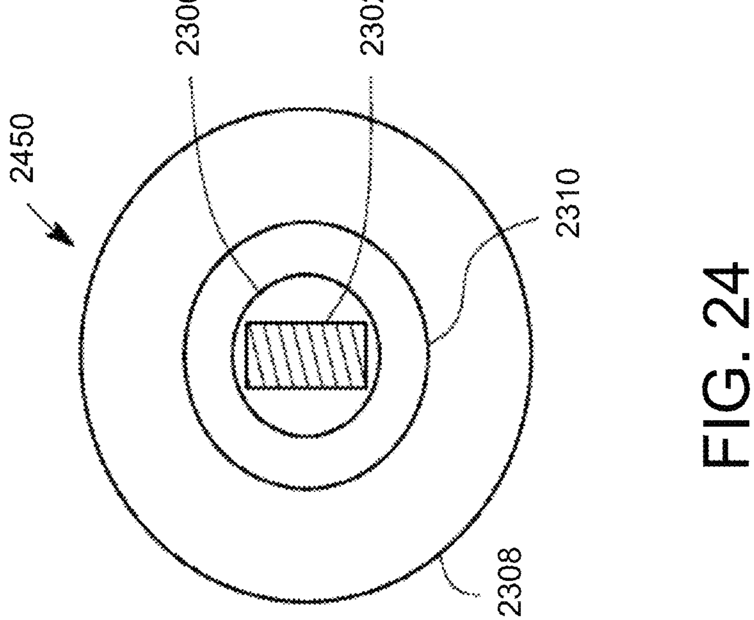
FIG. 24 is a side view of the sensing unit in accordance with the embodiment of FIG. 23.

FIG. 24 is a diagrammatical representation of a side view 2450 of the sensing unit 2300 of FIG. 23. In the illustrated embodiment, a portion of the sensing unit 2300 having the sensing region 2302 and the housing 2306 is shown. The housing 2306 includes the thread portion 2308, the flange portion 2312, and the body portion 2310. An outer periphery of the thread portion 2308, the flange portion 2312, and the body portion 2310 are shown.

Figure 25:
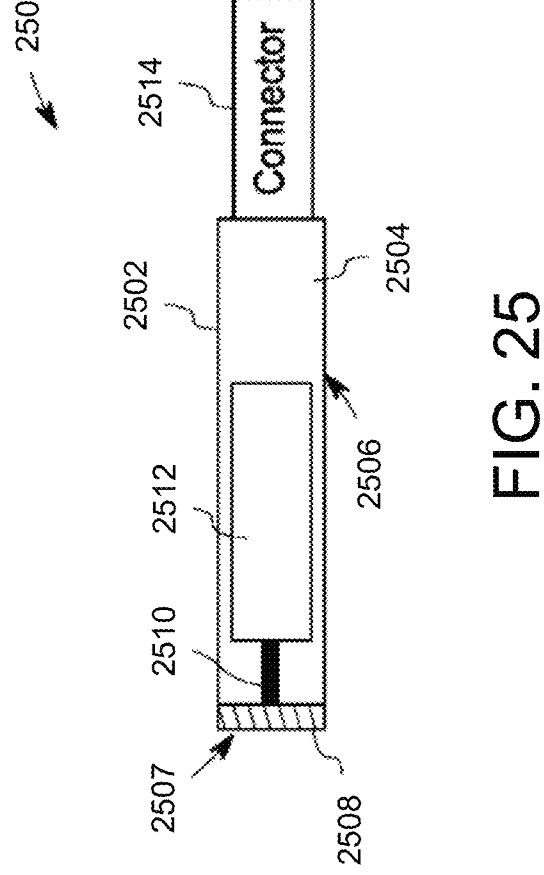
FIG. 25 is a top view of a sensor probe in accordance with another embodiment.

FIG. 25 depicts a top view of a sensor probe 2500 in accordance with another embodiment. In particular, only a portion of the sensor probe 2500 is depicted. The sensor probe 2500 includes a substrate 2502, a sensing region 2508, a coil 2512, and a connector 2514.

The coil 2512 is disposed on a first face 2504 (similar to first face 1950 of FIG. 19) of the substrate 2502. The connector 2514 is disposed on the second face 2506 (similar to the second face 1952 of FIG. 19) of the substrate 2502. The connector 2514 extends outward from the substrate 2502. The sensing region 2508 is disposed on a third face 2507 (similar to the third face 1954 of FIG. 19) of the substrate 2502. Further, the coil 2512 is galvanically coupled to the sensing region 2508 via a coupling 2510.

Figure 26:
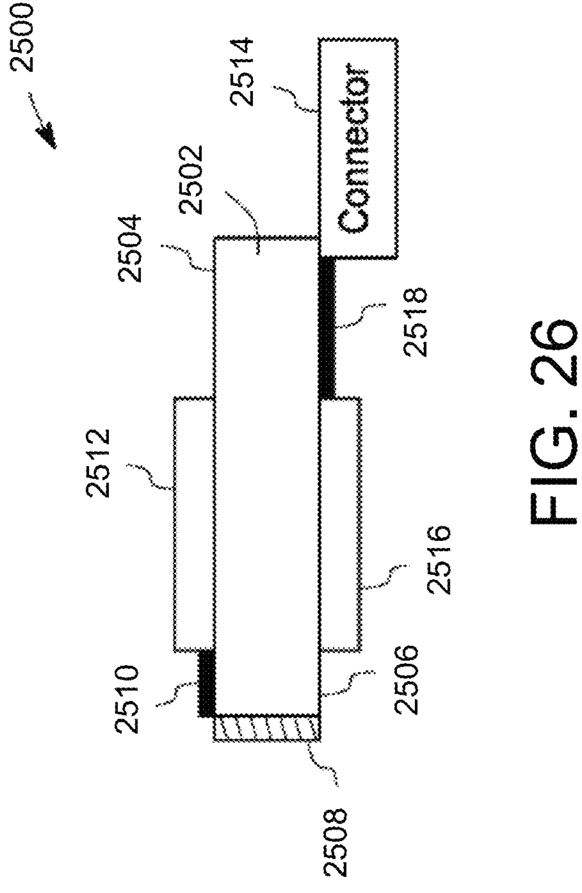
FIG. 26 is a side view of a sensor probe of FIG. 25 in accordance with another example embodiment.

Referring now to FIG. 26, a side view of a sensor probe 2500 of FIG. 25 is presented. The sensor probe 2500 includes a substrate 2502, a sensing region 2508, a first coil 2512, a second coil 2516, and a connector 2514.

The first coil 2512 disposed on the first face 2504 (similar to first face 1950 of FIG. 19) of the substrate 2502. The second coil 2516 is disposed on a second face 2506 (similar to the second face 1952 of FIG. 19) of the substrate 2502. The second coil 2516 is inductively coupled to the first coil 2512. The second coil 2516 may also be referred to as an inductive pick up coil. The second coil 2516 is configured to pick up signals from the first coil 2512. The second coil 2516 is further galvanically coupled to one end of the connector 2514 via a coupling 2518. The output signal is obtained at the other end of the connector 2514. The sensing region 2508 is disposed on a third face 2507 (similar to the third face 1954 of FIG. 19) of the substrate 2502. Further, the sensing region 2508 is galvanically coupled to the first coil 2512 via the coupling 2510. The first coil 2512 is configured to pick up the signals sensed by the sensing region 2508. The signals sensed by the sensing region 2508 are transmitted as an output signal via the first coil 2512, the second coil 2516, and the connector 2514. The connector 2514 extends outward from the substrate 2502.

Figure 27:
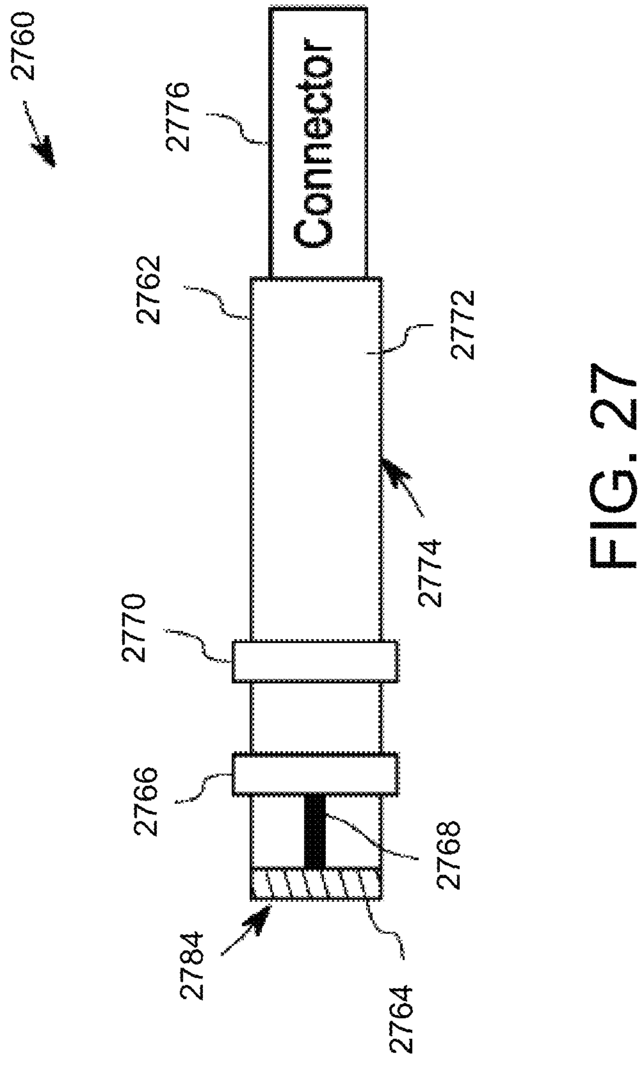
FIG. 27 is a top view of a sensor probe in accordance with another embodiment.

Referring to FIG. 27, a top view of a sensor probe 2760 in accordance with another embodiment is presented. In the illustrated embodiment, a portion of the sensor probe 2760 is shown. The sensor probe 2760 includes a substrate 2762, a sensing region 2764, a first coil 2766, a second coil 2770, and a connector 2776.

The first coil 2766 and the second coil 2770 extend coaxially along the substrate 2762. In one embodiment, the first and second coils 2766, 2770 are ring-like structures. Further, the first coil 2766 is disposed at a predetermined distance apart from the second coil 2770. In one non-limiting embodiment, the predetermined distance may be in a range from about 0.1 mm to about ten mm.

The connector 2776 is disposed on a second face 2774 (similar to the second face 1952 of FIG. 19) of the substrate 2762. Further, the connector 2776 extends outward from the substrate 2762. The sensing region 2764 is disposed on a third face 2784 (similar to the third face 1954 of FIG. 19) of the substrate 2762. The sensing region 2764 is galvanically coupled to the first coil 2766 via a coupling 2768.

Figure 28:
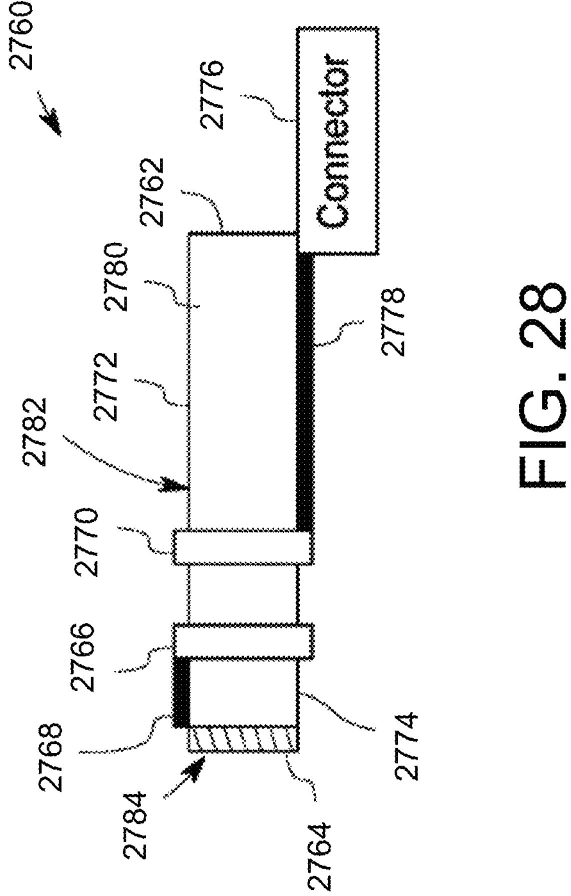
FIG. 28 is a side view of a sensor probe of FIG. 27 in accordance with another example embodiment.

Referring now to FIG. 28, a side view of a sensor probe 2760 of FIG. 27 is presented. The sensor probe 2760 includes a substrate 2762, a sensing region 2764, a first coil 2766, a second coil 2770, and a connector 2776.

The sensing region 2764, the first coil 2766, and the second coil 2770 are disposed on the substrate 2762. The first coil 2766 and the second coil 2770 extend coaxially along the substrate 2762. In particular, the first coil 2766 and the second coil 2770 are disposed partially on a portion of faces 2772, 2774, 2780, and 2782. The face 2772 is a first face (similar to the first face 1950 of FIG. 19), the face 2774 is the second face (similar to the second face 1952 of FIG. 19), the face 2780 is the fifth face (similar to the fifth face 1958 of FIG. 19), and the face 2782 is a sixth face (similar to the sixth face 1960 of FIG. 19) of the substrate 2762. The first coil 2766 and the second coil 2770 are coupled inductively. The sensing region 2764 is galvanically coupled to the first coil 2766 via the coupling 2768. Further, the second coil 2770 is galvanically coupled to the connector 2776 via the coupling 2782778. The connector 2776 is disposed on the substrate 2762 and extends outward from the substrate 2762.

Figure 29:
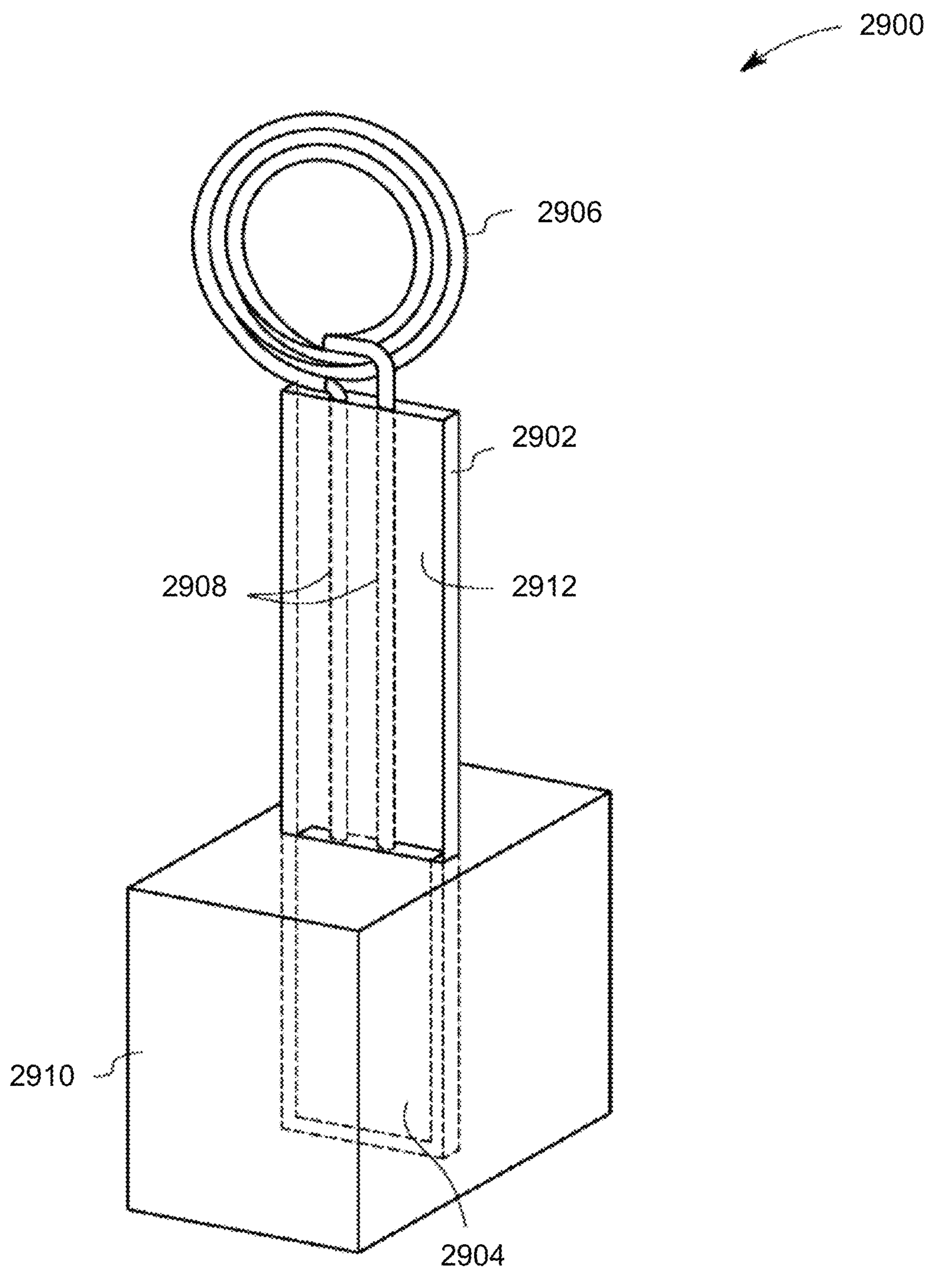
FIG. 29 is a diagrammatical representation of a sensor probe in accordance with the embodiment of FIG. 25.

FIG. 29 is a diagrammatical representation of one embodiment of a sensor probe 2900 of FIG. 17. The sensor probe 2900 includes a substrate 2902. In one embodiment, the substrate 2902 is a dielectric substrate. A sensing region 2904 is disposed on the face 2912 (similar to the first face 1950 of FIG. 19) of the substrate 2902. The sensing region 2904 includes an interdigital electrode. Further, a coil 2906 is coupled to the sensing region 2904 via a coupling 2908. The coil 2906 extends outward from the substrate 2902. Furthermore, the coupling 2908 is disposed along the substrate 2902. In the illustrated embodiment, the sensing region 2904 is disposed in operational contact with industrial fluids 2910. The properties of the industrial fluids 2910 may be determined using the sensor probe 2900.

Figure 30:
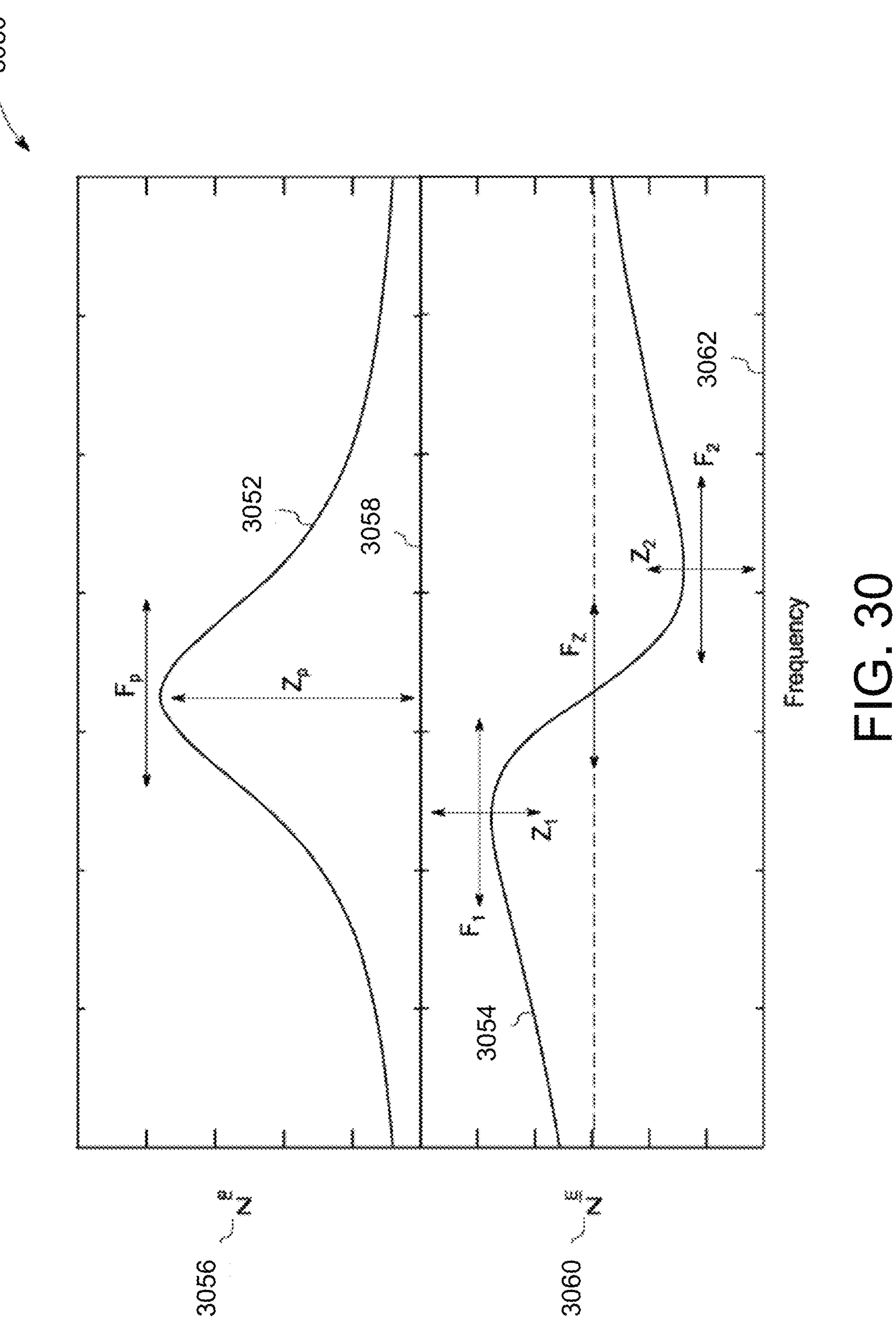
FIG. 30 is a diagrammatical representation of a resonance impedance spectrum of a sensor probe in accordance with the embodiment of FIG. 1 or FIG. 17.

FIG. 30 is a diagrammatical representation of a resonance impedance spectrum 3050 of a sensor probe in accordance with the embodiment of FIG. 17. In particular, FIG. 30 represents a resonance impedance spectrum 3050 of an LCR resonator. In one embodiment, the resonance impedance spectrum 3050 is measured using an inductive coupling or a direct connection to a sensor reader. The resonance impedance spectrum $\check{Z}(f)$ may be represented as:

$\check{Z}(f)=Zre(f)+jZim(f)$, where Zre(f) is a real impedance spectrum and jZim(f) is an imaginary impedance spectrum.

In the illustrated embodiment, reference numeral 3052 represents a real impedance spectrum Zre(f) and reference numeral 3054 represents an imaginary impedance spectrum Zim(f). Further, reference numerals 3056 and 3060 represent the real impedance and imaginary impedance in ohms respectively. Further, reference numerals 3058 and 3062 represent frequency in hertz. The parameters that may be determined using the $\check{Z}(f)$ resonance impedance spectrum include frequency position Fp and magnitude Zp of Zre(f) corresponding to frequency position Fp. Further, other parameters include a resonant frequency F1 and an anti-resonant frequency F2 and the impedance magnitudes Z1 and Z2 of imaginary impedance spectrum Zim(f) corresponding to frequencies F1 and F2. Also, yet another parameter that may be determined using the resonance impedance spectrum includes a zero-reactance frequency FZ of imaginary impedance spectrum Zim(f). In one embodiment, any variation in any of the abovementioned parameters of the resonance impedance spectrum may provide information regarding composition of an industrial fluid.

Figure 31:
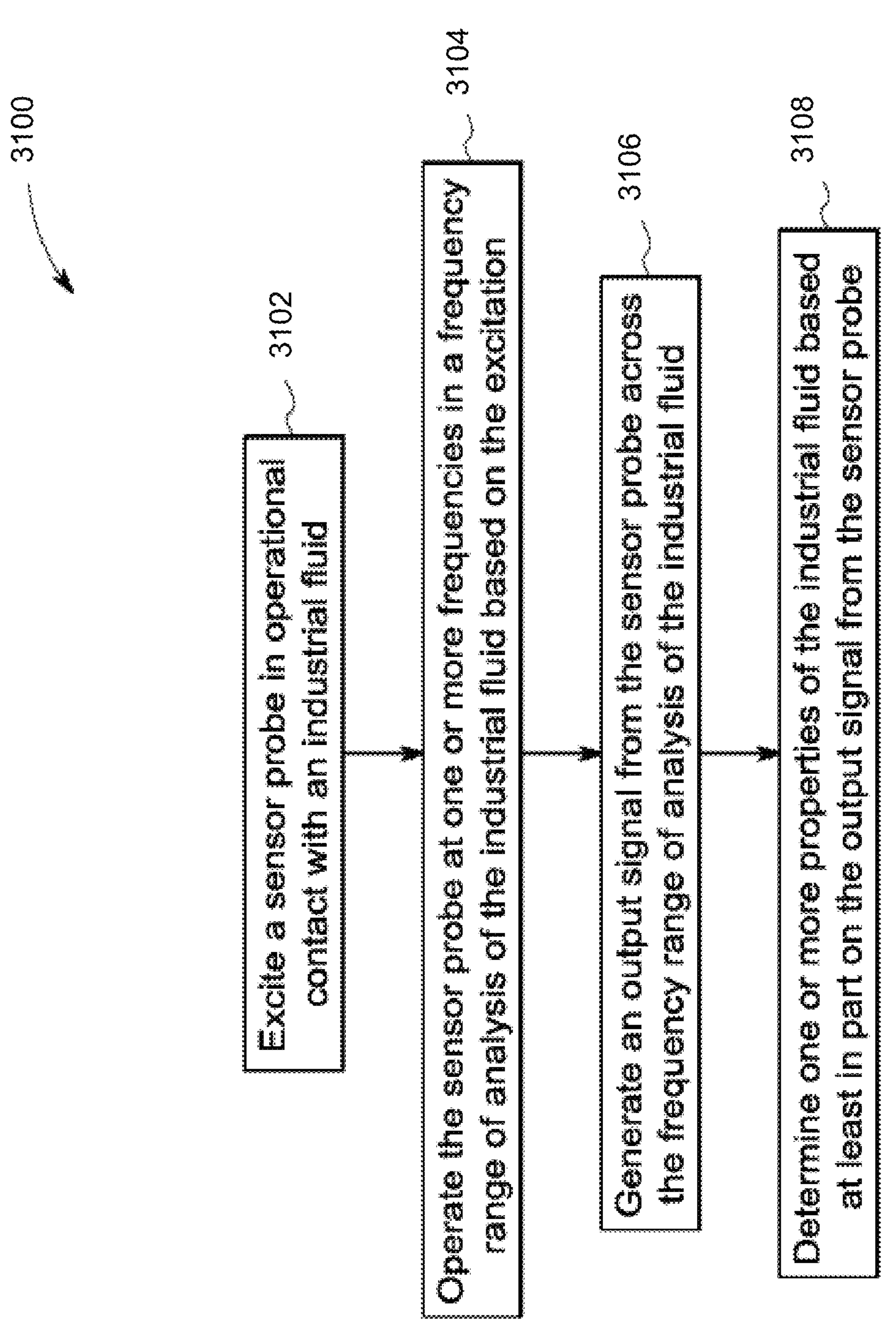
FIG. 31 is a flow chart representative of a method of operation of a sensing system in accordance with one or more embodiments.

Referring now to FIG. 31, a flow chart representative of a method for operating a sensing system in accordance with certain aspects of the present invention is presented. At block 3102, a sensor probe which is in operational contact with industrial fluid, is excited. The excitation of the sensor probe results in generation of an electrical field using the sensor probe. The electrical field is transmitted from the sensor probe to the industrial fluid.

Further, at block 3104, the sensor probe is operated at one or more frequencies in a frequency range of analysis of the industrial fluid based on the excitation. The sensor probe is a LCR resonator, where the LCR resonator is configured to operate at one or more frequencies in a frequency range of analysis.

At block 3106, an output signal from the sensor probe across the frequency range of analysis of the industrial fluid is generated. The output signal may be obtained at one end of a connector of the sensor probe. The output signal is representative of information about the industrial fluid. In one embodiment, the output signal is representative of a resonant impedance spectrum of the industrial fluid over a frequency range of analysis.

Furthermore, at block 3108, one or more properties of the industrial fluid based at least in part on the output signal from the sensor probe are determined. In one embodiment, one or more properties of the industrial fluid may be determined based at least in part on the resonant impedance spectrum. In one embodiment, the sensor probe may determine a complex permittivity of the industrial fluid. In particular, the complex permittivity of the industrial fluid may be determined based on the resonance impedance spectrum. In another embodiment, the complex permittivity of the industrial fluid may be representative of a measure of level of water in oil. The use of housing for packaging a sensor probe does not influence the sensitivity of the sensor probe.

Furthermore, the foregoing embodiments, and process steps may be implemented by suitable codes on a processor-based system, such as a general-purpose or special-purpose computer. It should also be noted that different implementations of the present technique may perform some or all the steps described herein in different orders or substantially concurrently. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

In accordance with the example embodiments discussed herein, the sensing system includes a housing at least partially enclosing the sensor probe. The housing aids in providing environmental sealing for the sensor probe, to withstand high temperature and provide RF shielding for the sensor probe. Furthermore, the housing is configured to protect the sensor probe from any damage. Moreover, in such embodiments, the sensor sensitivity and selectivity are not compromised. The specific design parameters of the housing and sensor probe packaging in the housing allows the sensor probe to provide sensitive, selective, and stable response. The non-limiting exemplary sensing system may be used in applications such as transportation, for example, locomotive, marine, automotive, and the like.

One or more embodiments herein describe systems and methods for environment sensing, specifically for detecting one or more analytes of interest within an environment. Exemplary existing and emerging applications of sensors include environmental monitoring and protection, industrial safety and manufacturing process control, monitoring of agricultural emissions, public safety, medical systems, wearable health and fitness, automation of residential homes and industrial buildings, transportation, and retail. Examples of classes and types of measured gases and volatiles of interest for these applications include environmental background (e.g. $O_2$, $CO_2$, $H_2O$), transportation/industrial/agricultural atmospheric pollutants (e.g. $CO_2$, CO, $O_3$, $H_2S$, $NH_3$, NOx, $SO_2$, $CH_4$, industrial fumes, waste odors), breath biomarkers (e.g. NO, $H_2S$, $NH_4$, acetone, ethane, pentane, isoprene, hydrogen peroxide), and public/homeland safety hazardous volatiles (e.g. toxic industrial chemicals, chemical warfare agents, explosives). Diverse types of volatiles are needed to be monitored over their broad range of concentrations ranging from part-per-trillion to percent, often mixed with chemical interferences such as ubiquitous variable background (indoor and outdoor urban air, industrial air, human odors and breath, exhaust of transportation engines, etc.), and at expected operation temperatures (ambient indoor and outdoor temperatures, body temperature, exhaust of transportation engines). Various embodiments utilize a sensing material electrically coupled to a pair of electrodes. An electrical stimulus is delivered to the metal oxide sensor or a transducer that includes a sensing material. Optionally, the sensor may include a resonant inductor L-capacitor C-resistor R (LCR) circuit and/or an RFID sensor.

An impedance response (e.g., impedance spectrum) of the sensor is measured via a controller circuit directly and/or inductive coupled between a pick up coil and the sensor. For example, the electrical response at certain frequencies or a single frequency corresponding to signal changes (e.g., impedance, resistance, capacitance, and/or the like) of the sensor is translated into the impedance changes of the sensor to form the impedance response. Based on the impedance response, the controller circuit may calculate one or more spectrum parameters. The "spectrum" or "spectral" parameters are calculated from a real portion and/or imaginary portion of the impedance response. The spectrum parameters are utilized to determine an environmental parameter of the analyte of interest. For example, the controller circuit may analyze the impedance response of the sensing material at frequencies calculated from the real portion of the impedance response that provide a linear response of the sensing material to the analyte of interest. It may be noted, the impedance response of the sensing material described herein provides a linearity improvement over the nonlinear (e.g. power law) resistance response of the sensing material in conventional environmental sensors. Additionally due to the linear response, the impedance response of the sensing material provides a monotonic response improvement over the non-monotonic resistance response (e.g., parabolic) of the sensing material in conventional environmental sensors. Additionally or alternatively, the spectrum parameters may be selected to reject and/or filter out effects of interference due to volatile analytes (e.g., analytes not of interest). For example, the impedance response of the sensing material provides reduction of effects of humidity over the resistance response of the sensing material in conventional environmental sensors.

Optionally, the sensors described herein may be utilized in a wireless sensor network as described in U.S. patent application Ser. No. 15/270,442 entitled, "SYSTEMS AND METHODS FOR ENVIRONMENT SENSING" having docket number 312706-1US, which is incorporated by reference in its entirety.

The fluids described herein can include gases, vapors, liquids, particles, biological particles, and/or biological molecules. Optionally, a fluid may refer to one or more solid materials.

A digital identification or ID can include data stored in a memory chip (or other memory device) of an RFID sensor. Non-limiting examples of this data include manufacturer identification, electronic pedigree data, user data, and/or calibration data for the sensor.

A monitoring process includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady state measurements of individual vapors and their mixtures.

Environmental parameters and/or select parameters can refer to measurable environmental variables within or surrounding a manufacturing or monitoring system (e.g., a sensing system). The measurable environmental variables comprise at least one of physical, chemical, and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

An analyte can include any desired measured environmental parameter.

Interference includes an undesired environmental parameter that undesirably affects the accuracy and precision of measurements with the sensor. An interference includes a fluid or an environmental parameter (that includes, but is not limited to temperature, pressure, light, etc.) that potentially may produce an interference response by the sensor.

A multivariate analysis can refer to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. A principal component analysis (PCA) includes a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

Spectral parameters or spectrum parameters may be used to refer to measurable variables of the impedance response of the sensor. The impedance sensor response is the impedance spectrum of the non-resonance sensor circuit of the CR (capacitance (C)-resistance (R)) sensor. The impedance sensor response is the impedance spectrum of the resonance sensor circuit of the LCR (inductance (L)-capacitance (C)-resistance (R)) or RFID (radio-frequency identification) sensor. In addition to measuring the impedance spectrum in the form of Z-parameters, S-parameters, and other parameters, the impedance spectrum (both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), and the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, “spectral parameters” or “spectrum parameters” calculated from the impedance spectra (such as non-resonance or resonance spectra), are called here “features” or “descriptors.” The appropriate selection of features is performed from all potential features that can be calculated from spectra. Multivariable spectral parameters are described in U.S. Pat. No. 7,911,345 entitled “Methods and systems for calibration of RFID sensors,” which is incorporated herein by reference.

A resonance impedance or impedance may refer to measured sensor frequency response from which the sensor spectral parameters are extracted.

Sensing materials and/or sensing films may include, but are not limited to, materials deposited onto a transducer’s electronics module, such as electrodes of the CR or LCR circuit components or an RFID tag, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the CR or the LCR or RFID sensor, the impedance sensor response changes as a function of pH. Thus, such as a CR or LCR or RFID sensor works as a pH sensor. When such a polyaniline film is deposited onto the CR or LCR or RFID sensor for detection in gas phase, the impedance sensor response also changes upon exposure to basic (for example, NH3) or acidic (for example, HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensing material. In order to prevent the material in the sensor film from leaching into the liquid environment, the sensing materials are attached to the sensor surface using standard techniques, such as covalent bonding, electrostatic bonding, and other standard techniques known to those of ordinary skill in the art. In addition, the sensing material has at least two temperature-dependent response coefficients related to temperature-dependent changes in material dielectric constant and resistance of the sensing material.

Transducer and/or sensor may be used to refer to electronic devices such as CR, LCR or RFID devices intended for sensing. Transducer can be a device before it is coated with a sensing film or before it is calibrated for a sensing application. A sensor may be a device typically after it is coated with a sensing film and after being calibrated for the sensing application.

Figure 32:
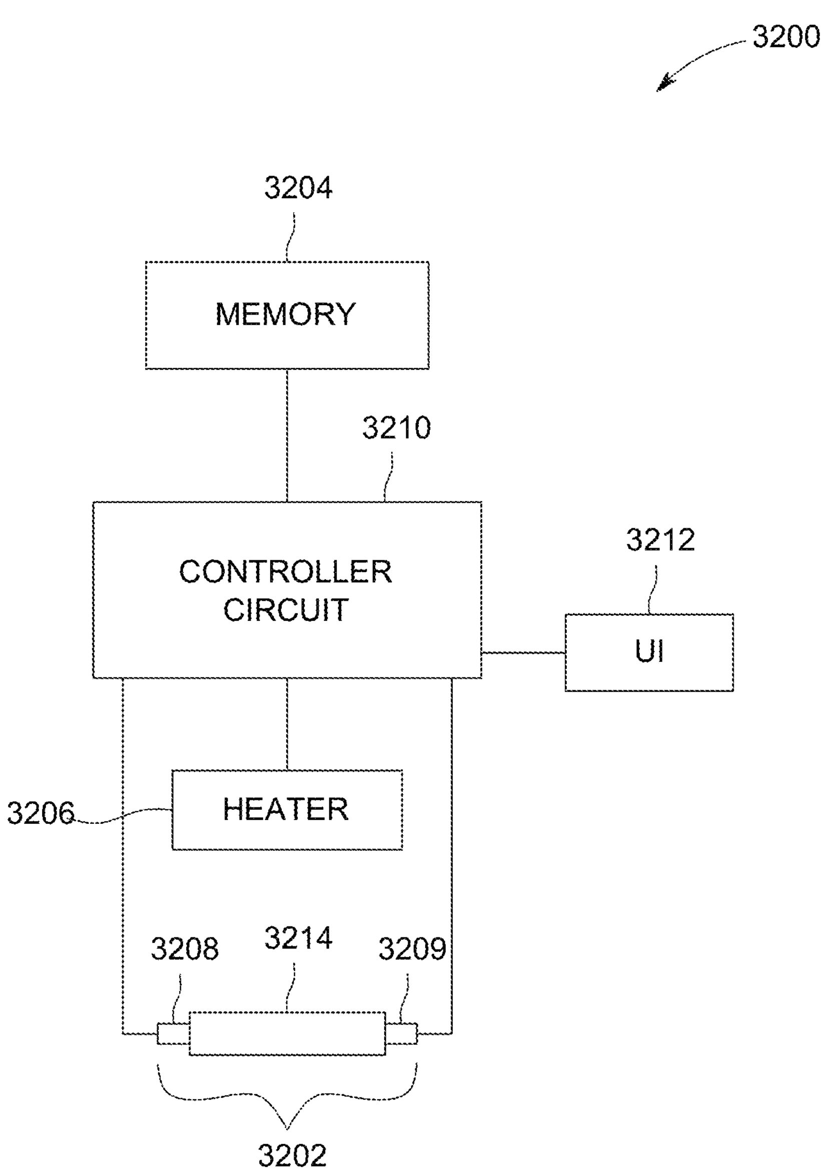
FIG. 32 is a schematic diagram of one embodiment of a sensing system.

FIG. 32 is a schematic diagram of a sensing system 33300, in accordance with an embodiment. The sensing system 33300 includes a controller circuit 33310, a memory 33304, a heater 33306, and a sensor 33302. The controller circuit 33310 can represent one or more of the controllers 122, 1708 described herein. The memory 33304 is an electronic storage device configured to store information acquired from the sensor 33302 (e.g., an impedance spectrum, a transfer function, and/or the like). The contents of the memory 33304 may be accessed by the controller circuit 33310, and/or the like. The memory 33304 may include flash memory, RAM, ROM, EEPROM, and/or the like. The sensor 33302 can represent one or more of the sensors, sensor probes, or sensor units described herein.

The controller circuit 33310 may control the operation of the sensing system 33300. For example, the controller circuit 33310 may be configured to apply a stimulation waveform to the sensor 33302. The stimulation waveform may be an electrical stimulus configured to be a sinusoidal waveform having an amplitude (e.g., voltage, current, and/or the like) and a dynamic frequency. Optionally, the controller circuit 33310 may adjust the frequency of the stimulation waveform over time. For example, the controller circuit 33310 may adjust the frequency of the stimulation waveform between frequencies of a non-resonant bandwidth of the sensor 33302. In another example, the stimulation waveform may adjust the frequency of the stimulation waveform between frequencies of a scanning bandwidth of the sensor 33302. The scanning bandwidth includes a range of frequencies that are non-resonant frequencies of the sensor 33302.

The controller circuit 33310 is configured to acquire an impedance response of the sensor 33302 in response to the stimulation waveform. For example, the controller circuit 33310 analyzes the impedance response of the sensor 33302 at frequencies that provide a linear response within a predetermined threshold (e.g., sufficiently linear) of the sensor 33302 to the one or more analytes of interest. The controller circuit 33310 may also be configured to analyze the impedance response of the sensor 33302 at frequencies that provide a non-linear response, monotonic response or a non-monotonic response within a predetermined threshold of the sensor 33302 to the one or more analytes of interest. The controller circuit 33310 may be embodied in hardware, such as a processor, controller, or other logic-based device, that performs functions or operations based on one or more sets of instructions (e.g., software). The instructions on which the hardware operates may be stored on a tangible and non-transitory (e.g., not a transient signal) computer readable storage medium, such as the memory 33304. Alternatively, one or more of the sets of instructions that direct operations of the hardware may be hard-wired into the logic of the hardware.

The heater 33306 may be thermally coupled to the sensor 33302. The heater 33306 is configured to generate thermal energy. For example, the heater 33306 may include one or more heating elements configured to convert electrical power (e.g., current, voltage) to generate thermal energy (e.g., heater). The amount of thermal energy generated by the heater 33306 may be based on instructions received by the controller circuit 33310. The thermal energy generated by the heater 33306 is received by the sensor 33302, and may increase a temperature of the sensor 33302 above an ambient temperature of the environment. For example, the heater 33306 may increase a temperature of the sensor 33302 at least fifty degrees Celsius above the ambient temperature. Additionally or alternatively, the heater 33306 may generate thermal energy to raise a temperature of the sensor 33302 based on a predetermined temperature stored in the memory 33304 (e.g., known to be above ambient temperature). For example, the controller circuit 33310 may instruct the heater 33306 to increase a temperature of the sensor 33302 to at least 33300 degrees Celsius. In another example, the controller circuit 33310 may instruct the heater 33306 to increase a temperature of the sensor 33302 to at least 3300 two hundred degrees Celsius. In yet another example, the controller circuit 33310 may instruct the heater 33306 to increase a temperature of the sensor 33302 to at least eight hundred degrees Celsius.

The heater 33306 may be a part of an asset or a part of equipment and may be thermally coupled to the sensor 33302. For example, the heater 33306 may be an internal combustion engine, a turbine, a gas stack, a chemical reactor vessel, a melting vessel and the like.

Optionally, the sensing system 33300 may include a user interface 33312. The user interface 33312 may correspond to a switch, a relay, a tactile button, and/or the like. The user interface 33312 may be used by the controller circuit 33310 to receive a user input to determine when to generate a stimulation waveform. In another example, the user interface 33312 may be used by the controller circuit 33310 to determine when to calibrate the sensor, such as defining a transfer function of the sensor 33302. Additionally or alternatively, the user interface 33312 may include one or more visual and/or audio indicators configured to alert a status of the sensing system 33300 to the user.

The sensor 33302 is configured to measure and/or detect a presence of one or more analytes of interest within the ambient (e.g., in operational contact with the sensing material 33314, proximate to, surrounding area, within a predetermined distance of a surface are of the sensing material 33314, and/or the like) environment of the sensor 33302. The sensor 33302 includes at least one pair of electrodes 33308-3209 and a sensing material 33314. The electrodes 33308-3209 are conductors that are electrically coupled to the sensing material 33314 and the controller circuit 33310. For example, the electrodes 33308-109 are in contact with the sensing material 33314. The electrodes 33308-109 are configured to deliver the stimulation waveform generated by the controller circuit 33310 to the electrodes 33308-109 and to the sensing material 33314.

The sensing material 33314 is configured to predictably and reproducibly affect and adjust the impedance of the sensor 33314 in response to changes in the environment. For example, characteristics (e.g., magnitude of the real part of the impedance, magnitude of the imaginary part of the impedance, phase of the impedance, and/or the like) of the impedance of the sensing material 33314 are adjusted based on a concentration, presence, and/or the like of the analyte of interest within the ambient environment of the sensor 33302. The sensing material 33314 is in operational contact with the ambient environment. For example, at least a portion of a surface area of the sensing material 33314 is exposed to and/or in contact with the environment adjacent to the sensor 33302, which changes an electrical property (e.g., inductance) of the sensing material 33314. The sensing material 33314 may be a semiconducting polymer (e.g., polyaniline film, Nafion) and/or a dielectric polymer (e.g., silicone adhesive). Additionally or alternatively, the sensing material 33314 may include organic, inorganic (e.g., sol-gel film), biological, composite film (e.g., polyisobutylene film), a nano-composite film (e.g., electrospun polymer nanofibers, gold nanoparticle-polymer film, metal nanoparticle-polymer film, electrospun polymer nanofibers, electrospun inorganic nanofibers, electrospun composite nanofibers), n-type oxide semiconductor, p-type oxide semiconductor, graphene, carbon nanotubes, and/or the like that are configured to change an electrical and/or dielectric property based on an environment exposed to the sensing material 33314.

Additionally or alternatively, the sensing material 33314 may be a metal oxide. For example, the sensing material 33314 may be a single-metal oxide such as ZnO, CuO, CoO, SnO2, TiO2, ZrO2, CeO2, WO3, MoO3, In2O3, and/or the like. In another example, the sensing material 33314 may be a perovskite oxide having differently sized cations such as SrTiO3, CaTiO3, BaTiO3, LaFeO3, LaCoO3, SmFeO3, and/or the like. In another example, the sensing material 33314 may be a mixed metal oxide composition such as CuO—BaTiO3, ZnO—WO3, and/or the like.

Base sensing materials may be further doped with metal salts, metal nanoparticles, conducting nanoparticles, semiconducting nanoparticles. Morphology of the base sensing materials may influence the working temperature of the sensing material. Sensing materials may be used for detection of analyte gases at a temperature of at least 30 degrees Celsius. Non-limiting examples of such sensing materials may include CeO, Fe2O3, In2O3, WO3, GaAs, SnO2, ZnO, NiO, V2O5, and/or the like.

Sensing materials may be used for detection of analyte gases at a temperature of at least 33300 degrees Celsius. Non-limiting examples of such sensing materials may include LaCoO3, GaAs. Sensing materials may be used for detection of analyte gases at a temperature of at least 300 degrees Celsius. Non-limiting examples of such sensing materials may include ZnO, AlVO4, SnO2, Bi4Fe2O9, La2CuO4, WO3, and/or the like. Sensing materials may be used for detection of analyte gases at a temperature of at least 800 degrees Celsius. Non-limiting examples of such sensing materials may include BaTiO3, SrTiO3, Ga2O3, WO3, Nb2O3, MoO3, CeO2, BaSnO3, and/or the like. Such sensing materials with the associated sensors may detect gases and volatiles of environmental background (e.g. O2, CO2, H2O), transportation/industrial/agricultural atmospheric pollutants (e.g. CO2, CO, O3, H2S, NH3, NOx, SO2, CH4, industrial fumes, waste odors), breath biomarkers (e.g. NO, H2S, NH4, acetone, ethane, pentane, isoprene, hydrogen peroxide), and public/homeland safety hazardous volatiles (e.g. toxic industrial chemicals, chemical warfare agents, explosives).

The sensor 33302 may be configured as a non-resonant circuit. Additionally or alternatively, the sensor 33302 may be configured as a resonant circuit by adding one or more components (e.g., inductor). Optionally, in connection with FIG. 33, a sensing system 3300 may include a sensor 3350 configured as a resonant circuit. It may be noted, that the sensor 3350 may be configured as a resonant circuit which may be implemented as the sensor 33302.

Figure 33:
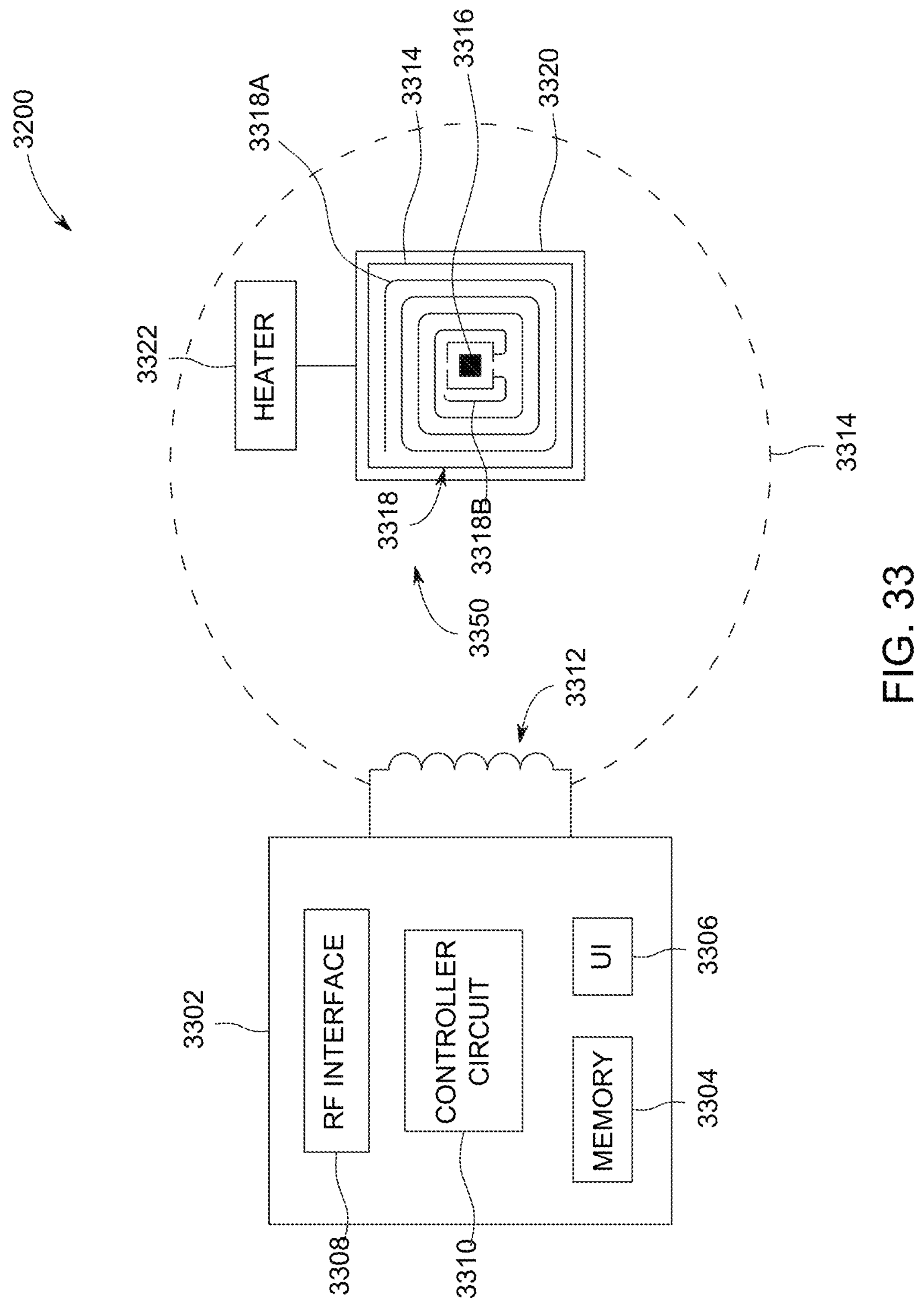
FIG. 33 is a schematic diagram of one embodiment of a sensing system.

FIG. 33 is a schematic diagram of the sensing system 3300, in accordance with an embodiment. The sensing system 3300 is having sensor reader 3302 and a sensor 3350. The sensor reader 3302 may include a memory 3304, a radio frequency (RF) interface 3308, an antenna 3318, and a controller circuit 3310. The sensor reader 3302 may be configured to receive an impedance of the sensor 3350, for example via a mutual inductance coupling between the sensor 3350 and a pickup coil 3312 of the sensor reader 3302. Optionally, the sensor reader 3302 may include a user interface 3306.

The RF interface 3308 may be electrically coupled to the memory 3304, the controller circuit 3310, and the pickup coil 3312. The RF interface 3308 may include a transmitter, a receiver, a transmitter and a receiver (e.g., a transceiver), and/or the like. The RF interface 3308 may be configured to transmit and/or receive information using an RFID protocol. The RFID protocol may be a short range wireless communication protocol defined in ISO/IEC 18092/ECMA-340, ISO/IEC 18000, ISO/IEC 14443, and/or the like. The RF interface 3308 may include hardware, such as a processor, controller, or other logic-based device to conform and/or encode information stored in the memory 3304 to the RFID protocol to transmit using the pickup coil 3312, and/or decode information received by the pickup coil 3312 to be processed by the RF interface 3308 and/or the controller circuit 3310.

The memory 3304 is an electronic storage device configured to store information received from the sensor 3350 (e.g., an impedance, a transfer function, and/or the like). The contents of the memory 3304 may be accessed by the controller circuit 3310, the RF interface 3308, and/or the like. The memory 3304 may include flash memory, RAM, ROM, EEPROM, and/or the like.

The controller circuit 3310 may control the operation of the sensor reader 3302. The controller circuit 3310 may be embodied in hardware, such as a processor, controller, or other logic-based device, that performs functions or operations based on one or more sets of instructions (e.g., software). The instructions on which the hardware operates may be stored on a tangible and non-transitory (e.g., not a transient signal) computer readable storage medium, such as the memory 3304. Alternatively, one or more of the sets of instructions that direct operations of the hardware may be hard-wired into the logic of the hardware.

The user interface 3306 may include a switch, a relay, a tactile button, and/or the like. The user interface 3306 may be used by the RF interface 3308 to determine when to receive information from and/or transmit information to the sensor 3350.

The sensor 3350 is configured to detect the one or more analytes of interest. Optionally, the sensor 3350 may be similar to the sensors described in U.S. Pat. No. 9,037,418 entitled "Highly selective chemical and biological sensors," U.S. Pat. No. 8,542,024 entitled "Temperature-independent chemical and biological sensors, and U.S. Publication No. 2012/0235690 entitled "Methods for analyte detection," all of which are incorporated by reference in their entirety. The sensor 3350 may include a heater 222 thermally coupled to the sensing material 3314. The heater 222 may be similar to and/or the same as the heater 33306.

The sensor 3350 includes a resonant inductor capacitor resistor (LCR) circuit with a sensing material 3314 overlaid on a substrate 3320. The resonant LCR circuit is formed and/or defined by a sensor antenna 3318 (e.g., 3318*a-b*). The sensor antenna 3318 may be divided into at least one pair of electrodes, such as a first electrode (e.g., the sensor antenna 3318*a*) and a second electrode (e.g., the sensor antenna 3318*b*). Additionally or alternatively, the sensor antenna 3318 may be a single electrode, such as a single conducting structure operationally coupled to a substrate. The sensing material 3314 is disposed and/or applied over a sensing region of the substrate 3320, which is interposed between the sensor antenna 3318. For example, the sensing material 3314 is attached to the sensor region of the substrate 3320 by covalent bonding, electrostatic bonding and/or the like. The sensing material 3314 material may be similar to and/or the same as the sensing material 3214 shown in FIG. 32.

Additionally or alternatively (not illustrated), a complementary sensor may be attached across the antenna 3318 that does not have the controller circuit 3316 and alters sensor impedance response. For example, the complementary sensor may be interdigitated sensor, resistive sensor, and capacitive sensor, and/or the like. Complementary sensors are described in U.S. Pat. No. 7,911,345 entitled "Methods and systems for calibration of RFID sensors," which is incorporated herein by reference.

Optionally, the sensor 3350 may also include a controller circuit 3316 electrically coupled to the antenna 3318. The controller circuit 3316 may be configured to apply the stimulation waveform to the antenna 3318. The controller circuit 3316 may include a memory and an RF signal modulation circuitry. The memory may include manufacturing, user, calibration, a transfer function, and/or other data stored thereon. The controller circuit 3316 may be an integrated circuit fabricated using a complementary metal-oxide semiconductor (CMOS) process and a non-volatile memory. The controller circuit 3316 may include an analog I/O input utilized for example as a resistance input, capacitance input, inductance input, and/or the like. The RF signal modulation circuitry may include a diode rectifier, a power supply voltage control, a modulator, a demodulator, a clock generator, and other components.

The sensor 3350 may be communicatively coupled to the sensor reader 3302 enabling the controller circuit 3316 to read (e.g., accessed) and/or store information received by the sensor reader 3302 via the antenna 3318. For example, the memory of the controller circuit 3316 may be read wirelessly by the sensor reader 3302 using a mutual inductance coupling between the antenna 3318 and the pickup coil 3312. The pickup coil 3312 may be positioned within an activation field 3314 of the antenna 3318. For example, an alternating current passes within the pickup coil 3312 to generate an RF and/or microwave field, which is passed through the antenna 3318. Optionally, the current may pass within the pickup coil 3312 in response to a user input received by the user interface 3306. The activation field 3314 may correspond to a region from the antenna 3318 where an RF and/or microwave field generated by the pickup coil 33312 can be received by the antenna 3318. A size of the activation field 3314 may be based on a frequency of the RF and/or microwave field, a power level and/or amplitude of the RF and/or microwave field, a size (e.g., dimensions, length, width, and/or the like) of the antenna 3318, and/or the like. An AC voltage is generated across the antenna 3318 based on the RF and/or microwave field emitted by the pickup coil 3312, which is rectified by the controller circuit 3316 via the RF signal modulation circuitry to result in a DC voltage for the operation of the sensor 3350 to form the mutual inductance coupling. Additionally or alternatively, the sensor 3350 may include a power source (not shown) that may be used to generate power (e.g., current, voltage) for the operation of the sensor 3350. Additionally or alternatively, the sensor 3350 may be communicatively coupled to the sensor reader 3302 via a wired interface.

Optionally, the AC voltage generated across the antenna 3318 may correspond to the stimulation waveform utilized to measure the impedance response. For example, sensing is performed via monitoring of the changes in the electrical properties (e.g., to form the impedance response) of the sensing material 3314 as probed by the electromagnetic field generated at the antenna 3318 in response to the RF and/or microwave field emitted by the sensor reader 3302. Upon reading the sensor 3350 with the pickup coil 3312, the electromagnetic field generated in the antenna 3318 extends out from the plane of the sensor 3350 and is affected by the dielectric property of a sensing material that is in contact with an ambient environment that adjusts an electrical characteristic to enable the controller circuit 33310 to measure the one or more analytes of interest.

Figure 34:
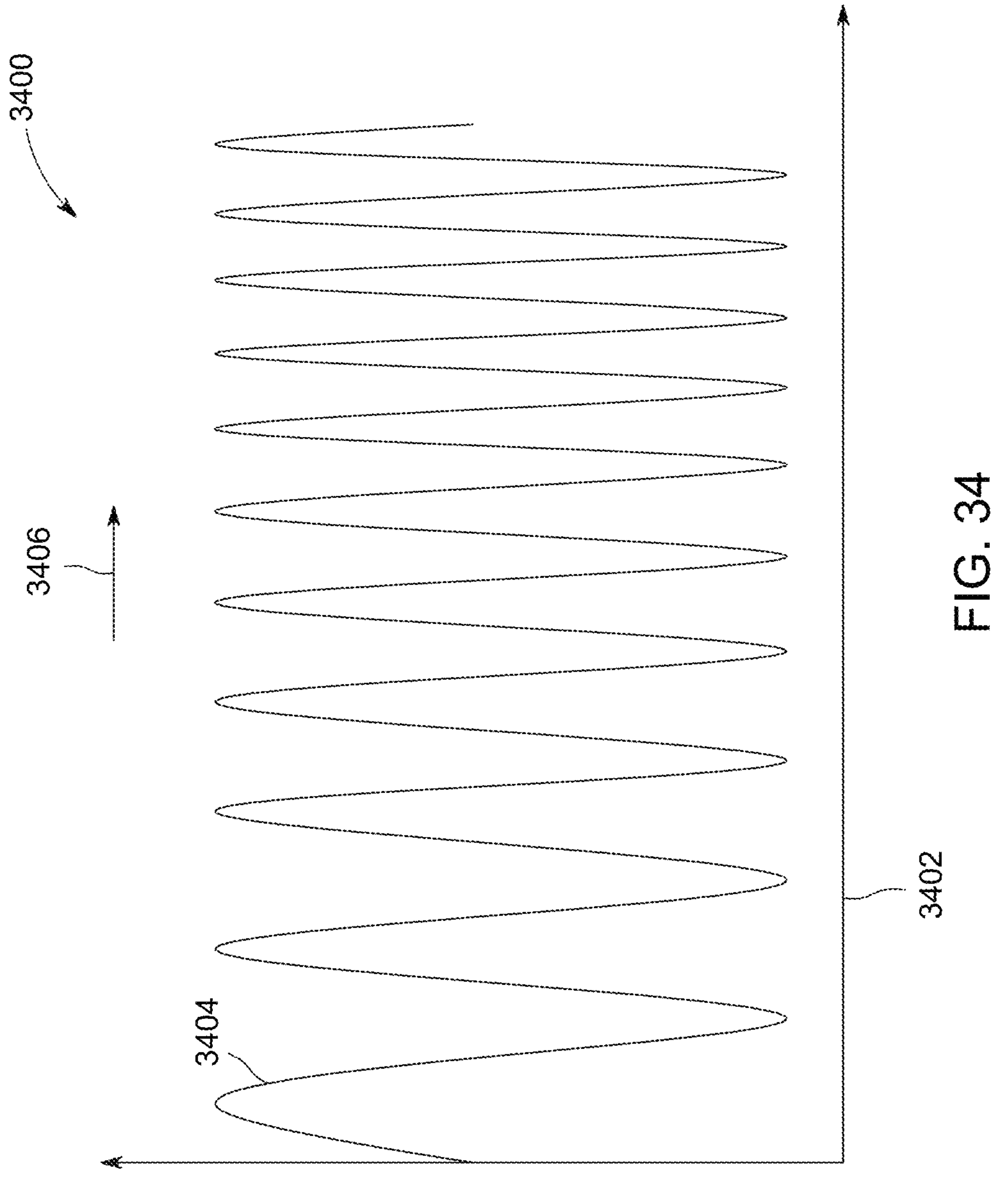
FIG. 34 shows a graphical illustration of one embodiment of a stimulation waveform applied to a sensing material of a sensor.

FIG. 34 is a graphical illustration 3400 of a stimulation waveform 3404 applied to the sensing material 33314, 3314 of a sensor 33302, 3350. The stimulation waveform 3404 may be generated by the controller circuit. The stimulation waveform 3404 may be an electrical stimulus having an amplitude (e.g., voltage, current, and/or the like) and a dynamic frequency. For example, the stimulation waveform 3404 is shown plotted along a horizontal axis 3402 representing time. Over time, the controller circuit may adjust (e.g., increase, decrease) the frequency of the stimulation waveform 3404. For example, as shown in FIG. 34, the controller circuit may increase the frequency of the stimulation waveform 3404 along the axis 3402 in a direction of an arrow 3406. In various embodiments, the stimulation waveform 3404 may be a chirp and/or sweep signal.

Optionally, a range of the frequencies of the stimulation waveform 3404 is adjusted by the controller circuit based on a frequency bandwidth. The frequency bandwidth may be a defined range of frequencies centered at a resonance frequency of the sensor 33302, 3350 (e.g., configured to a part of a non-resonant or a resonant circuit). Additionally or alternatively, the range the frequency of the stimulation waveform 3404 is adjusted by the controller circuit based on one or more scanning bandwidths. The scanning bandwidths may be a range of frequencies that are non-resonant frequencies of the sensor 33302, 3350. For example, the scanning bandwidths may be utilized by the controller circuit when the sensor 33302, 3350 is configured a part of a non-resonant circuit.

Figure 35:
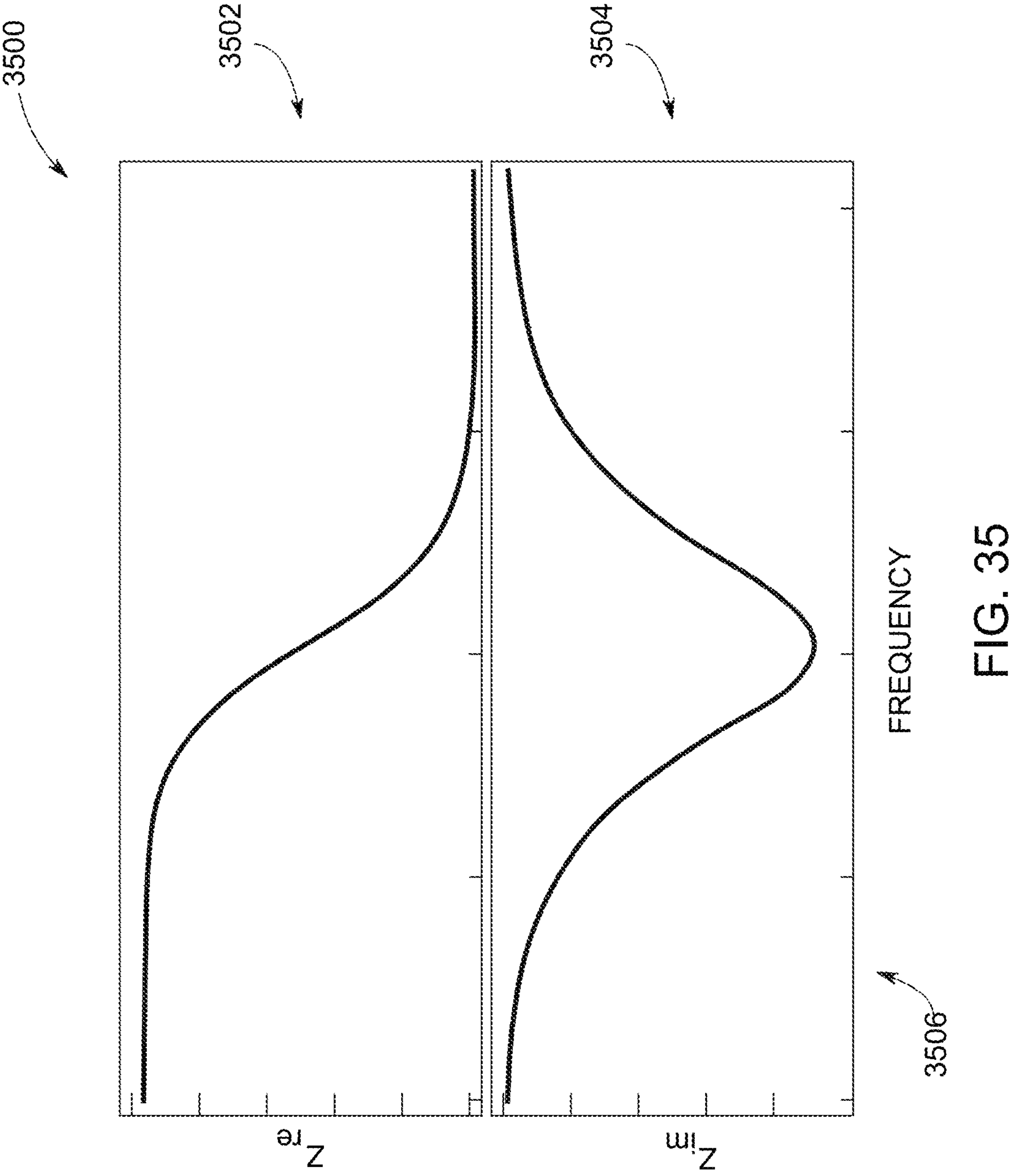
FIG. 35 shows a graphical illustration of a measured response corresponding to a non-resonance impedance response of a sensor, in accordance with an embodiment.
Figure 36:
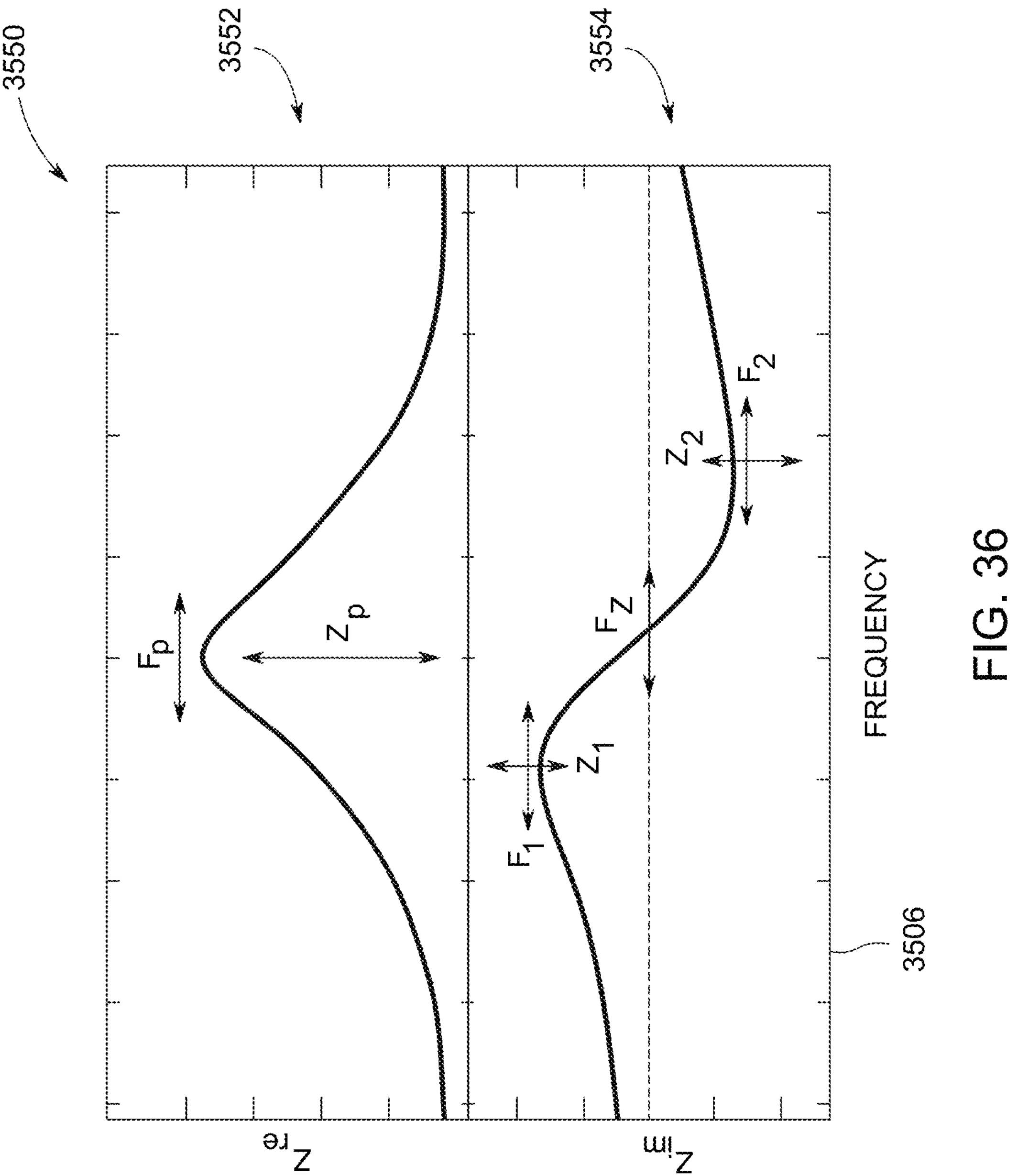
FIG. 36 shows a graphical illustration of a measured response corresponding to a resonance impedance response of a sensor, in accordance with an embodiment.

FIGS. 35 and 36 show graphical illustrations measured response 3500, 3550 corresponding to an impedance response 3502, 3504, 3552, 3554 of the sensors 33302 and 3350, respectively, in accordance with an embodiment.

For example, the impedance responses 3500, 3550 may represent the impedance sensor response of the sensor 33302, 3350 (respectively) based on the stimulation waveform 3404 generated by the controller circuit. The impedance responses 3500, 3550 includes several individually measured spectral parameters of the sensor 33302, 3350. The impedance responses 3500, 3550 are divided into real portions 3502, 3552 corresponding to the real impedance, Zre(f) of the impedance responses 3500, 3550, and imaginary portions 3504, 3554 of an imaginary impedance, Zim (f). The impedance responses 3500, 3550 are measured by the controller circuit based on a measurement signal. For example, the controller circuit may receive the measurement signal from the electrodes (e.g., the electrodes 3208-3209, the antenna 3318*a*-*b*) in contact with the sensing material. The measurement signal is an electrical signal generated by the sensing material in response to the stimulation waveform 3404 and the ambient environment. The measurement signal is representative of the impedance response of the sensing material. For example, the measurement signal may have electrical characteristics (e.g., voltage, current, frequency, and/or the like), which may be utilized by the controller circuit to calculate the impedance responses 3500, 3550.

Based on the impedance responses 3500, 3550, the controller circuit may calculate spectral parameters associated with the measured Zre(f) and Zim(f). For example, the spectral parameters may include the peak frequency position Fp and peak magnitude Zp of the real portion 3552, Zre(f). The spectral parameters may include the resonant F1 and anti-resonant F2 frequencies of the imaginary portion 3554, Zim(f), the impedance magnitudes Z1 and Z2 at F1 and F2 frequencies, respectively, and the zero-reactance frequency Fz. Additionally or alternatively, the controller circuit may calculate a quality factor.

In connection with FIG. 36, from the calculated spectral parameters, resistance, capacitance, and/r the like of the sensing material may also be determined by a multivariate analysis. The multivariate analysis may be used to reduce the dimensionality of the impedance response, either from the real portion 3502, 3552 Zre(f), and imaginary portion 3504, 3554, Zim(f), of the impedance responses 3500, 3550 or from the calculated spectral parameters Fp, Zp, F1 and F2, and possibly other parameters to a single data point in a multidimensional space for selective quantization of the one or more analytes of interest.

Figure 37:
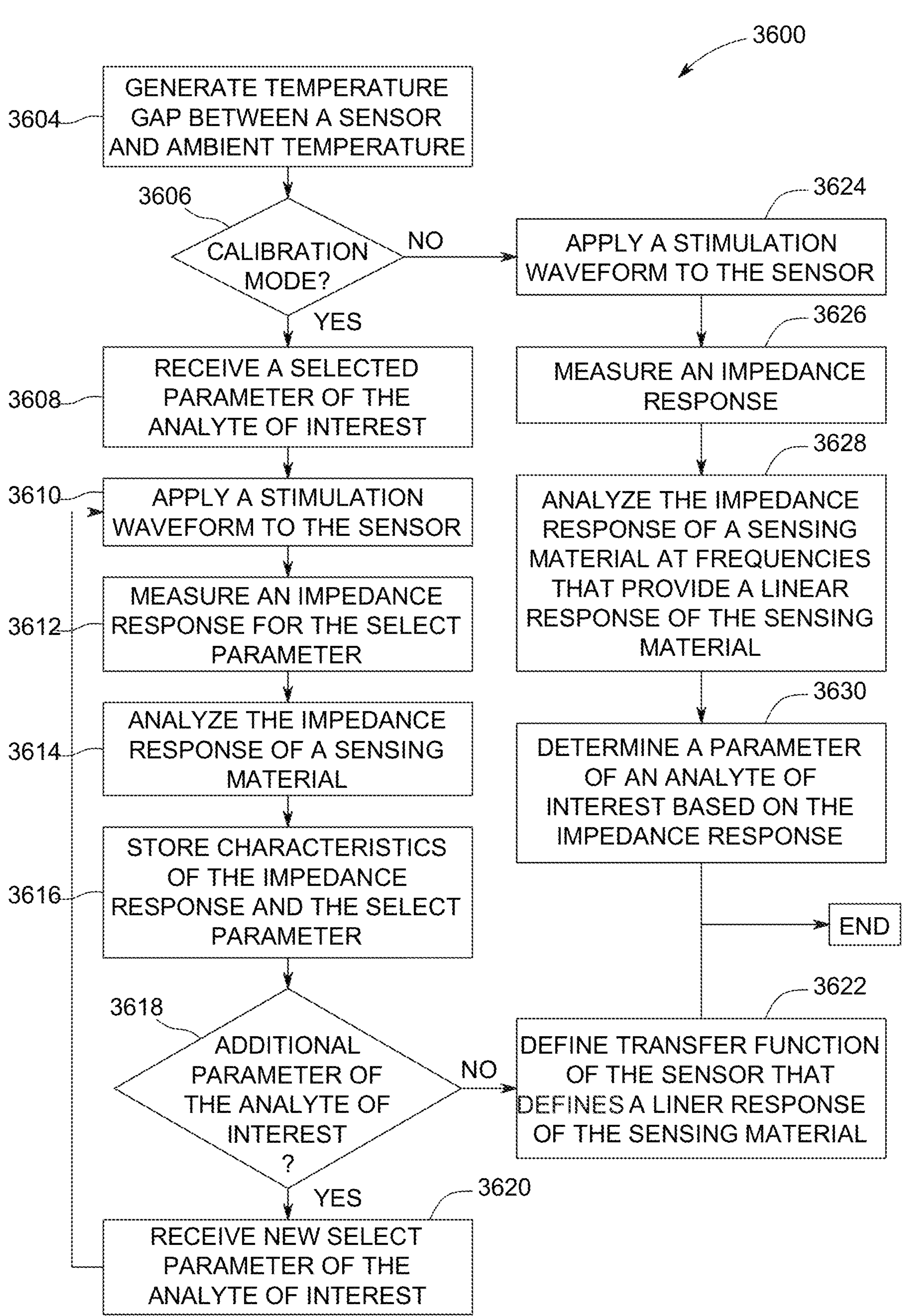
FIG. 37 is a flow chart of one embodiment of a method for detecting one or more analytes of interest.

FIG. 37 is a flow chart of a method 3600 for detecting one or more analytes of interest, in accordance with an embodiment. The method 3600, for example, may employ or be performed by structures or aspects of various embodiments (e.g., systems and/or methods) discussed herein. For example, the method 3600 includes operations performed by and/or changes to the memory, the controller circuit, the sensor, and/or the like. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. In various embodiments, portions, aspects, and/or variations of the method may be able to be used as one or more algorithms to direct hardware to perform one or more operations described herein.

It may be noted that although the method described below is in connection with the sensing system 3200, the operations described may be utilized by one or more other sensing systems described herein.

Beginning at 3604, the heater 3206 may generate a temperature gap (or difference) between the sensor and ambient temperature. The temperature gap may represent a difference in temperatures between the sensor and/or the components of the sensor (e.g., at least one pair of electrodes, the sensing material, etc.) and the ambient temperature based on thermal energy generated by the heater. For example, the controller circuit may instruct the heater to generate thermal energy, which is received by the sensor. An amount of thermal energy generated by the heater may be based on a temperature of the sensor relative to the heater. For example, the controller circuit may instruct the heater to increase a temperature of the sensor at least fifty degrees Celsius above the ambient temperature.

Additionally or alternatively, the temperature gap may be based on a predetermined temperature stored in the memory. For example, the controller circuit may instruct the heater to increase a temperature of the sensor to at least one hundred degrees Celsius. In another example, the controller circuit may instruct the heater to increase a temperature of the sensor to at least two hundred degrees Celsius or to at least eight hundred degrees Celsius.

At 3606, the controller circuit may determine if a user input is received indicative of a calibration mode. The calibration mode is utilized by the controller circuit to define a transfer function for the sensor. The transfer function is utilized by the controller circuit to determine a parameter (e.g., concentration) of the analyte of interest based on the impedance response, such as the measured spectral parameters of the impedance response. The controller circuit receives the user input from the user interface. For example, a user of the sensing system may utilize the user interface to select the calibration mode, which generates a user input received by the controller circuit. Based on the user input, the controller circuit may enter a calibration mode. Additionally or alternatively, the controller circuit may automatically determine a calibration mode based on predetermined periodicity of the calibration mode. Additionally or alternatively, the controller circuit may automatically determine a calibration mode based on a lack of transfer function stored in the memory.

If the sensing system is in a calibration mode, at 3608 the controller circuit may receive a select parameter of the analyte of interest. The select parameter may correspond to a concentration and/or quantitative measure of an amount of the analyte of interest within the ambient environment of the sensor. For example, the controller circuit may receive a user input from the user interface indicative on the concentration of the analyte of interest. It may be noted that in various embodiments the select parameter may correspond to a temperature, pressure, conductivity, dielectric property, number of dielectric, metallic, chemical, or biological particles in the proximity or in contact with the sensor, dose of ionizing radiation, light intensity, and/or the like.

At 3610, the controller circuit may apply a stimulation waveform to the sensor. The stimulation waveform may be similar to and/or the same as the stimulation waveform 3404 shown in FIG. 34. For example, the controller circuit may generate the stimulation waveform 3404 to the sensing material utilizing the pair of electrodes in contact with the sensing material. The stimulation waveform 3404 is conducted through the electrodes and received by the sensing material.

At 3612, the controller circuit may measure an impedance response for the select parameter. For example, the controller circuit may receive a measurement signal generated by the sensing material from the electrodes. The measurement signal is representative of an impedance response of the sensing material in operational contact with the ambient environment. For example, the measurement signal may have electrical characteristics (e.g., voltage, current, frequency, and/or the like), which is utilized by the controller circuit to calculate the impedance response. Optionally, the impedance response may be similar to and/or the same as the impedance response 3500 shown in FIG. 35.

Figures 40, 41:
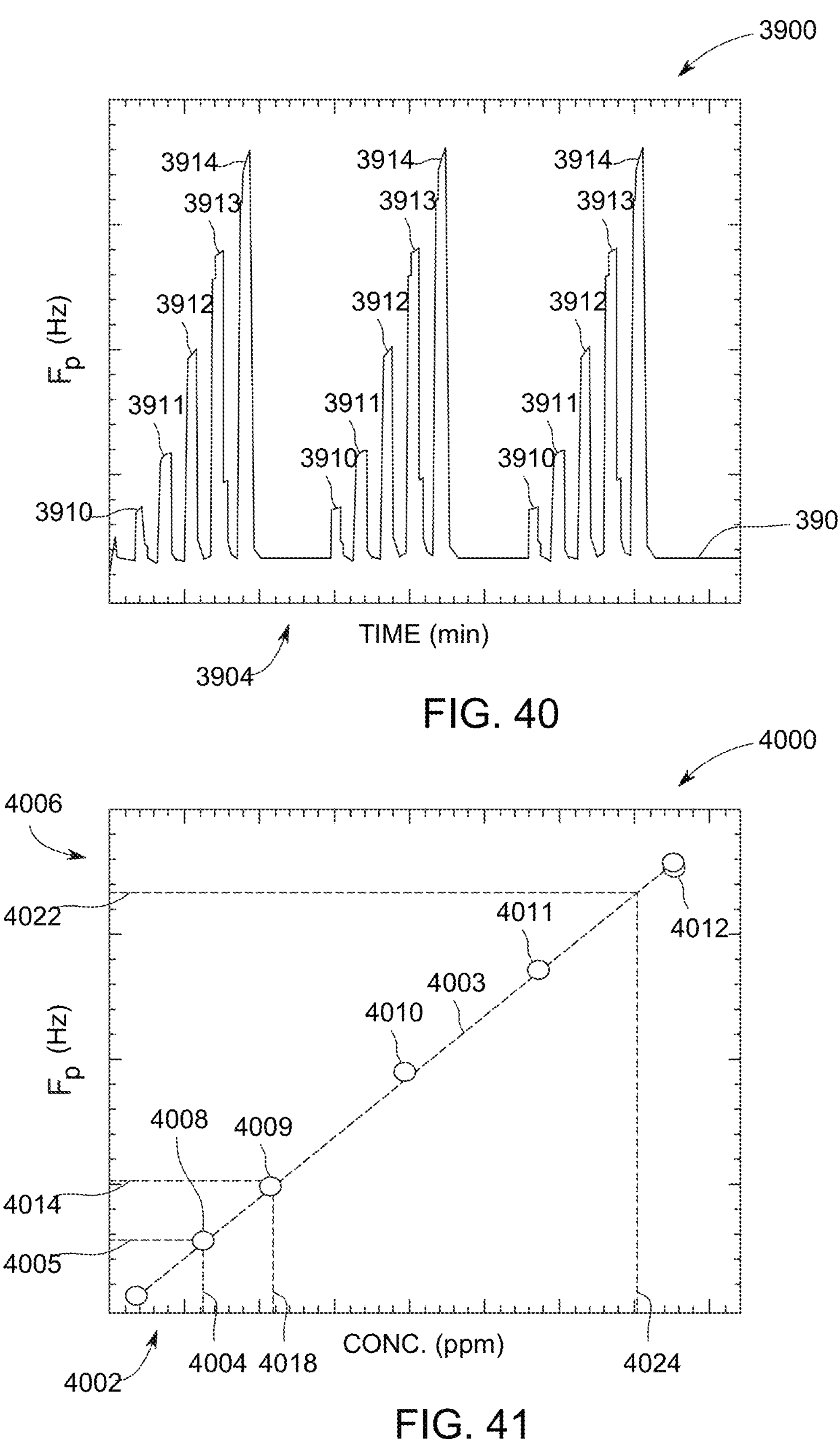
FIG. 40 is a graphical illustration of one embodiment of a spectral parameter calculated from a sensor.
FIG. 41 is a graphical illustration of a concentration curve of the sensor based on the spectral parameter shown in FIG. 40.

At 3614, the controller circuit may analyze the impedance response of the sensing material. For example, the controller circuit may calculate one or more spectral parameters based on a real portion (e.g., Fp, Zp) and/or imaginary portion (e.g., F1, F2, Fz, Z1, Z2) of the impedance response. The controller circuit may be configured to analyze the spectral parameters that provide a linear response (e.g., as shown in FIGS. 39 and 40) of the sensing material to the analyte of interest and reject effects of interference analytes (e.g., analytes that are not the analyte of interest).

Figures 38, 39:
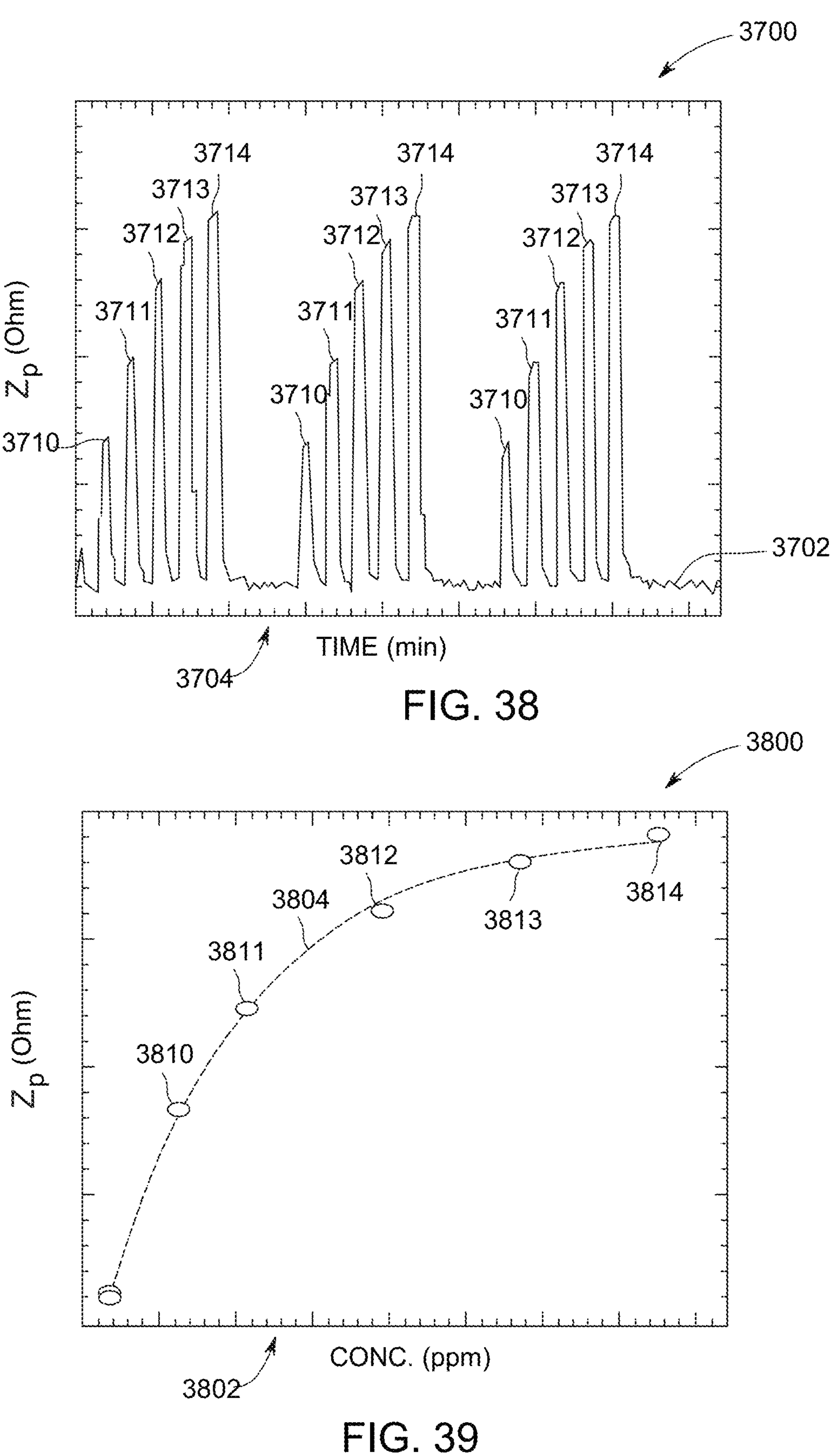
FIG. 38 is a graphical illustration of a spectral parameter calculated from a conventional sensor.
FIG. 39 is a graphical illustration of a concentration curve of the conventional sensor based on the spectral parameter shown in FIG. 38.

As a non-limiting example, in connection with FIGS. 37 and 38, a conventional resistance sensor is connected to a resonant circuit. This conventional resistance sensor is based on a SnO2 metal oxide and may detect an analyte of interest (e.g., methane gas, hydrogen, isobutane, ethanol).

For conventional sensor operation, the conventional sensor was heated to its prescribed working temperature of three hundred degrees Celsius. Measurements of resonant spectra were done using an impedance analyzer. Zp response of the resonant sensor circuit is directly proportional to the resistance of this conventional resistance sensor.

FIG. 38 is a graphical illustration 3700 of a spectral parameter 3702 calculated from a conventional sensor. The spectral parameter 3702 is a peak magnitude Zp plotted along a horizontal axis 3704 representing time.

The conventional sensor was exposed to different concentrations (e.g., 111 ppm, 222 ppm, 444 ppm, 667 ppm, 889 ppm) of the analyte of interest (e.g., methane gas) and a dry air in between the exposures over time.

The spectral parameter 3702 response based on the exposure to the different concentrations of the analyte of interest is represented by a non-linearity of the peaks 3710-3714 of the spectral parameter 3702. Each of the peaks 3710-3714 may have an amplitude based on the concentrations of the analyte of interest exposed to the conventional sensor. For example, the amplitude of the peak 3710 is less than the amplitude of the peak 3713 representing the concentration of the analyte of interest of the peak 3710 is less than at the peak 3713. In connection with FIG. 39, a calibration curve 3804 may be defined based on the peaks 3710-3714.

FIG. 40 is a graphical illustration 3800 of the concentration curve 3804 of the conventional sensor based on the spectral parameter 3702 response. The concentration curve 3804 is constructed from the spectral parameter 3702, such as using the peaks 3710-3714. For example, the concentration curve 3804 is constructed from using data points 3810-3814 based on the amplitudes of the peaks 3710-3714. It may be noted that the concentration curve 3804 is non-linear (e.g., power law).

Representing embodiments described herein, in connection with FIGS. 40 and 41, the spectral parameter 3902 of the impedance response of the sensor is analyzed by the controller circuit having a linear response.

Figure 42:
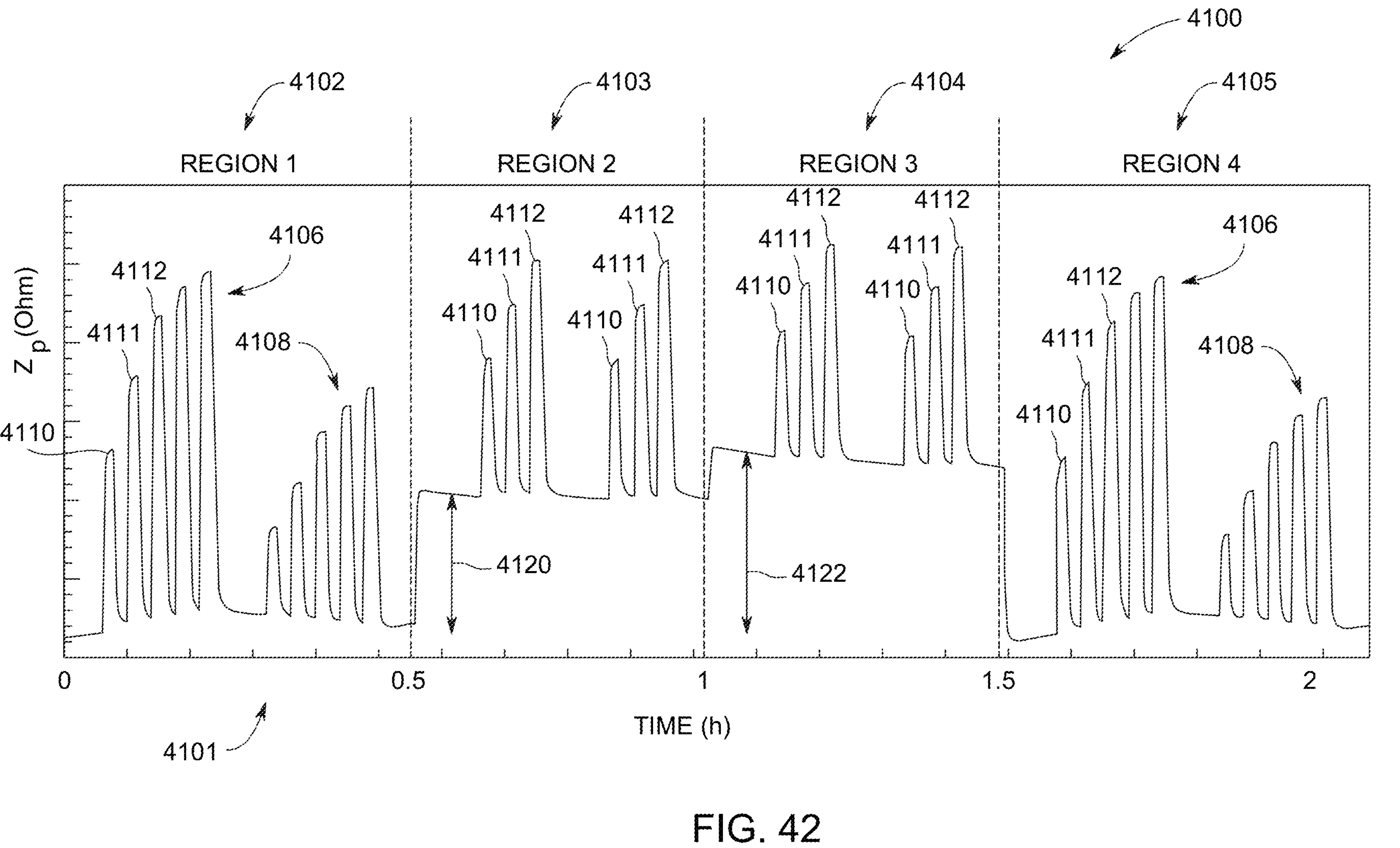
FIG. 42 is a graphical illustration of a typical effect of an analyte of interest and ambient humidity on a spectral parameter of a conventional sensor.

FIG. 42 is a graphical illustration 3900 of the spectral parameter 3902 calculated by the controller circuit of the sensor configured as a resonant sensor and/or the sensor. The spectral parameter 3902 is a peak frequency Fp plotted along a horizontal axis 804 representing time. The sensor, operating in the resonant mode, was exposed to different concentrations (e.g., 111 ppm, 222 ppm, 444 ppm, 667 ppm, 889 ppm) of the analyte of interest and a dry air in between the exposures over time.

The spectral parameter 3902 response based on the exposure to the different concentrations of the analyte of interest (e.g., methane gas) are represented by a linearity of peaks 3910-3914 of the spectral parameter 3902. Each of the peaks 3910-3914 may have an amplitude based on the concentration of the analyte of interest presented to the sensor. For example, the amplitude of the peak 3910 is less than the amplitude of the peak 3913 representing the concentration of the analyte of interest of the peak 3910 is less than at the peak 3913. In connection with FIG. 41, a calibration curve 4003 may be defined based on the peaks 3910-3914.

FIG. 41 is a graphical illustration 4000 of the concentration curve 4003 of the sensor 33302 based on the spectral parameter 3902 response. The concentration curve 4003 is constructed from the spectral parameter 3902, such as the peaks 3910-3914. For example, the concentration curve 4003 is constructed from using data points 4008-4012 based on the amplitudes of the peaks 3910-3914. It may be noted that the concentration curve 4003 is linear (e.g., not power law). This unexpected discovery shows that the sensor produces a highly linear response upon exposure to the different concentrations of an analyte of interest (e.g., methane gas) of the spectral parameter 802. Additionally or alternatively, the concentration curve 4003 is further shown having a monotonic response.

The graphical illustration 4000 represents the linear relationship of characteristics of an impedance response of the sensor and parameters of the analyte of interest, in accordance with an embodiment. The characteristics of the impedance response may correspond to the frequencies of the real portion of the impedance response, which is plotted along a vertical axis 4006. The parameters of the analyte of interest may correspond to the concentration of the analyte of interest (e.g., parts per million (ppm)) in the ambient environment of the sensor. The graphical illustration 4000 includes the plurality of data points 4008-4012. Each of the data points 4008-4012 may correspond to frequencies of the real portion of the impedance responses at different concentrations of the analyte of interest. For example, data point 4008 may correspond to a concentration at 4004 with the frequency at 4005 of the real portion of the impedance response. In another example, the data point 4009 may correspond to a concentration at 4018 with the frequency at 4014 of the real portion of the impedance response.

The data points 4008-4012 define a linear response of the concentration curve 4003 of the frequencies of the real portion of the impedance response of the sensor at different concentrations. Based on the linear response of the concentration curve 4003, the controller circuit may define a transfer function of the sensor. The transfer function may be utilized by the controller circuit to determine a characteristic of the analyte of interest based on one or more spectral parameters calculated from the impedance response (e.g., at 3630 in FIG. 36). The sensing material is configured to have the impedance response that provides a reduction of effect of interferences relative to the resistance response of a conventional sensor.

FIG. 42 is graphical illustration 4100 of a typical effect of an analyte of interest (e.g., methane gas) and ambient humidity on a spectral parameter of a conventional sensor. The spectral parameter shown in FIG. 42 is a peak magnitude Zp plotted along a horizontal axis 4101 representing time. The conventional sensor was exposed individually to the analyte of interest and water vapor as separate exposures and to the mixtures of the analyte of interest and water vapor. The graphical illustration 4100 includes four experimental regions 4102-4105 of gas exposures.

At the region 4102 and 4105, the conventional sensor was exposed to five concentrations of the analyte of interest (e.g., 111, 222, 444, 667, 889 ppm) and dry air in between the analyte of interest exposures to form a series of peaks 4106 of the spectral parameter. The series of peaks 4106 include peaks 4110-4112 based on concentrations at 111, 222, and 444 ppm of the analyte of interest. Subsequent to the concentrations of the analyte of interest, water vapor concentrations such as having different ambient humidity (e.g., at 9, 18, 36, 53, and 71 percent) is exposed to the conventional sensor and dry air in between the humidity exposures to form a series of peaks 4108.

At the region 4103, the conventional sensor was periodically exposed to three concentrations of the analyte of interest (e.g., 111, 222, 444 ppm) concurrently with a water vapor of eighteen percent relative humidity to form peaks 4110-4112 of the spectral parameter.

At the region 4104, the conventional sensor was periodically exposed to three concentrations of the analyte of interest (e.g., 111, 222, 444 ppm) concurrently with a water vapor of thirty-six percent relative humidity to form the peaks 4110-4112 of the spectral parameter.

It may be noted that FIG. 42 illustrates the conventional sensor is significantly affected by the ambient humidity exposed to conventional sensor, which shifts an amplitude of the peaks 4110-4112 of the spectral parameter. For example, the concentrations of the analyte of interest for the peaks 4110-4112 are the same for the regions 4102-4105. However, due to the ambient humidity of the regions 4103-4104, the amplitudes of the peaks 4110-4112 are shifted by shift magnitudes of 4120 and 4122, respectively, due to the ambient humidity relative to the amplitude of the peaks 4110-4112 shown in regions 4102 and 4105.

Figure 43:
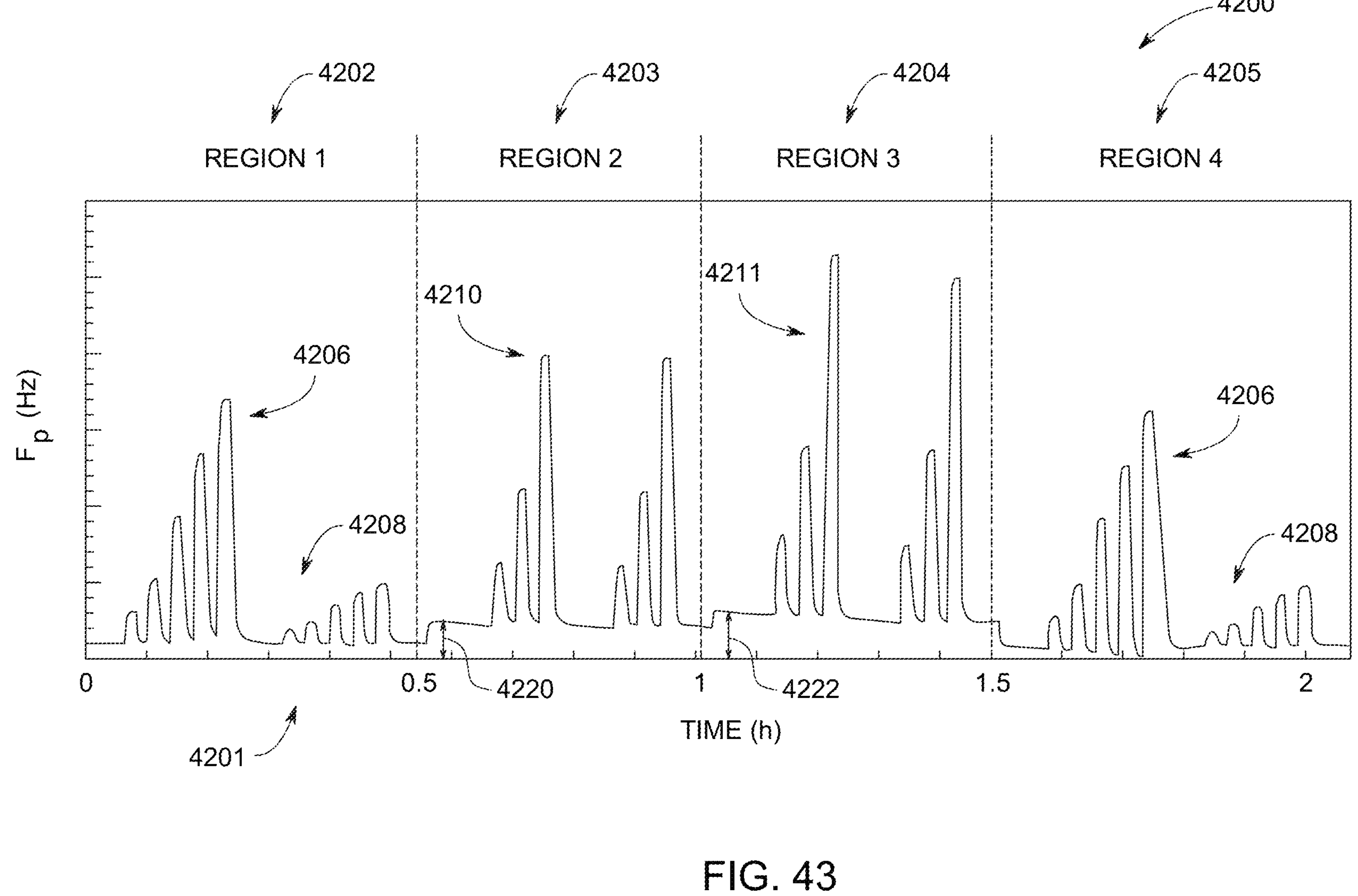
FIG. 43 is a graphical illustration of one embodiment of an analyte of interest and ambient humidity on a spectral parameter of a sensor.

FIG. 43 is graphical illustration 4200 of a typical effect of an analyte of interest (e.g., methane gas) and ambient humidity on a spectral parameter of the sensor. The spectral parameter shown in FIG. 42 is a peak frequency Fp plotted along a horizontal axis 4201 representing time. The sensor was exposed individually to the analyte of interest and water vapor as separate exposures and to the mixtures of the analyte of interest and water vapor. The graphical illustration 4200 includes four experimental regions 4202-4205 of gas exposures. Unexpectedly, we have found that when Fp measurements were performed with respect to the sensor, a significantly reduced effect of water vapor (e.g., ambient humidity) was observed as shown in FIG. 43. Thereby, the new disclosed principle of analyte of interest utilizing the sensor, provides significantly reduced effects of humidity.

For example, at the region 4202 and 4205, the conventional sensor was exposed to five concentrations of the analyte of interest (e.g., 111, 222, 444, 667, 889 ppm) and dry air in between the analyte of interest exposures to form a series of peaks 4106 of the spectral parameter. Subsequent to the concentrations of the analyte of interest, water vapor concentrations such as having different ambient humidity (e.g., at 9, 18, 36, 53, and 71 percent) are presented to the conventional sensor and dry air in between the humidity exposures to form a series of peaks 4208. At the region 4203, the conventional sensor was periodically exposed to three analyte of interest concentrations (e.g., 111, 222, 444 ppm) concurrently with a water vapor of 18 percent relative humidity to form a series of peaks 4210 of the spectral parameter. At the region 4204, the conventional sensor was periodically exposed to three analyte of interest concentrations (e.g., 111, 222, 444 ppm) concurrently with a water vapor of thirty-six percent relative humidity to form the peaks 4211 of the spectral parameter.

At regions 4203 and 4204, the series of peaks 4210 and 4211 of the spectral parameter is affected by the ambient humidity exposed to the sensor, which shifts an amplitude of the peaks 4210 and 4211 relative to the series of peaks 4206 by shift magnitudes 4220 and 4222, respectively. It may be noted, that the shift magnitudes 4220 and 4222 of the regions 4203 and 4204 are significantly less than the shift magnitudes 4120 and 4122 shown in regions 4102 and 4105. For example, the sensing material and/or sensor is configured to reduce effects of humidity of the impedance response by ten times relative to the conventional sensor shown in FIG. 41. Additionally or alternatively, the sensing material and/or sensor may be configured to reduce effects of humidity of the impedance response to approximately zero relative to the conventional sensor shown in FIG. 42.

The controller circuit may analyze the peak height Zp of the real portion of the resonant impedance response that includes multiple analytes (e.g., water, methane, tetrahydrofuran, benzene, ethyl acetate, ethanol, toluene, and/or the like). For example, a spectral parameter may be in response to the sensor being exposed individually to different analytes (e.g., vapors) as separate exposures with dry air interposed between the exposures of each analyte. It may be noted that the controller circuit may analyze additional spectral parameters concurrently and/or simultaneously with the each other. For example, the controller circuit may analyze the frequencies of the real portion of the impedance response concurrently and/or simultaneously with the impedance magnitudes of the real portion of the impedance response.

Figures 44, 45:
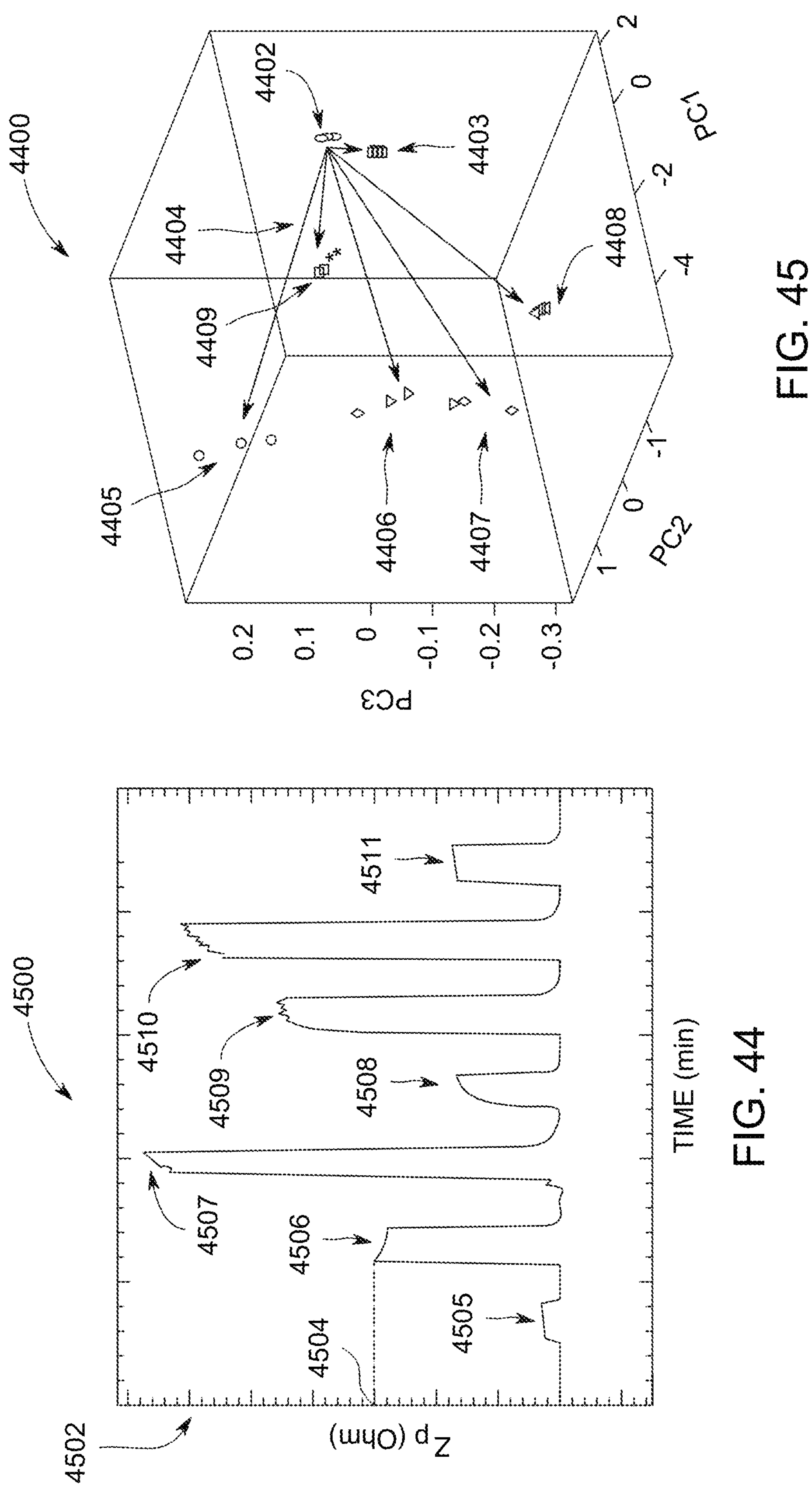
FIG. 44 is a graphical illustration of one embodiment of a spectral parameter of one embodiment of a sensor, in accordance with an embodiment.
FIG. 45 is a graphical illustration of one embodiment of a principal components analysis of a plurality of spectral parameters.

FIG. 44 is a graphical illustration of a spectral parameter 4500 calculated from an impedance response of the sensor, in accordance with an embodiment. The spectral parameter may correspond to impedance magnitude Zp calculated from a real portion of the resonant impedance response. The magnitudes of the impedance Zp are plotted along a vertical axis 4502. The spectral parameter shown in FIG. 44 shows the sensor has a cross-sensitivity to different analytes. For example, the spectral parameter based on the ambient environment in contact with the sensing material, includes multiple response peaks 4505-4511. Each of the peaks may correspond to a different analyte (e.g., gas or vapor) detected within the ambient environment of the sensor. For example, one of the peaks may correspond to water, methane, tetrahydrofuran, benzene, ethyl acetate, ethanol, toluene, and/or the like.

As depicted in FIG. 44, responses Zp to different gases or vapors have different magnitudes. The controller circuit may compare the magnitudes of the Zp response to an analyte parameter database to determine which of the frequency peaks correspond to the analyte of interest. The analyte parameter database may be stored in the memory. The analyte parameter database may include a plurality of analytes each having corresponding spectral parameters. For example, the analyte parameter database may include a plurality of analytes with corresponding real frequencies. The controller circuit may identify the analyte of interest within the analyte parameter database with corresponding real frequencies that include the frequency at 4304. The controller circuit may determine that the frequency peak 4306 that includes the frequency at 4304 corresponds to the analyte of interest, and filter and/or reject the responses 4305, 4307-4311 corresponding to interference and/or analytes not of interest.

Additionally or alternatively, the controller circuit may execute a multivariate analysis of the impedance response of the sensor to multiple analytes performed using spectral parameters Fp, Zp, F1, F2, Z1, and Z2 and processing these outputs using a principal components analysis (PCA). Based on the PCA, the controller circuit may eliminate the effects of volatiles (e.g., analytes not the analyte of interest, interference) and provide an accurate response and/or to isolate the analyte of interest into its unique response direction.

FIG. 45 is a graphical illustration 4400 of one embodiment of a principal components analysis of a plurality of spectral parameters. For example, the graphical illustration 4400 is calculated by the controller circuit by executing a PCA analysis of spectral parameters Fp, Zp, F1, F2, Z1, and Z2 calculated from an impedance response of the sensor. Based on the multiple outputs 4402-4409 of the PCA response, the controller circuit may discriminate between different analytes utilizing its unique response direction. Each of the multiple outputs 4402-4409 correspond to a different analyte. For example, the output 4402 may represent dry air (e.g., control having no analytes), the output 4403 may represent water, the output 4404 may represent benzene, the output 4405 may represent ethyl acetate, the output 4406 represent tetrahydrofuran, the output 4407 may represent ethanol, the output 4408 may represent methane, and the output 4409 may represent toluene.

Returning to FIG. 37, at 3616, the controller circuit may store characteristics of the impedance response and the corresponding select parameter in the memory. The characteristics of the impedance response may correspond to the spectral parameters calculated at 3614. For example, the controller circuit may store the response magnitude Zp of sensor resistance at 4504 (FIG. 44) based on the resistance magnitude peak 4306 corresponding to the analyte of interest and the corresponding select parameter in the memory. The controller circuit may link the magnitude at 4504 to the select parameter, such as concentration, of the analyte of interest in the memory. Optionally, the characteristic and the select parameter may be a data point (e.g., such as the data points 4008-4012 shown in FIG. 41) utilized to define a transfer function of the sensor. Additionally or alternatively, the select parameter may correspond to a response direction of the analyte of interest. For example, the controller circuit may store a direction of the output 4408 in the memory corresponding to the analyte of interest.

At 3618, the controller circuit may determine whether additional parameters of the analyte of interest are available. For example, the controller circuit may receive a user input from the user interface 3216 indicative of additional parameter of the analyte of interest is available. In another example, the controller circuit may have a predetermined threshold of parameters of the analyte of interest, and may determine that additional parameters are available until the predetermined threshold has been reached.

If additional parameters of the analyte of interest are available, at 3620 the controller circuit receives a new select parameter of the analyte of interest. For example, the controller circuit may receive a user input from the user interface indicative on the new select parameter (e.g., a new concentration) of the analyte of interest.

If there are no additional parameters of the analyte of interest, at 3622 the controller circuit may define a transfer function of the sensor that defines a linear response of the sensing material based on the analyte of interest. For example, in connection with FIG. 41, based on the concentration curve 4003 having a linear response, the controller circuit may define a transfer function of the sensor. The transfer function is utilized by the controller circuit to determine a characteristic of the analyte of interest based on one or more spectral parameters calculated from the impedance response.

Figure 46:
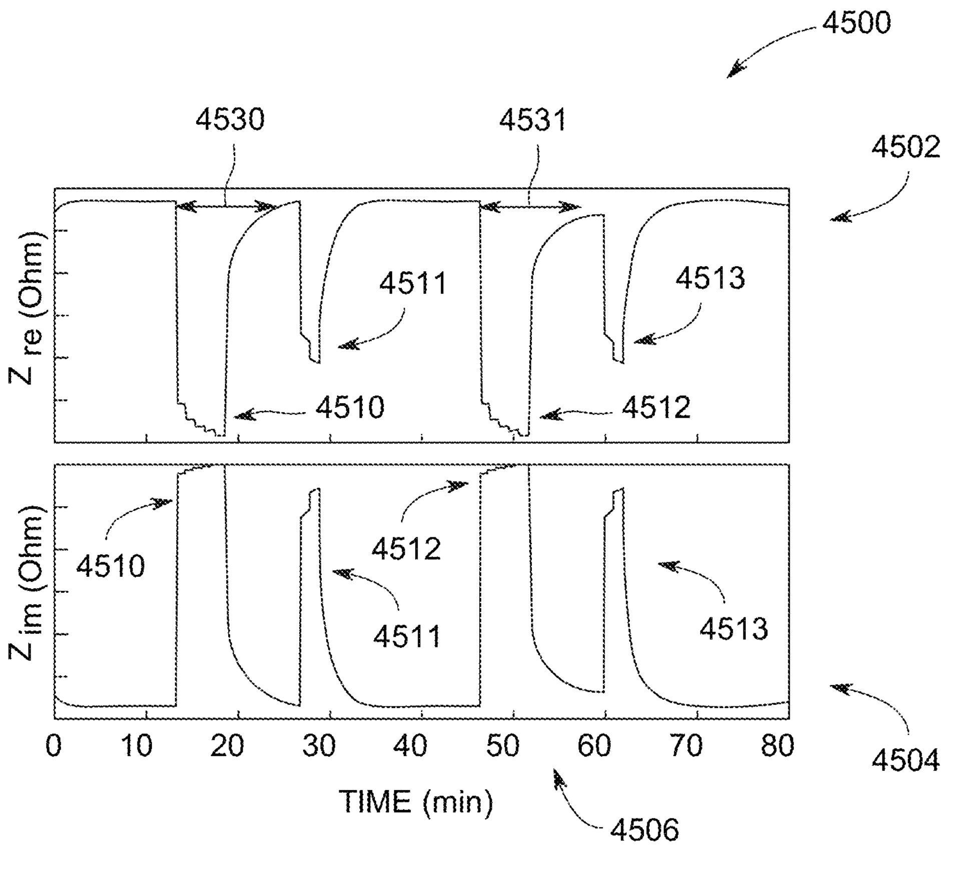
FIG. 46 are graphical illustrations of spectral parameters of one embodiment of a measured response of a sensor.
Figure 47:
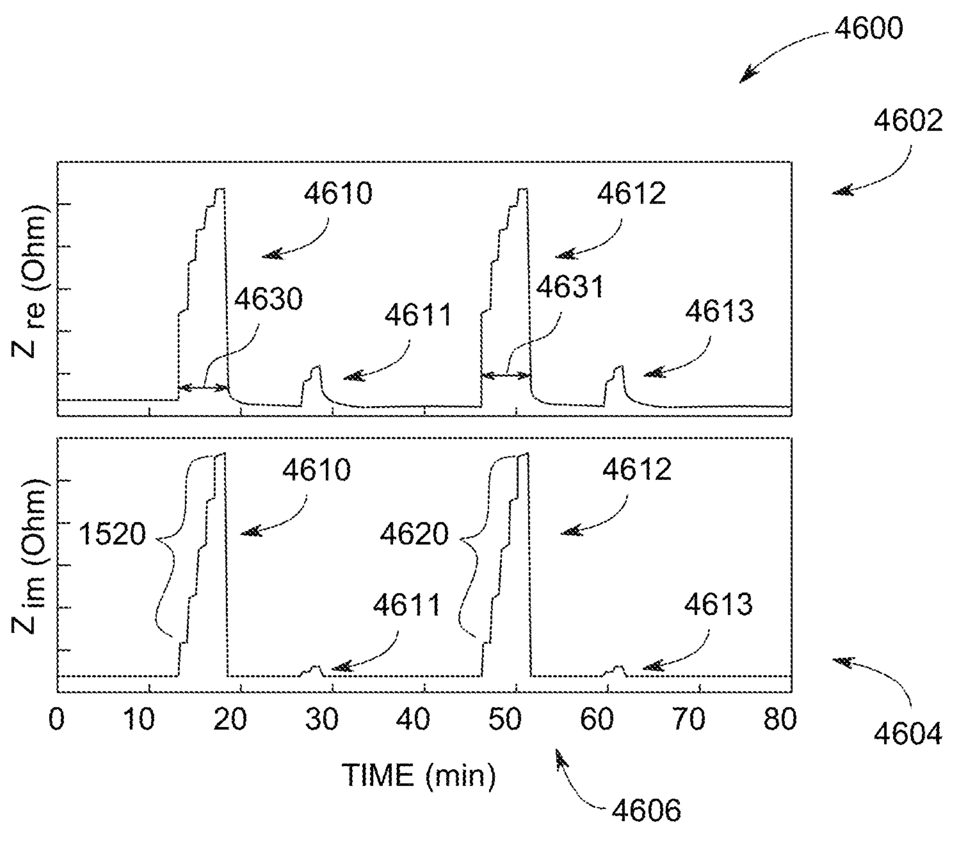
FIG. 47 are graphical illustrations of spectral parameters of one embodiment of a measured response of a sensor.

Additionally or alternatively, in connection with FIGS. 46 and 47, the sensor may be configured to perform in a non-resonance impedance mode. For example, the controller circuit may increase a temperature of the sensor, utilizing the heater to a temperature of three hundred degrees Celsius. The sensor may receive a stimulation waveform from the controller circuit having a frequency that is not at a resonance frequency of the sensor. While receiving the stimulation waveform, the sensor may be exposed individually to different analytes (e.g., methane, water vapor) at increasing concentrations at separate exposures interposed by dry air in between exposures of the analytes to form separate peaks. For example, a first analyte (e.g., methane) concentrations were at 555, 1111, 1667, 2222, and 2778 ppm. A second analyte, such as water vapor, concentrations generated were twenty-seven and fifty-three percent relative humidity.

FIG. 46 includes graphical illustrations 4500 of spectral parameters 4502, 4504 of one embodiment of a measured response of the sensor. For example, the controller circuit may generate a stimulation waveform received by the sensor having a frequency at 0.1 kHz. The sensor may generate a measurement signal, which is received and measured by the controller circuit representative of the impedance response of the sensor. The controller circuit may calculate the spectral parameters 4502, 4504 based on the impedance response over time, the horizontal axis 4506. For example, the spectral parameter 4502 may represent a real impedance Zre, and the spectral parameter 4504 may represent an imaginary impedance Zim of the impedance response. Each of the spectral parameters 4502, 4504 may include peaks 4510-4513 representing the analytes exposed by the sensor. For example, the peaks 4510 and 4512 may represent the exposure of the first analyte (e.g., methane), and the peaks 4511 and 4513 may represent he exposure of the second analyte, such as water vapor.

FIG. 47 includes graphical illustrations 4600 of spectral parameters 4602, 4604 of one embodiment of a measured response of the sensor. For example, the controller circuit may generate a stimulation waveform received by the sensor having a frequency at 100 kHz. The sensor may generate a measurement signal, which is received and measured by the controller circuit representative of the impedance response of the sensor. The controller circuit may calculate the spectral parameters 4602, 4604 based on the impedance response over time, the horizontal axis 4606. For example, the spectral parameter 4602 may represent a real impedance Zre, and the spectral parameter 4604 may represent an imaginary impedance Zim of the impedance response. Each of the spectral parameters 4602, 4604 may include peaks 4610-4613 representing the analytes exposed by the sensor. For example, the peaks 4610 and 4612 may represent the exposure to the first analyte, and the peaks 4611 and 4613 may represent the exposure to the second analyte.

It may be noted that the sensing material can be configured such that the stimulation waveform and/or operation of the sensor at high frequencies (e.g., at and/or above 100 kHz), as shown in FIG. 47, provides an improved response linearity to an analyte of interest (e.g., methane) relative to lower frequencies, as shown in FIG. 46. For example, the peaks 4610 and 4612 include a defined linear response 4620 based on the increase in concentration of the first analyte exposed to the sensor over time during the peaks 4610 and 4612.

Additionally or alternatively the sensing material is configured to have the impedance response that provides a reduction of effects of interferences over the resistance response of the sensing material. For example, the operation of the sensor at high frequencies (e.g., at and/or above 100 kHz) provides suppression of the impedance response to an interference by water vapor (e.g., humidity) exposed by the sensing material. In connection with FIGS. 45 and 46, the peaks 4511, 4513, 4611, and 4613 correspond to the exposure of the sensor to the second analyte representing water vapor. Based on the difference in operational frequency of the sensor, the peaks 4611 and 4613 have a lower amplitude than the peaks 4611 and 4613. It may be noted that the peaks 4611 and 4613 of the spectral parameter 4604 representing the imaginary part of impedance Zim provides a stronger suppression of response to the second analyte compared to the peaks 4611 and 4613 of the spectral parameter 4602 representing the real part of impedance Zre. For example, the sensing material and/or sensor is configured to reduce effects of humidity of the impedance response by ten times relative to the conventional sensor shown in FIG. 45. Additionally or alternatively, the sensing material and/or sensor may be configured to reduce effects of humidity of the impedance response to approximately zero relative to the conventional sensor shown in FIG. 45.

Additionally or alternatively, the sensing material is configured to have the impedance response that provides a reduction of recovery time based on a frequency of the stimulation waveform. For example, the peaks 4510 and 4512 have a corresponding peak width 4530 and 4531, respectively. During operation of the sensor at high frequencies (e.g., at and/or above 100 kHz), the peak width decreases relative to operation at lower frequencies (e.g., that formed the peak widths 4530 and 4531). For example, the peak widths 4630 and 4631 of the peaks 4610 and 4612, respectively, have a shorter length relative to the peaks widths 4530 and 4531 representing a reduced recovery time.

Additionally or alternatively, the sensing material is configured to have the impedance response that provides improvement of the baseline stability over the resistance response of a conventional sensor.

Figure 48:
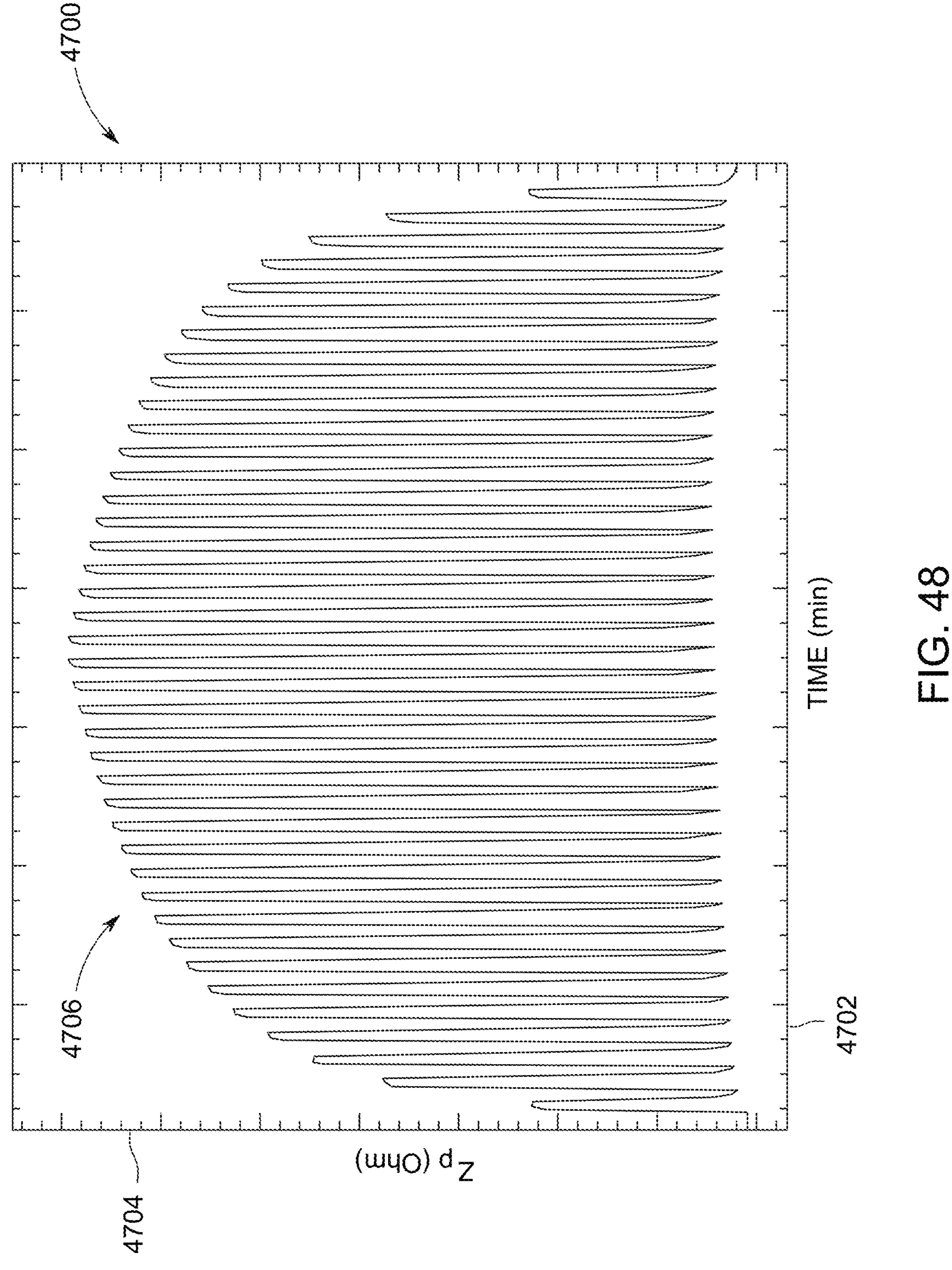
FIG. 48 is a graphical illustration of a spectral parameter calculated from a conventional sensor.

FIG. 48 is a graphical illustration 4700 of a spectral parameter 4706 of an embodiment calculated by the controller circuit of a conventional sensor configured as a resonant sensor. The spectral parameter 4706 includes a peak magnitude Zp (along a vertical axis 4704) plotted along a horizontal axis 4702 representing time. The conventional sensor operating in the resonant mode was exposed to different concentrations of the analyte of interest (e.g. methane) and a dry air in between the exposures over time. The different concentrations of the analyte of interest were presented to the sensor in the order of increasing concentrations (e.g., 0, 44.4, 88.9, 133, 178, 222, 267, 311, 356, 400, 444, 489, 533, 578, 622, 667, 711, 756, 800, 844 and 889 ppm) followed by the order of decreasing concentrations (e.g., 889, 844, 800, 756, 711, 667, 622, 578, 533, 489, 444, 400, 356, 311, 267, 222, 178, 133, 88.9, 44.4 and 0 ppm). Such presentation of the analyte concentrations provided the ability to access the sensor linearity upon increasing and decreasing analyte concentrations. As depicted in FIG. 48, the sensor had a non-linear response (e.g. power law) as a function of analyte concentrations.

Figure 49:
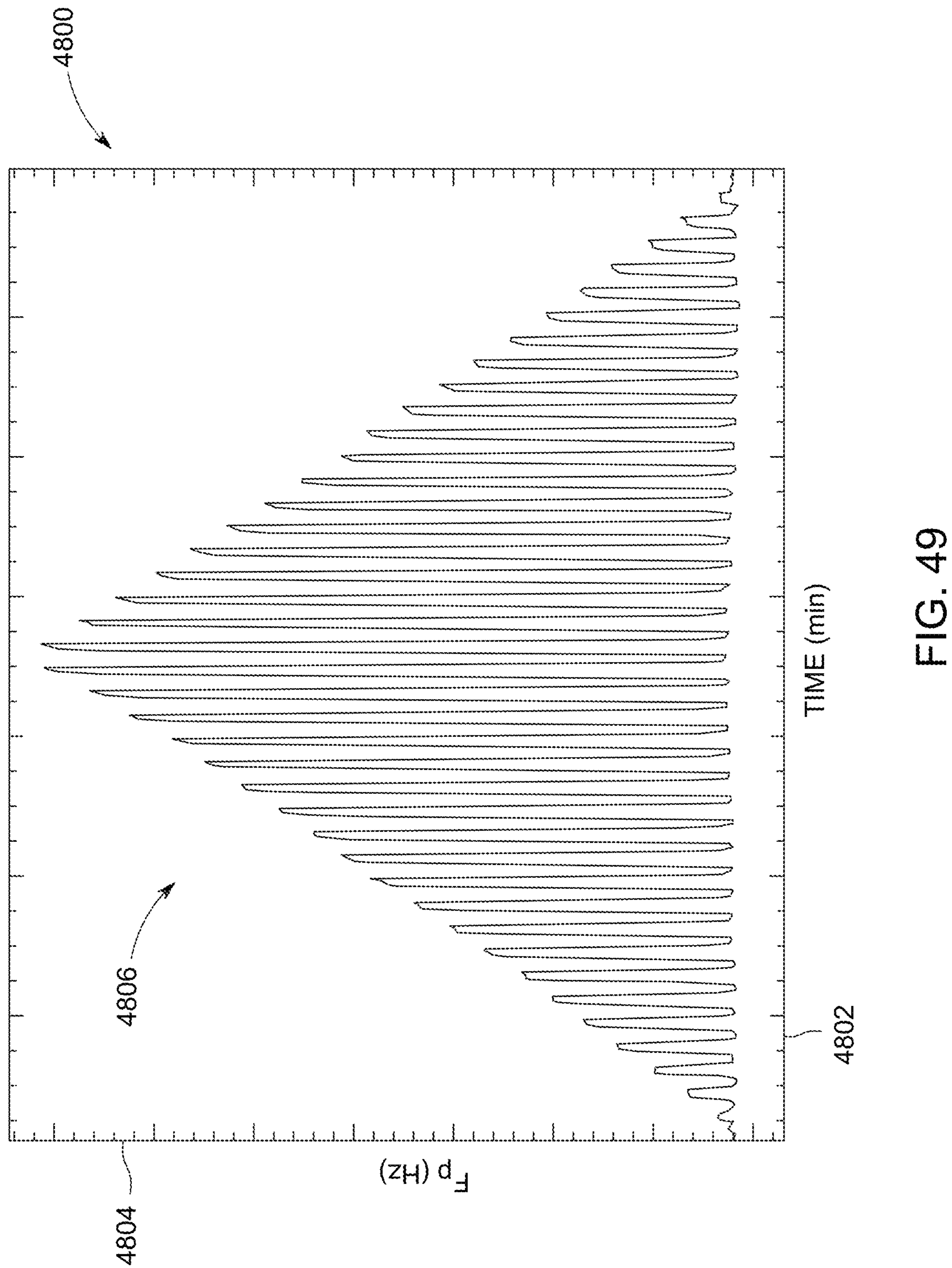
FIG. 49 is a graphical illustration of a spectral parameter of an embodiment calculated from a sensor.

FIG. 49 is a graphical illustration 4800 of the spectral parameter 4806 calculated by the controller circuit of the sensor configured as a resonant sensor. The spectral parameter 4806 is a frequency peak position Fp (along a vertical axis 4804) plotted along a horizontal axis 4802 representing time. The conventional sensor operating in the resonant mode was exposed to different concentrations of the analyte of interest (e.g. methane) and a dry air in between the exposures over time. The different concentrations of the analyte of interest were presented to the sensor in the order of increasing concentrations (e.g. 0, 44.4, 88.9, 133, 178, 222, 267, 311, 356, 400, 444, 489, 533, 578, 622, 667, 711, 756, 800, 844, and 889 ppm) followed by the order of decreasing concentrations (e.g. 889, 844, 800, 756, 711, 667, 622, 578, 533, 489, 444, 400, 356, 311, 267, 222, 178, 133, 88.9, 44.4, and 0 ppm). Such presentation of the analyte concentrations provided the ability to access the sensor linearity upon increasing and decreasing analyte concentrations. As depicted in FIG. 49, the sensor had a linear response as a function of analyte concentrations.

It may be noted that other types of metal oxide sensors may be utilized to benefit from the subject matter described herein of non-resonant and resonant impedance measurements to obtain improved response linearity to an analyte of interest, suppression of response to humidity and other interferences, rapid recovery time, improved baseline stability and the ability to discriminate between different analytes by bringing the response to gas of interest was into its unique response direction.

Additionally or alternatively, the sensing system may include additional sensors, such as a humidity sensor (not shown), a temperature sensor (not shown), and or the like. The controller circuit may adjust the impedance response based on the measurements of the additional sensors to define the transfer function. Additionally or alternatively, the controller circuit may include measurements of the humidity sensor and/or the temperature sensor to define the transfer function.

Returning to FIG. 37, if the sensing system is not in a calibration mode, at 3624 the controller circuit may apply a stimulation wave form to the sensor. The stimulation waveform may be similar to and/or the same as the stimulation waveform 304. For example, the controller circuit may generate the stimulation waveform 3404 to the sensing material utilizing the pair of electrodes in contact with the sensing material. The stimulation waveform 3404 is conducted through the electrodes and received by the sensing material.

At 3626, the controller circuit may measure an impedance response. For example, the controller circuit may receive a measurement signal generated by the sensing material from the electrodes. The measurement signal is representative of an impedance response of the sensing material in operational contact with the ambient environment. For example, the measurement signal may have electrical characteristics (e.g., voltage, current, frequency, and/or the like), which is utilized by the controller circuit to calculate the impedance response. Optionally, the impedance response may be similar to and/or the same as the impedance response 3500 shown in FIG. 36.

At 3628, the controller circuit may analyze the impedance response of the sensing material at frequencies that provide a linear response of the sensing material. The controller circuit may calculate one or more spectral parameters based on a real portion (e.g., Fp, Zp) and/or imaginary portion (e.g., F1, F2, Fz, Z1, Z2) of the impedance response. Optionally, the one or more spectral parameters calculated by the controller circuit may be based on a transfer function defining the linear relationship between the impedance response and a parameter of the analyte of interest.

For example, in connection with FIG. 41, the transfer function of the sensor may be based on a peak frequency (Fp) of the real portion of the impedance response, along the vertical axis 4006 and a concentration of the analyte of interest, along the horizontal axis 4002. The controller circuit may select frequencies of the real portion of the impedance response to reject and/or filter out effects of interferences (e.g., from analytes not of interest) based on the analyte parameter database stored in the memory as described above. For example, the controller circuit 3310 may determine the peak frequency of the impedance response corresponding to the analyte of interest is at 4022.

At 3630, the controller circuit may determine a parameter of an analyte of interest based on the impedance response. For example, the controller circuit may utilize the transfer function stored in the memory to determine a concentration of the analyte of interest within the ambient environment of the sensor.

Additionally alternatively, based on the parameter of the analyte of interest, the controller circuit may automatically perform one or more responsive actions. Optionally, the one or more responsive action may be configured to alert a user and/or remote system. For example, if the parameter (e.g., concentration) is above a predetermined threshold the controller circuit may display and/or initiate an auditory alert on the user interface.

The sensors described herein are applicable for diverse applications. In one non-limiting example, the sensor may be positioned and/or installed on an unmanned or manned vehicle. For example, the vehicle may be an aerial vehicle (e.g., drone, airplane, helicopter, and/or the like), automobile (e.g., car, truck, van, and/or the like). The vehicle may be positioned and/or traverse to one or more remote sites and configured to collect ambient air pollution data of the one or more remote sites. For example, the controller circuit may be configured to analyze an impedance response of the sensor to one or more analytes of interest that represent air pollution (e.g., sulfur oxide, nitrogen oxide, carbon monoxide, methane, ammonia, and/or the like). Based on the concentration levels of the one or more analytes of interest representing air pollution, the control circuit may determine the ambient air pollution of proximate to the vehicle within the remote site. Optionally, the vehicle may include an RF circuit configured to wirelessly transmit the air pollution data (e.g., concentration information of the one or more analytes of interest) to a remote system (e.g., server, air pollution monitoring system).

In another non-limiting example, the sensor may be installed to monitor natural gas transmission infrastructure. A particularly urgent problem with cities is the leakage of methane gas into the ambient environment. There are currently thousands of miles natural gas pipes under the streets of major US cities in the United States alone. Many of these cities have old natural gas piping that have been subjected to massive wear and tear, particularly at cities where old infrastructure exists. As a consequence, methane gas leaks have unfortunately become quite common at these cities. A sensing system configured for collecting ambient methane emission data from city streets that includes the sensing system and the sensor material located on existing urban infrastructure components (e.g. light poles within the city streets) and configured to detect ambient air methane molecules at the city streets, and data communication to service center to broadcast ambient methane concentrations.

In another non-limiting example, disclosed sensors facilitate better measurements and better regulations. Accurate methane emission inventory is now a top priority of regulatory agencies in the US. For decades, industry relies on estimated emission factors for leak sources in oil fields. The drive to refine these data relies on development of high fidelity sensors and analytics methods to refine the "default" methane emission factors and replace the current estimates, thereby informing policy and industrial decision making for potential mitigation opportunities.

In an embodiment a method (e.g., for detecting one or more analytes of interest) is provided. The method includes receiving a stimulation waveform at a sensor. The stimulation waveform is applied to a sensing material of the sensor via at least one pair of electrodes in contact with the sensing material. The sensing material is in contact with an ambient environment. The method includes receiving an electrical signal at a controller circuit from the at least one pair of electrodes representative of an impedance response of the sensing material, and analyzing the impedance response of the sensing material at frequencies that provide a linear response of the sensing material to an analyte of interest and at least partially rejects effects of interferences.

Optionally, the method includes operating the sensor at a temperature of at least fifty degrees Celsius above an ambient temperature.

Optionally, the impedance response includes at least one of a real portion or imaginary portion.

Optionally, the analyzing of the impedance response includes identifying a frequency peak of the impedance response. Additionally or alternatively, the frequency peak is configured to be based on a characteristic of the analyte of interest.

In an embodiment a system (e.g., sensing system) is provided. The system includes a sensor having a sensing material and at least one pair of electrodes in contact with the sensing material, the sensing material configured to be in contact with an ambient environment. The system includes a controller circuit electrically coupled to the at least one pair of electrodes. The controller circuit is configured to generate a stimulation waveform for application to the sensing material of the sensor via the at least one pair of electrodes. The controller circuit is configured to receive an electrical signal from the at least one pair of electrodes representative of an impedance response of the sensing material, and analyze the impedance response of the sensing material at frequencies that provide a linear response of the sensing material to an analyte of interest and at least partially reject effects of interferences.

In an embodiment a method (e.g., for detecting one or more analytes of interest) is provided. The method includes receiving a stimulation waveform at a sensor. The stimulation waveform is applied to a sensing material of the sensor via at least one pair of electrodes in contact with the sensing material. The sensing material is in contact with an ambient environment. The method includes receiving an electrical signal at a controller circuit from the at least one pair of electrodes representative of an impedance response of the sensing material, and analyzing the impedance response of the sensing material at frequencies that provide a monotonic or non-monotonic response of the sensing material to an analyte of interest and at least partially reject effects of interferences.

Optionally, the system includes a heater configured to set a temperature of the sensor at a temperature of at least fifty degrees Celsius above an ambient temperature associated with the sensor.

Optionally, the impedance response includes at least one of a real portion or imaginary portion.

Optionally, the frequencies correspond to a real portion of the impedance response.

Optionally, the frequencies include a frequency peak of the impedance response. The controller circuit may be configured to analyze the impedance response by identifying the frequency peak. Additionally or alternatively, the frequency peak is configured to be based on a characteristic of the analyte of interest.

Optionally, the at least one pair of electrodes and sensing material are configured to be part of a non-resonant circuit.

Optionally, the at least one pair of electrodes and sensing material are configured to be part of an inductor capacitor resistor (LCR) circuit.

Optionally, the sensing material is a metal oxide. Additionally or alternatively, the metal oxide is a single-metal oxide, a perovskite oxide having two differently sized cations, or a mixed metal oxide composition.

Optionally, the sensing material is a semiconductor.

Optionally, the sensing material is configured to have the impedance response with a monotonic response.

Optionally, the sensing material is configured to reduce effects of humidity of the impedance response.

Optionally, the controller circuit is configured to utilize a principal component analysis to reduce effects of interferences and isolate the analyte of interest.

Optionally, the sensing material is configured to have a recovery time of the impedance response based on a frequency of the stimulation waveform.

Optionally, the sensor is positioned on a vehicle. The analyte of interest may represent ambient air pollution relative to the vehicle.

In an embodiment a method (e.g., for detecting one or more analytes of interest) is provided. The method includes receiving a stimulation waveform at a sensor. The stimulation waveform is applied to a sensing material of the sensor via at least one pair of electrodes in contact with the sensing material. The sensing material is in contact with an ambient environment. The method includes receiving an electrical signal at a controller circuit from the at least one pair of electrodes representative of an impedance response of the sensing material, and analyzing the impedance response of the sensing material at frequencies that provide a monotonic or non-monotonic response of the sensing material to an analyte of interest and at least partially reject effects of interferences.

Embodiments described herein include various systems, assemblies, devices, apparatuses, and methods that may be used in a connection with obtaining one or more measurements of a machine. The measurement(s) may be representative or indicative of an operative condition of the machine. As used herein, an operative condition of the machine may refer to an operative condition of the machine as a whole or an operative condition of a component (e.g., element, assembly, or sub-system) of the machine. As used herein, the operative condition of a machine can relate to a present state or ability of the component and/or a future state or ability of the machine to perform one or more operations. For example, the measurement or operative condition may indicate that the machine or a component of the machine is not functioning in a sufficient manner, is damaged, is likely to be damaged if it continues to operate in a designated manner, is not likely to perform appropriately under designated circumstances, and/or is likely to cause damage to other components of the machine. Alternatively, the measurement or operative condition may indicate that the machine or component is operating normally or is not damaged.

As one example with respect to locomotives or other rail vehicles, one or more measurements obtained from a locomotive or other rail vehicle may indicate that a lubricant in the component (e.g., drive train, gearbox, engine, and the like) is low or has an insufficient quality. Embodiments set forth herein may generate an operating plan that is based on the measurement(s). For instance, the operating plan may include instructions to disable an axle or to limit tractive and/or braking efforts of the axle. The operating plan may indicate which element of the gearbox should be replaced and/or how the machine is to be operated until the gearbox is replaced. Such operating plans are described in greater detail below.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking. Embodiments may also comprise analyzing measurements from a plurality of sensors of the same type. For example, machines may include multiple gearboxes. Vibration measurements from the gearboxes may indicate that one of the gearboxes is operating differently than the others and, thus, may be damaged or in need of maintenance. Embodiments may also comprise analyzing different types of measurements to determine an operative condition of the machine. For example, the vibration measurements may be analyzed in light of the speed at which the gears are driven and/or current environmental conditions. Additional measurements or factors are set forth below.

The measurements may be wirelessly transmitted from a device to a reader, which may also be referred to as a receiver. For example, radio waves representative of the measurement(s) may be transmitted from a transmitter (e.g., antenna) of the wireless device to a remote reader. The reader may be a handheld reader (e.g., capable of being carried in a single hand by a technician) or an otherwise movable reader. In some embodiments, the reader may have a fixed position. For example, for embodiments in which the machine is a vehicle, the reader may have a stationary position along a designated path that is traversed by the vehicle (e.g., railroad tracks, weighing stations, tollbooths). When a vehicle passes the reader, the reader may interrogate one or more wireless devices to obtain measurements. Remote readers may also be located on-board the vehicle. For example, a locomotive or other rail vehicle may have a control system that receives data from multiple sources, including one or more wireless devices that communicate the measurements to the control system.

The measurement may be detected or obtained by a sensor when the device having the sensor is interrogated by the reader. Alternatively or additionally, the sensor may obtain data at designated intervals (e.g., one measurement/hour, one measurement/minute, and the like) and/or when a designated event occurs. For example, measurements may only be obtained after the vehicle has been interrogated or after the vehicle has remained stationary for a certain amount of time (e.g., ten minutes) or after the vehicle has started to move for a certain amount of time (e.g., one minute). In some embodiments, the wireless device includes a storage unit (e.g., memory) where multiple measurements may be stored or logged. The wireless devices may also include a power source that is integral to the device. Examples of electrical power sources include batteries and energy harvesting devices. Energy harvesting devices convert energy in the surrounding environment, such as kinetic energy (e.g., vibrations), thermal energy, and electromagnetic energy. In particular embodiments, the wireless devices may include or be coupled to a vibratory energy harvesting device that converts kinetic energy into electrical energy.

Embodiments described herein include various systems, assemblies, devices, apparatuses, and methods that may be used in a connection with obtaining one or more measurements of a machine. The measurement(s) may be representative or indicative of an operative condition of the machine. As used herein, an operative condition of the machine may refer to an operative condition of the machine as a whole or an operative condition of a component (e.g., element, assembly, or sub-system) of the machine. As used herein, the operative condition of a machine can relate to a present state or ability of the component and/or a future state or ability of the machine to perform one or more operations. For example, the measurement or operative condition may indicate that the machine or a component of the machine is not functioning in a sufficient manner, is damaged, is likely to be damaged if it continues to operate in a designated manner, is not likely to perform appropriately under designated circumstances, and/or is likely to cause damage to other components of the machine. Alternatively, the measurement or operative condition may indicate that the machine or component is operating normally or is not damaged.

As one example with respect to locomotives or other rail vehicles, one or more measurements obtained from a locomotive or other rail vehicle may indicate that a lubricant in the component (e.g., drive train, gearbox, engine, and the like) is low or has an insufficient quality. Embodiments set forth herein may generate an operating plan that is based on the measurement(s). For instance, the operating plan may include instructions to disable an axle or to limit tractive and/or braking efforts of the axle. The operating plan may indicate which element of the gearbox should be replaced and/or how the machine is to be operated until the gearbox is replaced. Such operating plans are described in greater detail below.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking. Embodiments may also comprise analyzing measurements from a plurality of sensors of the same type. For example, machines may include multiple gearboxes. Vibration measurements from the gearboxes may indicate that one of the gearboxes is operating differently than the others and, thus, may be damaged or in need of maintenance. Embodiments may also comprise analyzing different types of measurements to determine an operative condition of the machine. For example, the vibration measurements may be analyzed in light of the speed at which the gears are driven and/or current environmental conditions. Additional measurements or factors are set forth below.

The measurements may be wirelessly transmitted from a device to a reader, which may also be referred to as a receiver. For example, radio waves representative of the measurement(s) may be transmitted from a transmitter (e.g., antenna) of the wireless device to a remote reader. The reader may be a handheld reader (e.g., capable of being carried in a single hand by a technician) or an otherwise movable reader. In some embodiments, the reader may have a fixed position. For example, for embodiments in which the machine is a vehicle, the reader may have a stationary position along a designated path that is traversed by the vehicle (e.g., railroad tracks, weighing stations, tollbooths). When a vehicle passes the reader, the reader may interrogate one or more wireless devices to obtain measurements. Remote readers may also be located on-board the vehicle. For example, a locomotive or other rail vehicle may have a control system that receives data from multiple sources, including one or more wireless devices that communicate the measurements to the control system.

The measurement may be detected or obtained by a sensor when the device having the sensor is interrogated by the reader. Alternatively or additionally, the sensor may obtain data at designated intervals (e.g., one measurement/hour, one measurement/minute, and the like) and/or when a designated event occurs. For example, measurements may only be obtained after the vehicle has been interrogated or after the vehicle has remained stationary for a certain amount of time (e.g., ten minutes) or after the vehicle has started to move for a certain amount of time (e.g., one minute). In some embodiments, the wireless device includes a storage unit (e.g., memory) where multiple measurements may be stored or logged. The wireless devices may also include a power source that is integral to the device. Examples of electrical power sources include batteries and energy harvesting devices. Energy harvesting devices convert energy in the surrounding environment, such as kinetic energy (e.g., vibrations), thermal energy, and electromagnetic energy. In particular embodiments, the wireless devices may include or be coupled to a vibratory energy harvesting device that converts kinetic energy into electrical energy.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

Figure 50:
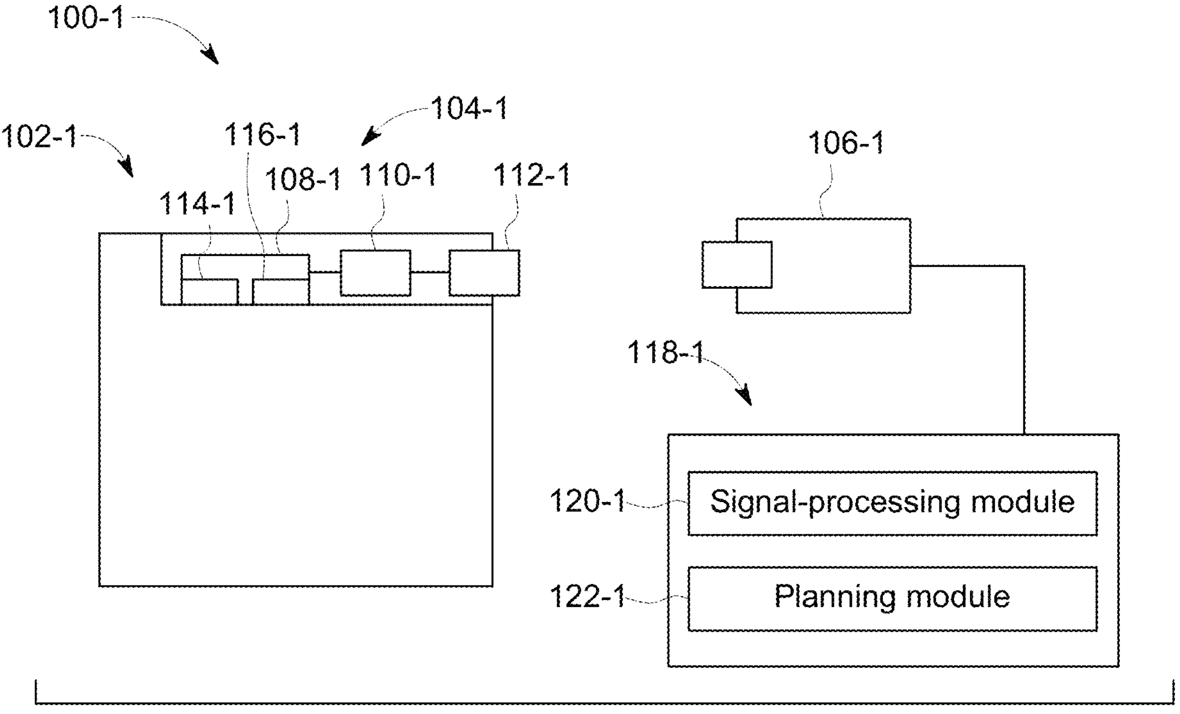
FIG. 50 is a schematic view of a system in accordance with an embodiment.

FIG. 50 is a schematic diagram of a monitoring or sensing system 100-1 formed in accordance with one embodiment. The system 100-1 is configured to obtain one or more measurements that are representative of an operative condition of a machine 102-1 or a component of the machine 102-1 (e.g., element, assembly, or sub-system of the machine 102-1). By way of example only, the machine 102-1 may be a motive machine or vehicle, such as an off-highway vehicle (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., train). In some embodiments, the machine is an automobile. In other embodiments, the machine is not configured to travel. For example, the machine may be a windmill or a power-generating turbine or a transformer.

The operative condition may relate to a health or status of a designated component of the machine. Non-limiting examples of such components include a gearbox, a gear case, an air compressor, a turbo-charger, or a drive train. The measurement may be analyzed to determine, for example, that a component is damaged, is operating improperly (e.g., insufficiently or not at all), and/or is operating in a manner that will lead to or cause greater damage to the component or other component of the machine 102-1.

In particular embodiments, the operative condition is determined based on an amount or quality of liquid used by the machine 102-1 and/or a vibratory state of the machine 102-1. For instance, in some embodiments, the component may be a gear case that has a reservoir for storing a lubricant liquid. A low level or quantity of the liquid in the reservoir may indicate that the gear case is damaged. In particular, a low level or quantity may indicate that the gear case is leaking the liquid. In other embodiments, a component may have a particular vibratory state(s) when the component is operating properly. For example, a mechanical element may be configured to oscillate in a known or expected manner during operation. However, if the mechanical element is damaged or operating improperly, the mechanical element may have a different vibratory state.

As shown, the system 100-1 may include a wireless device 104-1 that is configured to wirelessly communicate data signals to a remote reader 106-1. The data signals may represent the measurement(s) obtained by the wireless device 104-1. To this end, the wireless device 104-1 may include a sensor 108, a processing unit 110-1 (also referred to as a controller or computer), and a transmitter 112-1. The sensor 108-1 is configured to measure an operating parameter of the machine 102-1 and thereby obtain a measurement. In some embodiments, the sensor 108-1 includes a detector or transducer 114-1 and an activator 116-1. The activator 116-1 may be configured to provide a stimulus (e.g., sound waves, light, electric current, etc.) that causes a response by a component-of-interest or is affected by the component-of-interest. The detector 114-1 may be configured to detect the response that is caused by the stimulus or the affect that the component-of-interest has on the stimulus. For example, the stimulus may be sound waves that are detected to determine a liquid level (e.g., sonar). The stimulus may be light signals that are projected by a laser into a liquid to determine how much of the light signals are absorbed by the liquid. Another stimulus may be electric current. In other embodiments, the sensor 108-1 does not include an activator 116-1. Instead, the detector 114-1 may detect sound, vibrations, light, temperature, electrical properties, or other properties that occur in the environment without a stimulus provided by an activator.

The processing unit 110-1 is operably coupled to the sensor 108-1. The processing unit 110-1 is configured to receive measurement signals from the sensor 108-1 and process the measurement signals to provide data signals. The processing unit 110-1 may be an analog-to-digital converter (ADC). Alternatively or in addition to the ADC, the processing unit 110-1 may include a logic-based device that transforms the measurement signals into data signals. The data signals may then be configured to be transmitted to the reader 106-1 by the transmitter 112-1. For example, the processing unit 110-1 may be a computer processor, controller (e.g., microcontroller) or other logic-based device that performs operations based on one or more sets of instructions (e.g., software). The instructions on which the processing unit 110-1 operates may be stored on a tangible and non-transitory (e.g., not a transient signal) computer readable storage medium, such as a memory. The memory may include one or more types of memory, such as hard drives, flash drives, RAM, ROM, EEPROM, and the like. Alternatively, one or more of the sets of instructions that direct operations of the processing unit 110-1 may be hard-wired into the logic of the processing unit 110, such as by being hard-wired logic formed in the hardware of the processing unit 110-1-1.

The transmitter 112-1 is operably coupled to the processing unit 110-1 and is configured to wirelessly communicate the data signals to the reader 106-1. In some embodiments, the transmitter 112-1 is a transceiver that is configured to transmit the data signals and receive other signals, such as interrogation signals from the reader 106-1.

In some embodiments, the sensor 108-1, the processing unit 110-1, and the transmitter 112-1 are localized within and/or attached directly to the machine such that the sensor 108-1, the processing unit 110-1, and the transmitter 112-1 are proximate to each other and form a single device. In one embodiment, the sensor 108-1, processing unit 110-1, and transmitter 112-1 are located inside a single continuous or contiguous body, such as a single external housing. The sensor 108, the processing unit 110-1, and the transmitter 112-1 may be in a localized spatial region of the machine that is separate from a computing system that controls operation of the machine. For example, the processing unit 110-1 and the transmitter 112-1 may be integrated with the same component such that the processing unit 110-1 and the transmitter 112-1 have fixed positions with each other. More specifically, the processing unit 110-1 and the transmitter 112-1 may be at least partially integrated onto a common component (e.g., circuit board) and/or positioned within a common container or housing that is coupled to the machine. The common container may not be coextensive with the machine and, instead, may be a separate component that is attached to or disposed within the machine-of-interest. By way of example only, some or all the components of the processing unit 110-1 and the transmitter 112-1 may be located within 50 cm of each other, 2 cm of each other, 100 cm of each other or, more particularly, within 5 cm of each other.

In some embodiments, the processing unit 110-1 and the transmitter 112-1 may be part of a common radio frequency identification (RFID) unit (e.g., tag, chip, card, and the like). Optionally, the sensor 108-1 may also be part of the common RFID unit. In other cases, the sensor 108-1 is separate from, but operably coupled to, the RFID unit and is only a short distance from the RFID unit. For example, the sensor 108-1 may be located within 50-1 cm or less of the RFID unit and communicatively coupled via wires or wireless communication. The RFID unit may be formed in accordance with RFID technology, which may include integrated circuit technology. For example, the RFID unit may be an electronic circuit that is capable of wireless communication. In some instances, the RFID unit may satisfy one or more established RFID standards and/or guidelines, such as standards and guidelines formed by the International Organization for Standardization (ISO), the International Electrotechnical Commission (IEC), ASTM International, the DASH7 Alliance, EPCglobal, the Financial Services Technology Consortium (FSTC).

In certain embodiments, the wireless device 104-1 is not physically electrically connected (e.g., not connected by wires or other conductors) to any of the one or more computers or other controller-based units in the machine. For example, in the context of trains, the wireless device 104-1 may be partially disposed within a reservoir and/or attached to a wall that defines the reservoir and is not physically electrically connected to the computing system that controls operation of the train. In such embodiments, the data signals from the wireless device 104-1 may be wirelessly transmitted from the wireless device 104-1 to, for example, a reader that is on-board or off-board. More specifically, the data signals may not be transmitted via wire/cables or other physical electrical connections. In one or more embodiments, at least portions of the processing unit 110-1 and the transmitter 112-1 may be directly connected to a wall that defines the reservoir (e.g., a wall that bears a pressure of and/or contacts the liquid in the reservoir) and/or to a structure immediately connected to the wall (e.g., support structure of the reservoir, gear case, or the like).

Various forms of wireless communication may be transmitted and received by the wireless device 104-1. For example, the transmitter 112-1 may be configured to receive and/or transmit radio signals, optical signals, signals based on sound, or signals based on magnetic or electric fields. In particular embodiments, the transmitter 112-1 is configured to receive and/or transmit radio signals in one or more radio frequencies. The wireless signals may be transmitted along a narrow radio band. In narrow band transmission, a single carrier frequency is used. Alternatively, the wireless signals may be transmitted within a spectrum of radio frequencies. For example, in spread spectrum transmission, the signals may be transmitted over a number of different radio frequencies within a radio band. The data signals may be modulated for transmission in accordance with any one of a number of modulation standards, such as frequency-hopping spread spectrum (FHSS), direct-sequence spread spectrum (DSSS), or chirp spread spectrum (CSS). One wireless communication standard that may be used by embodiments described herein is IEEE 802.15.4. The IEEE 802.15.4 standard may operate within one of three frequency bands: (1) 868.0-868.6 MHz; (2) 902-928 MHz; or (3) 2400-2483.5 MHz. A number of channels may be used in each of the frequency bands. Embodiments may also use frequency bands that are associated with RFID technology, such as 120-150 kHz, 13.56 MHz, 865-868 MHz, 902-028 MHz, 2450-5800 MHz, or 3.1-10 GHz. Ultra wideband (UWB) may also be used.

In some embodiments, a transmission range of the data signals and/or the signals from the reader 106-1 is about 0-10 meters or from about 0-20 meters. In other embodiments, the transmission range may be greater, such as up to 100 meters or more.

Various embodiments may be based on or consistent with RFID technology. For example, the wireless device 104-1 may be a passive sensor, a semi-passive sensor, or an active sensor. A passive sensor may not include a power source. Instead, the power may be based on inductive coupling or backscatter coupling with the reader. A passive sensor may operate over a frequency range from about 1 kHz to about 10 GHz. A semi-passive sensor may include a power source for only designated functions. For example, a battery and/or an energy harvesting device may be used to increase the transmission distance. The passive and semi-passive sensors may be particularly suitable for when the reader is present (e.g., within transmission range so that the sensors can be powered by the reader). An active sensor may include a power source for powering multiple functions (e.g., detection, reception, and transmission). Active sensors may be used in embodiments in which the reader is configured to only receive data signals and not transmit interrogation signals.

The reader 106-1 may be operably connected to a control system 118-1 having a signal-processing or diagnostic module 120-1 and, optionally, a planning module 122-1. Like the processing unit 110-1, the modules 120-1, 122-1 may be a computer processor, controller (e.g., microcontroller), or other logic-based device that performs operations based on one or more sets of instructions. The instructions on which the modules 120-1, 122-1 operates may be stored on a tangible and non-transitory (e.g., not a transient signal) computer readable storage medium, such as a memory. Alternatively, one or more of the sets of instructions that direct operations of the modules 120-1, 122-1 may be hard-wired into the logic of the modules 120, 122-1. The module 120-1, 122-1 may be located on separate devices (e.g., separate processors) or may be located on common processor.

The signal-processing module 120-1 may be configured to determine, based on the data signals received by the reader 106-1, whether the machine 102-1 is operating improperly. The signal-processing module 120-1 may determine whether the machine 102-1 is operating properly or improperly by analyzing the data signals that are representative of the measurements. For example, the signal-processing module 120-1 may use a look-up table or other databases that provides acceptable ranges of operation. If the measurement based on the data signals is not within the range, the signal-processing module 120-1 may determine that the machine 102-1 is not operating properly. In some cases, based on the measurement(s), the signal-processing module 120-1 may be able to determine whether a particular component of the machine 102-1 is in need of maintenance, repair, or replacement or whether the machine 102-1 requires an overhaul of a sub-system.

Based on the measurement(s), the signal-processing module 120-1 may request that an operating plan be generated by the planning module 122-1. The operating plan may be configured to improve the performance of the machine 102-1 and/or to limit the performance of the machine 102-1 to prevent damage or additional damage. The operating plan may include instructions for replacing, maintaining, modifying, and/or repairing a designated component or components of the machine 102-1.

The operating plan may be based on the operative condition, which is at least partially a function of the measurement(s) obtained. For instance, if a capacitive measurement indicates that the liquid level is less than sufficient, but a substantial amount remains in the gear case, then the operating plan may include instructions for refilling the liquid at a first facility and then resealing the gear case at a second facility located further away. However, if a capacitive measurement indicates that the liquid level quickly reduced to little or no measurable amount of liquid, then the operating plan may instruct that the gear case be replaced at a designated facility.

In the context of a locomotive or other vehicle, the operating plan may include instructions for controlling tractive and/or braking efforts of the vehicle. In particular, the operating plan may be partially based on the measurements of the operative condition of the machine. The instructions may be expressed as a function of time and/or distance of a trip along a route. In some embodiments, travel according to the instructions of the operating plan may cause the vehicle to reduce a stress on a component-of-interest of the machine than the component would typically sustain during normal operation. For example, the operating plan may instruct the vehicle to reduce horsepower delivered to an axle, to intermittently drive the axle, or to disable the axle altogether. The vehicle may be autonomously controlled according to the operating plan or the instructions of the operating plan may be presented to an operator of the vehicle so that the operator can manually control the vehicle according to the operating plan (also referred to herein as a "coaching mode" of the vehicle).

In some embodiments, the operating plan that is generated when it is determined that the machine is operating improperly is a "revised" operating plan that supersedes or replaces another operating plan. More specifically, due to the newly acquired measurements, the control system may determine that the currently-implemented operating plan should be modified and, as such, may generate a revised operating plan to replace the other.

Operating plans may be optimized to achieve designated goals or parameters. As used herein, the term "optimize" (and forms thereof) are not intended to require maximizing or minimizing a characteristic, parameter, or other object in all embodiments described herein. Instead, "optimize" and its forms may include increasing or decreasing (as appropriate) a characteristic, parameter, or other object toward a designated or desired amount while also satisfying other conditions. For example, optimized stress levels on a component may not be limited to a complete absence of stress or that the absolute minimum amount of stress. Rather, optimizing the stress level may mean that the stress is controlled, while also satisfying other conditions (e.g., speed limits, trip duration, arrival time). For example, the stress sustained by a component may be controlled so that the vehicle may arrive at its destination without the component being severely damaged.

The planning module 122-1 is configured to use at least one of vehicle data, route data (or a route database), part data, or trip data to generate the operating plan. The vehicle data may include information on the characteristics of the vehicle. For example, when the vehicle system is a rail vehicle, the vehicle data may include a number of rail cars, number of locomotives, information relating to an individual locomotive or a consist of locomotives (e.g., model or type of locomotive, weight, power description, performance of locomotive traction transmission, consumption of engine fuel as a function of output power (or fuel efficiency), cooling characteristics), load of a rail vehicle with effective drag coefficients, vehicle-handling rules (e.g., tractive effort ramp rates, maximum braking effort ramp rates), content of rail cars, lower and/or upper limits on power (throttle) settings, etc.

Route data may include information on the route, such as information relating to the geography or topography of various segments along the route (e.g., effective track grade and curvature), speed limits for designated segments of a route, maximum cumulative and/or instantaneous emissions for a designated segment of the route, locations of intersections (e.g., railroad crossings), locations of certain track features (e.g., crests, sags, curves, and super-elevations), locations of mileposts, and locations of grade changes, sidings, depot yards, and fuel stations. The route data, where appropriate, may be a function of distance or correspond to a designated distance of the route.

Part data may include, for example, historical data or proprietary data regarding the lifetime operability of a component. The data may include baseline data for a designated speed and/or load on the machine. Additional factors may be part of the baseline data. For example, if the lubricant has a designated quantity in the gear case, the part data may include data from identical components that operated with an approximately equal lubricant level. The data may include how long the component is capable of operating at a designated speed.

Trip data may include information relating to a designated mission or trip, such as start and end times of the trip, start and end locations, route data that pertains to the designated route (e.g., effective track grade and curvature as function of milepost, speed limits), upper cumulative and/or instantaneous limits on emissions for the trip, fuel consumption permitted for the trip, historical trip data (e.g., how much fuel was used in a previous trip along the designated route), desired trip time or duration, crew (user and/or operator) identification, crew shift expiration time, lower and/or upper limits on power (throttle) settings for designated segments, etc. In one embodiment, the planning module 122-1 includes a software application or system such as the Trip Optimizer™ system developed by General Electric Company.

Figure 51:
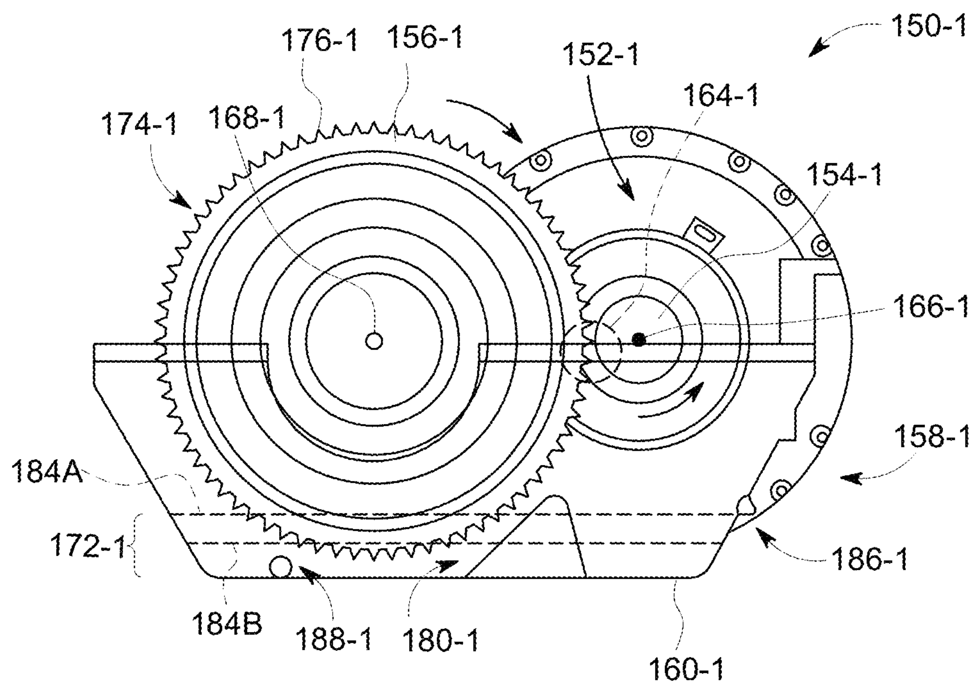
FIG. 51 is a side view of a drive train in accordance with an embodiment.
Figure 52:
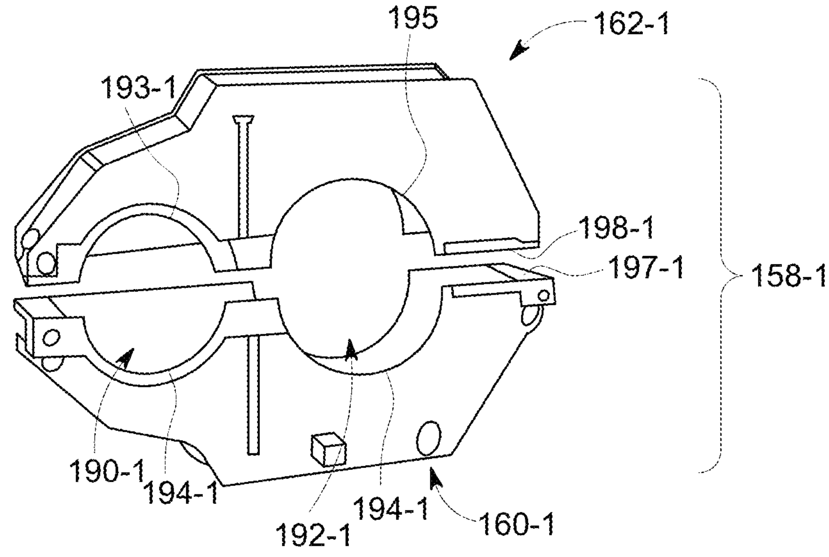
FIG. 52 is a partially exploded view of a gear case that may be used by the drive train of FIG. 51.

FIG. 51 is a side view of a drive train (or final drive) 150-1 in accordance with one embodiment. The drive train 150-1 includes a traction motor 152, a first (or pinion) gear 154-1, a second gear 156-1, and a base portion or shell 160-1 of a gear case 158-1. A top portion or shell 162-1 of the gear case 158-1 is shown in FIG. 52. As shown in FIG. 51, the first gear 154-1 and the second gear 156-1 engage each other at a gear mesh 164-1. During operation of the drive train 150-1 the traction motor 152-1 drives the first gear 154-1 by rotating an axle (not shown) coupled to the first gear 154-1 about an axis of rotation 166-1. The first gear 154-1 may be rotated, for example, in a counter-clockwise direction as viewed in FIG. 51. Due to the engagement at the gear mesh 164, the first gear 154-1 rotates the second gear 156-1 in a clockwise direction about an axis of rotation 168-1. The second gear 156-1 is coupled to an axle (not shown) that rotates with the second gear 156-1. The axle of the second gear 156-1 is coupled to wheels (not shown) that are rotated with the axle. The wheels engage a surface (e.g., rails or tracks) to move the machine.

The gear case 158-1 includes a reservoir 172-1 that is configured to hold a lubricant liquid 180-1 (e.g., oil). The gear case 158-1 has a fill or inlet port 186-1 and a drain or outlet port 188-1. The liquid 180-1 may be provided to the reservoir 172-1 through the fill port 186-1 and drained through the drain port 188-1.

As shown in FIG. 51, the second gear 156-1 has teeth 176-1 along an edge 174-1 of the second gear 156-1. When the liquid 180-1 is held within the gear case 158-1, the liquid 180-1 may have a fill level 184-1. FIG. 51 illustrates a first fill level 184A and a second fill level 184B. The second fill level 184B is lower than the first fill level 184A. In some embodiments, when the drive train 150-1 is operating properly, the quantity of the liquid 180-1 correlates to the first fill level 184A such that the edge 174-1 of the second gear 156-1 is sufficiently submerged within or bathed by the liquid 180-1-1. However, when the fill level is lowered to, for example, the fill level 184B, the edge 174-1 and teeth 176-1 may be insufficiently lubricated. Such circumstances may occur when the gear case 158-1 has a leak.

FIG. 52 is a partially exploded view of the gear case 158-1 and illustrates the base and top portions 160-1, 162-1 before the base and top portions 160-1, 162-1 are coupled to the drive train to surround the first and second gears 154-1, 156-1. As shown, the gear case 158-1 may include first and second gear-receiving openings 190-1, 192-1 that are sized to receive the first and second gears 154-1, 156-1 (FIG. 51), respectively. The gear-receiving openings 190-1, 192-1 may be defined by opening edges 193-1 to 196-1 and the base and top portions 160, 162-1 may engage each other along case edges 197-1, 198-1.

When the drive train 150-1 is fully constructed and operational, the opening edges 193-1 to 196-1 engage the portions of the drive train 150-1 along sealable interfaces. The case edges 197-1, 198-1 may also be coupled to each other along a sealable interface. During operation of the drive train 150-1, however, the interfaces may become damaged or worn such that the interfaces are no longer sufficiently sealed. For example, when the drive train 150-1 is part of a locomotive, the opening edges 193-1 to 196-1 or the case edges 197-1, 198-1 may become worn, damaged, or separated such that the liquid 180-1 is permitted to escape the reservoir 172-1. Accordingly, the amount of liquid 180-1 may reduce such that the fill level 184-1 (FIG. 51) lowers.

Embodiments described herein may be configured to detect that the amount of liquid 180-1 has reduced. In addition, due to the wear, damage, or separation of the base and top portions 160-1, 162-1, the gear case 158-1 (or portions thereof) may exhibit different vibratory characteristics. For example, a gear case that is sufficiently sealed with respect to the drive train 150-1 and has a sufficient fill level 184-1 may exhibit a first vibratory state when the drive train 150-1 is driven at a first speed. However, a gear case that is insufficiently sealed with respect to the drive train 150-1 and/or has an insufficient fill level 184-1 may exhibit a second vibratory state that is different than the first vibratory state when the drive train 150-1 is driven at the first speed. Embodiments described herein may be configured to detect and measure the different vibratory states. In certain embodiments, a wireless device, such as those described herein, is at least partially disposed within the reservoir 172-1 and/or directly attached to a portion of the gear case 158-1. For example, at least a portion of the wireless device 104-1 may be directly secured or affixed to a wall of the gear case 158, such as the wall that defines the reservoir 172-1. In some embodiments, the wireless device 104-1 is not physically electrically connected to other components of the machine, such as a computing system that controls operation of the machine.

In addition to liquid level and vibrations, embodiments may be configured to detect other characteristics. For example, other measurements may relate to a quality (e.g., degree of contamination) of the liquid. Contaminants may include water, metallic particles, and/or non-metallic particles. Furthermore, embodiments are not limited to the drive train or a gear case of the drive train. For example, measurements that may be obtained for a drive train may also be obtained for a turbo-charger, an air compressor, an engine, and the like. Other components of a machine may also be measured by wireless devices described herein.

Figure 53:
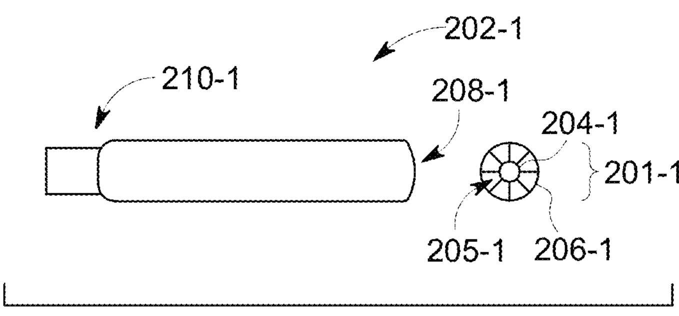
FIG. 53 is a side view of a capacitive-type sensor in accordance with an embodiment.
Figure 54:
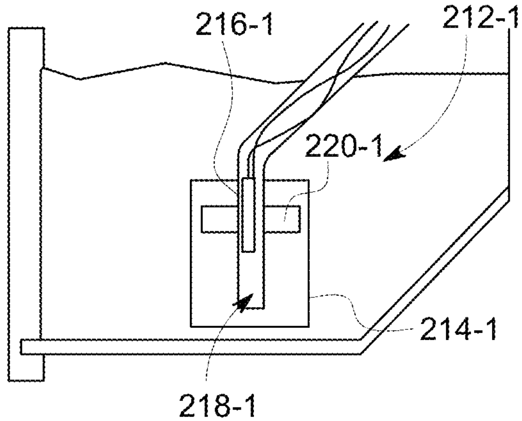
FIG. 54 is a schematic view of a magnetic float/reed switch sensor in accordance with an embodiment.
Figure 55:
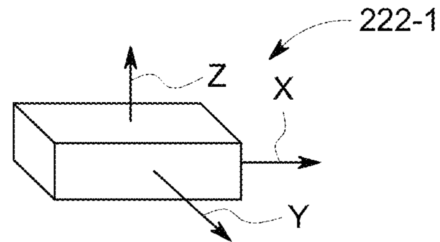
FIG. 55 is a schematic view of an accelerometer in accordance with an embodiment.

FIGS. 53 through 55 illustrate sensors 202-1, 212-1, 222-1, respectively. The sensors, which may also be referred to as transducers, may be a portion of the wireless devices described herein. Each of the sensors may be configured to measure (e.g., detect) a designated property or characteristic in the environment proximate to the sensor and provide a signal that is representative of the measured property or characteristic. The signal provided by the sensor may be the measurement.

Various types of measurements may be obtained by the sensors. Some non-limiting examples include a capacitance of a liquid, a temperature of a liquid and/or temperatures of certain parts of a machine, a fluid conduction of a liquid, a dielectric constant of a liquid, a dissipation factor of a liquid, an impedance of a liquid, a viscosity of a liquid, or vibrations of a mechanical element. A measurement may be directly obtained (e.g., temperature) by the sensor, or a designated measurement may be obtained after using information provided by the sensor to calculate the designated measurement. For example, the viscosity of the liquid may be calculated based on multiple level measurements obtained by a sensor.

Embodiments may include a single wireless device that is configured to measure and communicate only a single type of measurement (e.g., capacitance). However, in some embodiments, a single wireless device may be configured to measure and communicate multiple types of measurements (e.g., capacitance of the liquid, temperature of the liquid, temperature of the sensor, shock and/or vibration of the gear case, etc.). In such embodiments, the wireless device may have multiple sensors.

The sensor 202-1 is configured to measure a capacitance of a liquid, such as a lubricant in a tank (e.g., gear case). The sensor 202-1 is hereinafter referred to as a capacitive level probe 202-1. For reference, a cross-section 201-1 of the level probe 202-1 is also shown in FIG. 53-1. The level probe 202-1 extends lengthwise between a leading end 208-1 and a trailing end 210-1-1. The level probe 202-1 includes an inner or measurement electrode 204-1 and an outer or reference electrode 206-1. As shown, a space 205 exists between the inner and outer electrodes 204-1, 206-1. A capacitance of the material that exists within the space 205-1, such as a combination of a liquid and gas, may be measured by the level probe 202-1. In some embodiments, a wall of the tank that holds the liquid may be used as the reference electrode.

The level probe 202-1 is configured to be immersed into the liquid (e.g., oil) held by the tank. For example, the leading end 208-1 may be inserted into the liquid. As the leading end 208-1 is submerged, the liquid may flow into the space 205 thereby changing a ratio of liquid to gas within the space 205-1. As such, the measured capacitance changes as the level of the liquid within the space 205-1 changes. If the liquid is a lubricant, the measured value of capacitance decreases as an amount or level of the liquid decreases. As an amount or level of the liquid increases, the measured value of capacitance also increases.

The level probe 202-1 may also be configured to determine a quality of the liquid. More specifically, the level probe 202-1 may detect an amount or percentage of contaminations in the liquid based on capacitance measurements. For example, contaminant detection may be based on a dissipation factor of a dielectric of the liquid. In general, the dissipation factor is a function of an applied frequency, a liquid temperature, a composition of the liquid (e.g., the desired composition of the liquid), and contaminants. The dissipation factor may be substantially independent of the base capacitance or liquid level.

In some cases, movement of the machine may cause a displacement of the liquid which may introduce an error in the measurements. Accordingly, in some embodiments, the level probe 202-1 is only activated when the machine or component thereof is at rest (e.g., inactive). To this end, an accelerometer or other inertial type sensor may be part of or operably coupled to the wireless device that includes the level probe 202-1. The accelerometer may determine that the machine is in an inactive or stationary state such that measurements may be obtained by the level probe 202-1.

As shown in FIG. 54, the sensor 212-1 includes a body float 214-1 and a reed switch 216-1. The body float 214-1 includes a cavity 218-1 that is sized and shaped to receive the reed switch 216-1. The body float 214-1 is configured to float along the reed switch 216-1 (e.g., vertically) based on a level of the liquid in the reservoir. The body float 214-1 includes a permanent magnet 220-1, and the reed switch 216-1 includes a magnetically actuated switch or switches (not shown). As the body float 214-1 moves up and down, the permanent magnet 220-1 may activate or deactivate the switch (e.g., close or open a circuit, respectively, in the reed switch 216-1). The activated switch indicates that the body float 214-1 is at a designated level and, consequently, that the liquid is at a designated level.

As described above, one or more embodiments may also include a sensor that is an accelerometer. FIG. 55 illustrates one such sensor, which is referenced as an accelerometer 222-1. In some embodiments, the accelerometer 222-1 is a micro-electro-mechanical system (MEMS)tri-axis accelerometer. The accelerometer 222-1 may be used for a variety of functions. For example, the accelerometer 222-1 may be coupled to a mechanical element, such as a tank, and determine whether the mechanical element has remained stationary for a designated amount of time. In some embodiments, other measurements (e.g. liquid level) may be obtained only after it has been determined that the mechanical element has remained stationary for the designated amount of time.

Alternatively or additionally, the accelerometer 222-1 may be configured to detect vibratory states experienced by the mechanical element. For example, the accelerometer 222-1 may be configured to obtain numerous shock and vibrations measurements per second in each of x-, y-, and z-axes. For example, the accelerometer 222-1 may be able to log hundreds or thousands of data points per second in each of the x-, y-, and z-axes.

Figure 56:
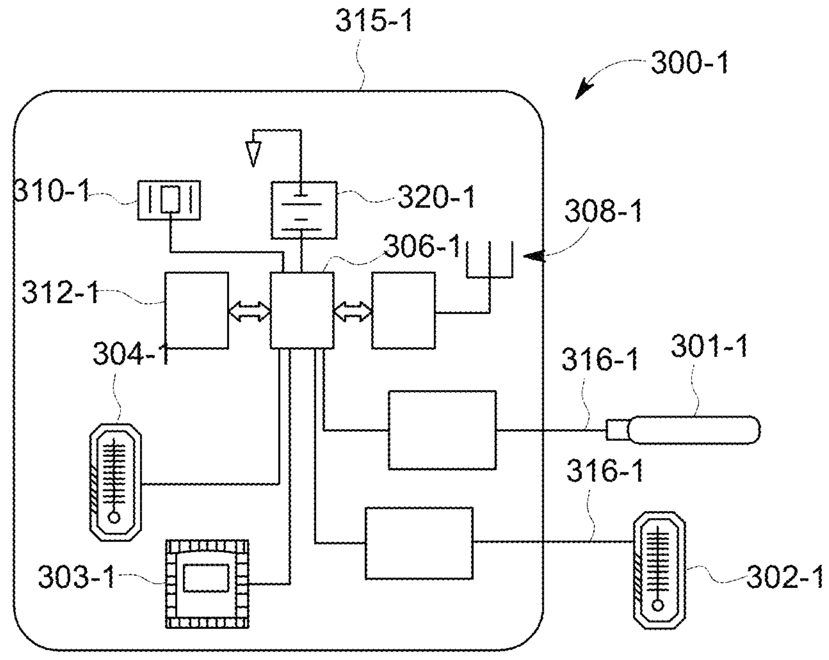
FIG. 56 is a schematic diagram of a wireless device formed in accordance with an embodiment.

FIG. 56 is a schematic diagram of a wireless device 300-1 formed in accordance with one embodiment. The wireless device 300-1 includes sensors 301-1 to 304-1, a processing unit 306-1 (e.g., microprocessor), a transmitter 308-1, an internal clock 310-1 (e.g., real-time clock crystal), and a memory 312-1 (e.g., non-volatile memory). The wireless device 300-1 has a device body 315-1, which may include a printed circuit board (PCB) or a die (e.g., semiconductor wafer) in some embodiments. In the illustrated embodiment, the device body 315-1 includes the sensors 303-1, 304-1, the processing unit 306-1, the transmitter 308-1, the internal clock 310-1, and the memory 312-1. In alternative embodiments, however, the wireless device 300-1 may have multiple bodies (e.g., multiple dies) that are coupled to each other and/or the components described herein may be separate from the device body 315-1. The sensors 301 and 302-1 may be operably coupled to the device body 315-1 through, for example, wires 316-1. In other embodiments, the sensors 301-1, 302-1 are wirelessly coupled to the device body 315-1.

The sensor 301-1 may be a level probe, such as the level probe 202-1. The sensor 301-1 is configured to be inserted into a liquid (e.g., lubricant) of a machine. The sensor 302-1 may be a thermometer that is configured to obtain a temperature of the liquid. The sensor 303 is an accelerometer, such as the accelerometer 222-1, and the sensor 304-1 is another thermometer that is configured to determine a temperature of the device body 315 of the wireless device 300-1. Each of the sensors 301-1 to 304-1 is communicatively coupled to the processing unit 306-1 and configured to communicate signals to the processing unit 306-1. The signals may be representative of a property or characteristic detected by the sensor.

The processing unit 306-1 may be configured to store or log data (e.g., data based on the signals obtained from the sensors) in the memory 312-1. In some embodiments, the processing unit 306-1 is configured to query the sensors to request measurements from the sensors. The queries may occur at predetermined times or when a designated event occurs. For example, the queries may occur once an hour as determined by the internal clock 310-1 until, for example, the wireless device 300-1 is interrogated by a reader (not shown). At such an event, the processing unit 306-1 may query the sensors for numerous data points. For example, the data points may be provided almost continuously after interrogation. The processing unit 306-1 may also receive data from the memory 312-1. The data received from the sensors and/or the memory 312-1 may be transformed into data signals that are communicated by the transmitter 308-1 to the reader.

The wireless device 300-1 may be characterized as an active or semi-passive device. For example, the wireless device 300-1 may include a power source 320-1, such as a battery (e.g., lithium thionyl chloride battery) and/or kinetic energy harvesting device. The wireless device 300-1 may utilize the power source 320-1 to increase the transmission range of the transmitter 308-1. In such embodiments, the reader may be located tens or hundreds of meters away from the wireless device 300-1. In addition to the transmitter 308-1, the power source 320-1 may be used to supply power to other components of the wireless device 300-1, such as the sensors or the processing unit 306-1.

Figure 57:
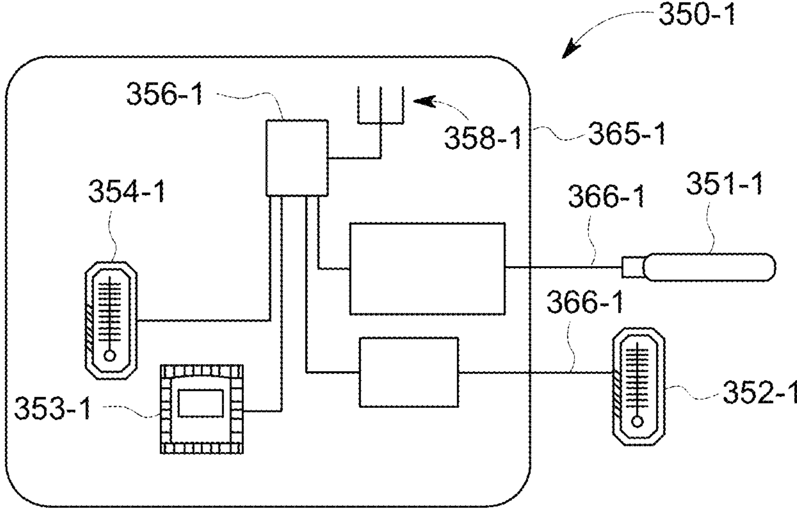
FIG. 57 is a schematic diagram of a wireless device formed in accordance with an embodiment.

FIG. 57 is a schematic diagram of a wireless device 350-1 formed in accordance with one embodiment. The wireless device 350-1 may be a passive device such that the wireless device 350-1 is powered by inductive or backscatter coupling with the reader (or some other non-internal power source). As shown, the wireless device 350-1 includes sensors 351-1 to 354-1, a processing unit 356-1, and a transmitter 358-1. The wireless device 300-1 has a device body 365 that includes, in the illustrated embodiment, the sensors 353-1, 354-1, the processing unit 356-1, and the transmitter 358-1. The device body 365-1 may be formed by integrated circuit technology. For example, the device body 365 may include one or more printed circuit boards (PCBs). The sensors 351-1 and 352-1 may be operably coupled to the device body 365-1 through, for example, wires 366-1. Similar to the wireless device 300-1 (FIG. 56), the sensors may be a level probe, external thermometer, an accelerometer, and an internal thermometer, respectively.

In some embodiments, the processing unit 356-1 executes fewer calculations or conversions of the signals from the sensors than the processing unit 306-1 (FIG. 56). For example, the processing unit 356-1 may be an ADC that converts the analog signals from the sensors 351-354-1 to digital signals. The digital signals may be the data signals that are then transmitted by the transmitter 358-1. In the illustrated embodiment, the processing unit 356-1 may only query the sensors after being interrogated by a reader (not shown). More specifically, the interrogation signals from the reader may power the processing unit 356-1 to query the sensors and transmit the data signals.

Figure 58:
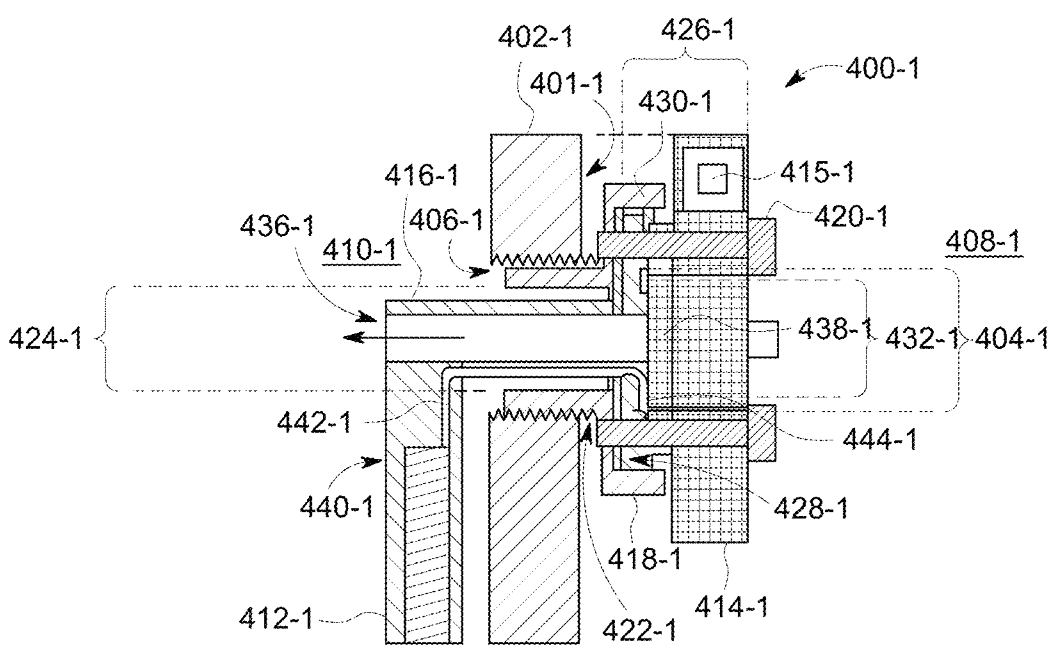
FIG. 58 is a cross-section of a portion of a wireless device utilizing the sensor of FIG. 53 in accordance with an embodiment.

FIG. 58 is a cross-section of a portion of a wireless device 400-1 attached to a wall 402-1 of a tank 401-1. The tank 401-1 may be part of a machine, such as a locomotive or other machine described herein. The tank 401-1 is configured to have a reservoir 410-1 for holding a liquid (not shown), such as a lubricant. The reservoir 410-1 is accessed through a fill port 404-1 of the wall 402-1 that is defined by interior threads 406-1 of the wall 402-1 as shown in FIG. 58. The fill port 404-1 provides access from an exterior 408-1 of the tank 401 to the reservoir 410-1.

As shown, the wireless device 400-1 includes a sensor 412-1, a device body 414-1, and an intermediate cable portion 416-1 that joins the sensor 412-1 and the device body 414-1. The wireless device 400-1 also includes a coupling component 418-1 that is configured to be secured to the device body 414-1 through, for example, fasteners 420-1 and attached to the wall 402-1. In the illustrated embodiment, the coupling component 418-1 includes threads 422-1 that complement and are configured to rotatably engage the threads 406-1 of the wall 402-1. However, in other embodiments, different methods of attaching the coupling component 418-1 to the tank may be used, such as latches, interference fits (e.g., plugs), and/or adhesives.

To assemble the wireless device 400-1, the coupling component 418-1 may be rotatably engaged to the wall 402-1. The sensor 412-1 and the cable portion 416-1 may be inserted through an opening 424-1 of the coupling component 418-1 and the fill port 404-1. As shown, the coupling component 418-1 has a mating face 428-1 that faces in a direction away from the wall 402-1. The cable portion 416-1 has a mating end 426-1 that is located in the exterior 408-1 of the tank 401 and may be pressed toward the mating face 428-1 with a gasket 430-1 located therebetween. The device body 414-1 has a cable opening 432-1 that receives an end of the cable portion 416-1. The device body 414-1 may be secured to the cable portion 416-1 and the coupling component 418-1 using the fasteners 420-1. As shown, the cable portion 416-1 includes a fill channel 436-1 that permits access to the reservoir 410-1. During operation, the fill channel 436-1 may be closed with a plug 438-1 at the mating end 426-1 of the cable portion 416-1.

The sensor 412-1 may be similar or identical to the level probe 202-1 described with respect to FIG. 53-1. For example, a trailing end 440-1 of the sensor 412-1 is shown in FIG. 58. The trailing end 440-1 is coupled to wires 442-1 that communicatively couple the sensor 412-1 to the device body 414-1. In other embodiments, the sensor 462-1 may be similar or identical to the sensor 212-1 (FIG. 54). The cable portion 416-1 is configured to surround and protect the wires 442-1 from the surrounding environment. As shown, the wires 442-1 terminate at a contact ring 444-1 along the device body 414-1. The sensor 412-1 is configured to transmit signals to the device body 414-1 through the wires 442-1 and the contact ring 444-1. The device body 414-1 is configured to process and transmit data signals that represent measurements obtained by the sensor 412-1. The device body 414-1 may include an integrated circuit unit 415-1. Although not shown, the integrated circuit unit 415 of the device body 414-1 may have a processing unit, power source, internal clock, additional sensors, and/or a transmitter, such as those described above. In some embodiments, the integrated circuit component 415 is formed as an RFID unit.

Figure 59:
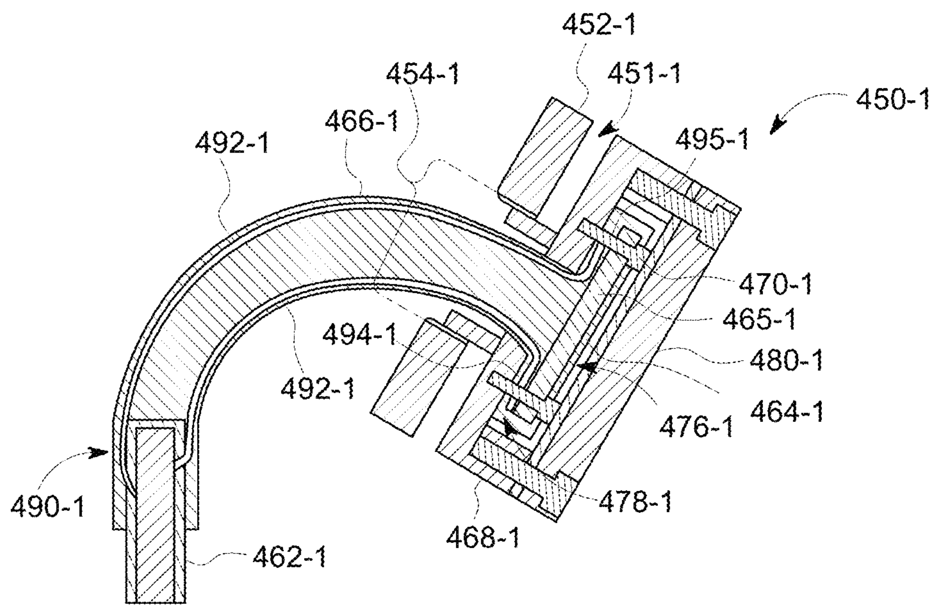
FIG. 59 is a cross-section of a portion of a wireless device utilizing the sensor of FIG. 53 in accordance with an embodiment.

FIG. 59 is a cross-section of a portion of a wireless device 450-1, which is also configured to be coupled to a wall 452-1 of a tank 451-1. The wireless device 450-1 may include similar features as the wireless device 400-1. For example, the wireless device 450-1 includes a sensor 462-1, a device body 464-1, and an intermediate cable portion 466-1 that joins the sensor 462-1 and the device body 464-1. The wireless device 450-1 also includes a coupling component 468-1 that is configured to be secured directly to the device body 464-1 and the cable portion 466-1 through fasteners 470-1. In the illustrated embodiment, the coupling component 468-1 is rotatably engaged to the wall 452-1 in a similar manner as the coupling component 418-1. However, other methods of attaching the coupling component 468-1 to the wall may be used.

To assemble the wireless device 450-1, the coupling component 468-1 may be rotatably engaged to the wall 452-1. The sensor 462-1 and the cable portion 466-1 may be inserted through the coupling component 418-1 and a fill port 454-1 of the wall 452-1. The device body 464-1 may be encased within a mating end 476-1 of the cable portion 466-1. As shown, the coupling component 468-1 has a mating face 478-1 that faces in a direction away from the wall 452-1. Accordingly, the cable portion 466-1 and the device body 464-1 may be secured to the coupling component 468-1 using the fasteners 470-1. A cover body 480-1 may then be positioned over the cable portion 466-1 to hold the device body 464-1 between the cover body 480-1 and the coupling component 468-1. Unlike the wireless device 400-1, the cable portion 466-1 does not include a fill channel that permits access to the reservoir.

The sensor 462-1 may be similar or identical to the level probe 202-1 described with respect to FIG. 53. For example, a trailing end 490-1 of the sensor 462-1 is shown in FIG. 59. The trailing end 490-1 is coupled to wires 492-1 that communicatively couple the sensor 462-1 to the device body 464-1. In other embodiments, the sensor 462-1 may be similar or identical to the sensor 212-1. As shown, the wires 492-1 terminate at contacts 494-1, 495 that are coupled to the device body 464-1. The device body 464-1 may include an integrated circuit component 465-1, which, in the illustrated embodiment, is a RFID unit. The sensor 462-1 is configured to transmit signals to the integrated circuit component 465 through the wires 492-1. Like the integrated circuit component 415-1, the integrated circuit component 465 is configured to process and transmit data signals that represent measurements obtained by the sensor 462-1. The integrated circuit component 465 may include a processing unit, power source, internal clock, additional sensors, and/or a transmitter, such as those described above.

FIG. 60 is a cross-section of a portion of a wireless device 500-1. The wireless device 500-1 may be similar to the wireless device 400-1 and the wireless device 450-1. However, as shown in FIG. 60-1, the wireless device 500-1 utilizes a sensor 502-1 that may be similar to or identical to the sensor 212-1. The wireless device 500-1 also includes a coupling component 504-1 that is configured to attach to a wall 506-1 of a tank 508-1, which is a gear case in the illustrated embodiment. The coupling component 504-1 may be similar to the coupling components described above. For example, the coupling component 504-1 may rotatably engage the wall 506-1.

Also shown, the wireless device 500-1 includes a device body 530-1 that is operably coupled to the sensor 502-1 through a base support 510-1 and an intermediate beam 512-1. The base support 510-1 is disposed within an opening 514-1 of the coupling component 504-1. The beam 512-1 extends between and joins the sensor 502-1 and the base support 510-1. The beam 512-1 may be fabricated from, for example, stainless steel and is configured to provide a passageway 516-1 for wires 518-1 that communicatively couple the device body 530-1 and the sensor 502-1.

The base support 510-1 includes a mating face 520-1 that faces away from the tank 508-1. The mating face 520-1 has contacts 524-1, 525-1 thereon. The contact 524-1 may be a contact pad, and the contact 525-1 may be a ring contact that extends around the contact pad. A device body 530-1 is configured to be rotatably engaged to the coupling component 504-1. The device body 530-1 includes a mounting surface 532-1 that faces the mating face 520-1 and has corresponding contacts that are configured to engage the contacts 524-1, 525-1. More specifically, when the device body 530-1 is rotated to engage the coupling component 504-1, the mounting surface 532-1 of the device body 530-1 may advance toward the mating face 520-1 so that the contacts of the device body 530-1 press against and engage the contacts 524-1, 525-1.

Accordingly, the device body 530-1 may be communicatively coupled to the sensor 502-1. Similar to the device bodies described above, the device body 530-1 may include an integrated circuit component 515-1 having a processing unit and a transmitter (not shown). Optionally, the integrated circuit component 515-1 may also include a memory, an internal clock, and one or more other sensors. The integrated circuit component 515-1 may transform the signals from the sensor 502-1 (or memory or other sensors) into data signals. The data signals may then be transmitted to a reader (not shown). In some embodiments, the integrated circuit component 515-1 is formed as an RFID unit.

FIG. 61 is a cross-section and FIG. 62 is a front view, respectively, of a portion of a wireless device 550-1. The wireless device 550-1 may include a sensor (not shown) and a device body 552-1 that are communicatively coupled through wires 554-1. The sensor may be similar to the sensor 202-1 or the sensor 212-1. The device body 552-1 is secured to a faceplate 556-1 that is coupled to an exterior surface of a tank 560-1. FIGS. 61 and 62 illustrate an embodiment in which no electrical contacts are required along the device body 552-1 to electrically join the sensor. Instead, wires 554-1 from the sensor may extend through potting 562-1 that mechanically couples the sensor to the tank 560-1. Like the wireless device 400-1, the wireless device 550-1 may permit access to a fill port 566-1 through a plug 568-1. Although not shown, the device body 552-1 may include an integrated circuit component, such as those described above, that processes data signals and transmits data signals. The integrated circuit component may be an RFID unit that is directly coupled to one of the wires 554-1.

Figure 63:
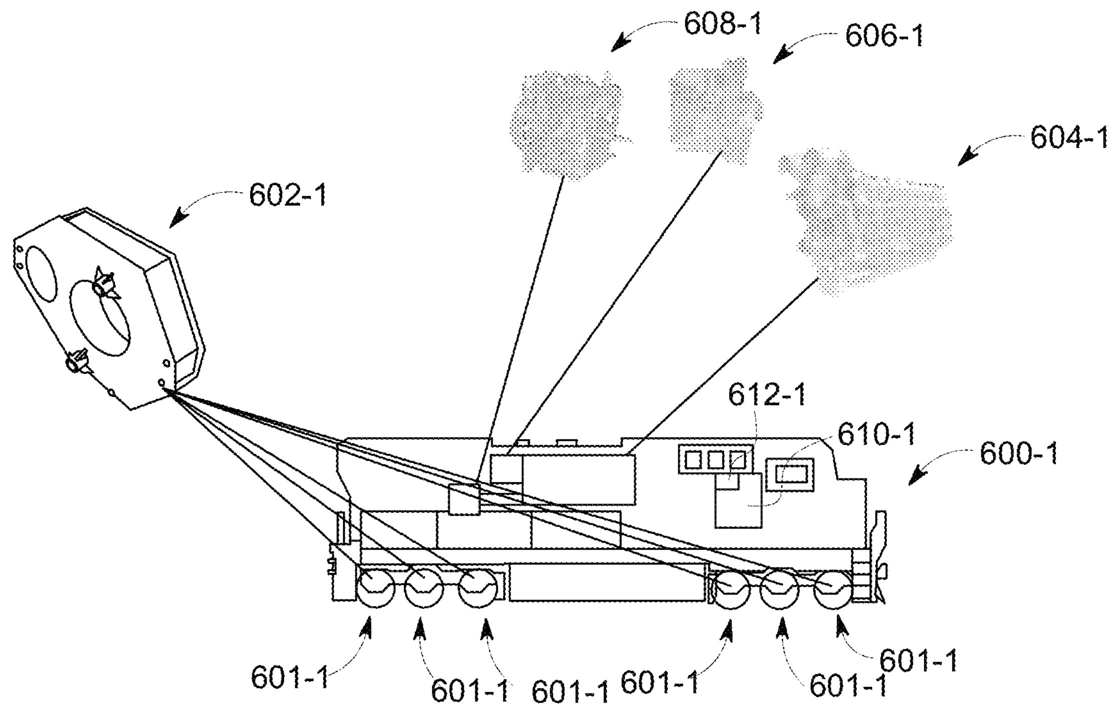
FIG. 63 is a schematic view of a locomotive and illustrates a plurality of components of the locomotive in accordance with an embodiment.

FIG. 63 is a schematic view of a locomotive 600-1 and illustrates a plurality of components of the locomotive 600-1 that may include one or more wireless devices, such as the wireless devices described herein. For example, the locomotive 600-1 may include a plurality of drive trains 601 that each has a gear case 602-1. The locomotive 600-1 may also include an engine 604-1, a turbo-charger 606-1 operably coupled to the engine 604-1, and an air compressor 608-1. Each of the components may have one or more of the wireless devices described herein operably coupled thereto. For example, the gear cases 602-1 and the engine 604-1 may have at least one of the wireless devices 202-1, 212-1, 222-1, 400-1, 450-1, 500-1, or 550-1 described above. In particular, each of the gear cases 602-1 and the engine 604-1 may have a reservoir that includes a liquid lubricant. The turbo-charger 606-1 and the air compressor 608-1 may use, for example, an accelerometer similar to the wireless device 222-1.

As shown, the locomotive 600-1 may also include an on-board control system 610-1. The control system 610-1 can control the tractive efforts and/or braking efforts of the locomotive 600-1 and, optionally, other locomotives that are directly or indirectly coupled to the locomotive 600-1. Operations of the control system 610-1 may be based on inputs received from an operator of the locomotive and/or remote inputs from, for example, a control tower, a dispatch facility, or the like. In addition, the control system 610-1 may receive inputs from various components of the locomotive 600-1. In some cases, the inputs may be data signals received through wireless communication. For example, the wireless devices of the gear cases 602-1, the engine 604-1, the turbo-charger 606-1, and the air compressor 608-1 may be configured to wirelessly communicate data signals to the control system 610-1. The control system 610-1 may include a reader 612-1 for receiving the wireless data signals. The control system 610-1 may also include a signal-processing module and a planning module that are similar to the signal-processing and planning modules 120-1, 122-1. The planning module may generate operating plans for the locomotive 600-1 based on the inputs received.

Figure 64:
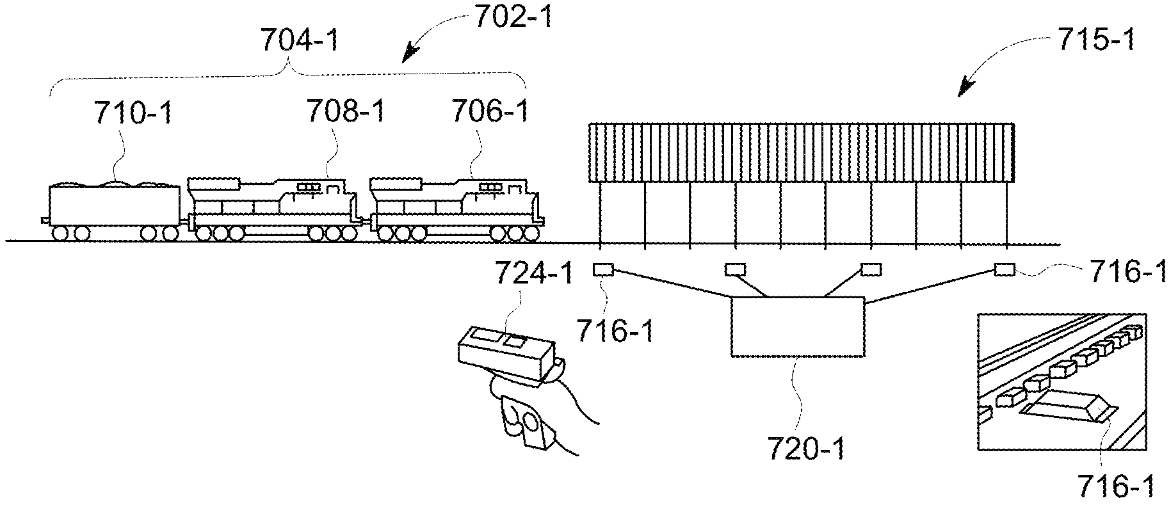
FIG. 64 illustrates a system in accordance with an embodiment for obtaining data signals from one or more wireless devices.
Figure 65:
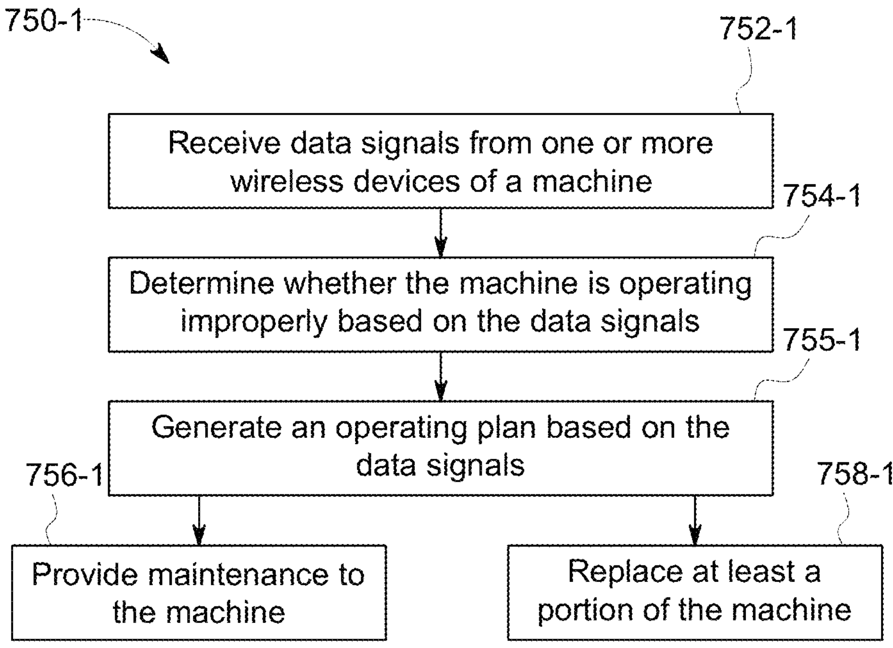
FIG. 65 is a flowchart illustrating a method in accordance with an embodiment.

FIG. 64 illustrates a system 700-1 in accordance with one embodiment for obtaining data signals from one or more wireless devices. FIG. 65 illustrates a flowchart of a method 750-1 that may be executed or performed by the system 700-1. In some embodiments, the locomotive 600-1 may also execute or perform the method 750-1. The system 700-1 and the method 750-1 may employ structures or examples of various embodiments discussed herein. In some embodiments, certain steps of the method 750-1 may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Likewise, the system 700-1 is not required to include each and every feature of each and every embodiment described herein.

With respect to FIG. 64, the system 700-1 includes a vehicle system 702-1 (e.g., train) including a locomotive consist 704-1. The locomotive consist 704-1 may include at least one locomotive that is linked (directly or indirectly) to one or more rail cars. For example, FIG. 64 shows the locomotive consist 704-1 including first and second locomotives 706-1, 708-1 and a rail car 710-1. In other embodiments, the vehicle system 702-1 may include more rail cars 710-1. Each of the locomotives 706-1 and 708-1 may include a plurality of components that are each monitored by one or more wireless devices. For example, each of the locomotives 706-1, 708-1 may include an engine, a turbo-charger, an air compressor, and a plurality of gear cases, such as those described herein.

As shown in FIG. 64, the vehicle system 702-1 is approaching a designated reading location 715-1. The reading location 715-1 is a maintenance facility in the illustrated embodiment. However, the reading location 715-1 may be a variety of other locations that are capable of receiving wireless data signals from the locomotives. For example, the reading location 715-1 may be a depot, fuel station, wayside location, rail yard entry point or exit point, designated sections of the track(s), and the like. The reading location 715-1 includes a plurality of readers 716-1. Each of the readers 716-1 is communicatively coupled (e.g., wirelessly or through communication wires) to a control system 720-1. Alternatively or additionally, a handheld reader 724-1 may be carried by an individual and used to receive the data signals. The reader 724-1 may also communicate data signals with the control system 720-1.

The control system 720-1 may include a signal-processing module and a planning module, such as the signal-processing and planning modules 120-1, 122-1. For example, the control system 720-1 may generate operating plans that include instructions for operating the vehicle system 702-1 and other similar vehicle systems.

The method 750-1 may include receiving (at 752-1) data signals from one or more of the wireless devices of a machine. In the illustrated embodiment, the machine is the vehicle system 702-1 or one of the locomotives 704-1, 706-1. However, embodiments described herein are not necessarily limited to locomotives. The machine may have one or components with moving mechanical elements or parts. For example, the machine may have a drive train, engine, air compressor, and/or turbo-charger. The data signals may be representative of a measurement of an operative condition of the component. By way of example the measurement may be at least one of a vibration measurement, a capacitance of a liquid, a temperature of a liquid, a fluid conduction of a liquid, a dielectric constant of a liquid, an impedance of a liquid, or a viscosity of a liquid. In particular embodiments, the measurement is representative of a vibratory state of a gear case or of a liquid condition of a lubricant held in the gear case.

The receiving operation (at 752-1) may include receiving the data signals at one or more fixed readers having stationary positions. For example, the readers 716-1 may have fixed positions with respect to tracks 730-1. The readers 716-1 may be located at designated distance from the tracks 730-1 so that the readers 716-1 are capable of receiving the data signals. The receiving operation (at 752-1) may also include receiving the data signals through one or more movable readers, such as the handheld reader 724-1.

In an alternative embodiment, as described above, the receiving operation (at 752-1) may occur with an on-board control system, such as the control system 610-1.

The method 750-1 also included determining (at 754-1), based on the data signals, whether the component of the machine is operating improperly. For example, the control system 720-1 may analyze the data signals and, optionally, other inputs to determine whether the component is operating sufficiently. If the component is operating improperly, the method 750-1 also includes generating (at 755-1) an operating plan that is based on the data signals. The operating plan may be a new (or revised) operating plan that is configured to replace a currently-implemented operating plan. The method 750-1 may also include at least one of providing maintenance (at 756-1) to the component or replacing (at 758-1) an element of the component.

In an embodiment, a system (e.g., a monitoring system) is provided that includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

In one example, the transmitter is configured to be energized by the reader when the reader interrogates the transmitter.

In one example, the system includes a power source that is configured to supply power to the transmitter for transmitting the data signals. The power source may include, for example, a battery and/or energy harvesting device.

In one example, the sensor is configured to be at least partially submerged in the liquid.

In one example, the measurement is at least one of a capacitance of the liquid, a temperature of the liquid, a fluid conduction of the liquid, a dielectric constant of the liquid, an impedance of the liquid, or a viscosity of the liquid.

In one example, the device body is configured to be affixed to a wall of the machine in which the wall at least partially defines the reservoir.

In one example, the sensor and the device body collectively form a first wireless device. The system may also include a second wireless device that is configured to obtain and wirelessly communicate second data signals that are representative of a measurement of a different reservoir.

In one example, the sensor is configured to be disposed in a gear case of a locomotive, the gear case having the reservoir.

In one example, the transmitter is included in a radio-frequency identification (RFID) element.

In one example, the sensor, the processing unit, and the transmitter collectively form a first wireless device. The system may also include a second wireless device that is configured to obtain and wirelessly transmit data signals that are representative of a measurement of a different reservoir. The system may include a signal-processing module. The signal-processing module may be configured to determine, based on the data signals, whether the machine is operating improperly by comparing the data signals of the first wireless device to the data signals of the second wireless device.

In one example, the data signals are configured to be transmitted to a handheld reader. In another example, the data signals are configured to be transmitted to a fixed reader located along a railway track. In yet another example, the data signals are configured to be transmitted to an on-board reader located on a locomotive.

In one example, the sensor includes a multi-conductor capacitive sensor configured to detect a capacitance of a fluid. The fluid may function as a dielectric, wherein a level of the fluid affects the capacitance detected. In another example, the sensor includes a body float and a position transducer configured to detect a position of the body float. The position transducer may include, for example, a reed switch.

In an embodiment, a system (e.g., a monitoring system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In one example, the system includes a power source configured to supply power to the transmitter for transmitting the data signals.

In one example, the system includes a memory. The memory is configured to log a plurality of the measurements obtained at different times. The transmitter is configured to transmit data signals that include the measurements.

In one example, the sensor, the processing unit, and the transmitter collectively form a first wireless device. The system may include a second wireless device configured to obtain and wirelessly transmit data signals that are based on a measurement of a different drive train.

In one example, the device body includes a radio-frequency identification (RFID) unit. The RFID unit may have the processing unit and the transmitter.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train.

In one example, the measurement is representative of vibratory state of a gear case or a liquid condition of a lubricant held in the gear case.

In one example, the measurement is at least one of a vibration measurement of a gear case, a capacitance of a lubricant stored by the gear case, a temperature of the lubricant, a fluid conduction of the lubricant, a dielectric constant of the lubricant, impedance of the lubricant, or a viscosity of the lubricant.

In one example, the data signals are received from a plurality of wireless devices. The data signals are based on a common type of measurement.

In one example, the data signals are received at a handheld reader.

In one example, the machine is a locomotive and the data signals are received at a fixed reader located along a railway track.

In one example, the machine is a locomotive and the data signals are received at a reader located on-board the locomotive.

In one example, the method also includes operating the machine according to a first operating plan and generating a second operating plan that is based on the operative condition.

In an embodiment, a system (e.g., a monitoring system) includes a signal-processing module that is configured to receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that is configured to generate an operating plan that is based on the operative condition.

In another embodiment, a system (e.g., wireless liquid monitoring system) comprises a sensor, a processing unit, and a transmitter. The sensor is configured to be disposed within a reservoir of a machine having moving parts that are lubricated by a liquid in the reservoir. The sensor is configured to obtain a measurement of the liquid that is representative of at least one of a quantity or quality of the liquid in the reservoir. The processing unit is operably coupled to the sensor and configured to generate first data signals representative of the measurement of the liquid. The transmitter is operably coupled to the processing unit and configured to wirelessly communicate the first data signals to a remote reader.

In another embodiment of the system, alternatively or additionally, the transmitter is an RFID unit, which may be, for example, similar to an RFID tag, chip, card, or label.

In another embodiment of the system, alternatively or additionally, the system is configured to be disposed in the machine (and when installed is actually disposed in the machine), which comprises a vehicle or other powered system comprising the reservoir, the moving parts, and one or more computers or other controller-based units (e.g., a vehicle controller) other than the processing unit. The system may not be physically electrically connected (e.g., not connected by wires or other conductors) to any of the one or more computers or other controller-based units in the machine. Thus, the first data signals may only wirelessly transmitted from the system to the reader or elsewhere, and are not transmitted via wire/cables or other physical electrical connections.

In another embodiment of the system, alternatively or additionally, the processing unit and transmitter are co-located proximate to one another (e.g., at least partially integrated onto a common circuit board, positioned within a common box/housing that is positioned within the machine—that is, the common box/housing is not coextensive with the outer body/structure of the machine, but is located within the outer body/structure—and/or some or all of the components of the processing unit and transmitter are located within 10-1 cm of each other, within 5 cm of each other, etc., for example), and/or at least portions of the processing unit and transmitter are directly connected to a wall of the reservoir (e.g., a wall that bears a pressure of and/or contacts the liquid in the reservoir) and/or to a structure immediately connected to such a wall (e.g., support structure of the reservoir, gear case, or the like).

In another embodiment of the system, alternatively or additionally, the transmitter is configured to wirelessly communicate the first data signals to the remote reader that comprises: a remote reader located within the machine (e.g., if the machine is a vehicle, the remote reader is located with the vehicle); a remote reader located on a wayside of a route of the machine, the machine comprising a vehicle; a portable (handheld, or otherwise able to be carried by a human operator) remote reader.

Additional embodiments are disclosed that relate to sensing methods and systems. The sensors, such as resonant sensors, may include inductor-capacitor-resistor (LCR) sensors that can be used as sensors or transducers for sensing fluids. Provided herein are sensors having a part that is a resonant structure that exhibits resolvable changes in the presence of a fluid and various components or contaminants in the fluid.

In one embodiment, the sensor may include an inductor-capacitor-resistor (LCR) resonator circuit with a resonance frequency response provided by the resonant impedance (Z) of this circuit. The sensors as provided herein may be capable of sensing properties of interest in the presence of variable noise sources and operating over the variable temperature conditions to provide stable sensor performance over time. Disclosed herein are sensors that include inductor-capacitor-resistor (LCR) resonators, which may function as a sensor or as a transducer. The resonant impedance spectrum of the sensor may be measured either via inductive coupling between pick up coil and sensor or directly by connecting to a sensor reader. The electrical response of the sensor may be translated into the resonant impedance changes of the sensor.

One or more embodiments herein describe systems and methods for environment sensing, specifically a wireless sensor network (WSN) having sensor nodes configured to detect one or more analytes of interest (e.g., methane gas, carbon monoxide gas, nitrogen oxide gas) within an environment. The sensor nodes include a sensor, such as a multivariable analyte sensor, and an environment sensor. The sensor may be similar to and/or the same as the sensor described in U.S. patent application entitled, "SYSTEMS AND METHODS FOR ENVIRONMENT SENSING" having docket number 285314-1US, which is incorporated by reference in its entirety. The environment sensor may be configured to acquire ambient parameters of the environment (e.g., not the analytes of interest), such as ambient temperature, ambient relative humidity, ambient atmospheric pressure, meteorological conditions, light detection, wind direction, wind speed, and/or the like.

The sensor nodes are powered by an ambient power source (e.g., solar panel, vibration, thermal power, ambient radio-frequency power, and/or the like). The sensor utilizes a sensing material electrically coupled to a pair of electrodes. An electrical stimulus is delivered to the sensor that includes a sensing material. Optionally, the multivariable analyte sensor may include a resonant inductor capacitor resistor (LCR) circuit and/or an RFID sensor.

An impedance response (e.g., impedance spectrum) of the sensor is measured via a controller circuit of the sensor node directly and/or inductive coupled between a pick up coil and the sensor. For example, the electrical response at certain frequencies or a single frequency corresponding to signal changes (e.g., impedance, resistance, capacitance, and/or the like) of the sensor is translated into the impedance changes of the sensor to form the impedance response. Based on the impedance response, the controller circuit may calculate one or more spectrum parameters. The spectrum parameters are calculated from a real portion and/or imaginary portion of the impedance response. The "spectrum" or "spectral" parameters are utilized to determine an environmental parameter of the analytes of interest. For example, the controller circuit may analyze the impedance response of the sensing material of the sensor at frequencies calculated from the real portion of the impedance response that provide a linear response of the sensing material to determine the environmental parameters (e.g., concentration) of the analytes of interest. It may be noted, the impedance response of the sensing material described herein provides a linearity improvement over the nonlinear (e.g. power law) resistance response of the sensing material in conventional environmental sensors. Additionally due to the linear response, the impedance response of the sensing material provides a monotonic response improvement over the non-monotonic resistance response (e.g., parabolic) of the sensing material in conventional environmental sensors. Additionally or alternatively, the spectrum parameters may be selected to reject and/or filter out effects of interference due to volatile analytes (e.g., analytes not of interest). For example, the impedance response of the sensing material provides reduction of effects of humidity over the resistance response of the sensing material in conventional environmental sensors.

The sensor node includes an RF circuit, which is configured to transmit the environmental parameters of the analytes of interest and the ambient parameters acquired by the environmental sensor to a remote system (e.g., central hub, WSN gateway, and/or the like). Optionally, the sensor nodes may transmit the environmental and ambient parameters at predetermined intervals. Additionally or alternatively, the remote system may receive additional ambient parameters from a remote weather station of the WSN.

The fluids described herein can include gases, vapors, liquids, particles, biological particles, and/or biological molecules. Optionally, a fluid may refer to one or more solid materials.

Each sensor node may have a digital identification or ID that can include data stored in a memory chip (or other memory device) of the sensor node. Non-limiting examples of this data include manufacturer identification, electronic pedigree data, user data, and/or calibration data for the sensor. Additionally or alternatively, the sensor node may have an IP address that may allow the sensor node connectivity to the Internet or other remote-based net, server, database, cloud or any other source of remote data storage and processing.

A monitoring process includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady state measurements of individual vapors and their mixtures.

Environmental parameters and/or select parameters can refer to measurable environmental variables within or surrounding a manufacturing or monitoring system (e.g., a sensing system). The measurable environmental variables comprise at least one of physical, chemical, and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

An analyte can include any desired measured environmental parameter.

Interference includes an undesired environmental parameter that undesirably affects the accuracy and precision of measurements with the sensor. An interference includes a fluid or an environmental parameter (that includes, but is not limited to temperature, pressure, light, etc.) that potentially may produce an interference response by the sensor.

A multivariate analysis can refer to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. A principal components analysis (PCA) includes a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

Spectral parameters or spectrum parameters may be used to refer to measurable variables of the impedance response of the sensor. The impedance sensor response is the impedance spectrum of the non-resonance sensor circuit of the CR (capacitance (C)-resistance (R)) sensor. The impedance sensor response is the impedance spectrum of the resonance sensor circuit of the LCR (inductance (L)-capacitance (C)-resistance (R)) or RFID (radio-frequency identification) sensor. In addition to measuring the impedance spectrum in the form of Z-parameters, S-parameters, and other parameters, the impedance spectrum (both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), and the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra (such as non-resonance or resonance spectra), are called here "features" or "descriptors." The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

A resonance impedance or impedance may refer to measured sensor frequency response from which the sensor spectral parameters are extracted.

Sensing materials and/or sensing films may include, but are not limited to, materials deposited onto a transducer's electronics module, such as electrodes of the CR or LCR circuit components or an RFID tag, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the CR or the LCR or RFID sensor, the impedance sensor response changes as a function of pH. Thus, such as a CR or LCR or RFID sensor works as a pH sensor. When such a polyaniline film is deposited onto the CR or LCR or RFID sensor for detection in gas phase, the impedance sensor response also changes upon exposure to basic (for example, NH3) or acidic (for example, HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensing material. In order to prevent the material in the sensor film from leaching into the liquid environment, the sensing materials are attached to the sensor surface using standard techniques, such as covalent bonding, electrostatic bonding, and other standard techniques known to those of ordinary skill in the art. In addition, the sensing material has at least two temperature-dependent response coefficients related to temperature-dependent changes in material dielectric constant and resistance of the sensing material.

Transducer and/or sensor may be used to refer to electronic devices such as CR, LCR or RFID devices intended for sensing. Transducer can be a device before it is coated with a sensing film or before it is calibrated for a sensing application. A sensor may be a device typically after it is coated with a sensing film and after being calibrated for the sensing application.

Figure 66:
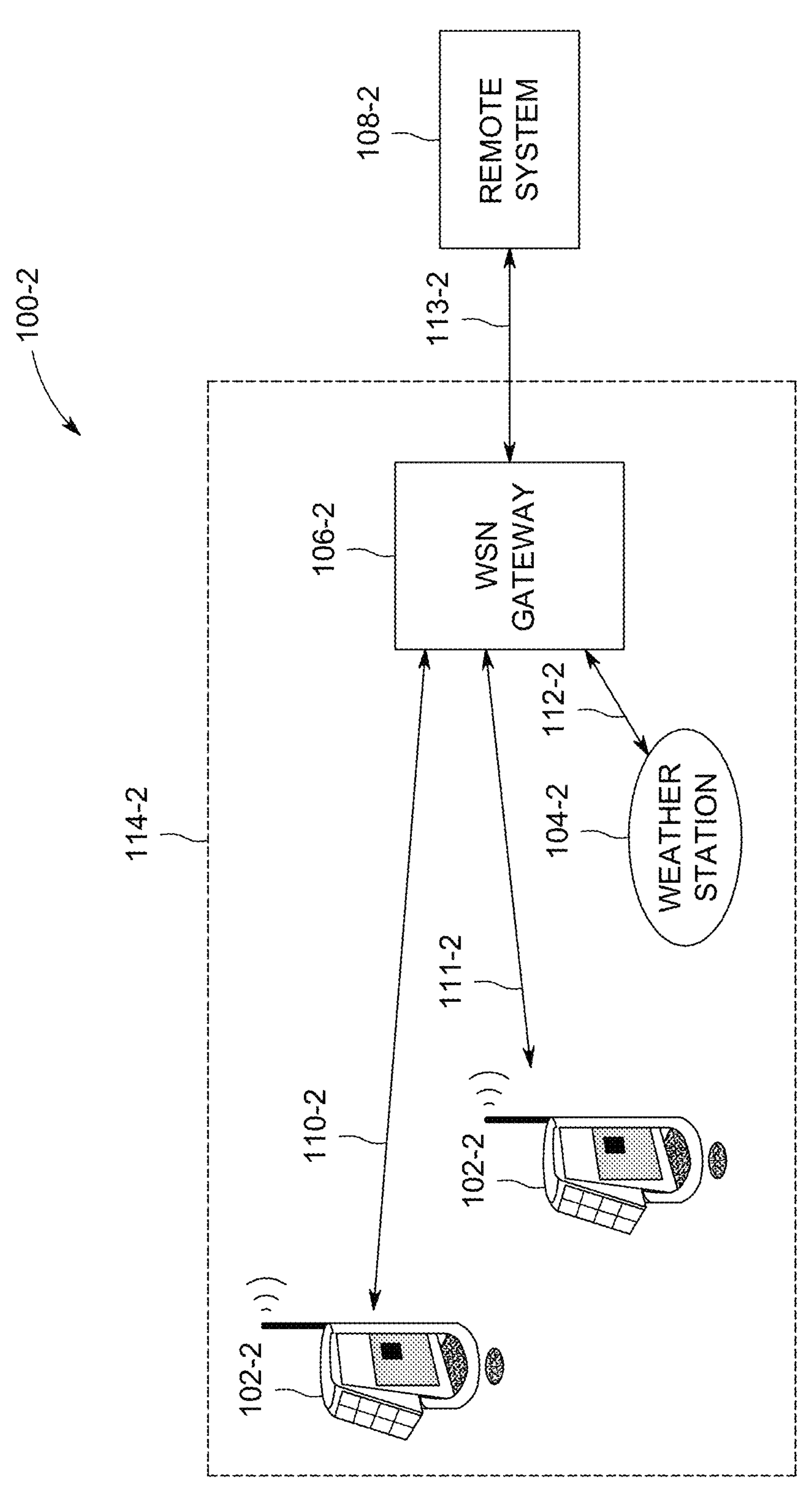
FIG. 66 is a schematic diagram of one embodiment of a wireless sensing network.

FIG. 66 is a schematic diagram of a wireless sensor network (WSN) 100-2, in accordance with an embodiment. The WSN 100-2 includes a remote system 108-2 and one or more sensor nodes 102-2. Optionally, the WSN 100-2 may include a weather station 104-2. The weather station 104-2 may be configured to acquire one or more ambient parameters (e.g., wind direction and/or speed, temperature, humidity, and/or the like) based on the environment of the WSN 100-2. The weather station 104-2 may include an anemometer, thermometer, barometer, hygrometer, pyranometer, rain gauge, and/or the like. For example, the weather station 104-2 may be configured to acquire a wind speed, a wind direction, temperature, and/or the like of a geographical area (e.g., a regional site 114-2) proximate to the sensor nodes 102-2 of the WSN 100-2. The nodes 102-2 and/or the weather station 104-2 may be communicatively coupled to the remote system 108-2 via one or more bi-directional communication links 110-2 to 113-2. Optionally, the data from the weather station 104-2 may be synchronized with responses of the sensor nodes 102-2 to provide more accurate sensor readings of the environmental parameters.

The remote system 108-2 is communicatively coupled to the sensor nodes 102-2 via one or more bi-directional communication links 110-2 to 113-2. The bi-directional communication links may be based on one or more standard wireless protocols such as Bluetooth Low Energy, Bluetooth, WiFi, 802.11, ZigBee, and/or the like. The bi-directional communication links may be configured to exchange data (e.g., environmental parameters, ambient parameters, operational status, and/or the like) between components (e.g., node 102-2, Weather station 104-2, remote system 108-2, and/or the like) of the WSN 100-2.

Optionally, the sensor nodes 102-2 may be connected wirelessly or wired to the Internet of Things and/or to the Industrial Internet via a PREDIX™ software platform (General Electric Company) for the use in asset optimization, industrial automation, machine diagnostics, optimization of industrial, healthcare, manufacturing and infrastructure management processes, to monitor asset production performance with a view to identifying trends, predicting outage, and other conditions.

Additionally or alternatively a WSN Gateway 106-2 may be communicatively interposed between the remote system 108-2 and one or more of the sensor nodes 102-2 and/or weather station 104-2. For example, the WSN Gateway 106-2 is configured to communicatively couple the nodes 102-2 and the weather station 104-2 together to form the regional site 114-2. The WSN Gateway 106-2 may communicatively couple the regional site 114-2 to the remote system 108-2 via the bi-directional communication link 113-2. It may be noted that in various embodiments, the remote system 108-2 may be communicatively coupled to a plurality of regional sites 114-2. For example, each of the regional sites 114-2 may correspond to different geographical locations. Additionally or alternatively, the regional sites 114-2 may correspond to an area proximate to a section of an industrial site and/or commercial site, an exhaust outlet, and/or the like. Optionally, the WSN Gateways 106-2 may be configured to bridge different wireless protocols. For example, the bi-directional communication links 110-2 to -112-2 within the regional site 114-2 may utilize a different wireless protocol relative to the bi-directional communication link 113-2.

The weather station 104-2 may be a federal, state and/or private weather station located in general area of interest outside the area 114-2. In this case the bi-directional communication link 112-2 may be replaced with a one-way communication of data from the weather station to the WSN Gateway 106-2 and/or to the remote system 108-2.

The remote system 108-2 may be a part of the Internet and/or other remote-based net, server, database, cloud and/or any other source of remote data storage and processing.

Optionally, the sensor nodes 102-2 of this invention may be combined with mobile robotic devices (e.g., for location and validation of pollution, homeland security threat, and other sources), GPS sub-systems, public or personal transportation vehicles for pollution and homeland security threat monitoring with a significant benefit of matching vehicle/sensor maintenance schedules.

Additionally or alternatively, the sensor nodes 102-2 may be implanted or incorporated in different objects, articles, items for real-time monitoring of chemical, biological, and physical parameters. Non-limiting examples of implanting or incorporation of the sensor nodes 102-2 into an industrial or consumer infrastructure or components may include stationary industrial infrastructure, moving industrial outdoors infrastructure, industrial indoors infrastructure, urban outdoors infrastructure, urban indoors infrastructure, roads, buildings, bridges, vehicles, wind power turbines, aircraft engines, single-use and multiple use bioprocess components, consumer products, home appliances, consumer appliances, sports equipment, laboratory equipment, laboratory analytical instrumentation, and/or the like.

Figure 67:
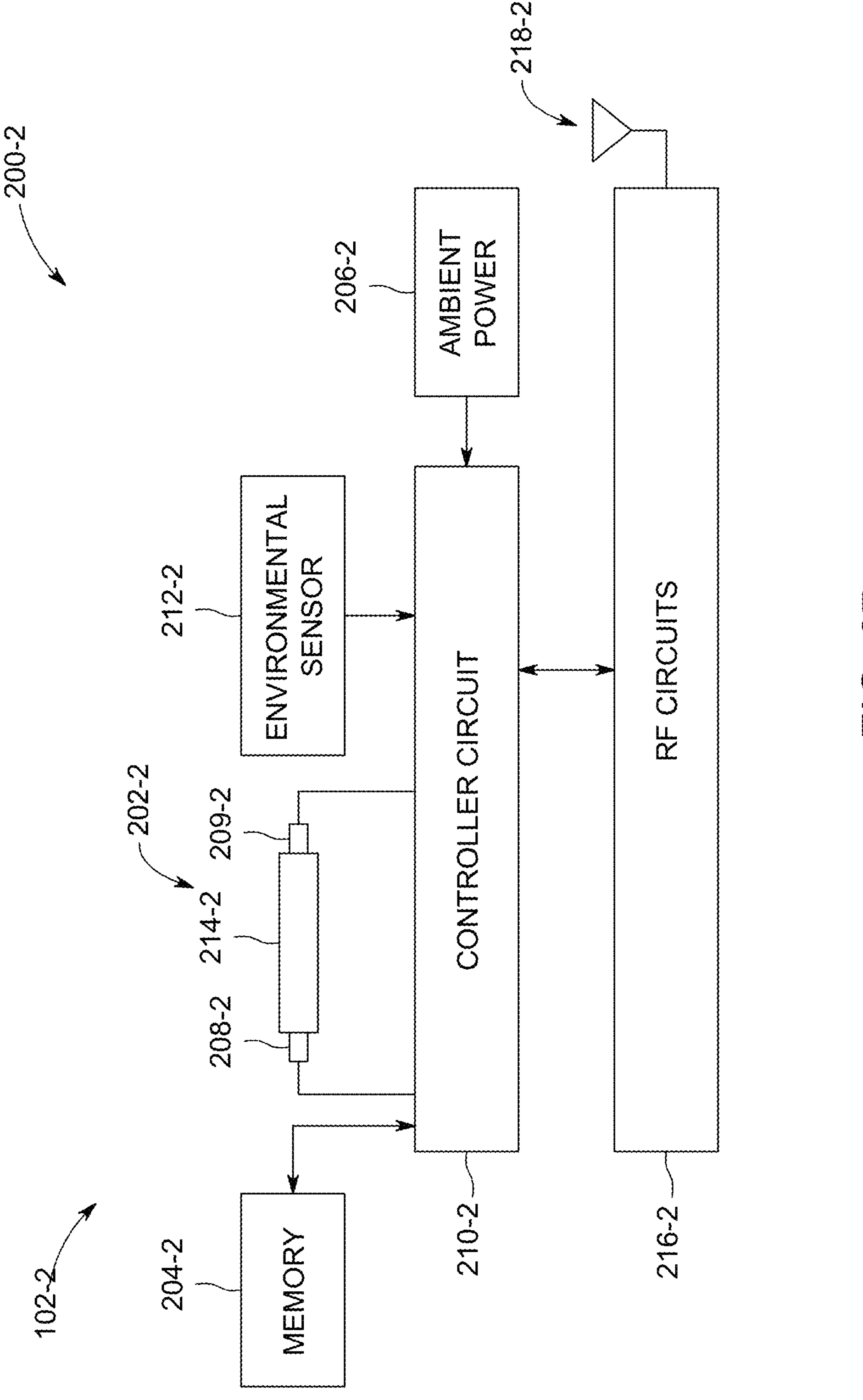
FIG. 67 is a schematic diagram of a sensor node of one embodiment of the wireless sensing network system of FIG. 66.

FIG. 67 is a schematic diagram 200-2 of the sensor node 102-2 of one embodiment of the WSN 100-2. The sensor node 102-2 includes a controller circuit 210-2, a memory 204-2, a sensor 202-2, an environmental sensor 212-2, a radio frequency (RF) circuit 216-2, and an ambient power source 206-2.

The memory 204-2 is an electronic storage device configured to store information acquired from the sensor 202-2 (e.g., an impedance spectrum, a transfer function, and/or the like), the environmental sensor 212-2, and/or the like. The contents of the memory 204-2 may be accessed by the controller circuit 210-2, the RF circuit 216-2, and/or the like. The memory 204-2 may include protocol firmware that may be accessed by the controller circuit 210-2. The protocol firmware may provide the wireless protocol syntax for the controller circuit 210-2 to assemble data packets, establish the bi-directional communication links 111-2 to -112-2 based on the wireless protocol, partition data from the data packets, and/or the like. The protocol syntax may include specifications on the structure of packets (e.g., frame size, packet specifications, appropriate number of bits, frequency, and/or the like) that are received and/or transmitted by the sensor node 102-2. The memory 204-2 may include flash memory, RAM, ROM, EEPROM, and/or the like.

The controller circuit 210-2 is configured to control the operation of the sensor node 102-2 and obtains measurements representing environmental and ambient parameters acquired by the sensor 202-2 and the environmental sensor 212-2. In various embodiments, the controller circuit 210-2 may be configured to apply a stimulation waveform to the sensor 202-2. The stimulation waveform may be an electrical stimulus configured to be a sinusoidal waveform having an amplitude (e.g., voltage, current, and/or the like) and a dynamic frequency. Optionally, the controller circuit 210-2 may adjust the frequency of the stimulation waveform over time. For example, the controller circuit 210-2 may adjust the frequency of the stimulation waveform between frequencies of a resonate bandwidth of the sensor 202-2. In another example, the stimulation waveform may adjust the frequency of the stimulation waveform between frequencies of a scanning bandwidth of the sensor 202-2. The scanning bandwidth includes a range of frequencies that are non-resonate frequencies of the sensor 202-2. Additionally or alternatively, the electrical stimulus may be configured to have a static frequency. For example, the electrical stimulus may have frequency at and/or about a resonant frequency of the sensor 202-2.

The controller circuit 210-2 is configured to acquire an impedance response of the sensor 202-2 in response to the stimulation waveform. The controller circuit 210-2 may be embodied in hardware, such as a processor, controller, or other logic-based device, that performs functions or operations based on one or more sets of instructions (e.g., software). The instructions on which the hardware operates may be stored on a tangible and non-transitory (e.g., not a transient signal) computer readable storage medium, such as the memory 204-2. Alternatively, one or more of the sets of instructions that direct operations of the hardware may be hard-wired into the logic of the hardware.

The RF circuit 216-2 may be configured to handle and/or manage the bi-directional communication links between the sensor node 102-2 and the remote system 108-2, the WSN Gateway 106-2, and/or the like. The RF circuit 216-2 is controlled by the controller circuit 210-2 and may support one or more wireless communication protocols. For example, the wireless communication protocols may include Bluetooth low energy, Bluetooth, ZigBee, WiFi, 802.11, and/or the like. Protocol firmware may be stored in the memory 204-2, which is accessed by the controller circuit 210-2. The protocol firmware provides the wireless protocol syntax for the controller circuit 210-2 to assemble data packets, establish one or more bi-directional communication links, and/or partition data received from other components of the WSN 100-2 (e.g., the remote system 108-2, WSN Gateway 106-2, weather station 104-2, another sensor node 102-2, and/or the like).

The environmental sensor (e.g., environmental sensor suite) 212-2 may be configured to acquire ambient parameters (e.g., temperature, humidity, and/or the like) of the environment (e.g., not the analytes of interest) proximate to the sensor node 102-2 and/or exposed by the environmental sensor 212-2. The environmental sensor 212-2 includes a thermistor, a thermocouple, a humidity sensor, a photosensor, an anemometer, and/or the like. The environmental sensor 212-2 may generate one or more sensor measurement signals, which are obtained by the controller circuit 210-2. The sensor measurement signals may be a digital signal representing one or more measurement values representing the one or more ambient parameters (e.g., temperature, humidity) acquired by the environmental sensor 212-2. Additionally or alternatively, the sensor measurement signals may be one or more analog signals having a predetermined electrical characteristic (e.g., frequency, amplitude, phase, and/or the like) representing the one or more measurement values representing the one or more ambient parameters acquired by the environmental sensor 212-2.

The ambient power source 206-2 may be configured to generate electrical power (e.g., current, voltage) for the one or more components of the sensor node 102-2. The ambient power source 206-2 may be an energy harvester configured to generate electrical power derived from the ambient environment (e.g., sunlight, thermal energy, wind energy, kinetic energy, electromagnetic radiation, and/or the like) proximate to the sensor node 102-2. For example, the ambient power source 206-2 may include a solar panel (e.g., photovoltaic generator), a thermoelectric generator, a wind turbine, piezoelectric material, and/or the like. Additionally or alternatively, the ambient power source 206-2 may be electrically coupled to an electrical storage device (not shown), such as a battery, capacitor, and/or the like. For example, the electrical storage device may be configured to supplement and/or complement electrical power generated by the ambient power source 206-2 when the power generated by the source 206-2 is deficient to power the components of the sensor node 102-2.

Additionally or alternatively, the sensor node 102-2 may include a heater (not shown). The heater may be thermally coupled to the sensor 202-2, and is configured to generate thermal energy. For example, the heater may include one or more heating elements configured to convert electrical power (e.g., current, voltage) to generate thermal energy (e.g., heater). The amount of thermal energy generated by the heater may be based on instructions received by the controller circuit 210-2. For example, the heater may increase a temperature of the sensor 202-2 at least 50 degrees Celsius above the ambient temperature measured by the environmental sensor 212-2.

The sensor 202-2 is configured to measure and/or detect a presence of one or more analytes of interest within the ambient (e.g., in operational contact with the sensing material 214-2, proximate to, surrounding area, within a predetermined distance of a surface are of the sensing material 214-2, and/or the like) environment of the sensor 202-2. For example, the sensor 202-2 may be a multivariable gas sensor. The sensor 202-2 includes at least one pair of electrodes 208-2-209 and a sensing material 214-2. The electrodes 208-2-209 are conductors that are electrically coupled to the sensing material 214-2 and the controller circuit 210-2. For example, the electrodes 208-2-209 are in contact with the sensing material 214-2. The electrodes 208-2-209 are configured to deliver the stimulation waveform generated by the controller circuit 210-2 to the electrodes 208-2-209 and to the sensing material 214-2.

The sensing material 214-2 is configured to predictably and reproducibly affect and adjust the impedance of the sensor 214-2 in response to changes in the environment. For example, characteristics (e.g., magnitude of the real part of the impedance, magnitude of the imaginary part of the impedance, phase of the impedance, and/or the like) of the impedance of the sensing material 214-2 are adjusted based on a concentration, presence, and/or the like of the analyte of interest within the ambient environment of the sensor 202-2. The sensing material 214-2 is in operational contact with the ambient environment. For example, at least a portion of a surface area of the sensing material 214-2 is exposed to and/or in contact with the environment adjacent to the sensor 202-2, which changes an electrical property (e.g., inductance) of the sensing material 214-2. The sensing material 214-2 may be a semiconducting polymer (e.g., polyaniline film, Nafion) and/or a dielectric polymer (e.g., silicone adhesive). Additionally or alternatively, the sensing material 214-2 may include organic, inorganic (e.g., sol-gel film), biological, composite film (e.g., polyisobutylene film), a nano-composite film (e.g., electrospun polymer nanofibers, gold nanoparticle-polymer film, metal nanoparticle-polymer film, electrospun polymer nanofibers, electrospun inorganic nanofibers, electrospun composite nanofibers), n-type oxide semiconductor, p-type oxide semiconductor, graphene, carbon nanotubes, and/or the like that are configured to change an electrical and/or dielectric property based on an environment exposed to the sensing material 214-2.

Additionally or alternatively, the sensing material 214-2 may be a metal oxide. For example, the sensing material 214-2 may be a single-metal oxide such as ZnO, CuO, CoO, SnO2, TiO2, ZrO2, CeO2, WO3, MoO3, In2O3, and/or the like. In another example, the sensing material 214-2 may be a perovskite oxide having differently sized cations such as SrTiO3, CaTiO3, BaTiO3, LaFeO3, LaCoO3, SmFeO3, and/or the like. In another example, the sensing material 214-2 may be a mixed metal oxide composition such as CuO—BaTiO3, ZnO—WO3, and/or the like.

Optionally, the sensor 202-2 may be configured as a non-resonant circuit. Additionally or alternatively, the sensor 202-2 may be configured as a resonant circuit. For example, the sensor 202-2 may be a resonant circuit as described in the U.S. patent application entitled, "SYSTEMS AND METHODS FOR ENVIRONMENT SENSING" having docket number 285314-1US, which is incorporated by reference in its entirety.

Optionally, sensor 202-2 may be configured to operate using any detection principle that is applicable to measure the needed analyte or analytes. Non-limiting examples of such detection principles include non-resonant and resonant impedance sensors, electromechanical resonant sensors, field-effect transistor sensors, and photonic non-resonant and resonant sensors (such sensors may be multivariable sensors).

Figure 68:
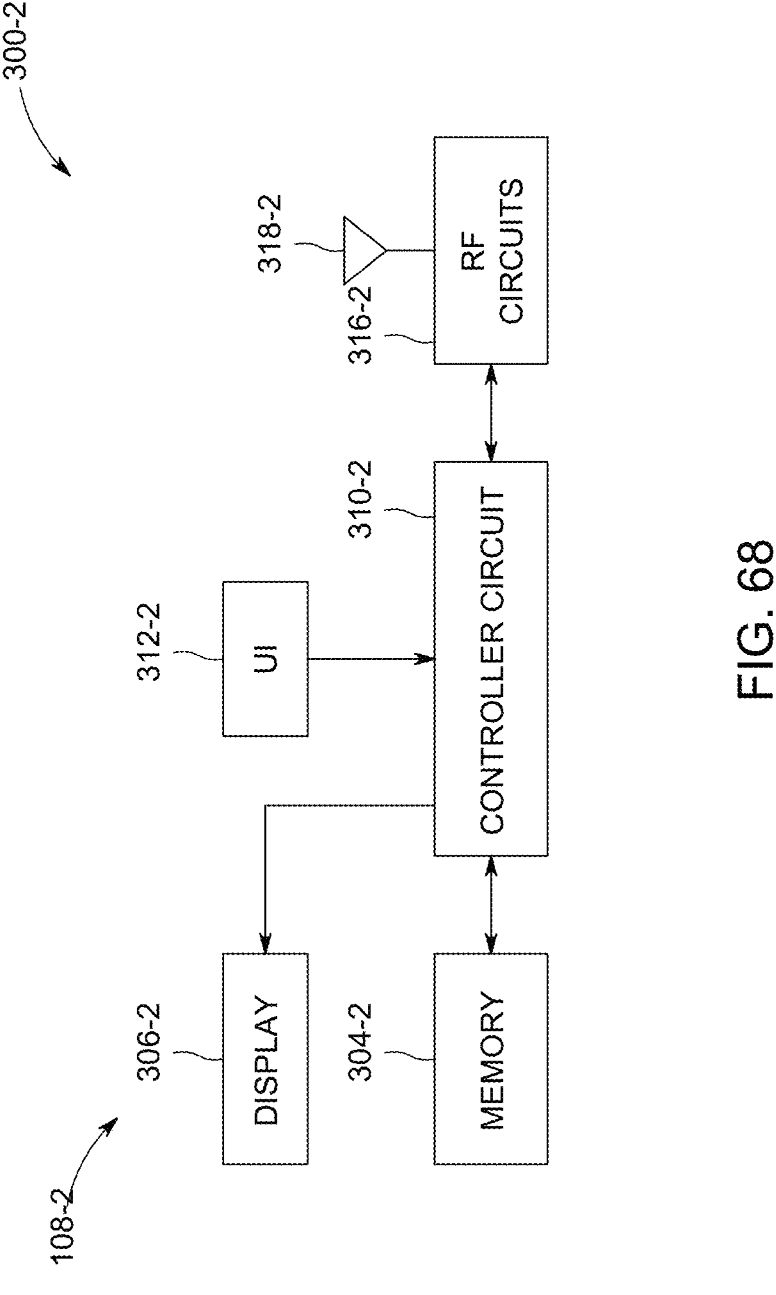
FIG. 68 is a schematic diagram of a remote system of one embodiment of the wireless sensing network system of FIG. 66.

FIG. 68 is a schematic diagram 300 of the remote system 108-2 of one embodiment of the WSN 100-2. The remote system 108-2 includes a controller circuit 310-2, a memory 304-2, a display 306-2, a user interface 312-2, and a radio frequency (RF) circuit 316-2. The memory 304-2 is an electronic storage device configured to store information acquired from one or more regional sites 114-2 of the WSN 100-2. For example, the memory 304-2 may include the environmental and ambient parameters received from one or more sensor nodes 102-2, ambient parameters received from the weather station 104-2, and/or the like. The memory 204-2 may include protocol firmware that may be accessed by the controller circuit 210-2. The protocol firmware may provide the wireless protocol syntax for the controller circuit 210-2 to assemble data packets, establish the bi-directional communication links 111-2 to 112-2 based on the wireless protocol, partition data from the data packets, and/or the like. The protocol syntax may include specifications on the structure of packets (e.g., frame size, packet specifications, appropriate number of bits, frequency, and/or the like) that are received and/or transmitted by the sensor node 102-2. The memory 204-2 may include flash memory, RAM, ROM, EEPROM, and/or the like. The contents of the memory 304-2 may be accessed by the controller circuit 310-2, the RF circuit 316-2, the display 306-2, and/or the like.

The RF circuit 316-2 may be configured to handle and/or manage the bi-directional communication links between the remote system 108-2 and the sensor nodes 102-2, the WSN Gateway 106-2, and/or the like. The RF circuit 316-2 is controlled by the controller circuit 310-2 and may support one or more wireless communication protocols. For example, the wireless communication protocols may include Bluetooth low energy, Bluetooth, ZigBee, WiFi, 802.11, and/or the like. Protocol firmware may be stored in the memory 304-2, which is accessed by the controller circuit 310-2. The protocol firmware provides the wireless protocol syntax for the controller circuit 310-2 to assemble data packets, establish one or more bi-directional communication links 113 and/or partition data received from other components of the WSN 100-2 (e.g., the WSN Gateway 106-2, the weather station 104-2, sensor nodes 102-2, and/or the like).

The controller circuit 310-2 is configured to control the operation of the remote system 108-2. In various embodiments, the controller circuit 310-2 is configured to analyze the impedance responses received from the sensor nodes 102-2 to determine the environmental parameters of the one or more analytes of interest. For example, the controller circuit 310-2 receives the impedance response of the sensor 202-2 measured by the controller circuit 210-2 along the bi-directional communication links 110-2, 111-2, 113-2 (FIG. 66). The controller circuit 310-2 analyzes the impedance response of the sensor 202-2 at frequencies that provide a linear response within a predetermined threshold (e.g., sufficiently linear) of the sensor 202-2 to the one or more analytes of interest. The controller circuit 310-2 may also be configured to analyze the impedance response of the sensor 202-2 at frequencies that provide a non-linear response, monotonic response or a non-monotonic response within a predetermined threshold of the sensor 202-2 to the one or more analytes of interest. The controller circuit 310-2 may be embodied in hardware, such as one or more processors, controller, or other logic-based device, that performs functions or operations based on one or more sets of instructions (e.g., software). The instructions on which the hardware operates may be stored on a tangible and non-transitory (e.g., not a transient signal) computer readable storage medium, such as the memory 304-2. Alternatively, one or more of the sets of instructions that direct operations of the hardware may be hard-wired into the logic of the hardware.

Additionally or alternatively, the controller circuit 310-2 may be configured to analyze the impedance response of the sensor 202-2 at a single or multiple frequencies. Nonlimiting examples of the controller circuit 310-2 include application specific integrated circuits (ASICs) such as SL900A (AMS AG) or AD5933 (Analog Devices), micro-network analyzers such as a Vector Network Analyzer MiniVNA Pro (Mini Radio Solutions), and/or the like.

The controller circuit 310-2 may be configured to include an electrical current sensor to monitor the current that is used by the sensor 202-2 and a gas flow sensor to monitor the air gas flow that is interacting with the sensor 202-2.

The controller circuit 310-2 is operably coupled to the display 306-2 and the user interface 312-2. The display 306-2 may include one or more liquid crystal displays (e.g., light emitting diode (LED) backlight), organic light emitting diode (OLED) displays, plasma displays, CRT displays, and/or the like. The display 306-2 may display one or more environmental parameters of the analytes of interest based on impedance responses received by the sensor nodes 102-2, geographical information of one or more regional sites 114-2 of the WSN 100-2, components of a graphical user interface, and/or the like received by the display 306-2 from the controller circuit 310-2.

The user interface 312-2 controls operations of the controller circuit 510 and is configured to receive inputs from the user. The user interface 312-2 may include a keyboard, a mouse, a touchpad, one or more physical buttons, and/or the like.

Optionally, the display 306-2 may be a touch screen display, which includes at least a portion of the user interface 312-2. For example, a portion of the user interface 312-2 may correspond to a graphical user interface (GUI) generated by the controller circuit 310-2, which is shown on the display. The GUI may include one or more interface components that may be selected, manipulated, and/or activated by the user operating the user interface 312-2 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

Figure 69:
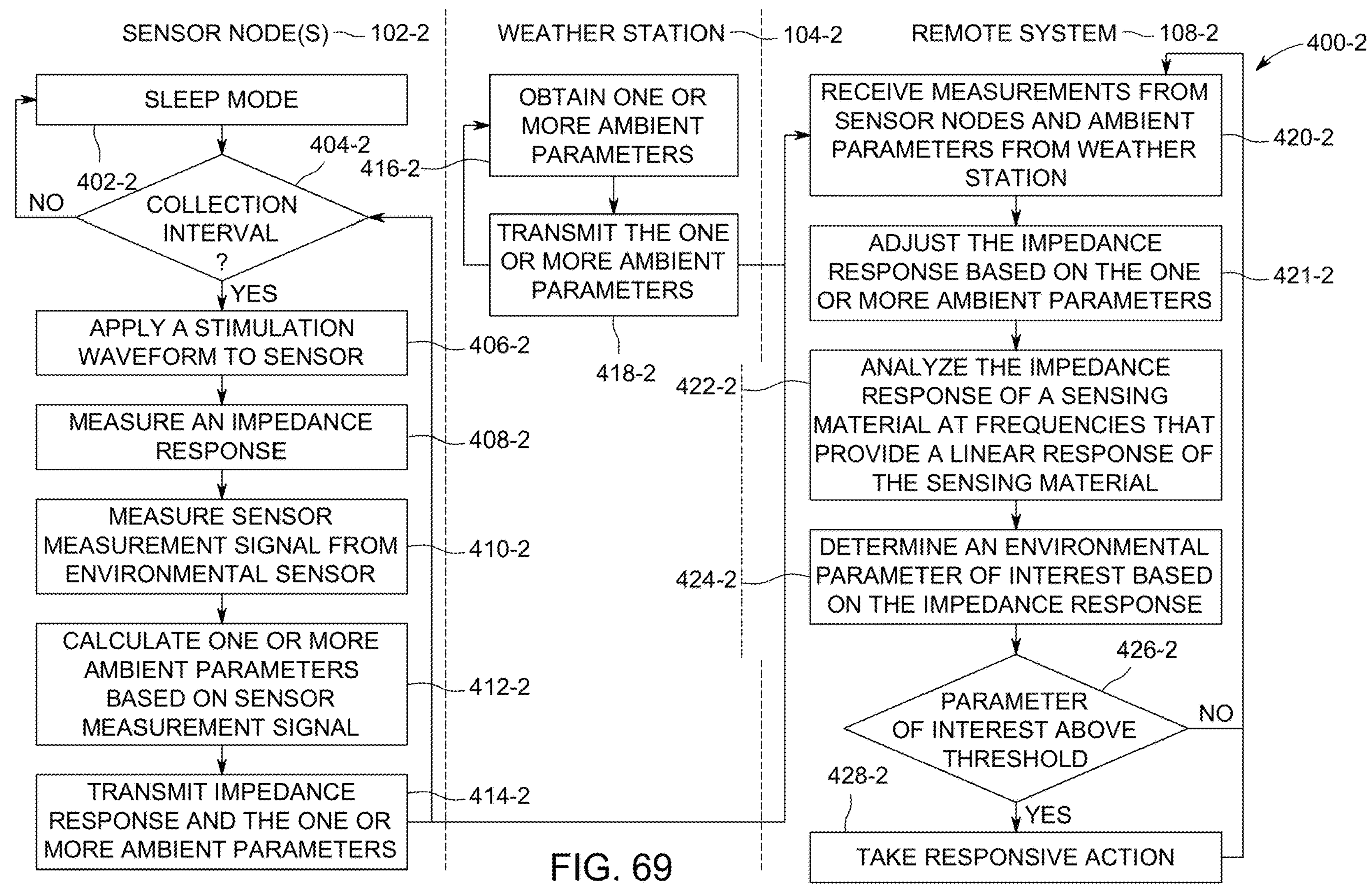
FIG. 69 is a "swim lane" diagram of one embodiment of a method for detecting one or more analytes of interest within a wireless sensor network.

FIG. 69 is a swim lane diagram of one embodiment of a method 400-2 for detecting one or more analytes of interest within a WSN 100-2. The method, for example, may employ or be performed by structures or aspects of various embodiments (e.g., systems and/or methods) discussed herein. For example, the method includes operations performed by and/or changes to the memory 204-2, 304-2, the controller circuit 210-2, 310-2, the sensor 202-2, and/or the like. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. In various embodiments, portions, aspects, and/or variations of the method may be able to be used as one or more algorithms to direct hardware to perform one or more operations described herein.

At 402-2, the controller circuit 210-2 of the sensor node 102-2 may enter a sleep mode (e.g., low power mode, hibernation mode, stand-by mode). During the sleep mode, the controller circuit 210-2 may be configured to reduce an amount of current utilized by the sensor node 102-2 relative to when not in the sleep mode. For example, during the sleep mode one or more components of the sensor node 102-2 do not receive power, such as the environmental sensor 212-2 and/or the RF circuit 216-2.

At 404-2, the controller circuit 210-2 may determine whether a collection interval is reached. The collection interval may be a length of time the controller circuit 210-2 is configured to obtain one or more impedance responses from the sensor 202-2 and/or the sensor measurement signal from the environmental sensor 212-2. The collection interval may be interposed between sleep intervals corresponding to durations when the controller circuit 210-2 enters a sleep mode. For example, the collection interval may be over a minute (e.g., range from 5-10 minutes) in length and is interposed between sleep intervals (e.g., ranging from 1-4 hours in length). It may be noted that the collection intervals and/or the sleep intervals may be similar to and/or the same for each sensor node 102-2 within the regional site 114-2.

When the controller circuit 210-2 determines that the collection interval is reached, at 406, the controller circuit 210-2 may apply a stimulation waveform to the sensor 202-2. In connection with FIG. 70, the controller circuit 210-2 may generate the stimulation waveform, which is received by the sensing material 214-2 utilizing the pair of electrodes 208-2-209 in contact with the sensing material 214-2. The stimulation waveform is conducted through the electrodes 208-2-209 and is received by the sensing material 214-2.

Figure 70:
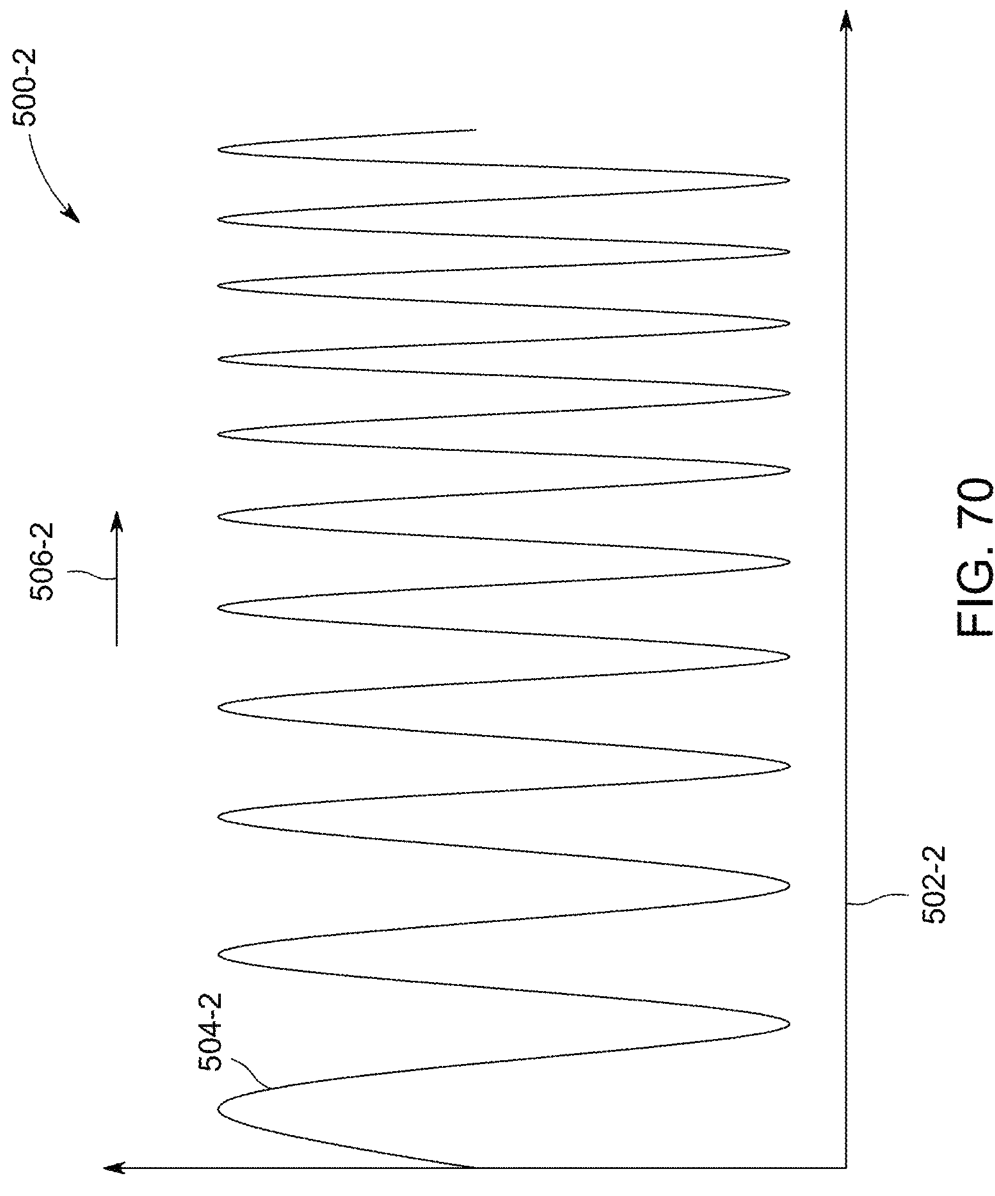
FIG. 70 shows a graphical illustration of one embodiment of a stimulation waveform applied to a sensing material of a sensor.

FIG. 70 is a graphical illustration 500-2 of a stimulation waveform 504-2 applied to the sensing material 214-2 of the sensor 202-2. The stimulation waveform 504-2 may be generated by the controller circuit 210-2. The stimulation waveform 504-2 may be an electrical stimulus having an amplitude (e.g., voltage, current, and/or the like) and a dynamic frequency. For example, the stimulation waveform is shown plotted along a horizontal axis 502-2 representing time. Over time, the controller circuit 210-2 may adjust (e.g., increase, decrease) the frequency of the stimulation waveform. For example, as shown in FIG. 70, the controller circuit 210-2 may increase the frequency of the stimulation waveform along the axis 502-2 in a direction of an arrow 506-2. In various embodiments, the stimulation waveform 504-2 may be a chirp and/or sweep signal.

Optionally, a range of the frequencies of the stimulation waveform is adjusted by the controller circuit 210-2 based on a frequency bandwidth. The frequency bandwidth may be a defined range of frequencies centered at a resonance frequency of the sensor 202-2 (e.g., configured to a part of a non-resonant or a resonant circuit). Additionally or alternatively, the range the frequency of the stimulation waveform is adjusted by the controller circuit 210-2 based on one or more scanning bandwidths. The scanning bandwidths may be a range of frequencies that are non-resonant frequencies of the sensor 202-2. For example, the scanning bandwidths may be utilized by the controller circuit 210-2 when the sensor 202-2 is configured a part of a non-resonant circuit.

At 408-2, the controller circuit 210-2 measures an impedance response of the sensor 202-2. For example, the controller circuit 210-2 may receive a measurement signal generated by the sensing material 214-2 from the electrodes. The measurement signal is representative of an impedance response of the sensing material 214-2 in operational contact with the ambient environment. For example, the measurement signal may have electrical characteristics (e.g., voltage, current, frequency, and/or the like), which is utilized by the controller circuit 210-2 to calculate the impedance response.

Figure 71A:
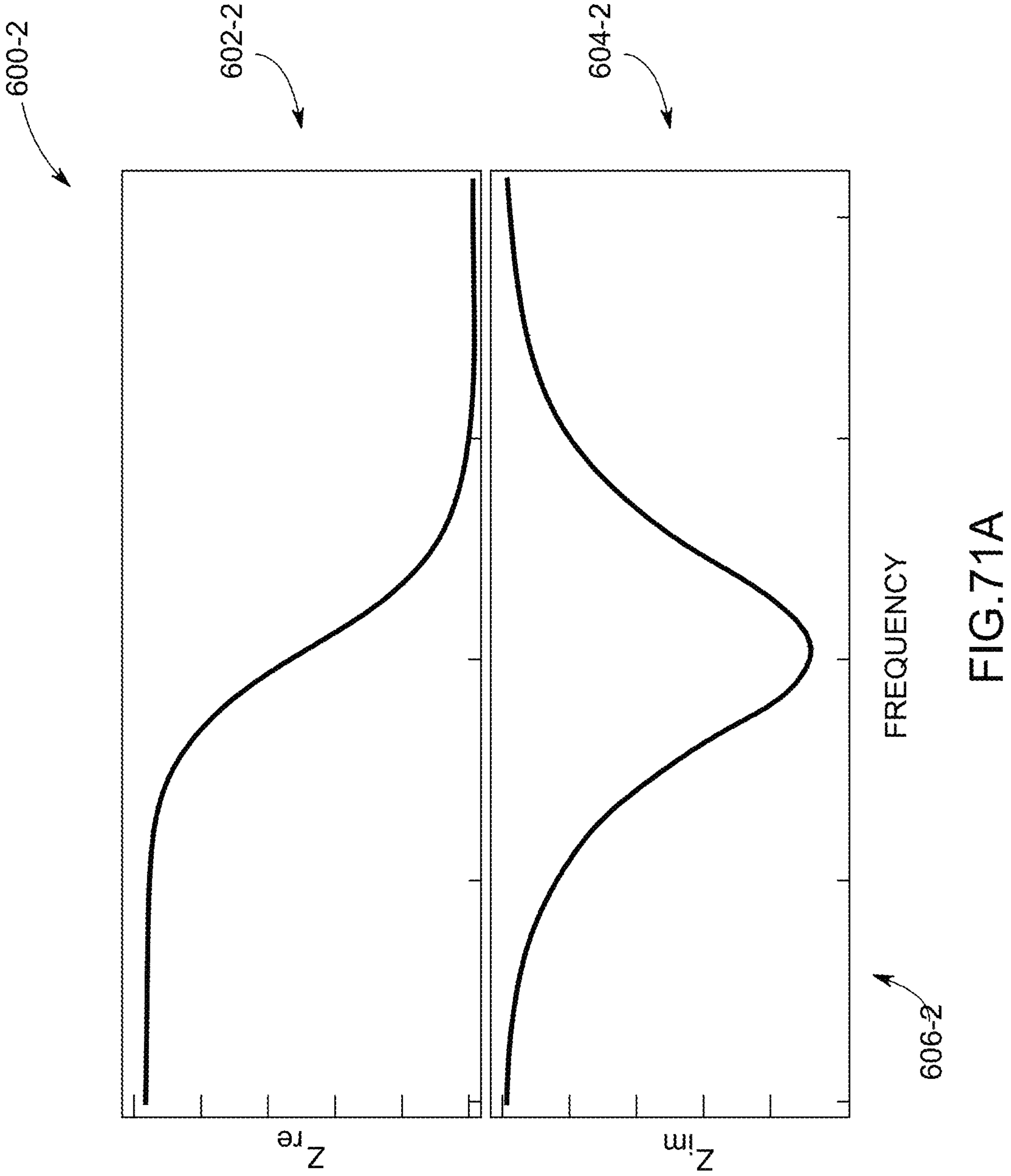
FIG. 71A shows graphical illustrations of a measured response corresponding to a non-resonance impedance response of a sensor, in accordance with an embodiment.
Figure 71B:
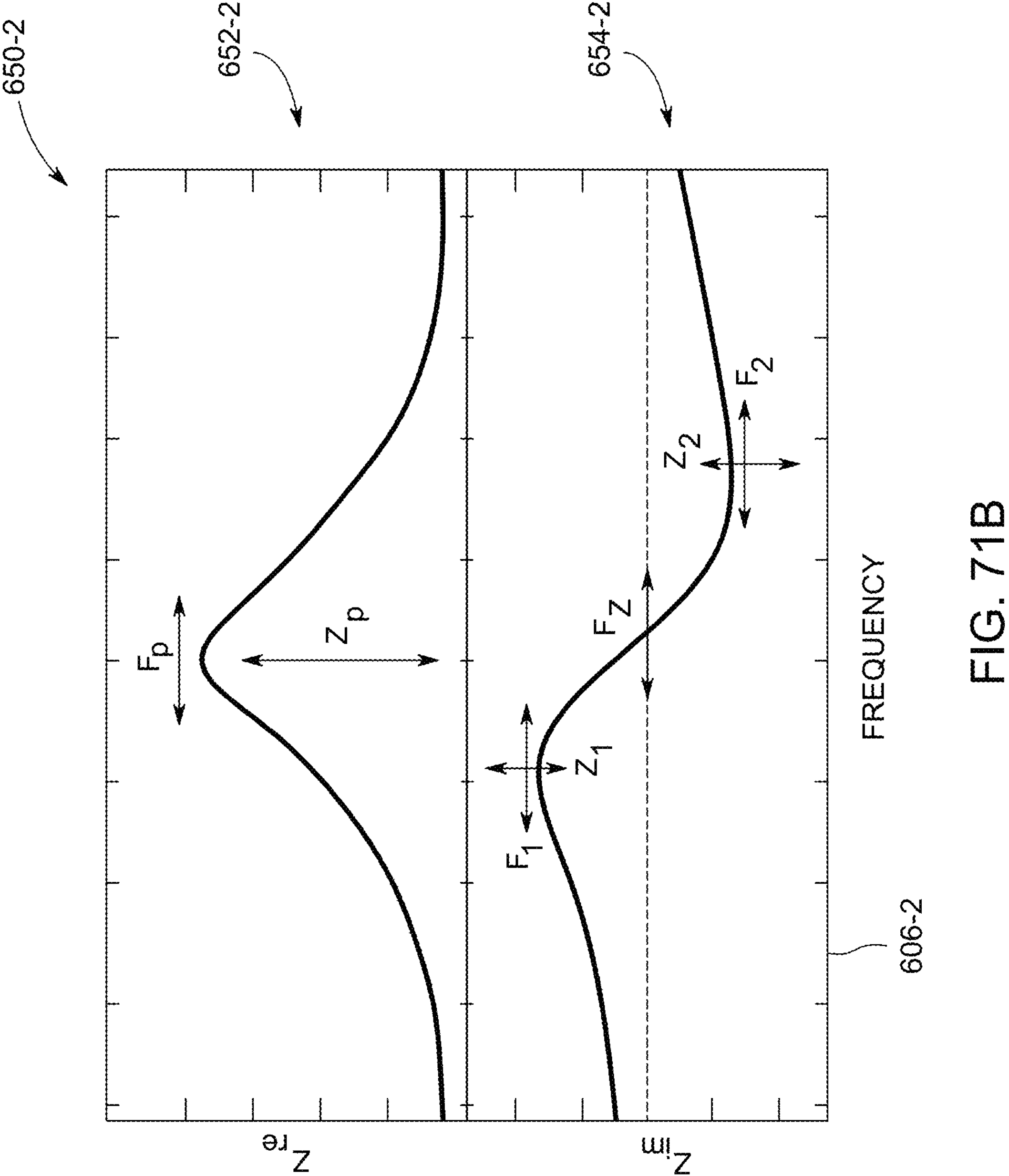
FIG. 71B shows graphical illustrations of a measured response corresponding to a resonance impedance response of a sensor, in accordance with an embodiment.

FIGS. 71A-B illustrate a graphical illustration of measured responses 600-2, 650-2 corresponding to a real and imaginary impedance responses 602-2, 604-2, 652-2, 654-2 of the sensor 202-2, in accordance with an embodiment.

For example, the impedance response 600-2 may represent the impedance sensor response of the sensor 202-2 configured as a non-resonant sensor based on the stimulation waveform 504-2 generated by the controller circuit 210-2. The impedance response 650-2 may represent the impedance sensor response of the sensor 202-2 configured as a resonant sensor based on a stimulation waveform generated by the controller circuit 210-2. The impedance responses 600-2, 650-2 are measured by the controller circuit 210-2 based on a measurement signal. For example, the controller circuit 210-2 may receive the measurement signal from the electrodes in contact with the sensing material 214-2. The measurement signal is an electrical signal generated by the sensing material 214-2 in response to the stimulation waveform 504-2 and the ambient environment exposed by the sensing material 214-2. The measurement signal is representative of the impedance response of the sensing material 214-2. For example, the measurement signal may have electrical characteristics (e.g., voltage, current, frequency, and/or the like), which may be utilized by the controller circuit 210-2 to calculate the impedance responses 600-2, 650-2. The impedance responses are divided into real portions 602-2, 652-2 corresponding to the real impedance, Zre(f) of the impedance responses, and imaginary portions 604-2, 654-2 of an imaginary impedance, Zim(f).

At 410-2, the controller circuit 210-2 may measure one or more sensor measurement signals from the environmental sensor 212-2. For example, the controller circuit 210-2 may receive the sensor measurement signals from the environmental sensor 212-2. Based on the electrical characteristics (e.g., amplitude, voltage, frequency, bit sequence, and/or the like) of the sensor measurement signals the controller circuit 210-2 may determine one or more values representing the ambient parameters (e.g., temperature, humidity, and/or the like).

At 412-2, the controller circuit 210-2 may calculate one or more ambient parameters (e.g., temperature, humidity, and/or the like) based on the sensor measurement signal. For example, based on a voltage of one of the sensor measurement signals the controller circuit 210-2 may determine a temperature measured by the environmental sensor 212-2.

At 414-2, the controller circuit 210-2 instruct the RF circuit 216-2 to transmit the impedance response and the one or more ambient parameters. For example, the controller circuit 210-2 may form a data packet based on the wireless protocol stored in the memory 204-2. The data packet includes information associated with the impedance response (e.g., impedance response 600-2, 650-2) that includes a real portion (e.g., real portions 602-2, 652-2) of the impedance response corresponding to the real impedance, Zre(f) of the impedance responses, and an imaginary portion (e.g., imaginary portion 604, 654) of an imaginary impedance, Zim(f). Additionally or alternatively (e.g., in subsequent and/or preceding data packet), the data packet includes information associated with the one or more ambient parameters (e.g., temperature, pressure, humidity, wind speed values) based on the sensor measurement signals generated by the environmental sensor 212-2.

The data packets transmitted by the RF circuit 216-2 may further include a time stamp. The time stamp may represent a global time value of the WSN 100-2 corresponding to when the data packet was transmitted by the RF circuit 216-2. Additionally or alternatively, the time stamp may represent when the impedance response and/or sensor measurement signals was measured by the controller circuit 210-2. The global time value is based on a network clock of the WSN 100-2. For example, the controller circuits 210-2, 310-2 and the weather station 104-2 may each utilize a system clock. When the bi-directional communication links are established, the components of the WSN 100-2 may synchronize the system clocks within the components of the WSN 100-2 to one of the system clocks designated as a network clock utilizing a clock synchronization protocol such as a network time protocol (NTP), a precision time protocol, based on global position system, and/or the like. For example, the controller circuits 210-2, 310-2 and/or the weather station 104-2 may execute the NTP to align the system clocks of the sensor nodes 102-2 and the weather station 104-2 to the system clock of the remote system 108-2, which may be designated as the network clock of the WSN 100-2.

During the collection interval, the controller circuit 210-2 may repeat operations 406-2 through 414-2. In various embodiments, the controller circuit 210-2 may continually repeat these operations until the collection interval is terminated and/or a sleep interval is reached. A rate at which the operations are performed may depend on a performance specification (e.g., processing speed) of the controller circuit 210-2. For example, the controller circuit 210-2 may be configured to continually collect and/or transmit the impedance response and the one or more ambient parameters every second.

At 416-2, the weather station 104-2 may obtain one or more ambient parameters (e.g., wind direction and/or speed, temperature, humidity, and/or the like). For example, the weather station 104-2 may determine a wind direction and speed utilizing one or more sensors (e.g., anemometer) of the weather station 104-2 of a geographical area proximate to the sensor nodes 102-2 of the WSN 100-2, such as the area formed by the regional site 114-2.

At 418-2, the weather station 104-2 transmits the one or more ambient parameters to the remote system 108-2. For example, the one or more ambient parameters may be included in a data packet based on the wireless protocol corresponding to the bi-directional communication link 112-2. The data packets transmitted by the weather station 104-2 may further include a time stamp similar to and/or the same as the time stamp included in the data packet transmitted by the RF circuit 216-2. Optionally, the weather station 104-2 may transmit the one or more ambient parameters continually not based on the collection interval, as shown in FIG. 69. For example, the weather station 104-2 may transmit data packets continually. Additionally or alternatively, the weather station 104-2 may transmit the one or more ambient parameters periodically. For example, the weather station 104-2 may transmit the one or more ambient parameters during the collection interval similar to and/or the same as the sensor nodes 102-2 of the WSN 100-2. Additionally or alternatively, the weather station 104-2 may not be included within the WSN 100-2.

At 420-2, the RF circuit 316-2 may receive the measurements (e.g., the impedance response, one or more ambient parameters) from the sensor nodes 102-2 and the one or more ambient parameters from the weather station 104-2. For example, the RF circuit 316-2 may receive the measurements from the sensor nodes 102-2 within via the bi-directional communication link 110-2, 111-2, and 113-2. In another example, the RF circuit 316-2 may receive the one or more ambient parameters from the weather station 104-2 via the bi-directional communication links.

The controller circuit 310-2 may align the received measurements and the one or more ambient parameters based on the time stamps included in the data packets received from the sensor nodes 102-2 and the weather station 104-2. By aligning the received measurements and the one or more ambient parameters, the controller circuit 310-2 may synchronize the data received from the sensor nodes 102-2 and the weather station 104-2 using the time stamps. For example, the controller circuit 310-2 may match the received measurements and the one or more ambient parameters having the same time stamps and/or time stamps within a predetermined threshold.

Additionally or alternatively, the alignment of the measurements (e.g., the impedance response, one or more ambient parameters) from the sensor nodes 102-2 and the one or more ambient parameters from the weather station 104-2 may be performed prior to being received by the RF circuit 316-2. For example, the WSN Gateway 106-2 may be configured to synchronize the data packets transmitted by the sensor nodes 102-2 and the weather station 104-2. The WSN Gateway 106-2 receives the data packets transmitted by the nodes 102-2 and the weather station 104-2 via the bi-directional communication links. The WSN Gateway 106-2 may partition the measurements and the one or more ambient parameters from received data packets having the same time stamps and/or time stamps within a predetermined threshold to generate a new aligned payload. The WSN Gateway 106-2 may form a new data packet having the aligned payload and transmit the new data packet to the remote system 108-2 via the bi-directional communication link 113-2. Additionally or alternatively, the WSN Gateway 106-2 may group the received data packets based on the time stamps to align the measurements and the one or more ambient parameters, which are transmitted successively to the remote system 108-2 via the bi-directional communication link 113-2.

At 421-2, the controller circuit 310-2 may adjust the impedance responses based on the one or more ambient parameters (e.g., temperature, humidity). The controller circuit 310-2 may compare the ambient parameters with an adjustment database stored in the memory 304-2. The adjustment database may include a plurality of candidate ambient parameters each having corresponding impedance adjustments to be performed by the controller circuit 310-2 based on the ambient parameter. When the controller circuit 310-2 matches an ambient parameter to the adjustment database, the controller circuit 310-2 adjust the impedance response according to the adjustment define within the adjustment database. For example, the controller circuit 310-2 may match an ambient parameter representing a humidity measured by the environmental sensor 121-2 in the adjustment database. Based on the humidity, the controller circuit 310-2 may adjust the impedance response by reducing or by increasing the impedance according to the adjustment database.

At 422-2, the controller circuit 310-2 may analyze the impedance response of the sensing materials 214-2 at frequencies that provide a linear response of the sensing materials 214-2. For example, the controller circuit 310-2 may calculate one or more spectral parameters based on a real portion (e.g., Fp, Zp) and/or imaginary portion (e.g., F1, F2, Fz, Z1, Z2) of the impedance response. The controller circuit 310-2 may be configured to analyze the spectral parameters that provide a linear response of the sensing material 214-2 to the analyte of interest and at least partially reject effects of interference analytes (e.g., analytes that are not the analyte of interest). Optionally, the one or more spectral parameters calculated by the controller circuit 310-2 may be based on a transfer function defining the linear relationship between the impedance response and a parameter of the analyte of interest.

Additionally or alternatively, the sensor nodes 102-2 may be configured to operate using any detection principle of a sensor that is applicable to measure the needed analyte or analytes of interest not utilizing non-resonant and resonant impedance detection principles as shown in FIG. 69. For example, such detection principles may include electromechanical resonant sensors, field-effect transistor sensors, photonic non-resonant and resonant sensors, and/or the like. Optionally, such sensors may be multivariable sensors.

The inspection apparatus and associated methods described herein facilitate improved collection of inspection data for industrial assets and, in particular, oil and gas equipment. More specifically, the inspection apparatus and methods described herein facilitate improved remote inspection of oil and gas equipment for purposes of locating and quantifying fluid leaks that may require intervention. To do so, the inspection apparatus described herein includes a range of sensors and equipment configured to collect data, to associate the collected data with a geographic location, and to transmit the data to a remote processing device for processing. Inspection apparatuses in accordance with this disclosure significantly reduce the amount of onboard processing required by the inspection apparatus by directly transmitting unprocessed data, including unprocessed image data, to the remote processing device. To facilitate transmission of the unprocessed data, the inspection apparatus includes at least two transmitters. The first transmitter is used for transmitting the unprocessed image data, while the second transmitter is used to transmit fluid concentration data and other signals from the inspection apparatus. By delegating data processing to the remote processing device, the inspection apparatus facilitates significant reductions in power consumption during an inspection mission. First, the inspection apparatus saves power by not performing on-board processing of the capture data. Second, by not requiring specialized data processing hardware, the overall weight of the inspection apparatus is reduced, thereby reducing the power required to navigate the inspection apparatus between points of interest. For example, by directly transmitting unprocessed image data to the remote processing device, the inspection apparatus does not require on-board image processing hardware, such as a graphics processing unit (GPU). The reduction in power facilitates longer inspection missions by the inspection apparatus and/or the inclusion of additional sensors on the inspection apparatus to provide a more complete inspection of the assets of interest.

Figure 72:
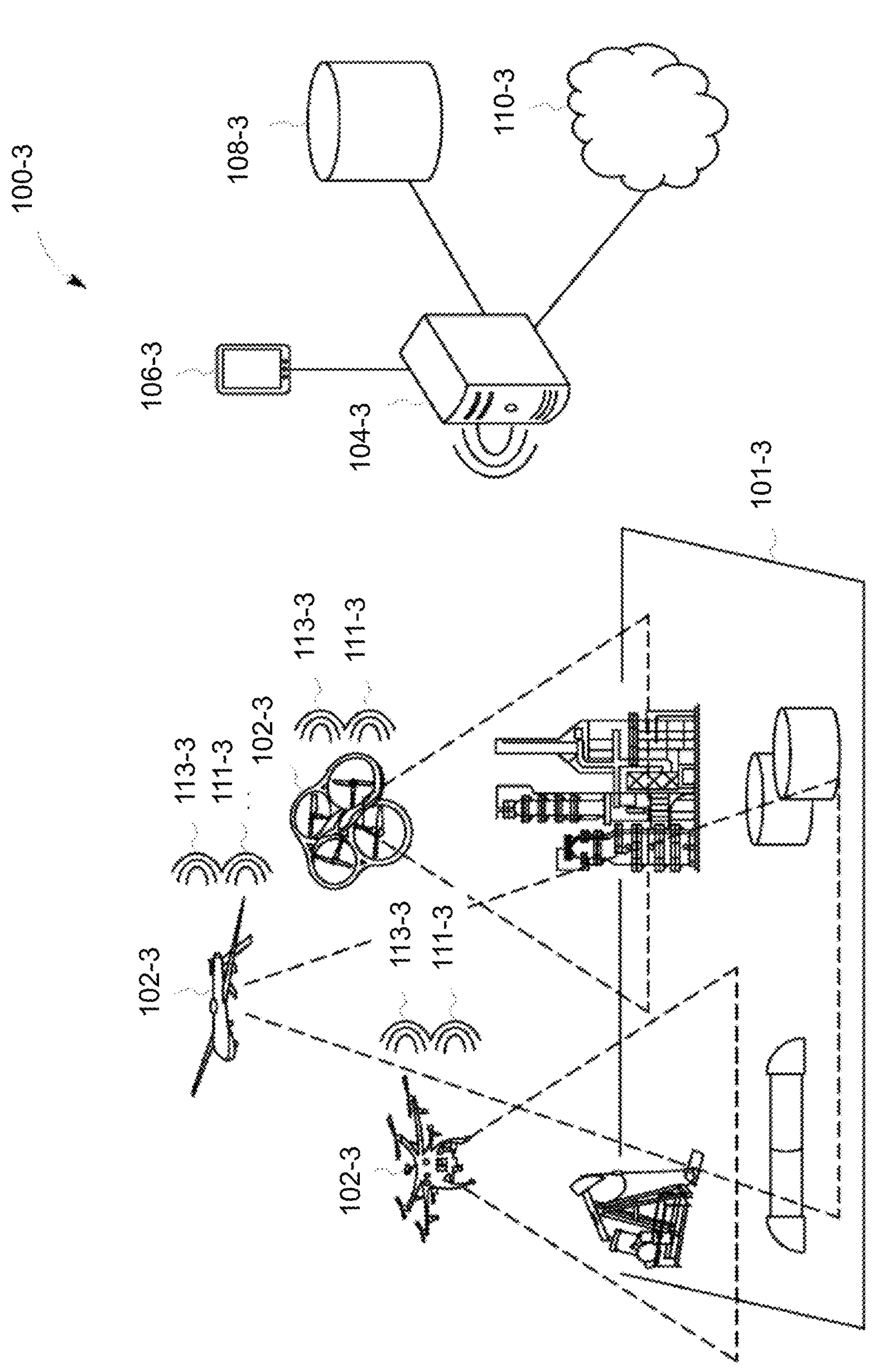
FIG. 72 is a schematic view of an example asset inspection system including one or more inspection apparatuses.

FIG. 72 is a schematic view of an exemplary asset inspection system 100-3 for inspecting industrial assets in a geographic region 101-3. In the exemplary embodiment, asset inspection system 100-3 is configured to inspect oil and gas equipment geographic region 101-3. Asset inspection system 100-3 includes one or more inspection apparatuses 102-3, which, in the exemplary embodiment, are inspection vehicles 102-3. Each of inspection vehicles 102-3 is capable of autonomous, semi-autonomous, and fully piloted navigation. Inspection vehicles 102-3 include, without limitation, aerial, ground-based, and water-based vehicles. Aerial vehicles include, without limitation, fixed wing aircraft, tilt-rotor aircraft, helicopters, multirotor drone aircrafts such as quadcopters, blimps, dirigibles, or other aircrafts. Ground-based inspection vehicles include, without limitation, wheeled vehicles, crawling or walking vehicles, vehicles with tracks, and air-cushioned vehicles (such as hovercrafts). Water-based vehicles include, without limitation, boats and other surface-based vehicles, submarines, and underwater rovers. Each of inspection vehicles 102-3 is communicatively coupled to a remote processing device 104-3, using one or more wireless communications standards. In the exemplary embodiment, remote processing device 104-3 is further communicatively coupled to mobile computing device 106-3, remote data source 108-3, and industrial cloud-based platform 110-3.

During operation, each of inspection vehicles 102-3 executes route plans configured to navigate inspection vehicles 102-3 to points of interest in geographic region 101-3 and to collect data regarding the points of interest. Each of inspection vehicles 102-3 further includes geolocation units for identifying their respective position. In the exemplary embodiment, each of inspection vehicles 102-3 includes at least one imaging sensor unit for capturing unprocessed image data and at least one quantitative fluid sensor unit configured to capture fluid concentration data. Accordingly, during execution of the route plan, inspection vehicles 102-3 navigate to the points of interest specified by the route plans and capture data using the imaging sensor unit and fluid sensor unit. The captured data is then geotagged with the current location of the capturing inspection vehicle and transmitted to remote processing device 104-3 for additional processing. The captured data is transmitted over multiple channels from each of inspection vehicles 102-3 to remote processing device 104-3. For example, each of inspection vehicles 102-3 transmit geotagged unprocessed image data to remote processing device 104-3 over a first channel 111-3 and geotagged fluid concentration data over a second channel 113-3.

Remote processing device 104-3 receives and processes data from each of inspection vehicles 102-3. For example, remote processing device 104-3 receives geotagged unprocessed image data from inspection vehicles 102-3 and converts the geotagged unprocessed image data and performs digital image processing on the geotagged unprocessed image data. Digital image processing includes, without limitation, resizing the image, compressing the image, and correcting one or more of color, white balance, brightness, and similar properties of the image. Digital image processing further includes, if necessary, converting the unprocessed image data into a readable and/or displayable file format. Remote processing device 104-3 also combines the geotagged fluid sensor data with the processed image data to generate a visual representation of the data collected by inspection vehicles 102-3. In certain embodiments, remote processing device 104-3 analyzes the geotagged fluid data received from inspection vehicles 102-3 and determines whether the geotagged fluid data meets predetermined criteria for additional inspection. For example, in certain embodiments, remote processing device 104-3 determines whether fluid concentration levels indicated by received geotagged fluid concentration data exceeds a predetermined fluid concentration threshold. If so, remote processing device 104-3 generates a new route plan or modifies an existing route plan to cause one or more of inspection vehicles 102-3 to reinspect the location associated with the high fluid concentration reading.

Remote processing device 104-3 is communicatively coupled over one or more networks to other computing devices including mobile computing device 106-3, remote data source 108-3, and industrial cloud-based platform 110-3. Mobile computing device 106-3 includes, without limitation, a laptop, smartphone, tablet computer, or similar portable device. During operation, an operator uses mobile computing device 106-3 to view and analyze data provided by inspection vehicles 102-3 and to issue commands to inspection vehicles 102-3. More specifically, remote processing device 104-3 provides mobile computing device 106-3 with data collected by inspection vehicles in a format displayable on a display (not shown) of mobile computing device 106-3. The operator then reviews the data collected by inspection vehicles 102-3 and, if necessary, issues additional commands to inspection vehicles 102-3 including, without limitation, requests to reinspect a given piece of equipment or point of interest, to inspect a different piece of equipment or point of interest, to end a current route plan, and to begin a different route plan.

Remote data source 108-3 stores supplemental data accessible by remote processing device 104-3 for purposes of supplementing the geotagged image and fluid data collected by inspection vehicles 102-3. Remote data source 108-3 generally includes one or more storage devices containing one or more databases. Examples of data stored in remote data source 108-3 include, without limitation, geographic data, meteorological data, previously collected fluid data, and general reference data (e.g., fluid properties and characteristics). By combining the supplemental data with the geotagged fluid and image data captured by inspection vehicles 102-3, remote processing device 104-3 generates data visualization with improved sophistication, improved accuracy, and improved utility as compared to data visualizations based only on the geotagged image and fluid data. For example, in one embodiment, remote processing device 104-3 retrieves supplemental data from remote data source 108-3 and generates a data visualization including a first layer corresponding to recently collected fluid data and one or more second layers including historical fluid data captured over time, with each layer overlaid on an image of geographic region 101-3. The data visualization is then transmitted to mobile computing device 106-3 where a user is able to animate the layers or otherwise turn certain layers of the data visualization on or off to analyze changes in the fluid data over time. Supplemental data from remote data source 108-3 can also be used to pinpoint the location of fluid leaks. For example, in certain embodiments, remote data source 108-3 includes weather data, such as wind patterns, that can be used to trace fluid leaks to a point of origin. In yet another example, supplemental data from remote data source 108-3 includes historical fluid concentration data taken over a period of time and is used to calculate fluid leak rates and total fluid leakage from a given source over the period of time.

Remote processing device 104-3 is also communicatively coupled to industrial cloud-based platform 110-3. Industrial cloud-based platform 110-3 is generally a system of networked computing devices configured to collect and analyze data from the networked computing devices. During operation, remote processing device 104-3 is configured to provide data collected by inspection vehicles 102-3 to industrial cloud-based platform 110-3, which performs various analytics on the provided data. The results of the analytics performed by industrial cloud-based platform 110-3 are then used to facilitate asset performance management. In certain embodiments, industrial cloud-based platform 110-3 performs analytics including, without limitation, fluid leak localization, leak rate determination from one or more industrial assets, and total leakage determinations from one or more industrial assets. In certain embodiments, industrial cloud-based platform 110-3 is communicatively coupled, either directly or indirectly through one or more intermediate computing devices, to one or more pieces of industrial equipment and is able to communicate with and/or control the one or more pieces of industrial equipment in response to the analytics. For example, during one operation, industrial cloud-based platform 110-3 receives data from remote processing device 104-3 and, based on an analysis of the received data, determines that a piece of inspected equipment has a fluid leak that exceeds a predetermined leak rate threshold. In response to such a determination, industrial cloud-based platform 110-3 may take one or more actions including, without limitation, generating and transmitting a report or similar message identifying the leak, issuing a command that modifies one or more control parameters of the equipment, activating or modifying operation of additional equipment associated with the inspected equipment, shutting down the inspected equipment, and issuing an alarm or alert to a control system communicatively coupled to the equipment.

In certain embodiments, at least one of remote processing device 104-3, and industrial cloud-based platform 110-3 use fluid concentration data collected by inspection vehicles 102-3 to analyze leakage from an industrial asset. More specifically, remote processing device 104-3 and/or industrial cloud-based platform 110-3 determines leakage based on fluid concentration data collected in a particular location or area over time. Leakage calculations by remote processing device 104-3 and/or industrial cloud-based platform 110-3 include determining, without limitation, one or more of a leakage rate, a change in leakage rate, and a total leakage over a period of time. Leakage may be determined based on either mass or volumetric basis. For example, in embodiments in which a leakage rate is calculated, the leakage rate may be expressed in either a volumetric flow rate, such as standard cubic feet per hour, or a mass flow rate, such as pounds per hour.

Figure 73:
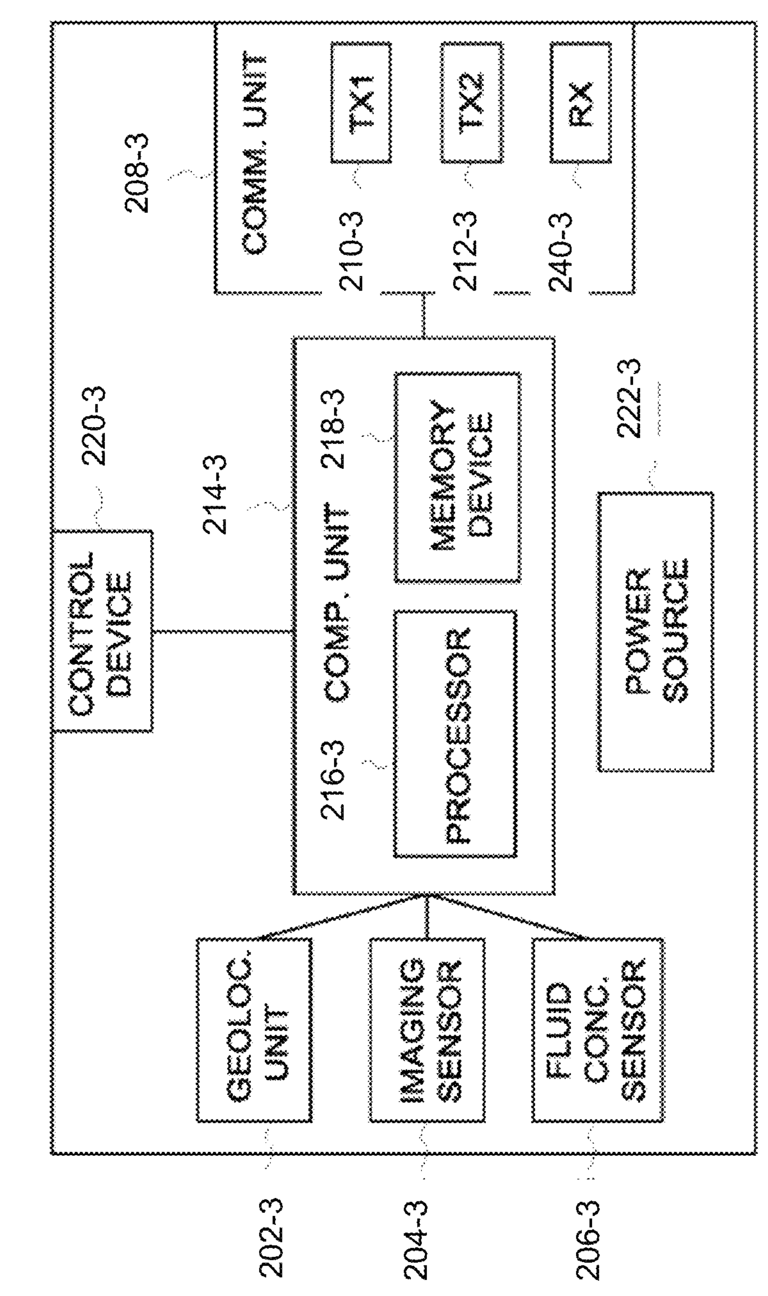
FIG. 73 is an example schematic view of an inspection apparatus for use in the asset inspection system of FIG. 72.

FIG. 73 is a schematic view of an inspection apparatus, namely inspection vehicle 102-3, of asset inspection system 100-3 (shown in FIG. 72).

Inspection vehicle 102-3 includes a geolocation unit 202-3, an imaging sensor unit 204-3, a quantitative fluid sensor unit 206-3, a communication unit 208-3, an on-board computing device 214-3, a control device 220-3, and a power source 222-3. Communication unit 208-3 further includes a first transmitter 210-3, a second transmitter 212-3, and a receiver 224-3. On-board computing device 214-3 further includes at least one processor 216-3 and a memory device 218-3 coupled to processor 216-3.

Processor 216-3 includes one or more of a microcontroller, a reduced instruction set circuits (RISC), an application-specific integrated circuits (ASICs), a logic circuit, and/or any other circuit or processor that is capable of executing the functions described herein. Processor 216-3 includes one or more processing units (not shown), such as, without limitation, an integrated circuit (IC), an application specific integrated circuit (ASIC), a microcomputer, a programmable logic controller (PLC), and/or any other programmable circuit. Processor 216-3 may include multiple processing units (e.g., in a multi-core configuration). Processor 216-3 executes instructions which perform the functions described herein. The above examples are exemplary only, and thus are not intended to limit in any way the definition and/or meaning of the term "processor."

Memory device 218-3 includes, without limitation, read-only memory (ROM) and/or random access memory (RAM). Memory device 218-3 stores executable instructions executable by processor 216-3 for performing the functions described herein.

Geolocation unit 202-3 is configured to determine the current position of inspection vehicle 102-3. More specifically, geolocation unit 202-3 is configured to generate a set of coordinates locating inspection vehicle 102-3 in space relative to a frame of reference. The frame of reference may be a global frame of reference or may be a frame of reference relative to another object having a known location. Geolocation unit 202-3 includes, without limitation, one or more global positioning system (GPS) receivers, laser rangefinders, altimeters, accelerometers, ultrasonic rangefinders, radiolocation systems, and radionavigation systems. Geolocation unit 202-3 generally produces geolocation data capable of accurately locating inspection vehicle 102-3 in three-dimensional space. For example, in embodiments in which inspection vehicle 102-3 includes a global positioning system receiver, geolocation unit 202-3 produces a set of coordinates including longitude, latitude, and altitude corresponding to the current position of inspection vehicle 102-3. In certain embodiment, geolocation unit 202-3 further includes one or more sensors configured to provide the orientation of inspection vehicle 102-3.

Imaging sensor unit 204-3 is generally configured to capture visual images of an area being inspected by inspection vehicle 102-3. Imaging sensor unit 204-3 includes, without limitation, one or more of a charge-coupled device (CCD) sensor, a complementary metal-oxide semiconductor (CMOS), and a n-type metal-oxide-semiconductor configured to capture (NMOS) sensor configured to capture electromagnetic radiation, such as light, and to convert the electromagnetic radiation into a digital representation of the captured electromagnetic radiation. Imaging sensor unit 204-3 includes, without limitation, sensors configured to capture one or more of color images, black-and-white images, infrared images (including mid-infrared images), and near infrared images and may include additional components, such as filters, to facilitate capture of such images.

Quantitative fluid sensor unit 206-3 is generally configured to determine a concentration of one or more fluids. For example, quantitative fluid sensor unit 206-3 is configured to determine a concentration of, without limitation, one or more of methane, water vapor, carbon dioxide, ammonia, hydrogen sulfide, nitrous oxide, non-methane volatile organic compounds, and sulfur dioxide. In certain embodiments, quantitative fluid sensor unit 206-3 determines fluid concentration based on one or more optical spectroscopy techniques. In the exemplary embodiment, quantitative fluid sensor unit 206-3 is a direct spectroscopy sensor unit, such as a tunable diode laser absorption spectroscopy (TDLAS) unit, configured to determine concentration of fluids based on absorption of absorption of a laser produced by the TDLAS unit by the fluid being tested. In other embodiments, quantitative fluid sensor unit 206-3 includes at least one of an electrochemical fluid sensor, an infrared point sensor, an infrared imaging sensor, a semiconductor fluid sensor, an ultrasonic fluid sensor, a holographic fluid sensor, a direct spectroscopy sensor unit, and an optical filter-based sensor unit. In embodiments including an electrochemical sensor unit, the electrochemical sensor unit further includes a sensing material and a transducer coupled to the sensing material.

The exemplary embodiment of inspection vehicle 102-3 includes one of each of geolocation unit 202-3, imaging sensor unit 204-3, and quantitative fluid sensor unit 206-3. In alternative embodiments, inspection vehicle 102-3 includes multiple of at least one of geolocation units, imaging sensor units, and quantitative fluid sensor units. In such embodiments, the additional geolocation units and sensors perform various functions including, without limitation, at least one of providing redundancy, collecting additional data of the same modal type, and collecting additional data of a different modal type. For example, in one embodiment, inspection vehicle 102-3 includes a first geolocation unit and a second geolocation unit as an emergency backup in case of failure of the first geolocation unit. In another embodiment, inspection vehicle 102-3 includes a first quantitative fluid sensor configured to measure a fluid concentration using spectroscopic methods and a second quantitative fluid configured to measure a fluid concentration using electrochemical fluid measurement methods.

Communication unit 208-3 facilitates communication to and from inspection vehicle 102-3. Communication unit 208-3 includes a first transmitter 210-3, a second transmitter 212-3, and a receiver 224-3 configured to communicate over at least one of a radio-frequency spectral range, a microwave spectral range, an optical spectral range, and an electromagnetic spectral range. In the exemplary embodiment, communication unit 208-3 is configured to communicate using first transmitter 210-3, second transmitter 212-3, and receiver 224-3 using a wireless communication standard such as Bluetooth™ or Z-Wave™, through a wireless local area network (WLAN) implemented pursuant to an IEEE (Institute of Electrical and Electronics Engineers) 802.11 standard (i.e., WiFi), and/or through a mobile phone (i.e., cellular) network (e.g., Global System for Mobile communications (GSM), 3G, 4G) or other mobile data network (e.g., Worldwide Interoperability for Microwave Access (WIMAX)), MAVLink, or a wired connection (i.e., one or more conductors for transmitting electrical signals).

Control device 220-3 produces a controlled force and maintains or changes a position, orientation, or location of inspection vehicle 102-3. Control device 220-3 is generally a device configured to change the speed and/or direction of inspection vehicle 102-3. In embodiments in which inspection vehicle 102-3 is an aerial vehicle, for example, control device 220-3 is one of thrust device or a control surface. A thrust device is a device that provides propulsion or thrust to inspection vehicle 102-3. For example, and without limitation, a thrust device is a motor driven propeller, jet engine, or other source of propulsion. A control surface is a controllable surface or other device that provides a force due to deflection of an air stream passing over the control surface. For example, and without limitation, a control surface is an elevator, rudder, aileron, spoiler, flap, slat, air brake, or trim device. Control device 220-3 may also be a mechanism configured to change a pitch angle of a propeller or rotor blade or a mechanism configured to change a tilt angle of a rotor blade. In embodiments in which inspection vehicle 102-3 is a water-based vehicle, control device 220-3 may include, without limitation, one or more of an engine, a motor, a propeller, a rudder, or any similar device configured to control speed and/or direction of inspection vehicle 102-3. Similarly, in embodiments in which inspection vehicle 102-3 is a ground-based vehicles, control device 220-3 may include, without limitation, one or more of an engine, a motor, a steering mechanism, or any similar device configured to control speed and/or direction of inspection vehicle 102-3. Control device 220-3 is communicatively coupled to on-board computing device 214-3 and configured to respond to real-time commands from processor 216-3. In certain embodiments, control device 220-3 is coupled to a control circuit (not shown) configured to convert real-time commands received from processor 216-3 into movement of an actuator. For example, and without limitation, real-time commands include instructions that, when executed, cause a throttle adjustment, flap adjustment, aileron adjustment, rudder adjustment, or other control surface or thrust device adjustment.

Power source 222-3 provides power to components of inspection vehicle 102-3. Power source 222-3 is, for example, and without limitation, one or more of a battery, solar cell, connection to a power grid, generator, or other source of electrical energy. In certain embodiments, power source 222-3 includes a wireless charging receiver (not shown) configured to receive electromagnetic energy wirelessly and to use the received electromagnetic energy to charge power source 222-3. For example, and without limitation, the wireless charging receiver is configured to charge power source 222-3 by at least one of inductive coupling, resonant inductive coupling, capacitive coupling, magnetodynamic coupling, microwaves, or light transmission to transmit electromagnetic energy. The wireless charging receiver includes one or more antenna devices configured to receive electromagnetic energy. For example, and without limitation, the wireless charging receiver includes wire coils, tuned wire coils, lumped element resonators, electrodes, rotating magnets, parabolic dishes, phased array antennas, lasers, photocells, lenses, and/or other devices for receiving electromagnetic radiation. Power source 222-3 includes at least one device for storing electrical energy such as a battery, capacitor, fuel cell, and/or other device for storing electrical energy. In alternative embodiments, inspection vehicle 102-3 is powered by liquid and/or solid fuel. Inspection vehicle 102-3 includes power source 222-3 that is a fuel tank or storage device and includes a refueling port (e.g., a probe configured to receive fuel from a drogue or other fuel source). In certain embodiments, power source 222-3 includes one or more energy harvesting modules configured to capture energy for use by inspection vehicle 102-3. Energy harvesting modules include, without limitation, modules configured to capture energy from the environment surrounding inspection module 102-3 and modules configured to capture energy from operation of inspection module 102-3. For example, energy harvesting modules include, without limitation, solar cells, wind turbines, piezoelectric generators, regenerative braking systems, thermal energy recovery systems, solid oxide fuel cells (SOFC), and kinetic energy recovery systems.

During operation, on-board computing device 214-3 captures image data using imaging sensor unit 204-3 and fluid data using quantitative fluid sensor unit 206-3, and geotags the captured data with location information obtained from geolocation unit 202-3. On-board computing device 214-3 then causes the geotagged captured data to be transmitted to remote processing device 104-3 (shown in FIG. 1) first transmitter 210-3 and second transmitter 212-3 of communication unit 208-3. To avoid the power requirements and added weight of image processing equipment, on-board computing device 214-3 transmits geotagged image data received from imaging sensor unit 204-3 using first transmitter 210-3 in a raw, unprocessed format. Due to the bandwidth required for such transmission, geotagged fluid data is transmitted using a second transmitter 212-3. By doing so, the extra bandwidth required for transmission of the geotagged unprocessed image data does not interfere with transmission of the geotagged sensor data and/or additional control signals that may be received from remote processing device 104-3.

During operation, on-board computing device 214-3 executes a route plan configured to cause inspection vehicle 102-3 to navigate to one or more points of interest within geographic region 101-3 and to capture sensor data at the one or more points of interest. More specifically, processor 216-3 is configured to retrieve and execute route plans stored in memory device 218-3. Each route plan contains one or more route instructions corresponding to at least one of navigation of inspection vehicle 102-3 or data capture using one or more sensors of inspection vehicle 102-3. A route plan can include all necessary route instructions for a complete inspection mission or include only a subset of route instructions corresponding to a portion of an inspection mission. Route instructions include, without limitation, general navigation instructions to move inspection vehicle 102-3 from a first location to a second location; specific instructions regarding control of a specific component of inspection vehicle 102-3, such as control device 220-3; and instructions regarding data capture using one of imaging sensor unit 204-3 and quantitative fluid sensor unit 206-3. Data capture instructions may include, without limitation, performing a single instance of data acquisition or performing periodic data acquisition. For example, a first set of route instructions causes inspection vehicle 102-3 to navigate to a first specified location and capture data upon arrival at the first specified location. A second set of route instructions then causes inspection vehicle 102-3 to navigate from the first specified location to a second specified location and to periodically capture data during transportation between the specified locations. Periodic data capture includes, without limitation, capturing data at a particular frequency (e.g., every 100-30 milliseconds (ms)) and capturing data based on a travelled distance (e.g., every 10 meters (m)).

In certain embodiments, route plans and route instructions correspond to pre-programmed logic as opposed to or in addition to a set of predetermined locations. For example, in certain embodiments, route plans include route instructions configured to cause an inspection vehicle to move within a geographic region until the inspection vehicle locates an area having a fluid concentration value that exceeds a predetermined threshold. In response, the route plan causes the inspection vehicle to track the heightened level of fluid concentration to a location at which the fluid concentration is at its highest and to capture data at that location.

During operation, route plans executed by processor 216-3 are subject to change and/or interruption in favor of executing an alternative route plan. For example, in certain embodiments, processor 216-3 is configured to analyze captured fluid data to determine whether a fluid concentration at a given location exceeds a predetermined threshold. If so, processor 216-3 modifies the current route plan or generates a second route plan including reinspection of the location associated with the high fluid concentration. For example, in one embodiment, processor 216-3 appends one or more route instructions to a currently executing route plan including instructions to return inspection vehicle 102-3 to the location associated with the high fluid concentration and to perform an additional data capture at that location. Alternatively, processor 216-3 generates a second route plan and executes the second route plan upon completion of the initial route plan. In a second embodiment, processor 216-3 temporarily suspends a first route plan, generates a second route plan including route instructions for reinspecting the location associated with the high fluid concentration, and executes the secondary route plan before resuming the second route plan.

In certain embodiments, processor 216-3 is configured to modify a route plan based on instructions received from communication unit 208-3 from remote processing device 104-3. Instructions received from remote processing device 104-3 include instructions generated by remote processing device 104-3 and instructions generated by at least one of mobile computing device 106-3 and industrial cloud-based platform 110-3. For example, during an inspection operation, inspection vehicle 102-3 transmits geotagged fluid concentration data to remote processing device 104-3 which then analyzes the geotagged fluid concentration data, combines the geotagged fluid concentration data with external supplemental data (for example from remote data source 108-3, and determines that at least a portion of the geotagged fluid concentration data or a fluid leak rate corresponding to the geotagged fluid concentration data exceeds a predetermined limit. In response, remote processing device 104-3 issues a command to inspection vehicle 102-3 to reinspect the area associated with the portion of the geotagged fluid concentration data. Alternatively, remote processing device 104-3 receives a similar request or command from one of mobile computing device 106-3 and industrial cloud-based platform 110-3. For example, in one embodiment, remote processing device 104-3 transmits a visualization of the geotagged fluid and image data for display on mobile computing device 106-3. An operator of mobile computing device 106-3, upon review of the visualization, selects one or more points of interest that the operator would like to reinspect. The selections are transmitted through remote processing device 104-3 to inspection vehicle 102-3 where they are incorporated into a new or existing route plan. In yet another example, remote processing device forwards collected fluid concentration and image data to industrial cloud-based platform 110-3 for additional analysis and processing. During such processing, industrial cloud-based platform 110-3 identifies one or more points of interest requiring additional inspection and transmits the points of interest to inspection vehicle 102-3 through remote processing device 104-3. Inspection vehicle 102-3 then incorporates the identified points of interest into a new or existing route plan.

Figure 74:
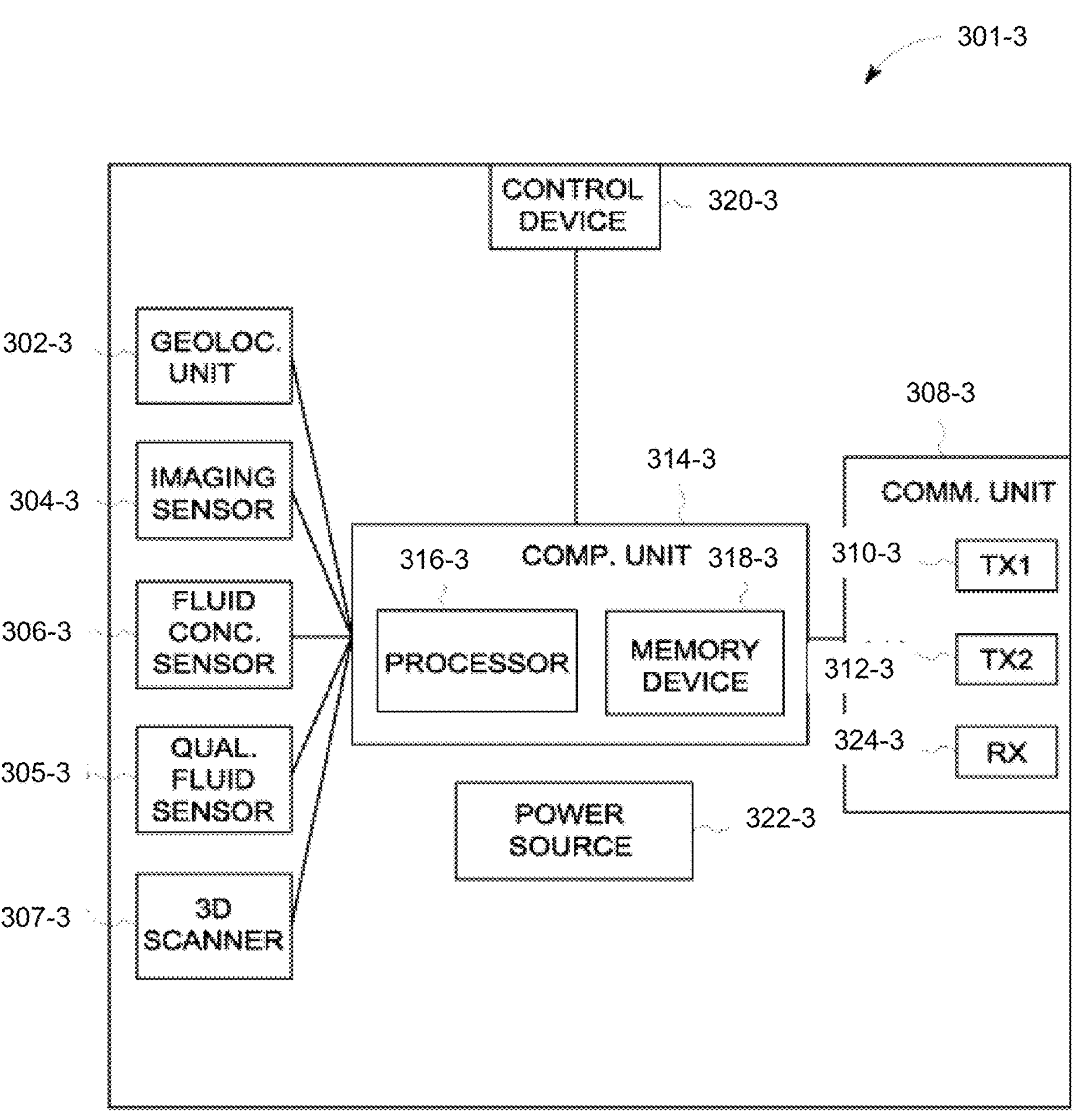
FIG. 74 is a schematic view of an alternative embodiment of an inspection apparatus for use in the asset inspection system of FIG. 72.

FIG. 74 is a schematic view of an alternative embodiment of an inspection apparatus 301-3, namely inspection vehicle 301-3, for use in inspection asset inspection system 100-3. Inspection vehicle 301-3 includes a geolocation unit 302-3, an imaging sensor unit 304-3, a qualitative fluid sensor 305-3, a quantitative fluid sensor unit 306-3, a three-dimensional scanning unit 307-3, a communication unit 308-3, an on-board computing device 314-3, a control device 320-3, and a power source 322-3. Communication unit 308-3 further includes a first transmitter 310-3, a second transmitter 312-3, and a receiver 324-3. On-board computing device 314-3 further includes at least on processor 316-3 and a memory device 318-3 coupled to processor 316-3. Except as noted below, each of geolocation unit 302-3, quantitative fluid sensor unit 306-3, communication unit 308-3, on-board computing device 314-3, control device 320-3, and power source 322-3 are configured as described above with respect to their counterparts in inspection vehicle 102-3.

In contrast to quantitative fluid sensor unit 306-3, which collects fluid concentration measurements, qualitative fluid sensor unit 305-3 is configured to capture qualitative fluid data. The term "qualitative fluid data" is used herein to denote fluid data related to the presence of a fluid. In the exemplary embodiment, qualitative fluid sensor unit 305-3 is an imaging device configured to capture images depicting the size and shape of a fluid plume emanating from a piece of equipment. Such data is particularly useful to characterize plumes of fluids that are otherwise invisible to the naked eye and/or imaging devices configured to capture light in the visible spectrum. In the exemplary embodiment, qualitative fluid sensor unit 305-3 is an infrared (IR) sensor configured to capture IR image data. IR image data differentiates between the IR characteristics of a fluid plume and the surrounding ambient air, thereby facilitating identification of the overall size and shape of the fluid plume even when the fluid plume is otherwise invisible to the naked eye or conventional imaging sensors. In other embodiments, qualitative fluid sensor unit 305-3 includes at least one of a mid- and near-infrared sensor.

During operation, processor 316-3 is configured to operate in conjunction with qualitative fluid sensor unit 305-3 to capture qualitative fluid data form qualitative fluid sensor unit 305-3. More specifically, qualitative fluid sensor unit 305-3 captures qualitative fluid data and transmits the captured qualitative fluid data to on-board computing device 314-3. Processor 316-3 then geotags the qualitative fluid data and transmits the geotagged qualitative fluid data to remote processing device 104-3 using second transmitter 312-3.

Inspection vehicle 301-3 further includes a three-dimensional scanning unit 307-3. Three-dimensional scanning unit 307-3, which in the exemplary embodiment is a light distancing and ranging (LIDAR) unit, generally includes at least one laser unit (not shown) configured to emit a laser, one or more detection units (not shown) configured to detect reflections of the laser, and internal circuitry (not shown) configured to calculate a time-of-travel of the laser and a corresponding distance to the object off of which the laser is reflected. Such distance measurements can then be used to construct a point cloud corresponding to the area scanned by the three-dimensional scanning unit 307-3.

During operation, processor 316-3 is configured to operate in conjunction with three-dimensional scanning unit 307-3 and to receive capture three-dimensional point data. More specifically, three-dimensional scanning unit 307-3 captures three-dimensional point data and transmits the captured three-dimensional point data to on-board computing device 314-3. Processor 316-3 then geotags the three-dimensional point data and transmits the geotagged three-dimensional point data to remote processing device 104-3 using second transmitter 312-3.

During operation of inspection vehicle 301-3, processor 316-3 is configured to control inspection vehicle 301-3 and to facilitate capture of data using the various sensors mounted thereon. More specifically, processor 316-3 obtains one or more of a current position using geolocation unit 302-3, image data from imaging sensor unit 304-3, qualitative fluid data from qualitative fluid sensor unit 305-3, quantitative fluid data from quantitative fluid sensor unit 306-3, and three-dimensional point data from three-dimensional scanning unit 307-3, to geotag each piece of data, and to transmit the geotagged data to remote processing device 104-3 for additional processing. More specifically, inspection vehicle 301-3 includes a communication unit 308-3 having a first transmitter 310-3 for exclusively transmitting geotagged unprocessed image data obtained from imaging sensor unit 304-3 and a second transmitter 312-3 for transmitting the remaining geotagged data. In certain embodiments, communication unit 308-3 includes one or more additional transmitters such that the remaining geotagged data is divided across multiple channels during transmission.

In certain embodiments, processor 316-3 merges the geotagged quantitative fluid data with one or both of the geotagged qualitative fluid data and the geotagged three-dimensional point data to generate a fluid data mesh prior to transmission by inspection vehicle 301-3. More specifically, processor 316-3 associates the geotagged quantitative fluid data obtained from quantitative fluid sensor unit 306-3 with one or both of the geotagged qualitative fluid data generated by qualitative fluid sensor unit 305-3 and the geotagged three-dimensional point data generated by three-dimensional scanning unit 307-3. In one embodiment, for example, processor 316-3 associates the geotagged quantitative fluid data with the geotagged qualitative image data to generate a two-dimensional array wherein each element of the array includes both qualitative and quantitative fluid data, the two-dimensional array representing a portion of geographic region 101-3.

Similarly, in alternative embodiments, the geotagged quantitative fluid data is associated with the geotagged three-dimensional point data to generate a three-dimensional fluid data mesh. In such embodiments, the fluid data mesh comprises a three-dimensional array wherein each array entry corresponds to a point in space of geographic region 101-3 and includes both quantitative fluid data and an indication of whether three-dimensional scanning unit 307-3 identified a point at that location. Accordingly, the three-dimensional data map may be used to define a topographic map including a fluid concentration reading at each point.

In certain embodiments, the geotagged quantitative fluid data may be correlated with each of the geotagged qualitative fluid data and the geotagged three-dimensional point data based on the geotags assigned to each piece of data. More specifically, the geotagged quantitative fluid data, geotagged qualitative fluid data, and geotagged three-dimensional point data are correlated and combined based, at least in part, on the geolocation represented by the geotag assigned to each piece of data. In alternative embodiments, association of the geotagged quantitative fluid data and each of the geotagged qualitative fluid data and the geotagged three-dimensional point data is further based on additional data including, without limitation, position and orientation on inspection vehicle 301-3 of each of the qualitative fluid sensor unit 305-3, the quantitative fluid sensor unit 306-3, and the three-dimensional scanning unit 307-3 during data capture on inspection vehicle 301-3; position and orientation relative to each other of the qualitative fluid sensor unit 305-3, the quantitative fluid sensor unit 306-3, and the three-dimensional scanning unit 307-3 during data capture; and direction and speed of travel of inspection vehicle 301-3 during data capture.

Figure 75:
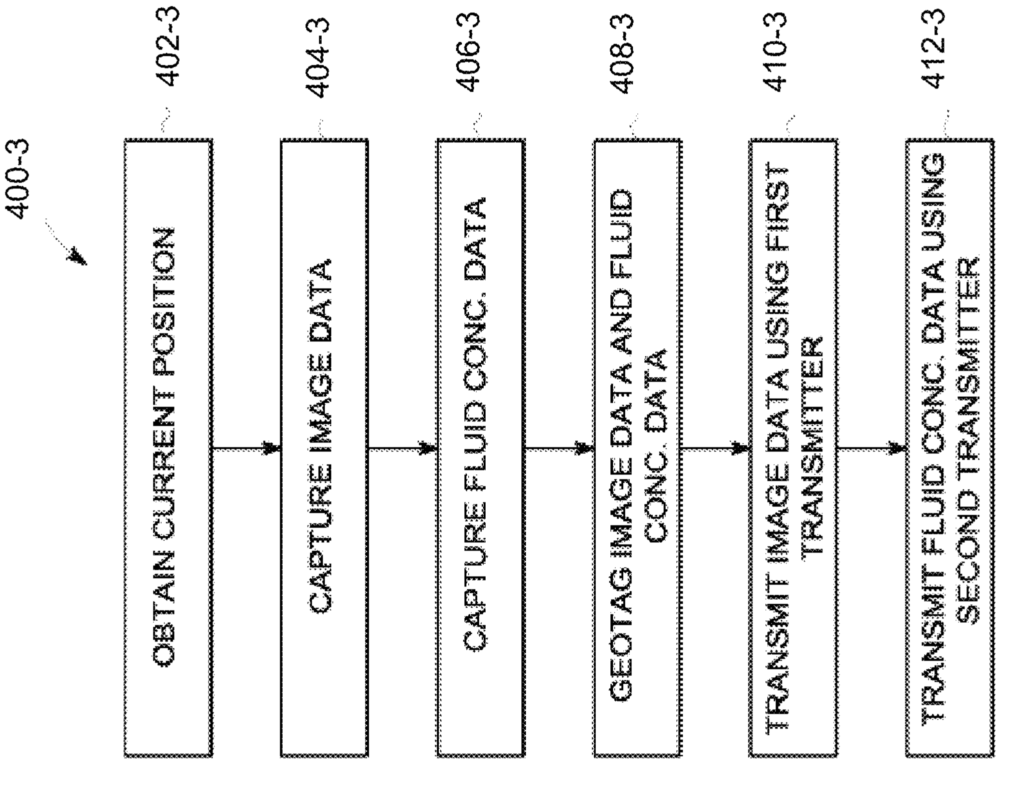
FIG. 75 is a flow chart of an example method of inspecting an industrial asset using the inspection apparatus of FIG. 73.

FIG. 75 is a flow chart of an exemplary method 400-3 of inspecting an industrial asset data using an inspection apparatus, namely inspection vehicle 102-3. As noted above, inspection vehicle 102-3 generally includes a geolocation unit 202-3, an imaging sensor unit 204-3, a quantitative fluid sensor unit 206-3, and a communication unit 208-3, which further includes a first transmitter 210-3 and a second transmitter 212-3.

Method 400-3 includes, at 402-3, obtaining a current position of inspection vehicle 102-3 from geolocation unit 202-3. For example, in certain embodiments, inspection vehicle 102-3 includes a processor, such as processor 216-3, communicatively coupled to geolocation unit 202-3. During operation, processor 216-3 issues one or more requests to geolocation unit 202-3 for the current position of inspection vehicle 102-3. In certain embodiments, geolocation unit 202-3 automatically periodically determines the current position of inspection vehicle 102-3 and transmits the most recently determined position to processor 216-3 in response to receiving a request from processor 216-3. Alternatively, geolocation unit 202-3 determines the current location dynamically upon receipt of a request from processor 216-3.

At 404-3 and 406-3, image and fluid concentration data are captured by inspection vehicle 102-3. More specifically, processor 216-3 issues instructions or requests to each of imaging sensor unit 204-3 and quantitative fluid sensor unit 206-3. In response, imaging sensor unit 204-3 and quantitative fluid sensor unit 206-3 capture image data and fluid concentration data, respectively.

At step 408-3, each of the image data and the fluid concentration data are geotagged with the position data provided by geolocation unit 202-3. Geotagging of the collected data can be performed in various ways including, without limitation, generating a data structure containing the captured data and the position of inspection vehicle 102-3; populating a metadata field of a data file containing the collected data with the current position of inspection vehicle 102-3; and constructing a message containing the collected data, wherein the message includes a message header including the current position of inspection vehicle 102-3. Inspection vehicle 102-3 transmits the geotagged image data and the geotagged quantitative fluid data at 410-3 and 412-3, respectively. More specifically, the geotagged image data is transmitted using first transmitter 210-3 and the geotagged fluid concentration data is transmitted using second transmitter 212-3.

The above-described apparatus and method provide for enhanced inspection of industrial assets using inspection vehicles. The method and systems described herein allow for enhanced inspection of an industrial asset by the inspection vehicle as the inspection vehicle is configured to include and operate using multi-modal sensors. More specifically, the inspection vehicle performs limited on-board processing, facilitating removal of unnecessary data processing systems or replacement of such data processing systems with additional sensors. Limited on-board processing also significantly reduces the amount of power consumed by data processing, thereby allowing for longer inspection missions and a greater quantity of sensor data collected on a given inspection mission.

An example technical effect of the apparatus and methods herein includes at least one of: (a) improving data collection by facilitating replacement of data processing equipment with additional sensor units; (b) improving inspection time by reducing inspection vehicle weight; (c) improving inspection time by reducing power consumption required for on-board data processing; (d) improving efficiency of inspection missions by quickly and accurately providing sensor data to one or more of a remote processing device, an operator remote processing device, and an industrial cloud-based platform configured to modify aspects of the inspection mission in response to collected data; and (e) facilitating data collection that more accurately reflects operational conditions of an industrial asset.

Example embodiments of method and systems for inspecting an industrial asset using an inspection vehicle are described above in detail. The method and systems described herein are not limited to the specific embodiments described herein, but rather, components of systems or steps of the methods may be utilized independently and separately from other components or steps described herein. For example, the apparatus and methods disclosed herein may be implemented in applications outside of the oil and fluid industry for purposes of monitoring operating conditions of other pieces of industrial equipment. Additionally, the methods may also be used with other components of devices, and are not limited to practice with only the components as described herein. Rather, the exemplary embodiments may be implemented and utilized in connection with many other unmanned vehicles and asset inspection systems.

Embodiments described herein include various systems, assemblies, devices, apparatuses, and methods that may be used in a connection with obtaining one or more measurements of a machine. The measurement(s) may be representative or indicative of an operative condition of the machine. As used herein, an "operative condition of the machine" may refer to an operative condition of the machine as a whole or an operative condition of a component (e.g., element, assembly, or sub-system) of the machine. As used herein, the term "operative condition" relates to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

As an example with respect to locomotives or other rail vehicles, one or more measurements obtained from a locomotive or other rail vehicle may indicate that a lubricant in the component (e.g., drive train, gearbox, engine, and the like) is low or has an insufficient quality.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

Other embodiments described herein may be configured to detect other characteristics besides liquid level, such as quality (e.g., degree of contamination) of the liquid. Contaminants may include water, soot, acid, base/alkali, metallic particles, and/or non-metallic particles. Furthermore, embodiments are not limited to the drive train or a gear case of the drive train. For example, measurements may be obtained for any machine including moving parts that use a lubricating fluid, such as a turbo-charger, an air compressor, a combustion engine, and the like.

Additional embodiments are disclosed that relate to sensing methods and systems. The sensors, such as resonant sensors, may include inductor-capacitor-resistor (LCR) sensors that can be used as sensors or transducers for sensing fluids. Provided herein are sensors having a part that is a resonant structure that exhibits resolvable changes in the presence of a fluid and various components or contaminants in the fluid.

In one embodiment, the sensor may include an inductor-capacitor-resistor (LCR) resonator circuit with a resonance frequency response provided by the resonant impedance (Z) of this circuit. The sensors as provided herein may be capable of sensing properties of interest in the presence of variable noise sources and operating over the variable temperature conditions to provide stable sensor performance over time. Disclosed herein are sensors that include inductor-capacitor-resistor (LCR) resonators, which may function as a sensor or as a transducer. The resonant impedance spectrum of the sensor may be measured either via inductive coupling between pick up coil and sensor or directly by connecting to a sensor reader. The electrical response of the sensor may be translated into the resonant impedance changes of the sensor.

Non-limiting examples of signal changes of an individual sensor may include combined and simultaneous resonant impedance change, inductance change, resistance change, and capacitance change (referred to herein as electrical characteristics). Suitable sensors and systems disclosed herein may enhance the ability to measure changes in a fluid, such as engine oil or fuel, by contacting it with the sensor between the electrodes that constitute a resonant circuit of the sensor. The resonant circuit of the sensor may be an electrical resonant circuit. Other resonant circuits may include a mechanical resonator, where a change of viscosity and/or density of the fluid cause a response of the mechanical resonators.

Suitable mechanical resonators may include tuning fork resonators, thickness shear mode resonators, quartz crystal microbalance resonators, surface acoustic wave resonators, bulk acoustic wave resonators, and others. Unlike these and other mechanical resonators, the electrical resonators may be not predictably affected by the changes change of viscosity and/or density of the fluid. Instead, electrical resonators may be predictably affected by the changes in the complex permittivity of the fluid. Electrical resonators may be complicated in their design. For example, marginal oscillators require complicated multi-component circuits.

The degradation of at least some oils and lubricants may generate molecules and/or other moieties that may be relatively more polar than the oil and lubricant from which they were formed. The base oil or lubricant may include long chain hydrocarbon molecules that are weakly polar. Thus, the presence of polar contaminants may increase of one or more parts of the oil's complex permittivity.

The degradation of at least some oils and lubricants may generate molecules and/or other moieties that may be relatively low molecular weight and may be in the form of volatiles or gases. For example, an insulating oil of an oil-fitted transformer is employed to insulate and suppress corona and arcing and to serve as a coolant. However, the insulating oil gradually deteriorates under the impact of electrical, thermal and environmental stresses during the life of the transformer. Different types of gases are generated in the insulating oil depending on the deterioration processes. Examples of these gases include hydrogen, carbon monoxide, carbon dioxide, methane, ethane, ethylene, and acetylene. For example, thermal decomposition of mineral oil produces hydrogen and methane. Thermal decomposition of cellulose and other solid insulation materials produces carbon monoxide, carbon dioxide, and water vapor. Such gases are detected and monitored in real time using multivariable sensors as described in more detail below. For this application the sensor is coated with a sensing material that is responsive to one or more gases of interest. When the sensor is in operational contact with the oil, dissolved gases in oil also interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material.

According to one aspect, the resonant transducers operate as re-configurable resonant structures and operate at multiple frequencies for monitoring of a status of fluids (and, further, for example, the health of equipment in contact with such fluids). Monitoring the health of fluids involves a determination of composition or a determination of contamination of such fluid.

Figure 76:
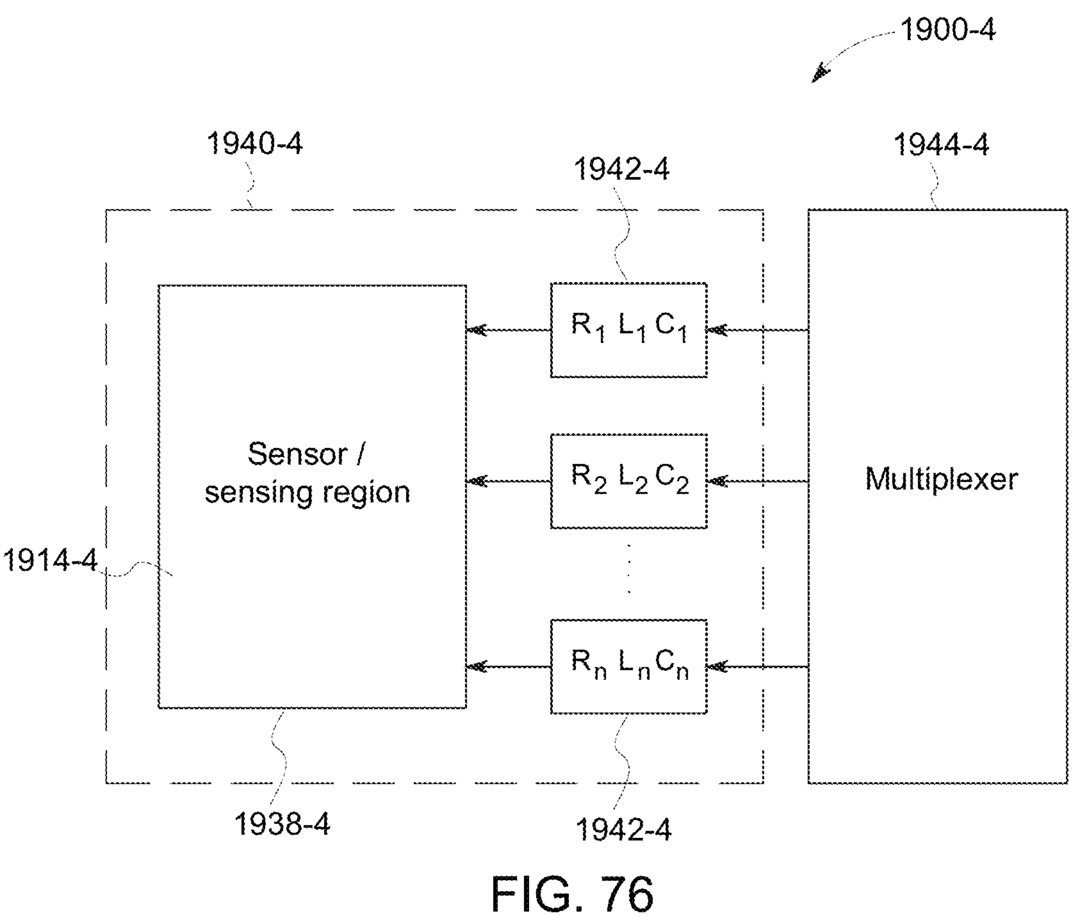
FIG. 76 is a schematic view of a portion of an example sensor system employing a sensor assembly configured for sensing of a fluid using a plurality of frequencies, in accordance with embodiments of the present disclosure.

FIG. 76 illustrates a portion of a resonant sensor system 1900-4 having a single sensing region 1938-4, and employed in a sensor assembly 1940-4 useful to probe a fluid sample using a plurality of frequencies. The sensing region may be disposed on a substrate and may include a suitable sensing material. In some embodiments, the substrate of the sensor may be a dielectric substrate. In some embodiments, the sensor assembly may include a plurality of tuning elements 1942-4. The plurality of tuning elements may be operatively coupled to the single sensing region to define a plurality of resonant circuits. The tuning elements along with the single sensing region may define a plurality of resonant circuits. Each resonant circuit of the plurality of resonant circuits may include one or more tuning elements of the plurality of tuning elements. Not shown is a semi-permeable film, semi-permeable membrane, or semi-permeable inorganic barrier (collectively a "selective barrier") that allows (or prevents) selective analytes or contaminants through the selective barrier and into the sensing region.

Suitable interdigital electrode structures for probing a fluid sample include two- and four-electrode structures. Suitable materials for electrodes include stainless steel, platinum, gold, noble metals, and others. Suitable materials of a substrate and/or a dielectric protective layer may include silicon dioxide, silicon nitride, parylene, silicone, fluorinated polymers, alumina, ceramics, and others. Suitable examples of sensing layers include semiconducting materials, metal oxides, nanocomposites, polymers, or the like. Suitable electrodes may be formed using metal etching, screen-printing, ink-jet-printing, and mask-based metal deposition techniques. The thickness of fabricated electrodes on the substrates may be in a range of from about 10 nanometers to about 1000 micrometers. The materials for the interdigital electrode structures, substrate, dielectric protective layer, sensing layer, and electrode formation methods may be selected based at least in part on the application specific parameters.

As shown in the illustrated embodiment, the plurality of tuning elements may be disposed external to the sensor. However, in one embodiment, the tuning elements may be disposed on the substrate of the sensor. In another embodiment, some of the plurality of tuning elements may be external to the sensor substrate, while other tuning elements may be disposed on the substrate. The tuning elements may comprise a resistor, a capacitor, an inductor, a resonator, impedance transformer, or combinations thereof.

The sensor assembly 1940-4 may include a controller that has a multiplexer 1944-4. The multiplexer may facilitate electronic switching between the tuning elements. The multiplexer may select one or more signals associated with the probing frequencies and forward the selected signal to an output device or a sensor reader. The multiplexer may send a plurality of signals simultaneously to a sensor reader.

During operation, each resonant circuit may resonate at a defined frequency. At least one resonant circuit may resonate at a frequency that may be different from the resonating frequency of the other resonant circuits. By way of example, if the sensing region includes a pair of electrodes, the tuning elements may be a resistor, a capacitor, and an inductor to form an inductor-capacitor-resistor (LCR) resonant circuit. The tuning elements may be electrically coupled to the sensing region. In one embodiment, the tuning elements may be in parallel connection to the sensing region. In certain embodiments, the different resonant circuits of the plurality of resonant circuits may be configured to resonate at different frequencies. The different resonant circuits may be configured to probe the fluid sample with a plurality of resonant frequencies. The different resonant frequencies may be used to probe a fluid sample over the frequency range of spectral dispersions of fluid components. The spectral dispersions of fluid components may include spectral dispersions of external contaminants and/or acidic and/or basic components of the fluid. As used herein, basic components may refer to alkaline components, and base concentration may refer to alkali/alkaline concentration. The spectral dispersions that may be monitored with the sensors of the present disclosure may be over a frequency range of from about 0.1 Hz to about 100 GHz and include alpha, beta, gamma, delta, and other types of spectral dispersions as constrained by application specific parameters.

FIG. 77 illustrates another sensor circuit 2010-4. The sensing region 1938-4 (shown with variable resistor and capacitor) is combined with tuning components 1942-4 (shown with variable inductor and capacitor). To realize sensor response at a different frequency range, additional circuit elements may be utilized to tune the frequency range.

Therefore, a sensor can be operating at multiple frequency ranges by using a defined or selected combination of extra circuit components—such as inductors, capacitors, and impedance transformers. These components may be connected in parallel or in series, as needed, to the sensor to vary the operating frequency range. The controller may control the impedance transformer ratio to affect the sensitivity. A sensor's frequency response and its magnitude may be based at least in part on the overall input resonant impedance changes due to the sensor's response to the fluid status, fluid behavior, and the like. Thus, the sensor's sensitivity may be controlled through the dynamic tunability of the transformer ratio. Tuning the response of each channel may be achieved, for example, by using one or more inductors. In one embodiment, wireless readout from the electrodes may provide an improvement in response selectivity and sensitivity. In one embodiment, transformer-based coupling may reject parasitic LCR components from instrumentation (analyzer, cables, amongst others). The LCR resonator in FIG. 77 has a relatively simple design as compared to other resonators, for example as compared to marginal oscillators that require complicated multi-component circuits for their operation that include a current feedback amplifier and other components.

As noted herein, a suitable wireless sensor may be radio-frequency identification (RFID) sensor where a passive RFID tag may be adapted to perform a sensing function. With reference to FIGS. 78 and 79, an embodiment is shown in which the resonant sensor may be an adapted RFID tag. In FIG. 78, a resonant antenna 2150-4 and memory chip 215-42 may be coated with a protective material or sensing material 2156. The sensing material may be a sensing region of the RFID tag. In FIG. 70, the sensing region 1938-4 (that can optionally include the protective or sensing material) may be attached across an antenna. In both cases (e.g., both FIGS. 78 and 79), the electrical response of the sensing region may be translated into changes in the resonant impedance response of the sensor. An RFID sensor having a memory chip may operate with a frequency determined at least in part by the operating frequency used by the memory chip. That is, some operating frequencies (of the sensor and the chip) may interfere with each other and may be less desirable to have disruptive harmonics or destructive waveforms. And, the sensor can have a circular, square, cylindrical, rectangular, or other appropriately-shaped sensing region and/or antenna.

The resonant frequency of an antenna circuit may be set to a higher frequency than a resonant frequency of the sensor circuit. The frequency differential may be in a range of from, for example, as much as about 4 times to about 1000 times higher. In one embodiment, the sensor circuit may have a resonant frequency that may respond to a determined sensed environmental condition. The two resonant circuits may be connected so that when alternating current (AC) energy is received by the antenna resonant circuit, it may apply direct current energy to the sensor resonant circuit. The AC energy may be supplied through the use of a diode and a capacitor, and the AC energy may be transmitted to the sensor resonant circuit through an LC tank circuit through either a tap within the L of the LC tank circuit or a tap within the C of the LC tank circuit. Further, the two resonant circuits may be coupled such that voltage from the sensor resonant circuit may change the impedance of the antenna resonant circuit. The modulation of the impedance of the antenna circuit may be accomplished through the use of a transistor, for example a FET (field-effect transistor).

The RFID sensor's memory chip may be optional. The RFID sensor without a memory chip can be a resonant LCR sensor and can operate at different frequency ranges from a kilohertz to several gigahertz. That is, the memory chip's absence may widen the available frequency range.

Suitable sensing materials and sensing films as disclosed herein may include materials deposited onto the sensor to perform a function of predictably and reproducibly affecting the resonant impedance sensor response upon interaction with the environment. For example, a conducting polymer, such as polyaniline, changes its conductivity upon exposure to solutions of different pH. That is, the resonant impedance sensor response changes as a function of pH when such a conducting polymer film is deposited onto the RFID sensor surface. Thus, such an RFID sensor works as a pH sensor.

As an example of gaseous fluid detection, when such a polyaniline film is deposited onto the RFID sensor for detection in gas phase, the resonant impedance sensor response also changes upon exposure to basic (for example, $NH_3$) or acidic (for example, HCl) gases. Suitable sensor films include polymer, organic, inorganic, biological, composite, and nano-composite films that change their electrical and or dielectric property based on the environment in which they may be placed. Other examples of sensor films may be a sulfonated polymer such as commercially available Nafion, an adhesive polymer such as silicone adhesive, an inorganic film such as sol-gel film, a composite film such as carbon black-polyisobutylene film, a nano-composite film such as carbon nanotube-Nafion film, gold nanoparticle-polymer film, metal nanoparticle-polymer film, zeolites, metal-organic frameworks, cage compounds, clathrates, inclusion compounds, semiconducting materials, metal oxides, electrospun polymer nanofibers, electrospun inorganic nanofibers, electrospun composite nanofibers, and other sensor materials selected based on application specific parameters. To reduce or prevent the material in the sensor film from leaking into the liquid environment, the sensor materials may be attached to the sensor surface using standard techniques, such as covalent bonding, electrostatic bonding and other techniques. Some sensing materials may require a certain temperature for efficient operation. A non-limiting range of operating temperatures of the sensing materials and associated sensors onto which the sensing materials are deposited is between −260 degrees Celsius and 1600 degrees Celsius.

In one embodiment, the system may measure a resonant impedance $\check{Z}(f)$ (represented by Eq. (1)) of the sensor.

$$\check{Z}(f) = Z_{re}(f) + jZ_{im}(f) \qquad \text{Eq. (1)}$$

where $Z_{re}(f)$ may be the real part of the resonant impedance and Zim(f) may be an imaginary part of the resonant impedance. In one embodiment, the resonant impedance spectral response of the sensor may be a multivariable response as more than one frequency may be utilized to measure sensor response across the resonance of the sensor. In some embodiments, the resonant impedance response of the sensor may be a multivariable response because more than one frequency may be utilized to measure sensor response outside the resonance peak of the sensor. In some embodiments, the sensor response may be measured at multiple frequencies across the resonance of the sensor. For example, if the sensor resonates at about 1 MHz, the measured frequencies and associated sensor responses may be measured from about 0.25 MHz to about 2 MHz. This multivariable response may be analyzed by multivariate analysis. The multivariable response of the sensor includes the sensor's full resonant impedance spectral response and/or several individually measured parameters, such as but not limited to $F_p$, $Z_p$, $F_z$, $F_1$, $F_2$, $Z_1$, and $Z_2$. As used herein, the term "resonant impedance spectral response" may be referred to as "impedance response," "resonant impedance spectra," and/or variations thereof.

FIG. 80 depicts a graph of measured resonant impedance parameters of an embodiment of the resonant sensor, in accordance with embodiments of the present technique. The properties include the frequency of the maximum of the real part of the resonant impedance ($F_p$, resonance peak position), magnitude of the real part of the resonant impedance ($Z_p$, peak height), zero-reactance frequency ($F_z$, frequency at which the imaginary portion of resonant impedance may be zero), resonant frequency of the imaginary part of the resonant impedance ($F_1$), and anti-resonant frequency of the imaginary part of the resonant impedance ($F_2$), signal magnitude ($Z_1$) at the resonant frequency of the imaginary part of the resonant impedance ($F_1$), and signal magnitude ($Z_2$) at the anti-resonant frequency of the imaginary part of the resonant impedance ($F_2$). Other parameters may be measured using the entire resonant impedance spectra, for example, quality factor of resonance, phase angle, and magnitude of resonant impedance.

Figure 81:
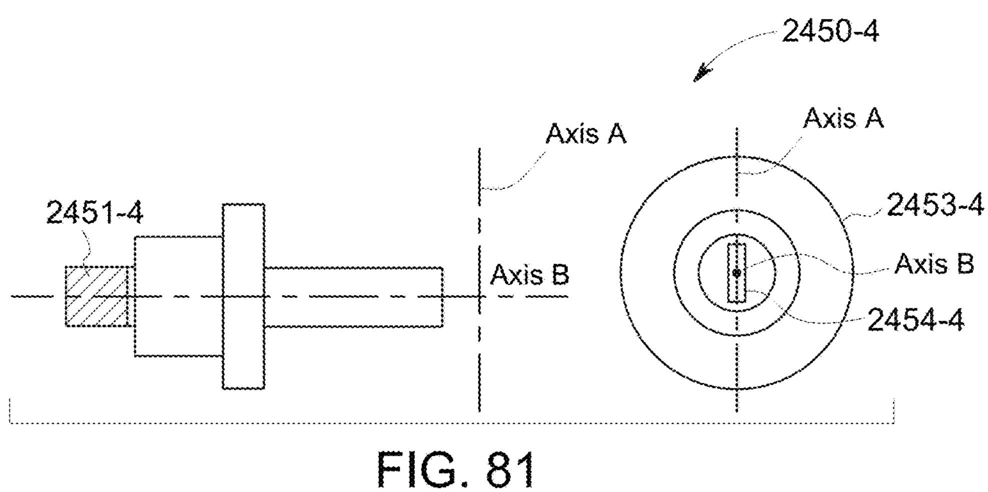
FIG. 81 illustrates a sensor with a sensing region designed to fit standard ports or specially made ports in a reservoir.
Figure 82:
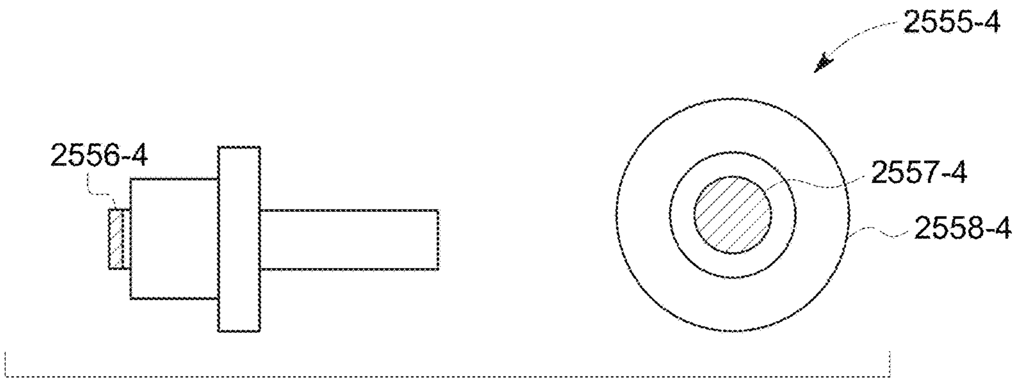
FIG. 82 also illustrates a sensor with a sensing region designed to fit standard ports or specially made ports in a reservoir.

For measurements of fluid properties in fluid reservoirs, sensors with their sensing regions can be designed to fit standard ports or specially made ports in the reservoirs. Suitable design examples are depicted in FIG. 81 and FIG. 82. An example is provided of a resonant sensor 2450-4 with an aligned sensing region 2451-4. The sensing region defines a first Axis A, which is perpendicular to a transverse axis labeled Axis B. An insertion port structure 2453-4 defines an insertion aperture 2454-4 that is elongated along Axis A. The sensing region, then, is arranged parallel to the port's elongated aperture, translation along Axis B allows for sensor region insertion into the port and to contact a measured fluid. An example of another resonant sensor 2555-4 in which the sensing region 2556-4 is not constrained by its shape relative to an aperture 2557-4 defined by a port structure 2558-4 is depicted in FIG. 82. Alignment pins, not shown, may be used to align the sensor, and the sensing region, relative to the port aperture, as may be desired.

Figure 83:
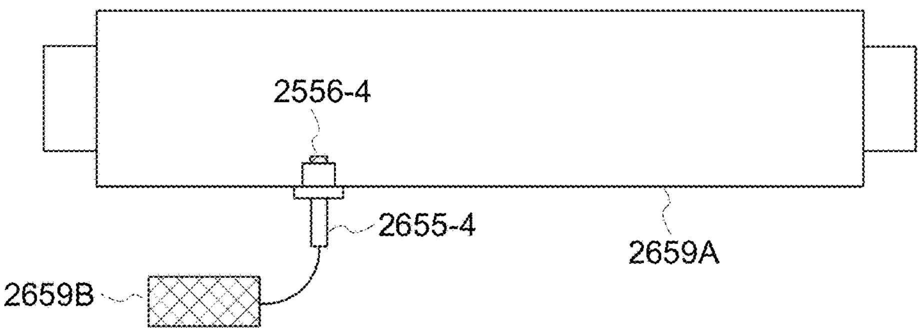
FIG. 83 illustrates a sensor having a sensing region exposed to a fluid.
Figure 84:
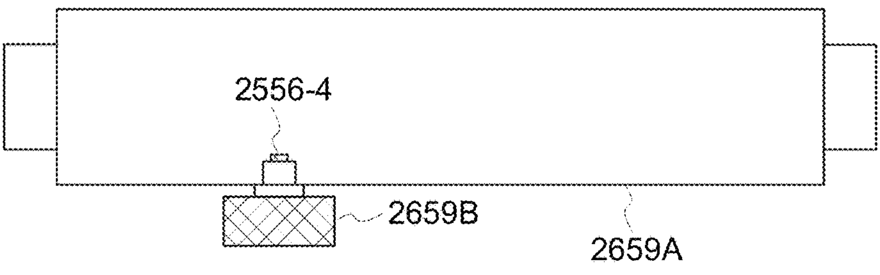
FIG. 84 also illustrates a sensor having a sensing region exposed to a fluid.

Measurements of fluid properties in fluid reservoirs may be performed using sensors with their sensing regions exposed to the fluid as shown in FIGS. 83 and 84. The sensor 2655-4 shown in FIG. 83 is installed in a fluid transfer pipe 2659A, and is coupled to a sensor reader 2659B. The sensor reader 2659B may be coupled by wire or cable, and located proximate to the sensor 2655-4 as shown in FIG. 83. In another embodiment, the sensor reader 2659B may be directly connected to the sensor without a cable—as shown in FIG. 84. During operation, a fluid flows through the pipe and contacts the sensing region 2556-4. As the sensing region 2556-4 senses an analyte of interest it signals the sensor reader 2659B.

Figures 85A, 85B, 85C:
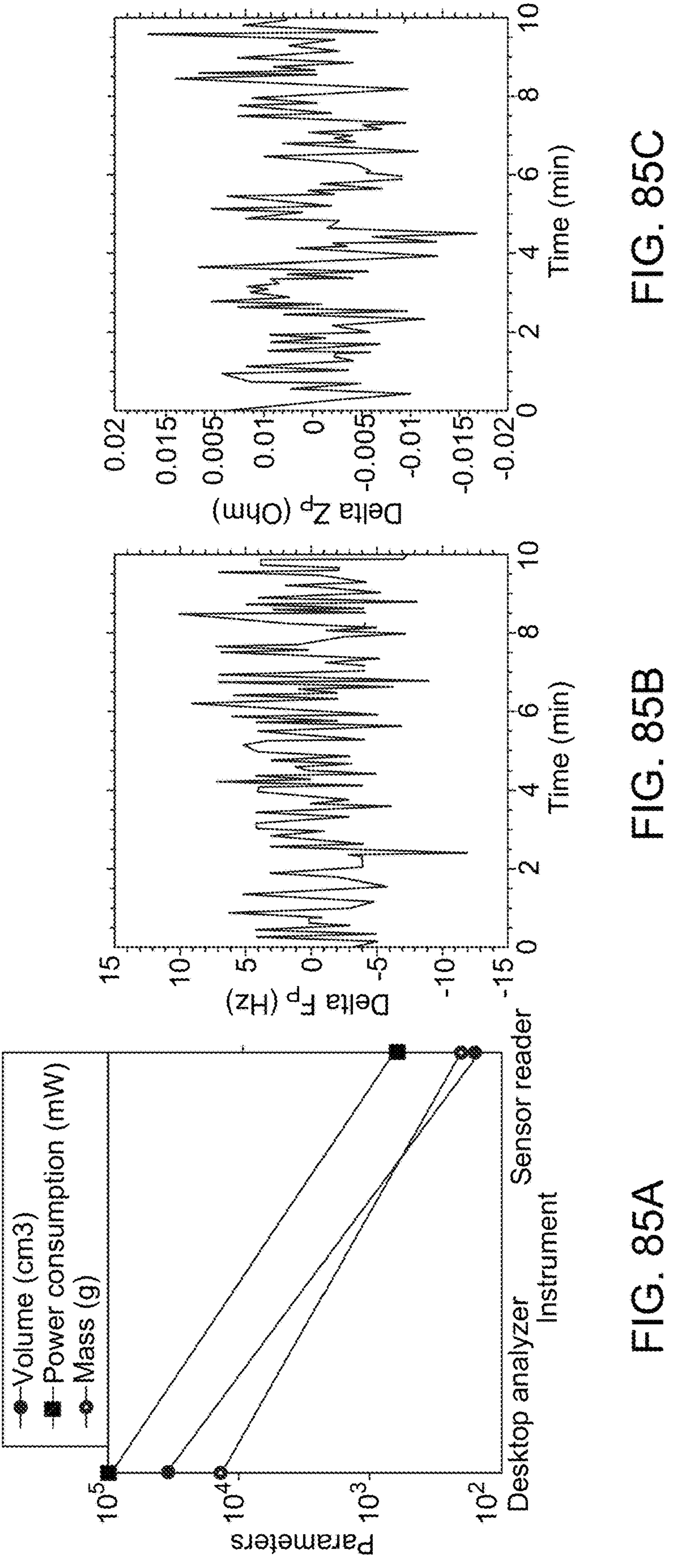
FIGS. 85A-C are graphs depicting measurements related to the sensor reader according to one embodiment.

The sensor reader (also referred to as micro-analyzer) has been developed with a small form factor, low power consumption and low cost of components. FIGS. 85A-C are graphs depicting measurements related to the sensor reader according to one embodiment. FIG. 85A is a comparison of power consumption, size, and weight between a desktop analyzer and the developed micro-analyzer. FIG. 85A depicts that the design of the micro-analyzer provided 100 to 500-fold reduction in power consumption, size, and weight as compared to desktop analyzers. These advancements make the sensor reader attractive for a wide range of applications including monitoring of industrial fluids, where laboratory analyzers are size-, power-, and cost-prohibitive. FIGS. 84B and 84C depict measured Fp and Zp noise levels of the developed micro-analyzer, respectively. The developed sensor reader has a 1σ Fp noise of ~5 Hz and 1σ Zp noise of 0.006 ohm. This electronic design of the sensor reader provided 4-14 times reduction in noise levels in measurements of Ž(f) spectra as compared to measurements with a laboratory desktop analyzer with Fp noise=60 Hz and Zp noise=0.025 Ohm.

Figure 86:
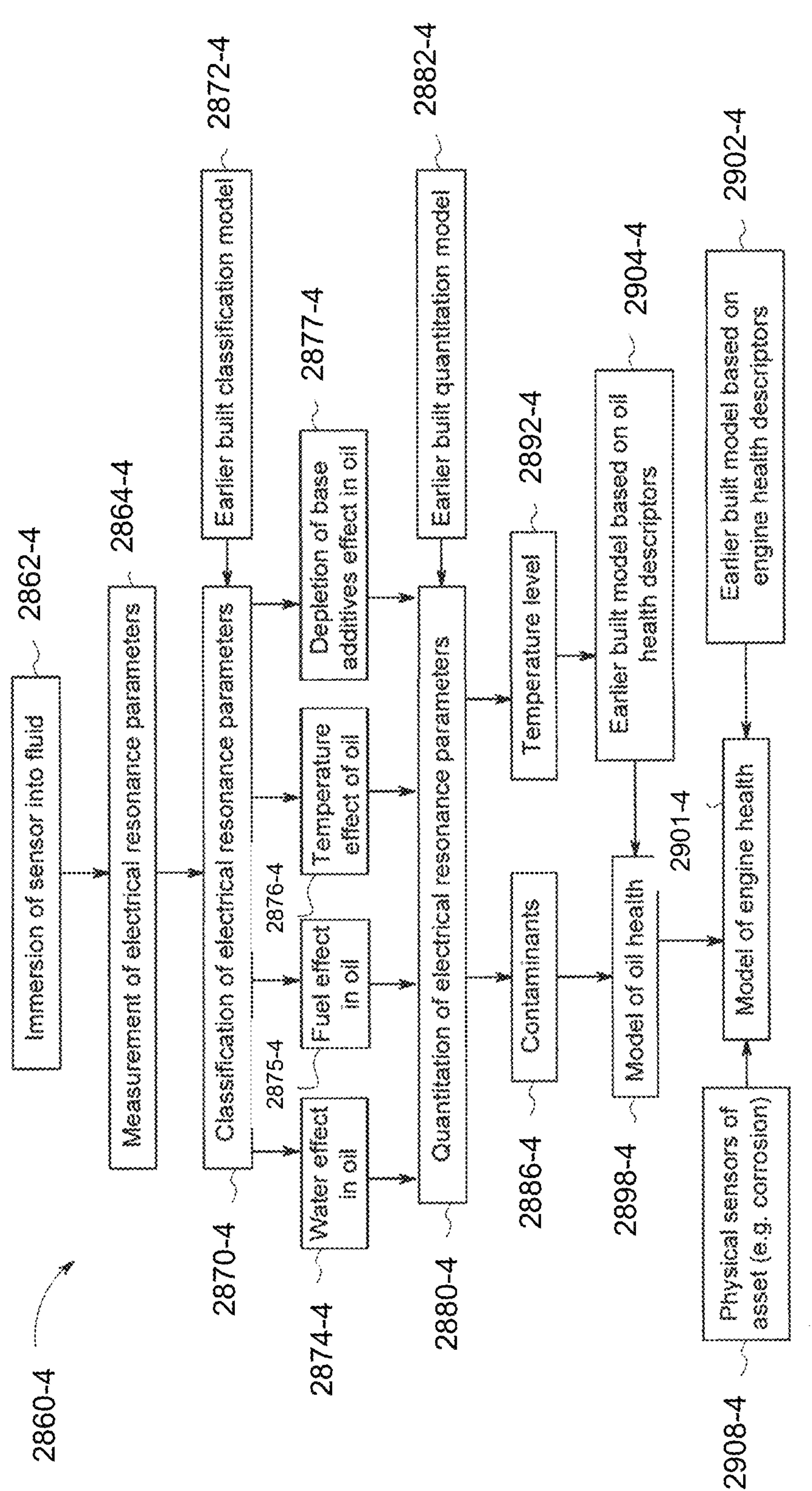
FIG. 86 illustrates a flowchart of one embodiment of a method for monitoring oil health.

A flow diagram of a method 2860-4 is shown in FIG. 86. In one embodiment, a method for monitoring of oil health includes immersion of the sensor into an oil (at 2862-4) and measurement of electrical resonance parameters of the resonance spectra (at 2864-4) at several resonances of a single sensor. For quantitation of contamination of engine oil by water, fuel leaks, and soot with a sensor, the sensor may be placed into operational contact with the fluid at 2862-4. In a specific embodiment, the resonant impedance spectra $\check{Z}(f)=Z_{re}(f)+jZ_{im}(f)$ of a sensor may be determined at 2864-4. For example, the parameters from the measured Ž(f) spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_Z$ of Zim(f), may be calculated. In another embodiment, the electrical resonance parameters may include capacitance parameters of the sensor in operational contact with the fluid, instead or in addition to impedance parameters.

The method 2860-4 classifies the electrical resonance parameters at 2870-4. This may be done using a determined classification model 2872-4 to assess, for example, one or more of water effects 2874-4, fuel effects 2875-4, temperature effects 2876-4, and depletion of base additives effects 2877-4 in oil. Quantitation of the electrical resonance parameters may be performed at step 2880-4 by using a predetermined, earlier saved quantitation model 2882-4, and determination of components 2886-4 in oil such as water, fuel, soot, and wear metal particles 2890-4 as well as the temperature 2892-4, and prediction of the oil health 2898-4 and the engine health 2901-4. This may be done by using one or more of determined engine health descriptors 2902-4 and oil health descriptors 2904-4 as well as inputs from any additional sensors 2908-4. Suitable additional sensors may include those sensing corrosion, temperature, pressure, system (engine) load, system location (e.g., by GPS signal), equipment age calculator, pH, and the like.

For example, in one embodiment, a sensor system may be an electrical resonator that may be excited with a wired or wireless excitation and where a resonance spectrum may be collected and analyzed to extract at least four parameters that may be further processed upon auto scaling or mean centering of the parameters and to quantitatively determine properties of the oil. The properties of the oil that are determined via analyzing the resonance impedance spectrum may include the concentration of water, acid, base, and/or fuel in engine oil. The properties may be used to predict the remaining life of the engine oil and/or the remaining life of the engine in which the oil is disposed. The spectral parameters of the resonance spectrum such as $F_p$, $Z_p$, $F_z$, $F_1$, $F_2$, $Z_1$, and $Z_2$ or the whole resonance spectrum with a single or multiple resonators can be used for data processing.

The classification model 2872-4 may be built using the predicted contributions of the spectral parameters for an uncontaminated fluid and for fluid contamination using previously determined component effects and their corresponding spectral parameters. Such effects may be quantified using the quantitation model 2882-4 to predict if a measured or sensed fluid has any water effects, acid effects, base effects, fuel leak effects, and/or temperature effects. That is, based on previously or empirically determined effects of components on a particular fluid, the resonance parameters, both real and imaginary, may be changed and/or affected in a quantifiable manner if specific components of interest are present. Further, based on the measured parameters, a concentration of a particular component may also be predicted, and multi-component models may be generated. The disclosed techniques may be used to sense a suitable fluid and to build a component and environmental effect model.

In one embodiment, measurements of impedance parameters of fluids may be performed at two or more temperatures of the fluid. Measurements at different temperatures provide information about species of interest and other species (chemical constituents) in the fluid when measured as the frequency dispersion profiles over the broad frequency range or when measured as frequency responses over the relatively narrow frequency range. Performing analysis of resonant impedance spectra of the sensor collected at different temperatures and determining two or more properties of the fluid per temperature based on the analyzed resonant impedance spectra allows an improvement of the sensor accuracy of determinations of properties of species of interest. This improvement may be due to differences of frequency responses of species of interest and other species in the fluid as a function of temperature caused by the molecular structure of these different species. Measurements at different temperatures may be performed with a resonant sensor that has a thermal element in thermal contact with the sensing region of the resonant sensor. The thermal element produces a local change in temperature of the fluid which may be in proximity to the sensing region. This local temperature change can be above or below the temperature of the bulk of the fluid in the container with the sensor. Non-limiting examples of thermal elements include a Peltier cooler, thin-film heater, and pencil heater. The thermal element can produce a local change in temperature of the fluid in the range from about 1 degree Celsius to about 50 degrees Celsius.

In one embodiment, measurements of parameters of fluids may be performed to determine dynamic signatures of the changes of chemical constituents in the fluid. The time scales of these dynamic signatures may vary greatly. Suitable timescale in a range of from about 1 second to about 200 days may be useful to determine different types of leaks of fluids in engines. Such determinations allow the identification of dynamic signatures of the leaks in an engine, relation of the identified signature with the known leak signature from a specific engine component, and determination of the location of the leak based on the signature.

Measurements of properties of fluids may be performed at extreme temperature conditions. Depending on the application, these conditions may range from temperatures down to about −260 degrees Celsius and to temperatures up to about +1600 degrees Celsius. Such harsh temperature conditions with negative temperature down to about −260 degrees Celsius may be useful in relation to liquefied natural gas (LNG) and in the storage of biological and other types of samples. Harsh temperature conditions with positive temperature of up to about +1600 degrees Celsius may be useful in monitoring equipment where the temperature of operating components of the equipment can reach about +1600 degrees Celsius. Examples of equipment that operates at about 250 degrees Celsius may include downhole equipment in oil and gas production and the operations of an internal combustion engine (diesel, natural gas, hydrogen (direct combustion or fuel cells), gasoline, combinations thereof, and the like) for one or more of the fuel, the lubrication system, and the cooling/radiator system. Another example of such equipment may include an oil-filled transformer. Examples of equipment that operates at about 1000 and up to 1500 degrees Celsius include gas turbines. Examples of equipment that operates at about 1600 degrees Celsius include aircraft jet engines.

The applicability of multivariable electrical resonators may be demonstrated by detection of engine oil contamination from water and diesel fuel and determinations of water in model fluid such as dioxane that has the dielectric constant similar to oil. Determination of resolution of the sensor measurements may be performed using hexane and toluene as model systems. Samples of some engine oil were obtained from GE Transportation, while other chemicals may be commercially obtained from Aldrich.

Measurements of the resonant impedance of sensors may be performed with a network analyzer (Agilent) or a precision impedance analyzer (Agilent), under computer control using LabVIEW. Collected resonant impedance data may be analyzed using KaleidaGraph (Synergy Software, Reading, Pa.) and PLS Toolbox (Eigenvector Research, Inc., Manson, Wash.) operated with Matlab (The Mathworks Inc., Natick, Mass.).

Different amounts of fuel and water leaks into oil may be determined quantitatively and experimentally with a single multivariable resonant sensor. Suitable oil may be railroad internal combustion engine oil. Suitable fuel may be diesel fuel. Binary and ternary mixtures of water and fuel in oil may be produced in different proportions. Concentrations of water may be 0, 0.1% and 0.2% (by volume). Concentrations of fuel may be 0, 3% and 6% (by volume).

In another example, sources of leaks in an engine may be determined by identifying dynamic signatures of the leaks, relating the identified signature with a known leak signature from a specific engine component, and determining the location of the leak based on the signature or relationship. Such approach may provide the ability for proactive maintenance, replacing reactive maintenance, and may increase the time-in-use for assets having lubrication systems or internal combustion engines.

Figure 87:
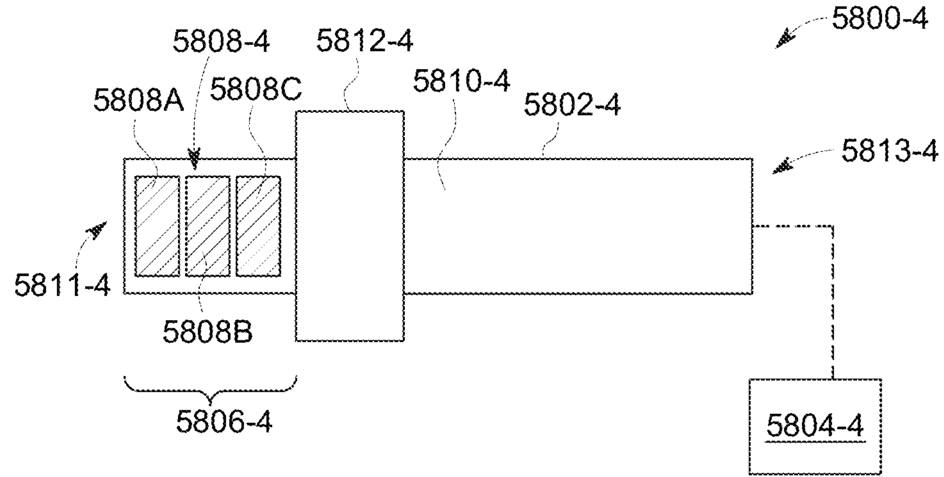
FIG. 87 is a schematic diagram of a sensing system that includes a sensor and a sensor reader.

FIG. 87 is a schematic diagram of a sensing system 5800-4 that includes a sensor 5802-4 and a sensor reader 5804-4. The sensor 5802-4 includes a sensing region 5806-4 that includes multiple electrodes 5808-4. The sensing region 5806-4 is configured to be placed in operational contact with an industrial fluid of interest, such as an oil, a fuel, or a solvent. The electrodes 580-48 may contact the industrial fluid directly or indirectly due to a dielectric sensing layer that may cover at least some of the electrodes. The sensing layer is applied to improve detection of water or other polar compounds in an industrial fluid. The sensing layer may be an inorganic sensing layer, unlike some conventional sensors that use polymeric sensing layers. Polymeric sensing layers in conventional resonant sensors operate by swelling and changing the resonant frequency of the sensor. In the sensor, water uptake by the sensing film does not produce swelling and does not change film thickness. Rather, water uptake produces a change in the dielectric property and the capacitance of the sensing film at multiple frequencies. Unlike conventional resonant sensors, the sensor produces dielectric property changes of the sensing film at multiple frequencies that allows more accurate determinations of the contaminants, such as water or other polar compounds. Such improved accuracy is provided by measurements of spectral dispersion of the sensing film before and after fluid contamination. Non-limiting examples of water sorbing or sensing layers include porous silicon porous ceramic, anodized aluminum oxide, and others. The sensing region 5806 has an electrode geometry that matches the measurement needs of the sensing region 5806-4.

The sensor 5802-4 in an embodiment includes a probe body 5810-4 that has a shoulder 5812-4 extending outward from the probe body 5810-4 such that the shoulder has a greater radial width or diameter than the probe body. The shoulder is disposed along an intermediate segment of the probe body. The sensing region extends from the shoulder to a distal end 5811-4 of the probe body. A proximal end 5813-4 of the probe body is operably coupled to the sensor reader. The electrodes are disposed on the sensing region at different distances relative to the shoulder such that the electrodes extend different depths into the industrial fluid. In an embodiment, at least two of the electrodes operate at one or more high frequencies and at least one of the electrodes (that is different than the electrodes that operate at high frequencies) operates at one or more low frequencies.

For example, the sensor 5802-4 in the illustrated embodiment includes multiple sensing sub-regions that each includes one or more electrodes disposed therein. The sub-regions with electrodes each contain electrode structures where these structures are two-electrode structures or four-electrode structures. The sensing sub-regions include a distal sensing sub-region 5808A, an intermediate sensing sub-region 5808B, and a proximal sensing sub-region 5808C. The electrodes 5808 in the intermediate sub-region 5808B are located between the distal sub-region 5808A and the proximal sub-region 5808C. The electrodes in the different sub-regions 5808A-C may operate at different frequencies and/or frequency ranges relative to one another. Some of the electrodes in the different sub-regions 5808A-C may be used for contaminant (such as water) concentration detection, while other electrodes 5808 in the different sub-regions 5808A-C may be used for fluid aging detection. As an alternative to water, some examples of other contaminants that may be detected by the sensing system include fuel, dust, and other external contaminants. The electrodes in the different sub-regions 5808A-C may have different electrode spacings between adjacent electrodes.

The distal sensing sub-region 5808A in an embodiment is covered by the sensing layer. The distal sensing sub-region 5808A may be configured to measure low concentration water or other contaminant leaks in oil. Each electrode in the distal sensing sub-region 5808A may be an interdigitated electrode that has an area in the range from 0.1 $mm^2$ to 100 $mm^2$. The electrode spacing for the electrodes in the sub-region 5808A may be relatively small, such as in the range from 0.1 μm to 10 μm. For example, the electrodes 5808 may have an area of 2 cm×2 cm with an electrode spacing of 0.15 mm. The electrodes 5808 may resonate at around 50 MHz in air. The electrodes in the distal sub-region 5808A may be operated at relatively high frequencies and/or frequency ranges compared to the electrodes 5808 in the intermediate and/or proximal sub-regions 5808B, 5808C.

The electrodes in the intermediate sensing sub-region 5808B are located more proximate to the sensor reader 5804 than the distal sensing sub-region 5808A. The intermediate sensing sub-region 5808B is provided for preferential measurements of leaks of nonpolar external contaminants and fluid aging detection. These electrodes in an embodiment are not coated with a sensing layer. The electrodes 5808 in the intermediate sub-region 5808B may have relatively small spacing in the range from 0.1 μm to 10 μm. The electrodes of the intermediate sub-region 5808B may be operated at relatively high frequencies and/or frequency ranges compared to the electrodes 5808 in the proximal sub-region 5808C.

The electrodes in the proximal sensing sub-region 5808C are disposed more proximate to the sensor reader 5804 than the sensing sub-regions 5808A and 5808B. The electrodes in the sub-region 5808C are provided for preferential measurements of fluid aging detection. These electrodes are not coated with a sensing layer and can have relatively large spacing in the range from 1 μm to 5000 μm. The electrodes of the proximal sub-region 5808B may be operated at relatively lower frequencies and/or frequency ranges compared to the electrodes in the distal and/or intermediate sub-regions 5808A, 5808B. In other embodiments, the sensing region may include different numbers and/or arrangements of electrodes and/or sensing sub-regions.

The sensor 5802-4 includes at least one inductor-capacitor-resistor (LCR) resonant circuit having one or more tuning elements 1942-4. The one or more resonant LCR circuits are configured to generate an electrical stimulus having a spectral frequency range. The electrical stimulus is applied to the industrial fluid at the sensing region via the electrodes. The electrical stimulus may include multiple electric fields and/or multiple frequencies.

The sensor is operably coupled to the sensor reader, such as via a mechanical fixed connection, a wired connection, or a wireless electrical connection. For example, the sensor may include a communication unit (e.g., a transceiver or discrete transmitter and receiver) that wirelessly transmits electrical signals to the sensor reader. The sensor reader 5804 includes one or more processors. The one or more processors may be one or more controllers (e.g., microcontrollers) or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed in the hardware of the one or more processors.

The one or more processors are configured to receive an electrical signal from the sensor that is representative of a resonant spectral response (or resonant impedance spectra) of the sensing region in operational contact with the industrial fluid in response to the electrical stimulus being applied to the industrial fluid.

The one or more processors are configured to analyze the resonant spectral response and determine properties of the fluid. For example, in one embodiment, the one or more processors may be configured to determine both a water concentration in the industrial fluid and an aging level of the industrial fluid based on the analyzed resonant spectral response.

The analysis of the resonant impedance spectra may be performed by comparing the extracted resonance parameters from the measured resonant impedance spectra from the electrodes in the sensing region (e.g., the sensing sub-regions 5808A, 5808B, and 5808C) to known resonance parameters of the same or a similar fluid at various controlled properties of the fluid, such as defined concentrations of water in the fluid or other external contaminant and at various age levels of the fluid. In an example in which water is the external contaminant, the tested fluid of interest may be determined to have a specific water concentration and a specific age level responsive to the measured set of resonance parameters matching a set of known resonance parameters associated with the specific water concentration and the given age level to a greater extent than the measured set of resonance parameters matches other sets of known resonance parameters associated with other concentrations of water and/or age levels. Statistical methods may be used to compare and "match" the measured resonance parameters to the known resonance parameters. The statistical method used may be a regression analysis, such as a linear regression, a nonlinear regression, or the like. In another example, a series of experiments may be performed using a single sensor to determine the measured resonance parameters of a resonant impedance spectral response of the sensor in a given industrial fluid at various concentrations of water or other external contaminant in the fluid and at various age levels of the fluid, which are the two or more variables that change across the series of experiments. The measured resonance parameters for the series of experiments may be plotted as data points on a graph, and may be used to develop a quantitative model that is used to predict the water or other external contaminant concentration and the age level of monitored fluids (where the water concentration or other external contaminant and the age are unknown). The quantitative model may be a transfer function for the sensing region 5808 broadly or for the individual sensing sub-regions 5808A, 5808B, and 5808C. Thus, measured resonance parameters from a resonance impedance spectral response may be input as variables into the quantitative model to predict water or other external contaminant concentration and aging level of the tested fluid.

The determination of the contaminant concentration in and/or age of the fluid of interest may be performed by establishing correlations between the spectral impedance responses of the sensing sub-regions 5808A, 5808B, and 5808C at multiple frequencies across the dispersion profiles of the fluid and the experimental impedance responses as determined initially via independent reference laboratory methods. Once these correlations (also known as transfer functions) are established, they are further utilized to predict the unknown measured concentrations. Such predictions may be performed by having the measured signals from the sensing sub-regions 5808A, 5808B, and 5808C at multiple frequencies across the dispersion profiles of the contaminant concentration and/or the age of the fluid, entering the values of these signals into the transfer functions or a single function, and obtaining the predicted values of the contaminant concentration and/or the age of the fluid. Depending on the transfer functions, one or more contaminants may be quantified from the measured signals from the sensing sub-regions 5808A, 5808B, and 5808C at multiple frequencies across the dispersion profiles of the contaminants concentration and/or the age of the fluid.

Figure 88:
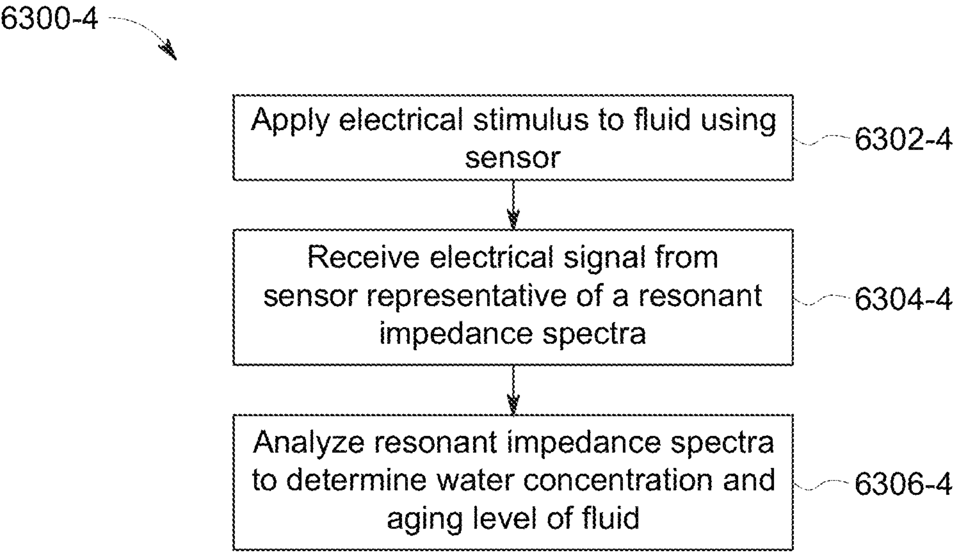
FIG. 88 is a flow chart representative of a method for determining multiple properties of an industrial fluid.

FIG. 88 is a flow chart representative of a method 6300-4 for determining multiple properties of an industrial fluid. At 6302-4, an electrical or electromagnetic stimulus is applied to an industrial fluid using a sensor. The "electrical stimulus" may additionally or alternatively be an electromagnetic stimulus. The sensor includes at least one resonant inductor-capacitor-resistor (LCR) circuit configured to generate the electrical stimulus. The electrical or electromagnetic stimulus is applied to the industrial fluid via multiple electrodes at a sensing region of the sensor in operational contact with the industrial fluid. Optionally, the sensor may include multiple LCR circuits that have different resonant frequencies. Applying the electrical or electromagnetic stimulus to the industrial fluid may include generating the electrical or electromagnetic stimulus to incorporate the resonant frequencies of the resonant LCR circuits such that the resonant impedance spectral response is measured over the resonant frequencies of the resonant LCR circuits. The method 6300 may also include tuning the electrical or electromagnetic stimulus generated by the at least one LCR circuit using one or more tuning elements. The tuning elements may include one or more inductors, capacitors, resistors, resonators, or impedance transformers.

At 6304-4, an electrical or electromagnetic signal is received from the sensor. The electrical or electromagnetic signal is representative of a resonant impedance spectral response of the sensing region in operational contact with the industrial fluid in response to the electrical or electromagnetic stimulus being applied to the industrial fluid. At 6306-4, the resonant impedance spectral response is analyzed to determine both a water concentration in the industrial fluid and an aging level of the industrial fluid based on the analyzed resonant impedance spectra. Although "water concentration" is mentioned, in other embodiments the concentration may be of another external contaminant other than water. The water or other external contaminant concentration in the industrial fluid and the aging level of the industrial fluid may be determined by comparing the extracted resonance parameters to known resonance parameters associated with various water or other external contaminant concentrations in the industrial fluid and various aging levels of the industrial fluid. The aging level of the fluid is determined by categorizing the fluid as three levels as one of fresh, old, or intermediate. The aging level of the fluid may be also determined by categorizing the fluid with more levels of aging where the number of levels of aging may be 8, 64, 128, or more. The number of aging levels determined by the sensor may depend on the developed transfer function between fluid aging and multivariable sensor response.

The determination of oil aging by levels is important for different applications. For example, a two-level aging of oil means that level 1 is a fresh oil and level 2 is aged oil that requires oil replacement or some other action. The higher number of resolution levels of oil aging, the more accurate performed actions can be, including prognostic algorithms to predict the remaining life of oil and/or the machine or an industrial system or site.

Analyzing the resonant impedance spectra may include extracting resonance parameters of the resonant impedance spectra. The resonance parameters are at least some of a frequency position (Fp) and magnitude (Zp) of a real part of the resonant impedance spectra, a resonant frequency (F1) and antiresonant frequency (F2) of an imaginary part of the resonant impedance spectra, an impedance magnitude (Z1) at the resonant frequency (F1) and an impedance magnitude (Z2) at the antiresonant frequency (F2), and a zero-reactance frequency (Fz) at the imaginary part of the resonant impedance spectra.

In an alternative embodiment, the resonant impedance spectra are analyzed to determine both water concentration and acid concentration in the fluid. Acid concentration of an oil is useful for estimating an amount of depletion of additives, an amount of acidic contamination, and/or an amount of fluid degradation. Some industrial fluids such as engine oil may have additives added to the fluids that are designed to increase the stability of the fluids in extreme temperature environments. The additives may be acidic compounds that elevate the acid concentration of the fluid. However, as the fluid ages, the additives deplete over time. The reduced amount of additives in the fluid reduces the acidity or acid concentration of the fluid. On the other hand, acidic contamination and fluid degradation may have the reverse effect of increasing the acid concentration of the fluid. Acidic contamination refers to external acidic components that are undesirably introduced into the fluid via leak paths through the reservoir housing that holds the fluid. For example, acidic components may be introduced into the fluid through a leak path with other external contaminants, such as water. As the amount of acidic contaminants increases, the acid concentration of the fluid increases and the performance or effectiveness of the fluid, such as for providing lubrication and/or heat dissipation, may decrease. The acids in the fluid may reduce the performance of the fluid and/or the machine in which the fluid is used by increasing the viscosity of the fluid and forming gums and resins.

Furthermore, the fluid may degrade over time as the fluid ages, such that the components of the fluid break up into smaller constituents. The rate of degradation may be affected by the high temperatures of the environment and/or the type and amount of additives and contaminants in the fluid. For example, the fluid may degrade at a higher rate once the stabilizing additives are depleted. The additives may include anti-oxidants, such that the fluid oxidizes at a greater rate once the additives are depleted. Typically, as the fluid degrades with age, the fluid may break down into corrosive acids which increase the acid concentration of the fluid. The corrosive acids also reduce the performance of the fluid and can cause component failure (e.g., engine failure) if the fluid is not replaced by new fluid.

Typical stabilizing additives may be basic (e.g., alkaline) in nature to neutralize acids in oil. Acids in oil may be generated from combustion of the fuels and the combustion byproducts being absorbed by oil and/or by organic acids due to oxidation of oil during engine operation.

Monitoring the acid concentration of the fluid over time may be used to determine when to replace the fluid. For example, a lubricating fluid may contain a basic (alkaline) additive package. The base concentration of the fluid may gradually decrease over time as the basic (alkaline) additives are gradually depleted. After the basic additives are depleted, the acid concentration may gradually increase due to at least one of acidic contaminants that leak into the fluid or degradation of the fluid. By monitoring the initial decrease in the base concentration in the fluid and the subsequent increase in the acid concentration, the sensing system can be used to predict the concentration of an additive package in the oil, when the additives are depleted, if there is a significant acid contamination, when the fluid should be replaced due to high acid concentration that exceeds a predetermined threshold level, and/or the like. For example, a low acid concentration may indicate that the fluid is relatively new or fresh and/or that the concentration of the basic additive package is relatively high. Based on the information provided by the sensing system, responsive actions may be taken to improve the fluid quality and/or increase the life of the fluid and/or machine in which the fluid is used. For example, the machine may be scheduled for repair and/or replacement responsive to detection of an acid contamination, and/or the fluid may be replaced responsive to determination of a high acid concentration that exceeds the predetermined threshold level.

Acidic components and water are both polar components. Conventional sensors, such as conventional capacitive sensors like the one described with reference to FIG. 52, are not able to discriminate between different polar components in a signal response to identify the individual contributions of water and acidic components in the fluid. However, the multivariable resonant sensor of the embodiments described herein can individually detect both water concentration and acid concentration of a fluid using only the single sensor.

Figure 89:
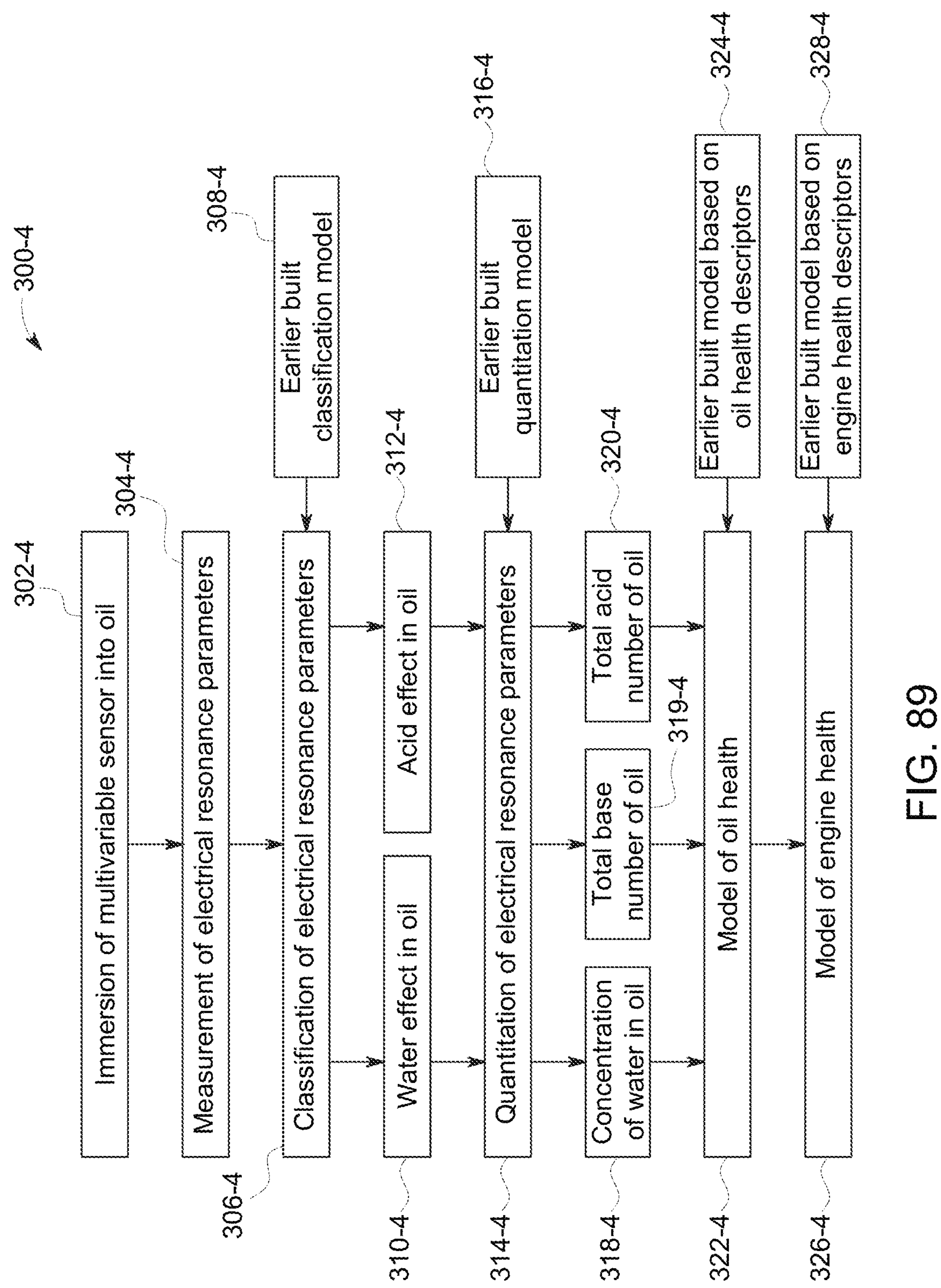
FIG. 89 is a flow diagram of method for monitoring and assessing a lubricating oil according to another embodiment.

FIG. 89 is a flow diagram of method 300-4 for monitoring and assessing a lubricating oil according to another embodiment. Although the method 300-4 is described with reference to a lubricating oil, the method 300-4 may be performed on a different industrial fluid other than a lubricating oil. The method 300-4 may be used to independently monitor a concentration of water in oil, a concentration of acid in oil (e.g., total acid number of oil), and/or a concentration of base in oil (e.g., total base number of oil), while other methods may be used to determine a concentration of water in oil, a concentration of fuel in oil, and a temperature of the oil.

At 302-4, a multivariable resonant sensor is immersed into oil. The oil may be used for lubricating a machine having moving parts, such as an engine. The sensor is immersed into the oil such that a sensing region of the sensor is in operational contact with the oil. The sensor includes electrodes and a sensing region circuit electrically connected to the electrodes. The sensor is configured to apply an electrical stimulus to the oil via the electrodes. The electrical stimulus may be generated by the sensing region circuit. The sensing region circuit in an embodiment includes one or more LCR resonant circuits. The electrical stimulus applied to the oil may include multiple electrical fields and/or multiple resonant frequencies. For example, in an embodiment, the sensing region circuit includes four LCR resonant circuits that have different resonant frequencies. The electrical stimulus has a spectral frequency range that includes the four resonant frequencies of the four LCR resonant circuits.

At 304-4, electrical resonance parameters are measured responsive to the application of the electrical stimulus to the oil. The electrical resonance parameters are measured by receiving an electrical signal from the sensor that is representative of a resonant impedance response or spectra of the sensing region of the sensor in operational contact with the oil. The electrical signal may be transmitted from the sensor to one or more processors-4. The resonant impedance response shows the response of the sensing region in contact with the oil over the frequency range that includes the multiple resonant frequencies of the LCR resonant circuits. As described above, the resonance parameters for the resonant impedance spectra (e.g., $\check{Z}(f)=Z_{re}(f)+jZ_{im}(f)$) may include one or more of the frequency position $F_p$ and magnitude $Z_p$ of $Z_{re}(f)$, the resonant $F_1$ and antiresonant $F_2$ frequencies, the magnitudes $Z_1$ and $Z_2$ of $Z_{im}(f)$, and zero-reactance frequency $F_z$ of $Z_{im}(f)$. In an embodiment, at least four resonance parameters are extracted from the impedance response. The one or more processors are configured to analyze the resonance parameters to quantitatively determine (e.g., estimate) the concentrations of water, acid, and/or base in the oil (as shown in 306-4, 308-4, 310-4, 312-4, 314-4, 316-4, 318-4, 319-4, 320-4). The one or more processors optionally may also be configured to estimate a health of the oil and/or the machine in which the oil is used based on the concentrations of water and acid in the oil (as shown in 322-4 and 324-4). Furthermore, the one or more processors may be configured to predict a remaining life of the oil and/or the machine based on the concentrations of water and acid in the oil (as shown in 326-4 and 328-4).

At 306-4, the electrical resonance parameters are classified, which may be done using an earlier-built classification model at 308-4, to assess the water effects in the oil at 310-4, the acid effect in the oil at 312-4, and/or the base effect in the oil at 319-4. The classification model may be built using spectral resonant parameters of a control group that is accumulated from previously-determined analyses of the effects of water and acid on the same or a similar type of oil. At 314-4, the electrical resonance parameters may be quantified using an earlier-built quantitation model at 316-4, to independently determine a concentration of water in the oil at 318-4, a concentration of base in the oil (e.g., a total base number (TBN) of the oil) at 319-4, and a concentration of acid in the oil (e.g., a total acid number (TAN) of the oil) at 320-4. Total Base Number (TBN) is the measure of basic chemical components or compounds in the oil. The basic components in engine oil may be components of additive packages. The basic components are used to neutralize acidic combustion products within the engine oil. The Total Acid Number (TAN) is the measure of acidic components of compounds in the oil. The acidic components in engine oil may be components of additive packages, by-products of combustion reactions, by-products of the chemical breakdown of oil, external acidic contaminants, or the like.

In an embodiment, the analysis of the resonant impedance response may be performed by comparing the extracted resonance parameters from the measured resonant impedance response to known resonance parameters of a control group. The parameters in the control group may be recorded resonance parameters of the same or a similar type of oil at various controlled properties of the oil, such as at different specific concentrations of water in the oil, different specific concentrations of acid in the oil, and/or different specific concentrations of base (alkali) in the oil. For example, a first subset of the resonance parameters in the control group may be associated with the same type of oil having a negligible amount of water and a first concentration of acid; a second subset of the resonance parameters in the control group may be associated with the same type of oil having a first concentration of water and the first concentration of acid; and a third subset of the resonance parameters in the control group may be associated with the same type of oil having the first concentration of water and a negligible amount of acid. The resonance parameters may also correspond to different specific concentrations of base in the oil. The data for the resonance parameters in the control group may be obtained via previous tests in the field and/or in the laboratory. The data for the previous tests may be stored and used to build the classification model and/or the quantitation model.

For example, a series of experiments may be performed using a single multivariable resonant sensor to determine the measured resonance parameters of a resonant impedance spectral response of the sensor in a given type of oil at various concentrations of water, acid, and base of the oil. The concentrations of water, acid, and base are variable that are modified across the series of experiments. The measured resonance parameters for the series of experiments may be plotted as data points on a graph, and may be used to develop the quantitative model that is used to predict the water concentration, the acid concentration, and/or the base concentration of monitored oil. The quantitative model may be a transfer function. Thus, the measured or extracted resonance parameters from a resonance impedance spectral response may be input as variables into the quantitative model to predict water concentration and acid concentration of the tested oil.

In an embodiment, the properties of the oil that is monitored by the sensor may be determined by comparing the extracted resonance parameters from the measured impedance response to the resonance parameters in the control group that are associated with known properties of the oil (e.g., known water, acid, and base concentrations). For example, the water concentration, the acid concentration, and the base concentration in the oil may be determined by matching the extracted resonance parameters to a specific subset of resonance parameters in the control group. For example, if the extracted resonance parameters more closely match or align with the resonance parameters of the second subset of resonance parameters described above (relative to the matching or alignment with the resonance parameters of the first and third subsets), then the measured oil is determined to have the first concentration of water and the first concentration of acid. Statistical methods may be used to compare and match the measured resonance parameters to the control group of known resonance parameters. The statistical method used may be a regression analysis, such as a linear regression, a nonlinear regression, or the like. Although only three subsets of resonance parameters are mentioned above, the quantitation model may have more than three subsets in order to provide more accurate determinations of the water concentration, the acid concentration, and/or the base concentration in a sample of oil. For example, the one or more processors may be configured to determine the concentration of water in an oil at 100, 300, 500, or more different levels or concentrations such as part per million concentrations, and may be configured to independently determine the concentration of acid and base within the same oil sample at 100, 300, 500, or more different levels or concentrations in order to provide an accurate determination of both properties.

At 322-4, the concentrations of water, acid, and base in the oil may be used to generate or update a model of oil health, which may be based on an earlier-built model using oil health descriptors at 324-4. In general, a relatively high concentration of water and/or a relatively significant increase in the concentration of water in the oil may signal poor oil health. The significant increase in water concentration may indicate a leak condition that should be addressed. Furthermore, a relatively high concentration of acid and/or a relatively significant increase in the acid concentration may signal poor oil health, especially if the oil is not fresh or new. For example, if the oil is new, the high concentration of acid may be at least partially due to the presence of stabilizing additives added to the oil, such that the oil may be in good health. But, as the oil ages and the additives deplete, an increase in acid concentration (and/or a decrease in base concentration) may indicate the introduction of an acidic contaminant and/or degradation (e.g., oxidation) of the oil, indicating poor oil health. The oil health descriptors may include threshold levels or ranges of water, acid, and base, and may also include threshold rates of change for the concentrations of water, acid, and base. The oil may be considered to have good health if the determined concentrations of water, acid, and base are all within the designated threshold levels. The oil health descriptors may include multiple thresholds for the water concentration, acid concentration, and base concentration. For example, if the acid concentration of the oil exceeds a first threshold, the model of oil health may indicate that the oil should be replaced within a designated period of time (or miles, revolutions, etc.) to avoid the oil degrading to a level of poor health that could damage the machine. Furthermore, if the acid concentration of the oil exceeds a second threshold that is greater than the first threshold, the model of oil health may indicate that the oil has a poor quality and should be replaced immediately without further operation of the machine until the oil is replaced and/or the machine is repaired (e.g., if a contamination leak is detected).

At 326-4, the concentrations of water, acid, and/or base in the oil may be used to generate or update a model of the health of the engine (e.g., or another machine in which the oil is disposed), which may be based on an earlier-built model using engine health descriptors at 328-4. For example, if the engine is operated with a poor quality of oil, the health of the engine may suffer, reducing the expected performance and/or operational lifetime of the engine. On the other hand, if the oil in the engine is maintained in good health such that the oil is replaced before the oil degrades to a poor health condition, then the engine may be determined to have a good health. The health of the oil and the engine may be used to predict the remaining operational lifetimes of the oil and the engine using the models at 322-4 and 326-4.

In one embodiment, a sensing system is provided that includes a sensor and one or more processors. The sensor includes a sensing region configured to be in contact with an industrial fluid. The sensing region includes electrodes and a sensing region circuit electrically connected to the electrodes. The sensing region circuit is configured to generate an electrical stimulus having multiple different frequencies that are applied to the industrial fluid via the electrodes. The one or more processors are configured to receive one or more electrical signals from the sensor representative of an impedance response of the sensing region to the electrical stimulus. The one or more processors are configured to analyze the impedance response and determine at least one of a contaminant concentration of an external contaminant in the industrial fluid, an acid concentration of acidic components in the industrial fluid, or a base concentration of basic components in the industrial fluid based on the impedance response.

Optionally, the one or more processors are configured to determine the contaminant concentration, the acid concentration, and the base concentration in the industrial fluid based on the impedance response.

Optionally, the sensing region of the sensor is configured to be disposed with the industrial fluid within a reservoir of a machine having moving parts. The industrial fluid lubricates the moving parts of the machine.

Optionally, the industrial fluid is at least one of an oil, a fuel, a gas, or a solvent.

Optionally, the one or more processors are configured to analyze the impedance response by extracting resonance parameters of the impedance response. The resonance parameters include one or more of a frequency position (Fp) and magnitude (Zp) of a real part of the resonant impedance spectral response, a resonant frequency (F1) and antiresonant frequency (F2) of an imaginary part of the resonant impedance spectral response, an impedance magnitude (Z1) at the resonant frequency (F1) and an impedance magnitude (Z2) at the antiresonant frequency (F2), and a zero-reactance frequency (Fz) at the imaginary part of the resonant impedance spectral response.

Optionally, the sensing region circuit includes an inductor-capacitor-resistor (LCR) resonant circuit.

Optionally, the sensing region includes a sensing material.

Optionally, the one or more processors are configured to analyze the impedance response by extracting resonance parameters of the impedance response. The one or more processors are configured to determine at least one of the contaminant concentration or the acid concentration of the industrial fluid by comparing the resonance parameters that are extracted to known resonance parameters associated with at least one of different contaminant concentrations, different acid concentrations, or different base concentrations in the industrial fluid.

Optionally, the one or more processors are configured to determine the acid concentration of the industrial fluid within one of at least three different acid levels. The one or more processors are further configured to determine the contaminant concentration of the industrial fluid within one of at least three different contaminant levels.

Optionally, the external contaminant is water.

Optionally, the industrial fluid is an oil and at least some of the acidic components in the industrial fluid are products of oxidation of the oil. The one or more processors are configured to determine the acid concentration in the industrial fluid to estimate at least one of an amount of acidic contamination of the oil, an amount of the basic components in the oil, or an amount of degradation of the oil.

In another embodiment, a method is provided that includes applying an electrical stimulus having multiple different frequencies to an industrial fluid via electrodes of a sensor that is in contact with the industrial fluid. The electrical stimulus is generated by a sensing region circuit of the sensor that is electrically connected to the electrodes. The method also includes receiving one or more electrical signals from the sensor at one or more processors. The one or more electrical signals are representative of an impedance response of the sensor to the electrical stimulus. The method further includes analyzing the impedance response using the one or more processors to determine at least one of a contaminant concentration of an external contaminant in the industrial fluid, an acid concentration of acidic components in the industrial fluid, or a base concentration of basic components in the industrial fluid based on the impedance response.

Optionally, the impedance response is analyzed by extracting resonance parameters of the impedance response. The method further includes comparing the resonance parameters that are extracted to known resonance parameters associated with at least one of different contaminant concentrations, different acid concentrations, or different base concentrations in the industrial fluid.

Optionally, the impedance response is analyzed to determine both the contaminant concentration and the acid concentration in the industrial fluid based on the impedance response.

Optionally, the impedance response is analyzed to determine both the contaminant concentration and the base concentration in the industrial fluid based on the impedance response.

Optionally, the impedance response is analyzed to determine both the contaminant concentration and a concentration of an additive package in the industrial fluid based on the impedance response.

In another embodiment, a sensing system is provided that includes a sensor and one or more processors. The sensor includes a sensing region configured to be in contact with an industrial fluid. The sensing region includes electrodes and a sensing region circuit electrically connected to the electrodes. The sensing region circuit includes an inductor-capacitor-resistor (LCR) resonant circuit. The sensing region circuit is configured to generate an electrical stimulus having multiple different frequencies that is applied to the industrial fluid via the electrodes. The one or more processors are configured to receive one or more electrical signals from the sensor representative of an impedance response of the sensing region to the electrical stimulus. The one or more processors are configured to analyze the impedance response and determine a contaminant concentration of an external contaminant in the industrial fluid, a base concentration of basic components in the industrial fluid, and an acid concentration of acidic components in the industrial fluid based on the impedance response.

Optionally, the electrodes in the sensing region include at least one pair of electrodes.

Optionally, the sensing region circuit includes multiple LCR resonant circuits that have different resonant frequencies. The electrical stimulus applied to the industrial fluid has a spectral frequency range that includes the different resonant frequencies of the multiple LCR resonant circuits.

Optionally, the industrial fluid is an oil and at least some of the acidic components in the industrial fluid are products of oxidation of the oil. The one or more processors are configured to determine the acid concentration in the industrial fluid to estimate at least one of an amount of acidic contamination of the oil, an amount of depletion of the basic components in the oil, or an amount of degradation of the oil.

Optionally, the sensing region includes a sensing material.

Optionally, the industrial fluid is an oil and at least some of the basic components in the industrial fluid are additives added to the oil. The one or more processors are configured to determine the base concentration in the industrial fluid to estimate at least one of an amount of depletion of the additives, an amount of basic contamination of the oil, or an amount of degradation of the oil.

In another embodiment, the multivariable resonant sensor described herein is a component of an asset monitoring system that is configured to monitor an asset (e.g., an engine, a gearbox, a transmission, a turbocharger, and the like). As used herein, "assets" refer to machines and/or devices with tangible mechanical structures. The asset monitoring system may be configured to determine a health of the machine asset and may take responsive action, such as to provide an alert or automatically schedule maintenance, responsive to determining that the health of the machine asset, or an industrial fluid therein, is below a designated threshold health level. In one or more embodiments, the asset monitoring system may provide a prognostic outlook for the machine asset, such as by estimating a remaining operational lifetime of the machine asset and/or an industrial fluid therein.

Figure 90:
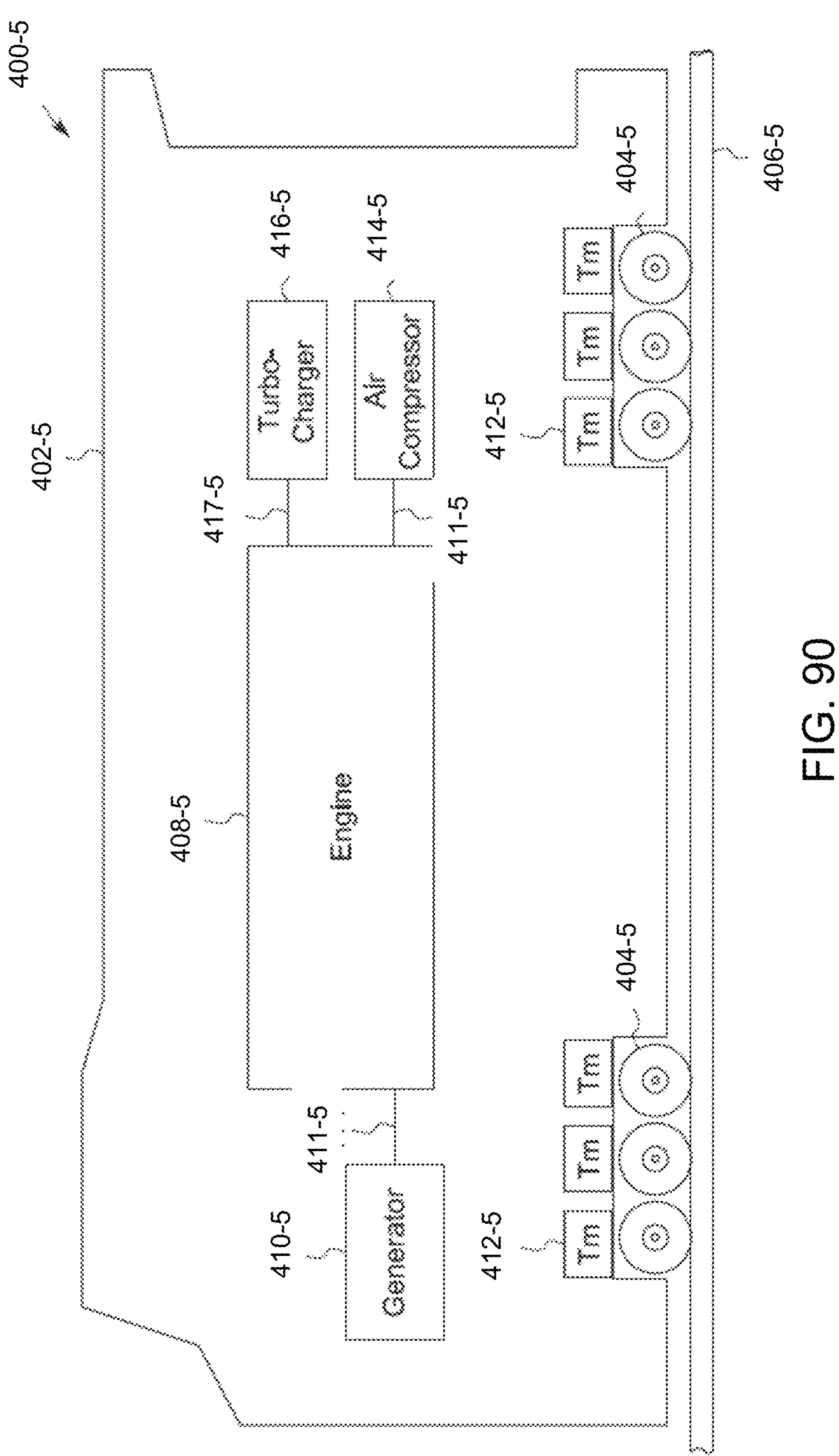
FIG. 90 is a perspective view of a portion of a portion of a vehicle system according to an embodiment.

FIG. 90 is a perspective view of a portion of a portion of a vehicle system 400-5 according to an embodiment. The vehicle system in the illustrated embodiment is a propulsion-generating rail vehicle 402-5 (such as a locomotive), but in other embodiments the vehicle system may be an onroad vehicle (e.g., a semi-truck, an automobile, etc.), an off-road vehicle (e.g., a construction vehicle), a marine vehicle, or the like. Although only the locomotive is shown in FIG. 90, the vehicle system optionally may include multiple vehicles that are configured to travel together along a route. For example, the multiple vehicles may be mechanically coupled to one another, such as in a train, or may be mechanically spaced apart and communicatively coupled to one another such that movements of the multiple vehicles are coordinated. The locomotive includes multiple wheels 404-5 configured to engage and move along a rail 406-5 of a track.

The vehicle system includes an engine 408-5 configured to generate power to propel the vehicle system along a route. In the illustrated embodiment, the engine of the locomotive may be a diesel-powered engine. The engine may include multiple cylinders arranged in a straight line or in a V-shape within a cylinder block. The engine is operatively coupled to a generator 410-5 (e.g., an alternator) via a drive shaft 411-5. The generator converts mechanical energy from the engine to electrical energy, such as AC current or DC current. The electrical energy is transmitted conductively via electrical cables (not shown) to multiple traction motors 412-5 associated with axles (not shown) coupled to the wheels. The traction motors use the electrical energy to mechanically rotate the wheels to move the vehicle system along the route. Some of the electrical energy generated by the generator may be transmitted to a battery and/or to non-propulsion loads, such as heating, ventilation, and air-conditioning (HVAC) loads, lighting, and electrical computing systems.

The vehicle system may also include an air compressor 414-5 and a turbo-charger 416-5. The air compressor is configured to provide a constant supply of compressed air for the brakes of the vehicle system. The air compressor optionally may be driven via the drive shaft of the engine. The turbo-charger is used to increase the amount of air that is supplied to the engine relative to naturally-aspirated engines, and therefore provides an increase in engine power. The turbo-charger may be driven by exhaust gas from the engine via an exhaust gas conduit 417-5, such that no additional fuel is burned to operate the turbo-charger. Although not shown, the vehicle system may also include a plurality of drive trains that each has a gear case. The gear cases of the drive trains include a reservoir that holds a lubricating fluid, such as oil. The gear cases may be associated with the axles and the wheels. For example, the gear cases may be operably coupled between the traction motors and the axles.

The engine, the generator, the turbo-charger, the traction motors, the air compressor, and the gear cases are vehicle machines or equipment (also referred to herein as machine assets) of the vehicle system. At least some of the machines of the vehicle system have industrial fluids therein for lubrication, heat-dissipation, pneumatics, or the like. For example, the engine includes oil housed within one or more reservoirs, such as a crankcase, a gearbox, the cylinder block, and/or the like. Although the engine is described herein as the monitored machine of the vehicle system, it is understood that other machine devices of the vehicle system may also include movable components that engage lubricating industrial fluids, such as oil. The oil engages movable components of the engine to provide lubrication, reducing the frictional forces and providing improved efficiency (relative to engines without lubricating fluids).

However, as described above, the health of oil may diminish over time due to oil aging and/or the introduction of external contaminants, such as water and acidic components. As the health of the oil declines, not only does the lubricating performance of the oil suffer (e.g., due to oil contamination and aging), but so too may the health of the asset that uses the oil (e.g., the engine). For example, contaminants such as acids and water may cause, or at least exacerbate, corrosion of the walls of the engine reservoir that contain the oil. The water and acid may increase the rate of oxidation of the metallic walls of the engine. The corrosion may result in cracks that allow additional contaminants into the engine. Eventually, the corrosion may cause the engine to operationally fail (e.g., the engine stalls or breaks), which can cause the vehicle system to shut down until a replacement engine can be installed. The failure of the engine due to corrosion may cause damage to other assets and/or components of the vehicle system, such as the generator, increasing the cost of the repairs and possibly extending the down-time of the vehicle system.

The external contaminant in the oil of the engine may be water that enters the oil reservoir of the engine from the ambient environment due to condensation. For example, the engine may not be hermetically sealed, and leak paths in the engine may allow contaminants such as water from the ambient environment to interact with the oil. Besides condensation, water may be introduced into the oil via a coolant leak, equipment cleaning, or as a by-product of a reaction. The amount of water in the oil may vary based on multiple factors including the amount and size of the leak paths (e.g., the accessibility of the oil), the temperature of the oil, and the temperature and relative humidity of the ambient environment. For example, while the vehicle system operates, the temperature of the oil may exceed the temperature of the ambient environment and/or an evaporation temperature of water. At least some of the water within the oil may evaporate into the ambient environment, reducing the concentration of water within the oil. Conversely, when the temperature of the oil is less than the evaporation temperature of water, the concentration of water within the oil may increase due to condensation of water from the ambient environment into the oil. The condensation of water into the oil may typically occur when the vehicle system is in a non-operating state, as the temperature of the oil decreases relative to the temperature of the oil while the engine is in an operating state. In order to avoid the costs associated with reduced performance of the vehicle system, repairs, shutdowns, and/or reduced operating lifetimes of assets such as the engine, an asset monitoring system 500-5 (shown in FIG. 92) is configured to provide real-time monitoring of the health of the lubricating oil in an asset, such as the engine. The asset monitoring system is configured to provide data for early detection of leaks of process fluids into engine oil, to provide data for early detection of oil degradation and aging, to provide a status of the engine, and/or to predict the remaining life of the oil and/or the engine.

Figure 91:
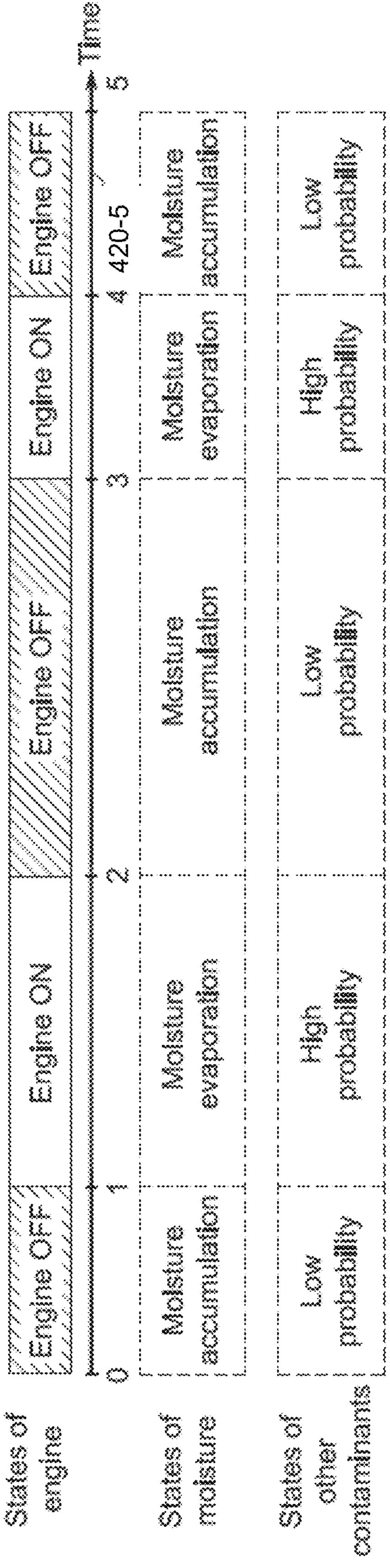
FIG. 91 is a schematic diagram showing a relationship between operating state of the vehicle system and a change in water concentration within the oil of the vehicle system over time.

FIG. 91 is a schematic diagram showing a relationship between operating state of the engine of the vehicle system and a change in water concentration within the oil of the engine over time. FIG. 91 plots the state of the engine and the state of moisture (e.g., water) in the oil along an axis 420-5 representing time in relative units. During a first time period between times 0 and 1, the engine is in an OFF or non-operating state. When the engine is in the OFF state, the engine does not supply power to the generator. For example, the engine may be shut down such that no fuel and/or no air is injected into the cylinders to drive the movement of the pistons and rotate the crankshaft. Therefore the engine in the OFF state may be attributed with a lack of fuel and air injection, a lack of noise and vibration of the engine, a lack of exhaust gas, non-operation of the turbo-charger, non-operation of the generator, and the like. The engine may be switched to the OFF state when the vehicle system is parked in a railyard and/or the vehicle system is scheduled to be stationary for at least a designated amount of time (e.g., for longer than a typical duration of a temporary stop).

When the engine is in an ON or operating state, fuel is injected into the cylinders to force pistons within the cylinders to move and drive rotation of a crankshaft. The engine in the ON state generates power that is used to power loads on the vehicle system, such as to propel the vehicle system along the route. Therefore, the ON state of the engine is attributed with fuel injection, air injection, rotation of the crankshaft and drive shaft, vibration of the engine, noise produced by the engine, exhaust gas output, operation of the turbo-charger due to the exhaust gas, operation of the generator, electrical energy supplied to the tractive motors, and/or the like. It is noted that the engine may be kept in the ON state in idle during temporary stops, even though the vehicle system is stationary. Some examples of temporary stops of the vehicle system include stops for meets and passes with other vehicle systems, traffic signal stops, stops at designated stations to load and/or unload cargo and passengers, and the like. The engine may be controlled to operate in the ON state during a first trip of the vehicle system, and then may be controlled to be in the OFF state after the first trip and before a second trip begins.

As shown in FIG. 91, moisture accumulates in the oil between times 0 and 1 (where time is in relative units) while the engine is in the OFF state. The moisture may accumulate due to condensation from the ambient environment while the temperature of the oil is relatively low. In the subsequent time period between times 1 and 2, the engine is in an ON or operating state, and the moisture evaporates from the oil into the ambient environment due to the high temperature of the oil. The diagram in FIG. 91 illustrates a general trend that a concentration of water in the oil of the engine increases or accumulates while the engine is OFF and the concentration of water in the oil decreases via evaporation while the engine is ON. The rates of water accumulation and/or reduction may change over time based on various factors such as temperature of the oil, temperature and relative humidity of the ambient environment, existing concentration of water in the engine, size and/or amount of leak paths in the engine, and the like. For example, if the engine operates for a sufficient duration and at a sufficient temperature, most if not all of the water may evaporate from the oil such that the rate of moisture evaporation may effectively stop due to the lack of moisture in the oil, although the engine continues to operate in the ON state.

Since water may accumulate in the oil while the engine is OFF and evaporates from the oil while the engine is ON, the concentration of water in oil while the engine is OFF may be greater than the concentration of water while the engine is ON. As a result, the corrosive effect of water in the engine may be more severe during the periods of time that the engine is OFF relative to when the engine is ON and operating. For example, a greater concentration of water in the oil and/or a greater amount of time that the engine is OFF cause an increased amount of corrosion or degradation of the engine relative to a reduced concentration of water in the oil and/or a reduced amount of time that the engine is OFF. Therefore, the health of the oil and/or the engine may be preserved by reducing the amount of water that is introduced into the oil and/or reducing the amount of time that the engine is OFF, such as by operating the engine in the ON state for longer durations of time. The asset monitoring system 500-5 is configured to continuously (e.g., at set time intervals) monitor the operating states of the engine and the concentration of one or more polar analytes, such as water, in the oil to determine the health of the oil and the engine.

During the time periods that the engine is OFF between times 0 and 1, between times 2 and 3, and between times 4 and 5, there is a low probability of other contaminants (e.g., other than water) present in the oil of the engine. The other contaminants may refer to acids, fuel, soot, and the like that may enter the oil reservoir of the engine through a leak path. For example, there is a low probability of fuel leakage into the oil when the engine is OFF because fuel is not being injected into the engine. During the time periods that the engine is ON between times 1 and 2 and between times 3 and 4, there is a higher probability of other contaminants present in the oil of the engine. For example, as the engine operates, the high temperatures and high pressures within the engine may cause or enlarge leak paths that allow contaminants, such as fuel, acids, and soot or other debris, to enter the engine.

Figure 92:
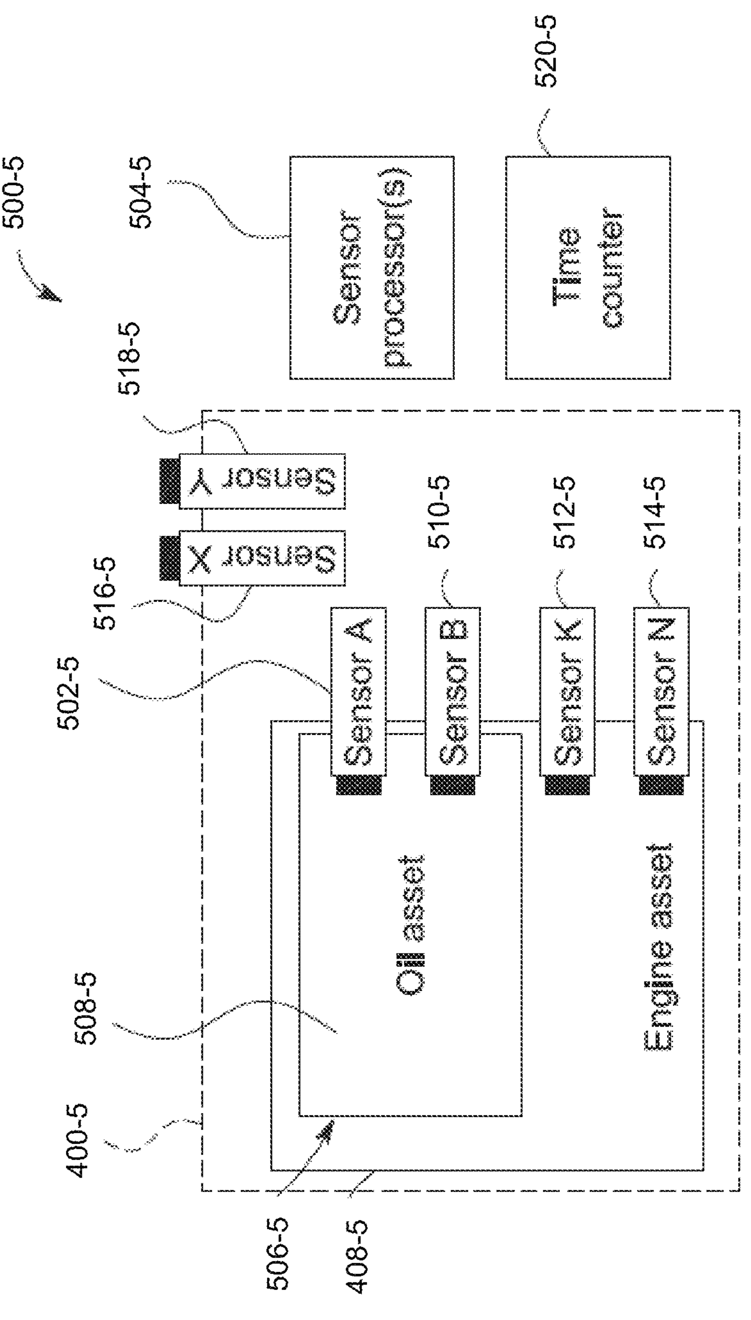
FIG. 92 is a schematic diagram of an asset monitoring system according to an embodiment.

FIG. 92 is a schematic diagram of an asset monitoring system 500-5 according to an embodiment. The asset monitoring system includes at least a resonant sensor 502-5 (e.g., Sensor A shown in FIG. 92) and one or more sensor processors 504-5 operatively connected to the resonant sensor 502-5. The asset monitoring system 500-5 is configured to monitor an asset of the vehicle system 400-5, which in the illustrated embodiment is the engine 408-5. The engine 408-5 defines a reservoir 506-5 that contains a lubricating oil 508-5 for lubricating the various gears, pistons, and other moving components of the engine 408-5. The resonant sensor 502-5 is mounted to the engine 408-5 in operational contact with the oil 508-5. The asset monitoring system 500-5 is configured to provide real-time monitoring of the health of the oil 508-5 and the engine 408-5. The asset monitoring system 500-5 may be configured to use the determined health of the oil 508-5 and/or the engine 408-5 to predict a remaining operational life of the oil 508-5 and/or the engine 408-5. Furthermore, the asset monitoring system 500-5 may be configured to take responsive actions based on the determined health of the oil 508-5 and/or the engine 408-5, such as automatically scheduling maintenance, providing an alert or message to an operator representative of the health status, and/or prohibiting operation of the vehicle system 400-5 until maintenance is performed.

One or more technical effects of the asset monitoring system 500-5 is the ability to provide maintenance on an asset device based on a health or condition of the asset, such that the maintenance is performed when necessary. The asset monitoring system 500-5 is configured to avoid problems associated with monitoring the asset only on a fixed schedule, such as every twelve months, every six months, or every three months. For example, such maintenance may require an operator manually accessing the engine to inspect the health of the oil and the engine. If the oil and engine are determined to be in good health during an inspection, the effort and cost of manually inspecting the engine are unnecessary. On the other hand, leaks can quickly cause damage to the engine and the oil therein, and the fixed maintenance schedule may not be able detect a poor health condition of the oil and/or the engine in time to prevent reduced performance of the vehicle system and/or damage to the vehicle system. The asset monitoring system 500-5 is configured to continuously monitor the health of the oil and/or the engine, such as by obtaining a measurement every second, every minute, every hour, every day, or any other predetermined time interval.

By estimating the remaining operational life of the oil and/or engine, the asset monitoring system 500-5 allows an operator to plan for future maintenance, such as by ordering replacement parts and scheduling a maintenance appointment, before such maintenance is necessary. Furthermore, by taking an automatic responsive action upon detecting a poor health of the oil and/or engine (instead of waiting until regularly-scheduled maintenance), the asset monitoring system 500-5 is configured to reduce damage to the engine which extends the operational lifetime of the engine and/or other components of the vehicle system. Therefore, the condition-based maintenance provided by the asset monitoring system 500-5 provides the ability to operate the vehicle system more reliably and to avoid costly shut-downs and repairs.

The resonant sensor 502-5 is configured to measure a concentration of at least one polar analyte in the oil 508-5. The resonant sensor 502-5 may be the same or at least similar to the sensor 5802-5 or another sensor described herein. For example, the sensor 502-5 has a sensing region circuit that includes at least one LCR resonant circuit, and optionally includes multiple LCR resonant circuits having different resonant frequencies relative to each other. The sensing region circuit is configured to generate an electrical stimulus that is applied to the oil via electrodes of the sensor 502-5. The electrical stimulus applied to the oil is generated over a spectral frequency range that includes or incorporates the resonant frequencies of the resonant LCR circuits. The sensor 502-5 generates the electrical stimulus having multiple different frequencies in order to obtain a measurement of one or more polar analytes in the oil.

The sensor 502-5 is communicatively connected to the one or more sensor processors 504-5. For example, the sensor 502-5 may be wirelessly connected to the one or more sensor processors 504, such as via inductive coupling, or may be conductively connected to the one or more sensor processors 504-5, such as via a wired connection. The one or more sensor processors 504-5 may be components of the sensor reader 5804-5 and/or the reader 2659B. Although shown as one discrete component or device, the one or more sensor processors 504-5 may include multiple processors that are distributed in different devices or housings. For example, one processor 504-5 may be disposed in a sensor reader proximate to the sensor 502-5, and another processor 504-5 of the sensor processors 504-5 may be disposed remotely, such as in a remote server that is not disposed on the vehicle system 400-5.

The sensor 502-5 is configured to transmit an electrical signal to the one or more processors 504-5. The electrical signal is representative of an impedance response of the sensor 502-5, in contact with the oil, to the electrical stimulus. The impedance response is measured over the resonant frequencies of a single or multiple LCR resonant circuits of the sensor 502-5. As described above, the one or more sensor processors 504-5 are configured to receive the electrical signal from the resonant sensor 502-5 and analyze the impedance response to determine a concentration of the polar analyte in the oil. The one or more sensor processors 504-5 may analyze the impedance response by extracting (e.g., calculating) resonance parameters from the impedance response, such as Fp, Zp, F1, F2, Z1, Z2, and/or Fz.

The one or more polar analytes that are measured by the sensor 502-5 are at least one of an oil-aging compound or an external contaminant. Examples of oil-aging compounds may include stabilizing additives added to the oil and acidic components that are produced during the chemical breakdown of the oil and/or the stabilizing additives added to the oil. Examples of external contaminants include water, acids, fuel, soot, metallic particles, and the like that enter the reservoir 506-5 via leak paths in the engine 408-5 or generated within the engine 408-5. As described above, each measurement of the impedance response of the oil to an electrical stimulus pulse may be used to determine a concentration of water and/or a concentration of acid (e.g., total acid number) in the oil. Therefore, the sensor 502-5 can be used to determine a measurement of the concentration of water, the concentration of acid, or both based on the impedance response to an electrical stimulus. In one embodiment, the sensor 502-5 and processors 504-5 may monitor the water concentration only, and in another embodiment the sensor 502-5 and processors 504-5 may monitor the water concentration and the acid concentration or just the acid concentration.

The sensor 502-5 and one or more processors 504-5 are configured to monitor the concentration of the one or more polar analytes of interest in the oil over time by obtaining multiple different measurements of the concentration at different times. For example, in an embodiment, the sensor 502-5 and the one or more processors 504-5 may periodically measure the concentration of a selected polar analyte to track changes of the concentration of the selected polar analyte over time. For example, the sensor 502-5 and one or more processors 504-5 may obtain a measurement of the concentration at regular intervals that are no greater than five minutes in duration (between measurements). The concentration of the selected polar analyte may be measured every two minutes, every minute, every thirty seconds, every ten seconds, every second, or the like. The concentration of the polar analyte is measured periodically by the sensor 502-5 applying an electrical stimulus having multiple different frequencies to the oil at a regular time interval.

The one or more processors 504-5 are configured to analyze the impedance response of the oil (e.g., the sensor in contact with the oil) to each application of the electrical stimulus to determine the concentration of the polar analyte at multiple different times. For example, a first determined concentration of the polar analyte is associated with a first time that the sensor 502-5 applies a first electrical stimulus to the oil, and a second determined concentration of the polar analyte is associated with a second time (e.g., such as thirty seconds after the first time) that the sensor 502-5 applies a second electrical stimulus to the oil. The relatively high frequency of measurements, compared to monthly or bi-yearly measurements for example, allows the asset monitoring system 500-5 to provide early detection of, and remedial responses to, contaminant leaks, poor oil health and/or engine health, and the like. By obtaining measurements of the concentration of the one or more selected polar analytes in the oil at multiple different times, the asset monitoring system 500-5 can monitor and track how the concentration changes during an operational life of the engine.

In one embodiment, the output of the resonant sensor 502-5 may be coupled to a data-based and/or physics-based model that predicts the frequency position (Fp) and magnitude (Zp) with water, fuel, acid, and/or soot contamination. The Fp and Zp may be directly correlated to the level or concentration of the contaminant in the engine oil. Data fusion may be performed via a Kalman filter-based approach or a derivative approach, such as the extended Kalman filter. A particle filter-based approach may also be implemented. The filter(s) are used with the model of the resonant sensor output. Data fusion may yield a prediction of the percent of water contamination and the percent of fuel contamination in the oil based on the current measurements of Fp and Zp. Future predictions or projections of the contaminant concentrations in the oil can be made via slope-based methods to obtain estimates of the time until water and/or fuel percentage contamination exceeds predetermined thresholds or condemnation limits. As additional data is collected, the estimates of time remaining until thresholds are crossed may become more accurate. Other filters may also be used to compute the remaining amounts of time, including exponential and moving average filters.

In an embodiment, the rate of change of the resonant parameters Fp and Zp are tracked between time periods. A threshold-based control logic is used to determine, based on the rate of change of the parameters Fp and Zp, whether a water leak, fuel leak, or other contaminant leak has occurred.

The asset monitoring system 500-5 optionally may include one or more additional sensors configured to monitor various properties of the oil, the vehicle system, and/or the ambient environment. For example, in the illustrated embodiment, the asset monitoring system 500-5 includes a temperature sensor 510-5 (e.g., Sensor B) that is mounted to the engine 408-5 and/or disposed within the reservoir 506-5. The temperature sensor 510-5 is in operational contact with the oil 508-5 and is configured to monitor a temperature of the oil 508-5 over time. For example, the temperature sensor 510-5 may measure the temperature of the oil 508-5 periodically, such as every second, every ten seconds, every thirty seconds, every minute, or the like. The temperature sensor 510-5 optionally may measure the temperature of the oil 508-5 with the same or similar periodicity as the resonant sensor 502-5. In one embodiment, the temperature sensor 510-5 may be a part of the sensor 502-5 and share the same housing and communication components with the sensor 502-5.

The asset monitoring system 500-5 also can include additional sensors that are configured to monitor relevant properties of the oil 508-5, the engine 408-5, and the ambient environment. For example, the asset monitoring system 500-5 may include a temperature sensor 512-5 (e.g., Sensor K) and a vibration sensor 514-5 (e.g., Sensor N) mounted to the engine, such as installed on or in a housing of the engine. The temperature sensor is configured to monitor a temperature of the engine. The temperature sensors disclosed herein may be thermocouples, resistive temperature devices, infrared sensors, bimetallic devices, silicon diodes, thermometers, change of state sensors, or the like. The vibration sensor is configured to monitor vibration of the engine and/or the vehicle system. The vibration sensor may be or include an accelerometer, a piezoelectric component, a piezoresistive component, a variable capacitance component, and/or a servo sensor.

The asset monitoring system may also include a temperature sensor 516-5 (e.g., Sensor X) and a humidity sensor 518-5 (e.g., Sensor Y) mounted to the vehicle system remote from the engine. The temperature sensor 516-5 is configured to monitor a temperature of the ambient environment, and the humidity sensor monitors the relative and/or absolute humidity of the ambient environment. The humidity sensor may be a capacitive-based electronic hygrometer, a resistive-based electronic hygrometer, or the like. All of the sensors of the asset monitoring system are communicatively coupled to the one or more sensor processors via a wireless or wired connection. For example, the sensors are configured to obtain measurements of the corresponding properties and transmit the measurements in the form of electrical signals having data parameters to the one or more sensor processors for data collection and analysis. The sensors, other than the resonant sensor, may be optional. In other embodiments, the asset monitoring system may have greater or less than the six sensors shown in FIG. 92, and/or may include at least one different type of sensor than the types of sensors described, such as an optical sensor, an electromagnetic sensor (e.g., a Hall effect sensor), or the like.

Some of the sensors of the asset monitoring system may be configured to monitor properties that are used to determine the operating state of the engine. For example, the temperature sensor 510-5 in the oil, the temperature sensor 512-5 on the engine, and the vibration sensor may be used by the sensor processor(s) to monitor whether the engine is in the ON (or operating) state or the OFF (or non-operating)

state. Such sensors are referred to herein as operating condition sensors, as the sensors are used to detect when the engine is in the operating state and when the engine is in the non-operating state. For example, if the vibration sensor detects that the engine is vibrating at an amount, characterized as a frequency or intensity, that exceeds a corresponding vibration threshold, the one or more sensor processors may determine that the engine is in the operating state because operation of the engine may cause vibration due to the moving components. Conversely, if the vibration sensor detects that the vibration of the engine is below the vibration threshold, then the engine may be determined to be in the non-operating state.

In another example, if at least one of the temperature of the oil or the temperature of the engine exceeds a corresponding threshold temperature, the one or more sensor processors may determine that the engine is in the operating state because operation of the engine generally heats the engine and the oil therein. Conversely, detection of the temperature of the oil or the temperature of the engine falling below the corresponding threshold temperature may indicate that the engine is in the non-operating state because the engine and the oil therein may generally cool down responsive to the engine shutting down. Optionally, the corresponding threshold temperatures may vary dependent on the temperature of the ambient environment as detected by the temperature sensor 516-5. For example, the one or more sensor processors may analyze the temperature difference between the ambient environment and the oil and/or the engine. For example, if the ambient environment is hotter than an average or median temperature, then the corresponding threshold temperature may be raised to account for the temperature change of the oil and/or engine attributable to the ambient environment. Furthermore, if the ambient environment is colder than the average or median temperature, then the corresponding threshold temperature may be lowered.

In other embodiments, additional or different sensors may be used to determine and monitor the operating state of the engine, such as an optical sensor, an electromagnetic sensor, an angular rotation sensor, or the like. The asset monitoring system may be configured to continuously monitor the operating state of the engine over time to determine durations of time periods that the engine is ON, durations of time periods that the engine is OFF, the frequency at which the engine switches operating states, and the like. In an embodiment, the asset monitoring system includes a time counter 520-5 that is configured to keep a record of time. The one or more processors are configured to determine the durations in each of the ON and OFF operating states and the frequency of switching based on received parameters from the operating condition sensors and the time counter. Although the time counter is shown as a separate and discrete component or device relative to the sensor processor(s), the time counter optionally may be an integral component of the one or more sensor processors. For example, at least one of the one or more processors and the time counter may be contained within a same computer or server.

Different processes occur while the engine is in the ON state relative to when the engine is in the OFF state, such as water condensation and accumulation in the oil while the engine is in the OFF state. Therefore, the information about the times, durations, and frequency that the engine is in the OFF state may be used to determine the health of the oil and the engine, because the corrosion of the engine due to water may be more severe when the engine is in the OFF state due to the higher water concentration in the oil.

Figure 93:
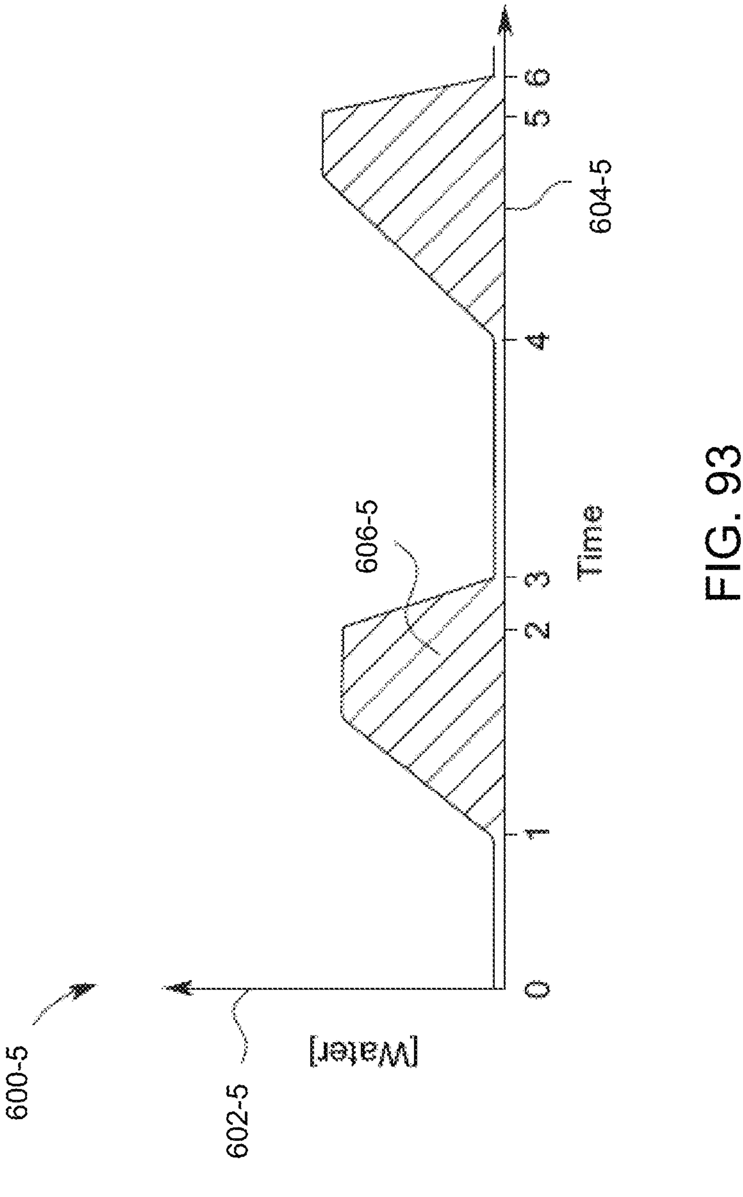
FIG. 93 is a plot of a concentration of water in oil over time according to an embodiment.

FIG. 93 is a plot 600-5 of a concentration of water in oil over time according to an embodiment. The y-axis 602-5 represents the concentration of water in oil, which may be in parts per million or the like. The x-axis 604-5 represents time. The duration of the x-axis 604-5 from times 0 to 6 may be days, weeks, months, or years. The time values 1 to 6 shown in FIG. 93 are not representative of regular, uniform time intervals, such that the time between times 1 and 2 is greater than the time between times 2 and 3. The oil may be the oil within the engine of the vehicle system. In an embodiment, water is a polar analyte that is measured by the resonant sensor and one or more sensor processors. The resonant sensor and the one or more processors are configured to measure the concentration of water within the oil at multiple times during the operational life of the engine (e.g., by applying an electrical stimulus to the oil at different times and analyzing the resonant impedance spectral responses to the electrical stimuli). The resonant sensor and the one or more processors 504 may measure the concentration of water within the oil periodically at a regular interval, such that the data obtained can be plotted as shown in FIG. 92.

As shown in FIG. 93, between times 0 and 1, the concentration of water is at a negligible amount, such that no water or only a residual amount of water is present in the oil. The time period between times 0 and 1 may represent a time period that the engine is in the operating (e.g., ON) state. For example, while the engine operates, the temperature of the oil may be sufficiently high that water from the ambient environment does not condense into the oil and water previously within the oil evaporates, resulting in a negligible amount of water. Between times 1 and 2, the concentration of water increases to a non-negligible amount. For example, the concentration of water increases and then generally levels off. The time period between times 1 and 2 may represent a time period that the engine is in the non-operating (e.g., OFF) state, such as between trips of the vehicle system. For example, after the engine shuts down, the temperature in the oil may decrease towards the temperature of the ambient environment. When the temperature of the oil is sufficiently low, water from the ambient environment may accumulate in the oil due to condensation and other known factors, causing the illustrated increase in the concentration of water. The concentration of water may level off due to various factors, such as the humidity of the ambient environment, the temperature of ambient environment, the temperature of the oil, and properties of the oil such as water solubility of the oil.

Between times 2 and 4, the concentration of water in the oil decreases until the concentration of water is at a negligible amount from time 3 to time 4. The time period between times 2 and 4 may represent another time period that the engine is operating. In an initial period between times 2 and 3, the concentration of water in the oil decreases, which may be attributable to an increased temperature of the oil as the engine warms up and operates. The time period between times 2 and 3 may include a warm-up period of the engine. For example, as the oil heats up, the temperature of the oil may exceed an evaporation threshold temperature, causing the water in the oil to evaporate into the ambient environment or a headspace of the engine oil reservoir. Between times 3 and 4, most if not all of the water in the oil at time 2 has evaporated. Between times 4 and 5, the concentration of water in the oil increases again due to the engine switching back to the non-operating state. The engine may shut down after completing a trip. The engine may also shut down responsive to a delay during a trip that exceeds a threshold amount of time, such as responsive to a derailment, traffic congestion, a delayed meet and pass event, or the like. In such situations, shutting the engine down may conserve fuel relative to operating the engine at idle for the duration of the delay. Furthermore, the engine may shut down during maintenance or other scheduled tasks. At time 5, the engine is switched ON again, which causes the resulting decrease in the concentration of water shown in the plot 600-5 after time 5.

A high concentration of water in the oil of the engine generally reduces the health of the engine and the oil relative to a negligible amount of water in the oil. For example, the water causes corrosion of the engine and also increases oxidation and breakdown of various components in the oil, such as stabilizing additives. As shown in FIG. 93, the time periods in which the engine is OFF, such as between times 1 and 2 and between times 4 and 5, have a higher concentration of water relative to the time periods that the engine is ON, such as between times 0 and 1, 2 and 4, and after time 5. Therefore, the health of the oil and the health of the engine deteriorate more, due to water in the oil, when the engine is OFF than when the engine is ON.

In one or more embodiments, the one or more sensor processors are configured to calculate a degradation value for the engine based on the concentration of one or more polar analytes of interest in the oil as a function of time. The degradation value represents a level of asset degradation. The degradation value is inversely proportional to the health and remaining life of the asset, such as the engine and/or the oil within the engine. For example, a low degradation value may represent a relatively healthy oil and/or engine with a long remaining life, and a high degradation value represents a relatively unhealthy oil and/or engine with a short remaining life. The remaining life represents an estimated amount of time before the asset should be replaced or repaired to avoid causing poor performance of the vehicle system and/or damage to other components of the vehicle system. The degradation value typically increases over time as the asset ages and the quality or health of the asset decreases. Optionally, the one or more processors may calculate a degradation value of the oil and a separate degradation value of the engine. For example, an oil change in the engine may trigger a reset of the degradation value of the oil without resetting the degradation value of the engine, which may continue to gradually increase.

The degradation value is calculated based on the concentration of the polar analyte in oil over time during the operating life of the asset. For example, in embodiments in which water is the polar analyte of interest, the degradation value may be calculated as the product of the water concentration and the duration of time. Since the concentration of water in the oil fluctuates over time due to condensation, evaporation, and the like, the degradation value may be calculated as the integral of the water concentration over time during the life of the asset. The integral is calculated to determine the area under the curve 606-5 shown in the plot 600-5 of FIG. 93. Since the water concentration may be measured periodically by the resonant sensor, the one or more processors may integrate using the trapezoidal rule to approximate the area under the curve 606-5 using the periodic measurements of water concentration in the oil. The degradation value of an asset can only increase or stay the same over time, such that the degradation value of the asset at time 5 is greater than the degradation value of the same asset earlier in time, such as at time 4.

The degradation value is proportional to the concentration of water, so the degradation value increases when there is a non-negligible water concentration, which usually occurs when the engine is non-operating and the temperature of the oil is relatively cool. Due to the trend between water concentration in oil and operating state of the engine, in an embodiment, the degradation value may be calculated based on the concentration of water in the oil during the time periods that the engine is in the non-operating state. For example, the degradation value may be calculated as the integral of the concentration of water between times 1 and 2 and between times 4 and 5. The times that the engine switches between operating states, such as at time 1 and at time 2, may be determined based on one or more of the operating condition sensors of the vehicle system, such as the vibration sensor 514-5, the temperature sensors 510-5, 512-5, or the like. In an alternative embodiment, the one or more sensor processors 504-5 may calculate the degradation value of the asset based on the entire duration from times 0 to 6 shown in FIG. 93, such as by calculating the integral of the concentration of water over the entire time period from 0 to 6. By including the entire duration in the calculation, some intermediate time periods in which the engine is operating while water is still present in the oil, such as between times 2 and 3 and times 5 and 6, are accounted for in the calculation of the degradation value.

In another embodiment, the one or more sensor processors 504-5 may calculate the degradation value of the asset based on temperature of the oil as monitored by the temperature sensor 510-5. For example, the degradation value may be calculated based on the concentration of water in oil measured during time periods that the temperature of the oil is less than an evaporation threshold temperature. The evaporation threshold temperature of water in the oil may be approximately 60, 80, or 100 degrees Celsius, depending on the vapor pressure of the ambient environment. Such time periods in which the oil temperature is less than the evaporation threshold temperature may be associated with the time periods that the engine is non-operating, such as between times 1 and 2 and between times 4 and 5. It is recognized that the time periods in which the oil temperature is less than the evaporation threshold temperature may be offset at least slightly from the time periods that the engine is non-operating due to warming up and cooling down of the oil. For example, after switching from the operating state to the non-operating state, there may be a lag period before the oil temperature cools to a temperature below the evaporation threshold temperature and water from condensation begins to accumulate in the oil. Similarly, after switching from the non-operating state to the operating state, there may be another lag period before the oil temperature exceeds the evaporation threshold temperature and the concentration of water in the oil begins to decrease due to evaporation.

In one or more embodiments herein, the calculation of the degradation value for the oil and/or the engine may account for intermediate states or sub-states of the engine, such as engine start, engine warm-up, engine cool-down, and engine stop. For example, the degradation value may be calculated as the concentration of the polar analyte in the oil during time periods in which the engine is non-operating and during time periods in which the engine is warming up, since significant water may remain in the oil as the engine warms up after switching into the operating state from the non-operating state. The intermediate states of the engine may be determined using the one or more operating condition sensors, such as a temperature sensor, a vibration sensor, or the like.

In addition to monitoring the concentration of one or more polar analytes in oil over time, the degradation value may also factor the specific component characteristics (e.g., type of engine, oil, etc.) and the specific usage or operating conditions (e.g., operating environment and operating intensity). Different types of engines and oils have different operational lifetimes due to varying materials/compounds and mechanics among the different types of components. For example, a first type of engine may be better able to withstand a certain concentration of a polar analyte in the oil than a second type of engine, such that the first type of engine degrades at a slower rate due to the polar analyte in the oil than the second type of engine. In addition, even similar types of engines having similar concentrations of a polar analyte in the oil may degrade at different rates based on different operating conditions. For example, a first engine may degrade at a faster rate than a second, similar engine if the first engine is operated at a higher speed or output, for a longer period of time, in a hotter and/or more humid environment, and/or in the presence of more dust, dirt, sand, or other debris than the second engine. The component characteristics may be determined by accessing an electronic vehicle database that stores information about the engine. The operating conditions may be determined based on an array of one or more sensors on the vehicle and/or by accessing an electronic trip plan or speed profile that is stored in a memory onboard the vehicle and used to control the movement of the vehicle during a trip.

Optionally, a physics-based model may be used to predict the degradation value for a specific engine of a vehicle based on the concentration of one or more polar analytes in the oil, the component characteristics of the engine, and/or the operating conditions of the engine. For example, the physics-based model may compare the polar analyte concentration in the oil and the operating conditions of a specific engine to historical data of polar analyte concentrations in the oil and operating conditions of similar engines (with similar types of oil) that were previously monitored and recorded in a database. Based on the historical data including recorded operational lifetimes of similar engines, the physics-based model may predict the degradation value and the remaining operational life of the specific engine.

Figure 94:
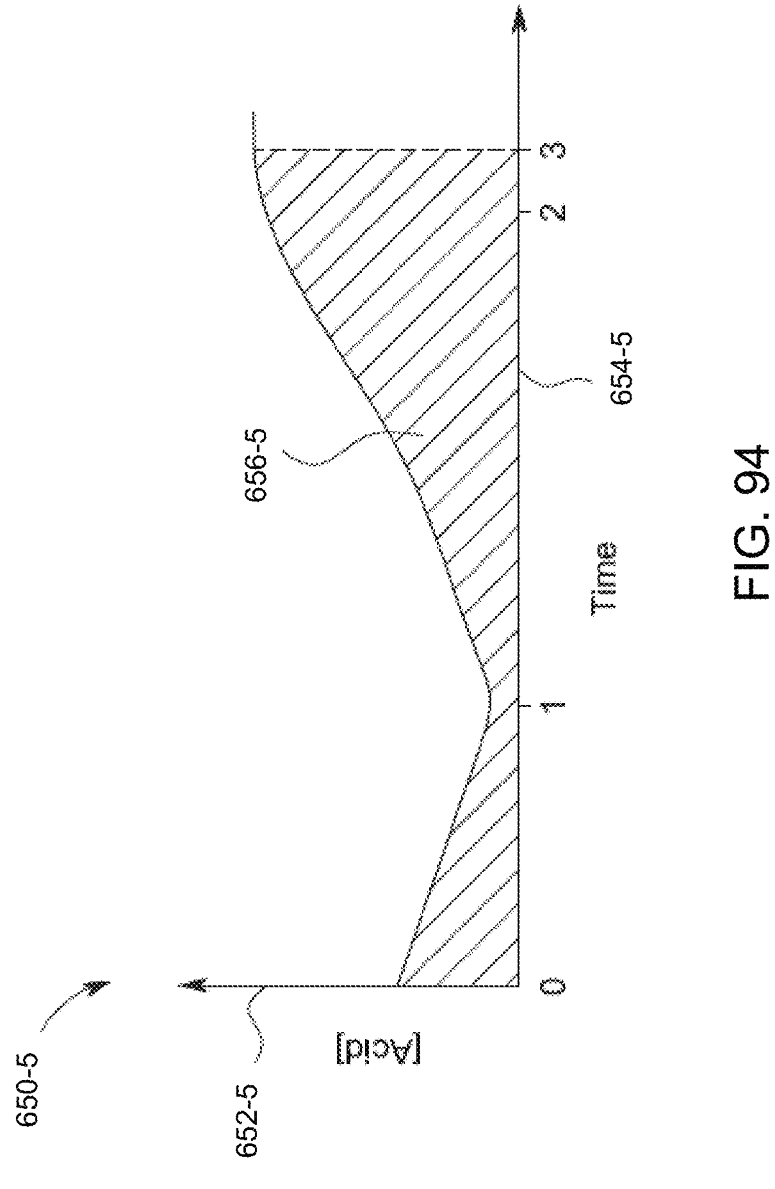
FIG. 94 is a plot of a concentration of acid in oil over time according to an embodiment.

FIG. 94 is a plot 650-5 of a concentration of acid in oil over time according to an embodiment. The y-axis 652-5 represents the concentration of acid in oil, which may be in parts per million or the like, and/or the total acid number (TAN) of the oil as an equivalent of mg KOH/g. The x-axis 654-5 represents time. The duration of the x-axis 654-5 from times 0 to 2 and beyond may be months or years. The time values 1 and 2 shown in FIG. 94 are not representative of regular, uniform time intervals. Between times 0 and 1, the concentration of acid in the oil slowly decreases, which may be due to depletion of stabilizing additives in the oil. The stabilizing additives may be or include acidic compounds, such that the acid concentration in the oil may decrease as the additives are depleted due to use of the oil in the engine. Between times 1 and 2, the concentration of acid in the oil increases due to one or more factors, such as breaking down of the oil into acidic compounds, introduction of acidic contaminants, and the like. For example, the oil may break down more rapidly after time 1 due to the lack of stabilizing additives in the oil due to depletion. The concentration of acid in the oil may begin to level out after time 2. A greater level of acid in the oil, particularly after the additives have depleted, can increase the amount of degradation of the oil and/or the engine. For example, the acid can cause corrosion of the engine and oxidation or other chemical reactions with different compounds in the oil, reducing the health of the engine and the oil. The detrimental effect of the acid in the oil is more severe at time 2 than at times 0 and 1 due to the greater concentration of acid in the oil at time 2 and the lack of stabilizing additives.

In an embodiment in which acid is the polar analyte of interest, the degradation value may be calculated as the product of the water concentration and the duration of time. Since the concentration of acid in the oil changes over time, the degradation value may be calculated as the integral of the acid concentration over time during the life of the asset. The integral is calculated to determine the area under the curve 656-5 between times 0 and 3 as shown in the plot 650-5 of FIG. 94.

Optionally, the degradation value of the asset (e.g., the engine and/or the oil in the engine) may account for degradation due to both water and acid. For example, a first component of the degradation value may be based on the concentration of water over time and a second component of the degradation value may be based on the concentration of acid over time. The first and second components may be weighted differently (e.g., using respective constants) in order to factor in the relative effect that each polar analyte has on the degradation of the asset. For example, the water may have a more severe detrimental effect on the asset than the acid, so the first component of the degradation value attributable to the water may be weighted greater than the weight of the second component of the degradation value attributable to the acid. Alternatively, the second component of the degradation value attributable to the acid may be weighted greater than the first component attributable to the water or the two components may be weighted equally.

Figure 95:
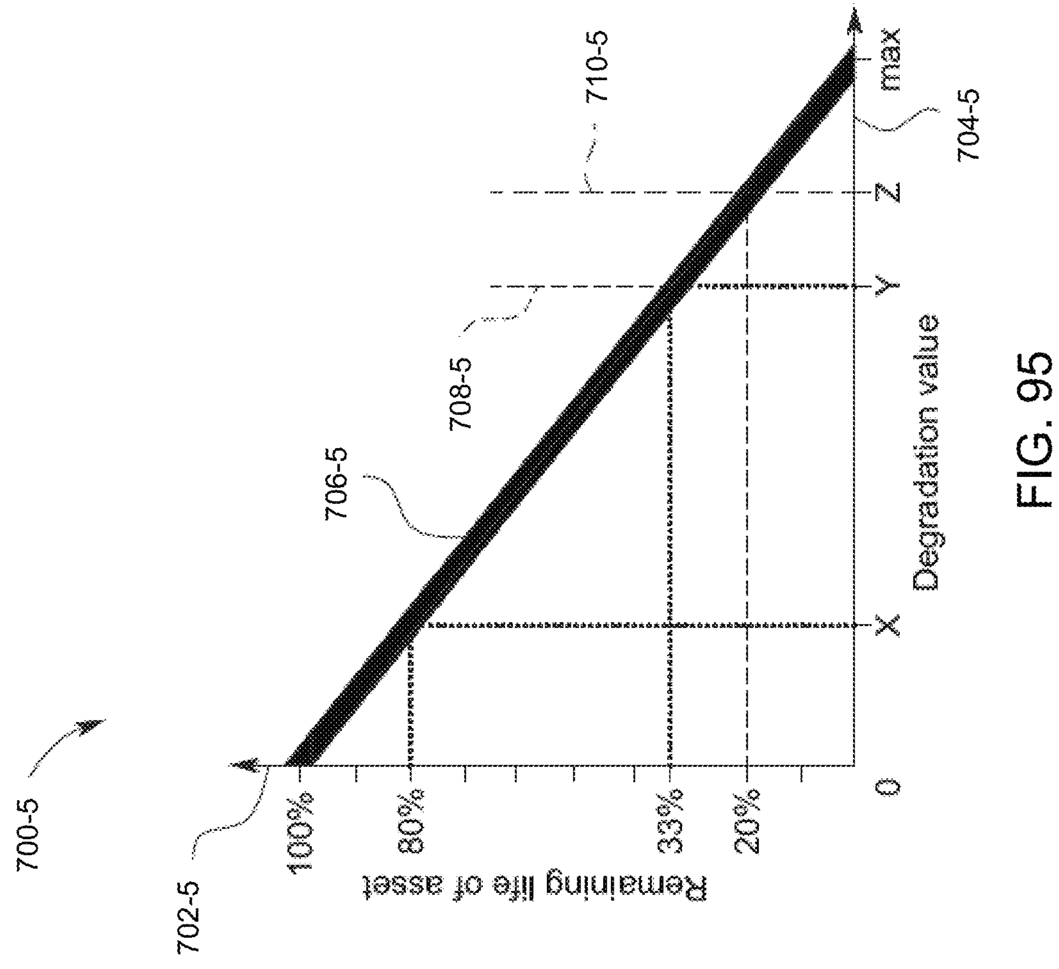
FIG. 95 is a plot of a remaining life of an asset over a degradation value of the asset according to an embodiment.

FIG. 95 is a plot 700-5 of a remaining life of an asset over a degradation value of the asset according to an embodiment. The y-axis 702-5 represents the remaining life of the asset, as demarcated by percentage of the remaining life. The x-axis 704-5 represents the degradation value. The degradation value may have units such as $ppm_{analyte}$, $ppm_{analyte}$*hour, or $ppm_{analyte}$/hour, or alternatively may be unitless. The x-axis 704-5 extends from 0 to a max degradation value. Although only three different values X, Y, and Z are marked on the x-axis 704 between 0 and the max degradation value, the x-axis 704-5 may have any number of values. The plot 700-5 includes a plot line 706-5 that shows the relationship between the remaining life of the asset and the degradation value. As shown in FIG. 95, the plot line 706-5 has a negative slope, which indicates that the remaining life of the asset is inversely proportional to the degradation value. For example, a new asset, such as fresh oil and/or a new engine, has 100% remaining life and a degradation value of 0. As the degradation value of the asset increases, the estimated remaining life of the asset decreases as shown by the plot line 706-5. In an embodiment, one or more processors (e.g., the one or more sensor processors) may generate the function (e.g., slope) of the plot line 706-5 based on historical data that compares calculated degradation values to monitored amounts of time remaining in a life of a similar asset. For example, the plot line 706-5 may represent a transfer function that associates calculated degradation values to corresponding percentages of remaining life of the asset based on historical data.

In an embodiment, after calculating the degradation value of an asset, the one or more processors may be configured to estimate the remaining amount of time in the operational life of the asset by plugging the degradation value into the function represented by the plot line 706-5 to yield an estimated remaining life of the asset. For example, as shown in FIG. 95, a degradation value of X for the engine translates to an estimated 80% of the life of the engine remaining. In another example, a greater degradation value of Y translated to an estimated 33% of the life of the engine remaining. During use of the asset, the degradation value gradually increases, moving along the x-axis 704-5 from 0 towards the max degradation value. The rate at which the degradation value increases (e.g., moves along the x-axis 704-5) is based on factors such as the concentration of the one or more polar analytes in the oil and the length of time that the one or more polar analytes are present in the oil. For example, a first oil with a greater concentration of water and a greater amount of time that the water is in the oil would predictably degrade faster (e.g., reaching the max degradation value quicker) than a second oil having a lower concentration of water and a reduced amount of time that the water is present in the oil.

Providing an estimate of the remaining life of an asset, such as an engine or oil within the engine, allows for planning maintenance in advance. Therefore, the maintenance is performed when desirable or necessary, instead of performing the maintenance before necessary (which may be wasteful) or after the maintenance is necessary (which may be harmful to performance or other components of the vehicle system). The one or more processors may convey the estimated remaining life of the asset to an operator, such as via transmitting a message containing the estimated remaining life to a computer, workstation, or personal handheld device.

In one or more embodiments, the one or more processors may monitor the degradation value of an asset relative to one or more designated degradation thresholds. The one or more degradation thresholds may be selected based on historical data of the similar assets. The degradation thresholds may be stored in memory of the one or more processors. The degradation thresholds are designed to trigger the one or more processors to take remedial actions to prevent reduced performance of the vehicle system, extended shut-downs, and/or damage to the vehicle system. Therefore, responsive to the degradation value of an asset exceeding a designated degradation threshold, the one or more processors are configured to automatically take a specified remedial action. For example, the processors may schedule maintenance for the vehicle system, such as to change the oil in the engine, repair the engine, or replace the engine or a part thereof. The processors may be communicatively coupled to a computer, server, or operating system that schedules maintenance for the asset.

Additionally, or alternatively, the remedial action of the processors may be to provide an alert for an operator to schedule or perform maintenance for the vehicle system. For example, the processors may trigger a message that is displayed to the operation via a workstation display screen or a handheld device display screen (e.g., a cell phone, tablet, wearable device, or the like). The alert for the operator may include visual text and/or graphics on a display, audible sounds or speaking via a speaker, and/or vibrations. Additionally, or alternatively, the remedial action may be to prohibit additional operation of the vehicle system until maintenance is performed on the vehicle system. The prohibition of operation of the vehicle system may include the processors controlling the engine in the operating state to shut down and/or preventing the engine in the non-operating state from switching to the operating state. The engine may be prohibited from operating to protect the other components of the vehicle system from possible damage due to the degraded oil and/or engine. For example, the vehicle system is prohibited from operating to prevent a corroded engine from breaking down and damaging the generator, the drive shaft, the air compressor, or other components of the vehicle system. The one or more processors may prevent the engine from operating by transmitting a message to a controller device of the vehicle system and/or by triggering a switch that deactivates the operation of the engine.

Optionally, the one or more processors may monitor the degradation value of an asset relative to multiple degradation thresholds. For example, a first degradation threshold 708-5 may be the degradation value Y shown in FIG. 95, and a second degradation threshold 710-5 may be the degradation value Z, which is greater than the value Y. The first degradation threshold 708-5 is at 33% of the remaining life of the asset, and the second threshold 710-5 is at 20% of the remaining life of the asset. Responsive to the degradation value exceeding the first degradation threshold 708-5, the processors may be configured to schedule replacement of the oil within the engine and/or provide an alert to schedule replacement of the oil within the engine. Replacing the oil in the engine may reduce the rate at which the engine degrades due to the reduced corrosive contaminants in the healthy oil. In an embodiment, responsive to the degradation value exceeding the second degradation threshold 710-5, the processors may be configured to schedule servicing of the engine (e.g., repair or replacement of the engine) and/or provide an alert to schedule servicing of the engine. Although not shown in FIG. 95, a third degradation threshold greater than the value Z may be associated with 10%, 5%, 2%, or 1% of the remaining life of the asset. Upon exceeding the third degradation threshold, the one or more processors may be configured to prevent additional operation of the vehicle system until after maintenance is performed on the vehicle system.

Figure 96:
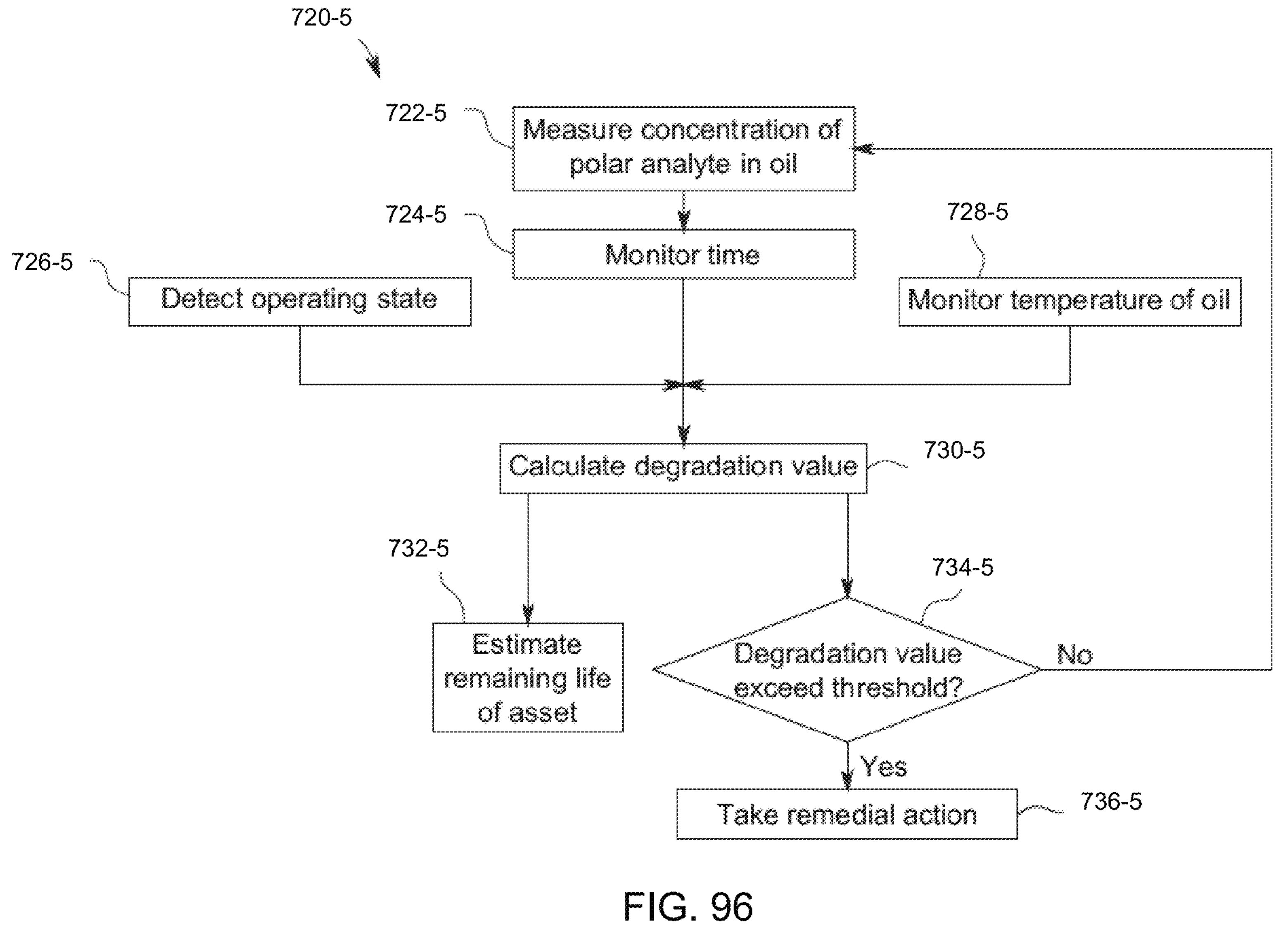
FIG. 96 is a flow chart of a method for monitoring an asset in a vehicle system according to an embodiment.

FIG. 96 is a flow chart of a method 720-5 for monitoring an asset in a vehicle system according to an embodiment. The asset may be an engine of the vehicle system, oil within the engine, or another component or fluid of the vehicle system. In the illustrated embodiment, the asset is the engine. At 722-5, a concentration of a polar analyte in the oil of the engine is measured. The polar analyte may be at least one of water or acid (e.g., an acidic component within the oil). The concentration may be measured by a multivariable resonant sensor and one or more processors, such as the multivariable resonant sensor and the one or more processors. A measurement of the concentration may be obtained at different times during the operational life of the asset, such as periodically at a regular interval of one measurement every thirty seconds, every one minute, every two minutes, or the like. For each measurement, the multivariable resonant sensor generates an electrical stimulus having multiple different frequencies that is applied to the oil in contact with the multivariable resonant sensor, and an electrical signal representative of a resonant impedance spectral response to the electrical stimulus is conveyed to the one or more processors. The one or more processors analyze the impedance response and extract or calculate resonant parameters from the impedance response to determine the concentration of the polar analyte in the oil at the time that the electrical stimulus is applied to the oil. At 724-5, the time is monitored, such as via the time counter. Therefore, the measured concentrations of the polar analyte can be associated with time to track the concentration of the polar analyte over time.

Operations 726-5 and 728-5 are optional, such that the method 720-5 may be performed without either 726-5 or 728-5, with both 726-5 and 728-5, or with only one of 726-5 or 728-5. At 726-5, the operating state of the engine is detected, such as whether the engine is in an operating state or a non-operating state. The operating state of the engine may be detected via an operating condition sensor, such as a vibration sensor mounted to the engine, an optical sensor that monitors the rotation of the crankshaft or drive shaft, or an electromagnetic sensor that detects the flow of current from the generator. At least some of the measurements of the concentration of the polar analyte in the oil may be obtained while the engine is in the non-operating state. At 728-5, the temperature of the oil within the engine is monitored, such as via a temperature sensor.

At 730-5, a degradation value for the asset is calculated based on the concentration of the polar analyte in the oil as a function of time. The degradation value may be calculated by one or more processors, such as the one or more sensor processors. The degradation value may be calculated based on the concentration of the polar analyte, and how the concentration changes, over time during the operating life of the asset. For example, the degradation value may be calculated as an integral of the concentration of the polar analyte in the oil over a time period that the concentration measurements are obtained. Optionally, if the polar analyte is water, the degradation value for the asset is calculated, at least in part, based on measurements of the concentration of water in the oil that are obtained during time periods that the engine is non-operating as determined at 726-5. The detrimental effect of water in the oil may be more significant in the non-operating state relative to the operating state because water can accumulate in the oil due to condensation when the engine is not operating. Optionally, the degradation value may be calculated based, at least in part, on measurements of the concentration of the polar analyte in the oil that are obtained during time periods that the temperature of the oil is less than an evaporation threshold temperature as determined at 728-5. For example, the detrimental effect of the polar analyte in the oil may be more significant when the temperature of the oil is below the evaporation threshold temperature because the polar analyte may be present. At a higher temperature of the oil above the evaporation threshold temperature, the polar analyte may evaporate from the oil, reducing the concentration of the analyte as well as the associated harmful effects of the analyte.

At 732-5, a remaining amount of time in the operational life of the asset is estimated based on the degradation value for the asset. The remaining amount of time is inversely proportional to the degradation value as described above with reference to FIG. 95. The estimated remaining life of the asset may be conveyed to an operator and/or to a remote control facility and used for planning future maintenance or other service for the vehicle system.

At 734-5, a determination is made whether the degradation value exceeds a designated degradation threshold. The one or more processors may determine whether one or more set degradation thresholds are exceeded. If at least one degradation threshold is exceeded by the calculated degradation value, then flow proceeds to 736-5 and remedial action is automatically taken. For example, the remedial action may include scheduling maintenance for the vehicle system (e.g., such as to replace the oil within the engine or replace the engine or a component thereof), providing an alert to schedule maintenance for the vehicle system, and/or prohibiting operation of the engine until maintenance is performed on the vehicle system. If, on the other hand, the degradation value does not exceed a designated degradation threshold, flow may return to 722 for additional monitoring of the polar analyte concentration in the oil.

Figure 97:
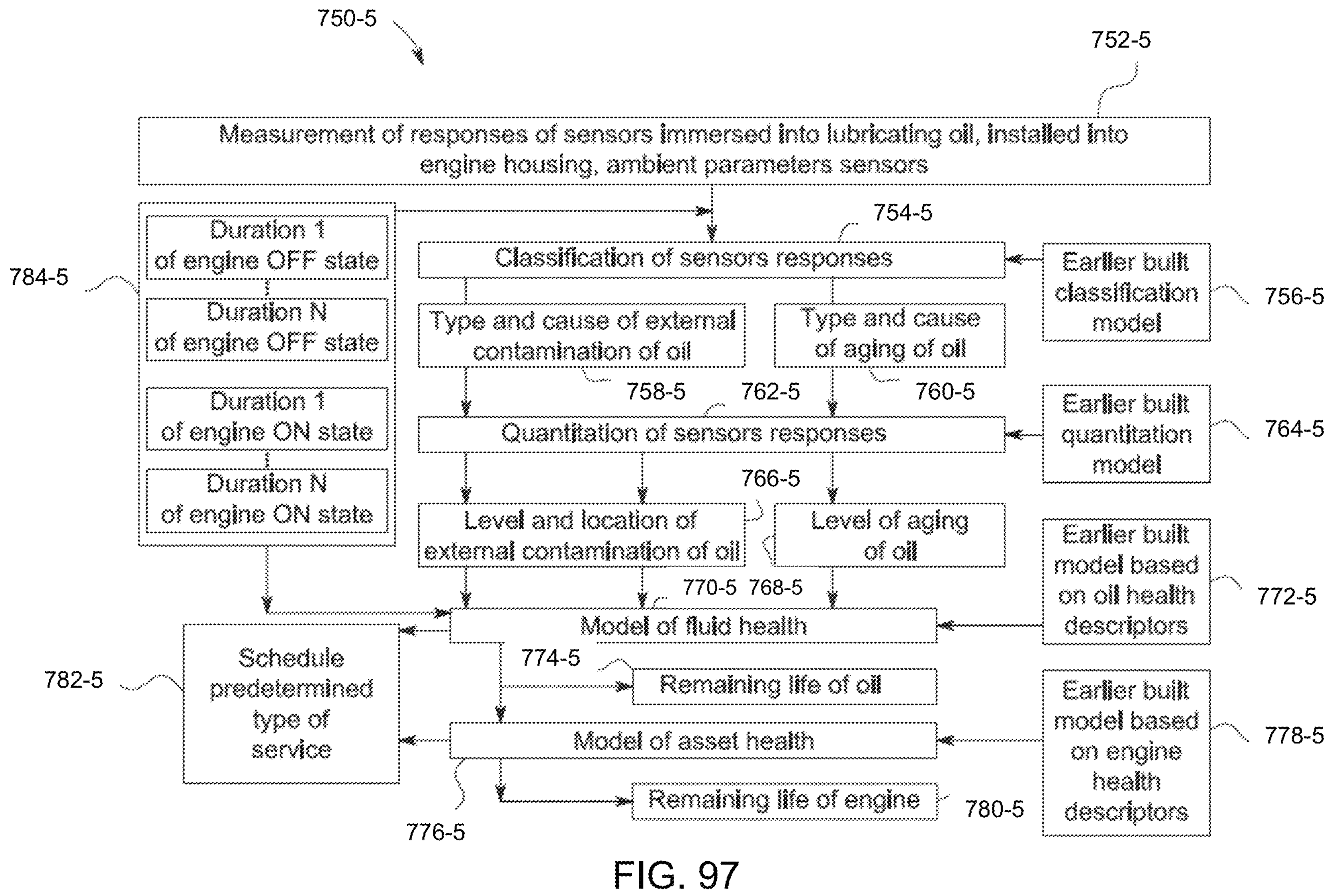
FIG. 97 is a flow chart of a method for predictive assessment of oil health and engine health according to an embodiment.

FIG. 97 is a flow chart of a method 750-5 for predictive assessment of oil health and engine health according to an embodiment. The method 750-5 may be similar to the method 720-5 of monitoring an asset in a vehicle system. The method 750-5 may include some of the same steps from the method 300-5 for monitoring and assessing a lubricating oil and/or the method 2860-5 for monitoring oil, and such operations are not described in detail with reference to FIG. 97.

At 752-5, various measurements are obtained from different sensors, including sensors immersed into lubricating oil (e.g., resonant sensor and/or temperature sensor), sensors installed into the engine housing (e.g., vibration sensor and/or temperature sensor), and/or ambient-parameter sensors (e.g., temperature sensor and/or humidity sensor). At 754-5, the sensor responses are classified by using a predetermined, earlier saved classification model at 756-5. At 758-5 and 760-5, determination of the individual effects of oil-aging compounds and external contaminants in engine oil is made. For example, the type and cause of external contamination of oil, such as acid or water, is determined at 758-5, and the type and cause of oil aging is determined at 760-5. At 762-5, the sensors responses are quantified by using a predetermined, earlier saved quantitation model at 764-5 to quantify the individual effects of oil-aging compounds and external contaminants in engine oil. For example, at 766-5 the level and location of external contamination of oil is determined, and at 768-5 the level of aging of the oil is determined.

At 770-5, a model of fluid health is generated and/or updated using an earlier-built model based on oil health descriptors at 772-5. The oil health descriptors may be based on sensor responses to changes in the properties of the oil, the engine, and/or the ambient environment. The obtained sensor responses are compared to the model of fluid health to estimate the remaining life of the oil at 774-5. At 776-5, a model of asset health (e.g., health of the engine) is generated and/or updated using an earlier-built model based on engine health descriptors at 778-5. The engine health descriptors may be based on sensor responses to changes in the properties of the oil, the engine, and/or the ambient environment. The obtained sensor responses are compared to the model of asset health to estimate the remaining life of the engine at 780-5.

The oil health descriptors may include level and type of external contaminant such as water, molecularly dissolved water, dispersed (emulsified) water, wear particles, water in the air within the headspace of the engine, dust particles, and other external contaminants. The engine (or asset) health descriptors may include corrosion state, wear state of the engine (or asset), and the like. Oil health descriptors and/or engine health descriptors may also include time of operation since the previous maintenance of the engine and time periods when the engine was in ON and OFF states.

In an embodiment, the model of the fluid health and/or the model of the asset health are used to schedule a predetermined type of service for the vehicle system at 782-5. For example, if a calculated amount of degradation of the engine based on the model of fluid health and/or the model of asset health exceeds a designated threshold, the predetermined type of service may be scheduled. The type of service may include replacing the oil in the engine, repairing or servicing the engine, replacing the engine, or the like. The type of service that is scheduled may be based on the extent of degradation of the engine, ranging from replacing the oil responsive to a first level of degradation to replacing the entire engine responsive to a second, greater level of degradation. An appropriate service location for the service may also be selected, such as a railyard that has capability to perform the designated type of service.

In an embodiment, the time periods in which the engine of the vehicle system is in various operating states are monitored at 784-5, such as via a global time counter and one or more sensors that detect the operating state of the engine. For example, the engine may cycle between an operating or ON state and a non-operating or OFF state. The durations of time in each ON state and each OFF state are monitored. Optionally, other intermediate states of the engine may also be monitored, such as engine start, engine warm-up, engine cool-down, and engine stop. The durations of time in each of the operating states may be used to classify the sensor responses at 754-5 and/or determine the model of fluid health at 770-5.

Sensors that may be utilized to accomplish the method 750-5 (for predictive assessment of oil health and engine health) may have several operational characteristics such as the ability to detect oil aging, the ability to detect the presence of water in oil, the ability to resolve oil aging vs presence of water, and the ability to separately quantify a level of oil aging vs the concentration of water in the oil.

In an embodiment, a system is provided that includes a resonant sensor and one or more processors. The resonant sensor is configured to be in contact with oil within an engine of a vehicle system. The sensor includes electrodes and a sensing region circuit that is configured to generate electrical stimuli at different times during an operational life of the engine. Each electrical stimulus has multiple different frequencies that are applied to the oil via the electrodes. The one or more processors are configured to receive multiple electrical signals from the resonant sensor. The electrical signals represent impedance responses of the oil to the electrical stimuli. The one or more processors are configured to analyze the impedance responses and determine a concentration of a polar analyte in the oil at each of the different times based on the impedance responses. The one or more processors are further configured to calculate a degradation value for the engine based on the concentration of the polar analyte in the oil. Responsive to the degradation value exceeding a designated degradation threshold, the one or more processors are configured to at least one of schedule maintenance for the vehicle system, provide an alert to schedule maintenance for the vehicle system, or prohibit operation of the vehicle system until maintenance is performed on the vehicle system.

Optionally, the resonant sensor is a multivariable sensor.

Optionally, the resonant sensor individually quantifies a concentration of at least one contaminant in the oil and a level of aging of the oil.

Optionally, the resonant sensor individually quantifies a concentration of molecularly dissolved water and a concentration of dispersed water in the oil.

Optionally, the polar analyte in the oil is at least one of an acidic component or water.

Optionally, the polar analyte in the oil is water, and the system further includes a temperature sensor configured to monitor a temperature within the engine. The one or more processors are configured to calculate the degradation value for the engine based on the concentration of water in the oil during time periods that the temperature within the engine is less than an evaporation threshold temperature.

Optionally, the polar analyte in the oil is water, and the system further includes a vibration sensor mounted to the vehicle system. The vibration sensor is configured to detect the engine is in a non-operating state based on an amount of vibration of the vehicle system. The one or more processors are configured to calculate the degradation value for the engine based on the concentration of water in the oil during time periods that the engine is in the non-operating state.

Optionally, the resonant sensor is configured to generate the electrical stimuli periodically at intervals no greater than five minutes in duration in order for the one or more processors to periodically determine the concentration of the polar analyte in the oil during the operational life of the engine.

Optionally, the one or more processors are configured to calculate the degradation value as an integral of the concentration of the polar analyte in the oil over a time period in which the electrical stimuli are applied to the oil.

Optionally, the one or more processors are further configured to estimate an amount of time remaining in the operational life of the engine based on the degradation value for the engine. The remaining amount of time is inversely proportional to the degradation value.

Optionally, the one or more processors are configured to analyze the impedance response by extracting resonance parameters of the impedance response. The resonance parameters include one or more of a frequency position (Fp) and magnitude (Zp) of a real part of the impedance response, a resonant frequency (F1) and antiresonant frequency (F2) of an imaginary part of the impedance response, an impedance magnitude (Z1) at the resonant frequency (F1) and an impedance magnitude (Z2) at the antiresonant frequency (F2), and a zero-reactance frequency (Fz) at the imaginary part of the impedance response.

Optionally, the sensing region circuit of the resonant sensor includes at least one inductor-capacitor-resistor (LCR) resonant circuit.

In an embodiment, a method is provided that includes obtaining multiple measurements of a concentration of at least one polar analyte in oil within an engine of a vehicle system. The measurements are obtained at different times during an operational life of the engine via a resonant sensor in operational contact with the oil. The resonant sensor includes electrodes and a sensing region circuit that is configured to generate an electrical stimulus having multiple different frequencies that are applied to the oil via the electrodes. The concentration of the at least one polar analyte in the oil is determined based on an impedance response of the oil to the electrical stimulus. The method also includes calculating a degradation value for the engine based on the concentration of the at least one polar analyte in the oil within the engine. Responsive to the degradation value exceeding a designated degradation threshold, the method includes at least one of scheduling maintenance for the vehicle system, providing an alert to schedule maintenance for the vehicle system, or prohibiting operation of the vehicle system until maintenance is performed on the vehicle system.

Optionally, the measurements of the concentration of the at least one polar analyte in the oil are obtained periodically at intervals no greater than five minutes in duration.

Optionally, the method further includes detecting that the engine is in a non-operating state. At least some of the measurements of the concentration of the at least one polar analyte in oil are obtained while the engine is in the non-operating state.

Optionally, the designated degradation threshold is a first degradation threshold. Responsive to the degradation value exceeding the first degradation threshold, the method includes at least one of scheduling replacement of the oil within the engine or providing an alert to schedule replacement of the oil within the engine.

Optionally, responsive to the degradation value exceeding a second degradation threshold that is greater than the first degradation threshold, the method includes at least one of scheduling servicing of the engine or providing an alert to schedule servicing of the engine.

Optionally, the at least one polar analyte in the oil that is measured is at least one of an acidic component or water.

Optionally, the degradation value is calculated as an integral of the concentration of the at least one polar analyte in the oil over a time period that the measurements of the concentration are obtained.

Optionally, the method further includes estimating an amount of time remaining in the operational life of the engine based on the degradation value for the engine. The remaining amount of time is inversely proportional to the degradation value.

Optionally, the at least one polar analyte that is measured is water, and the method further includes monitoring a temperature of the oil within the engine. The degradation value for the engine is calculated based on measurements of the concentration of water in the oil that are obtained during time periods that the temperature of the oil is less than an evaporation threshold temperature.

In an embodiment, a system is provided that includes a resonant sensor, one or more processors, and an operating condition sensor. The resonant sensor is configured to be in contact with oil within an engine of a vehicle system. The sensor includes electrodes and a sensing region circuit that is configured to generate electrical stimuli at different times during an operational life of the engine. Each electrical stimulus has multiple different frequencies that are applied to the oil via the electrodes. The one or more processors are configured to receive multiple electrical signals from the resonant sensor. The electrical signals represent impedance responses of the oil to the electrical stimuli. The one or more processors are configured to analyze the impedance responses and determine a concentration of water in the oil at each of the different times based on the impedance responses. The operating condition sensor is mounted to the vehicle system. The operating condition sensor is configured to detect when the engine is in a non-operating state and when the engine is in an operating state. The one or more processors are configured to calculate a degradation value for the engine based on the concentration of water in the oil during time periods that the engine is in the non-operating state. Responsive to the degradation value exceeding a designated degradation threshold, the one or more processors are configured to at least one of schedule maintenance for the vehicle system, provide an alert to schedule maintenance for the vehicle system, or prohibit operation of the vehicle system until maintenance is performed on the vehicle system.

Optionally, the operating condition sensor is at least one of a vibration sensor, a temperature sensor, an electrical switch sensor, or an optical sensor.

Some oil sensors are based on an inductor-capacitor-resistor (LCR) resonator structure that monitors aspects of oil health, such as levels of oil degradation and levels of external contaminants into oil. The LCR resonator operates in a multivariable mode where multiple outputs from the resonator are measured and used to detect independent changes in the oil health due to the leaks of water and fuel into the oil, and oil aging.

These types of sensors can involve a sensor probe comprised of two distinct components such as a sensing substrate onto which an electrode structure was deposited. The sensor probe is a region of the sensor that is in operational contact with the measured industrial fluid (e.g., oil). Other portions of the sensor (such as sensor housing, transformer, electronics, electrical connectors, etc.) are not in operational contact with the measured industrial fluid. The sensing substrate is an inert material that allows the sensing electrodes to be presented to the fluid.

The sensing electrodes may be deposited only on one side of the substrate. This type of design has significant limitations. First, the need for a substrate may not allow the entire surface of the electrodes to be in contact with the fluid under examination. Second, the substrate material can add a significant parasitic capacitance that reduces the sensitivity of the response of the sensor. Third, the substrate material can add a significant parasitic capacitance that reduces the selectivity of the response of the sensor to different constituents in the fluid under examination.

In one embodiment of the inventive subject matter described herein, a sensor probe assembly for monitoring of fluid (e.g., a gas or liquid, such as a lubricant) health and/or other industrial fluid health has significant structural and manufacturing differences as compared to known sensor probes, and has a significant improvement in sensor performance such as sensor sensitivity and sensor selectivity as compared to the known sensor probes. One structural difference in the design of the sensor probe assemblies described herein is in the design of electrodes that does not require a sensor substrate. These free-standing electrodes have a larger area that is in contact with the oil or fluid when compared to the electrodes of the same size of previous sensor probes that were deposited or otherwise mounted on substrates. The larger area can include a material that is sensitive to the presence of impurities in a fluid under examination. Examples of such materials include metal oxide semiconductor materials, such as tin oxide ($SnO_2$), inorganic sorbing materials such as porous alumina, porous silicon, or polymeric sorbing materials such as poly [4,5-difluoro-2,2-bis(trifluoromethyl)-1,3-dioxole-co-tetrafluoroethylene] (Teflon AF) or poly[4,4'-oxydiphenylene-pyromellitimide] (Kapton), or another sensing material. These free-standing electrodes with or without sensing material are a part of a resonant circuit of the sensor probe. Another structural difference in the design of the sensor probe assembly as compared to the known sensors is that the electrodes have openings for an improved flow path of the measured oil or fluid across the electrodes. Another structural difference in the design of the sensor probe assembly as compared to the known sensors is that the free-standing electrodes simultaneously serve as an inductor of the resonant sensor.

The sensor probe assembly can be manufactured using additive manufacturing (e.g., three-dimensional printing) and electrical discharge machining to produce the free-standing electrodes. The resonant components of a circuit of the sensor probe assembly also can be produced using additive manufacturing and electrical discharge machining. Electrical discharge machining is also known as spark machining, spark eroding, burning, die sinking, wire burning, or wire erosion. This type of machining creates a desired shape using electrical discharges, such as sparks.

Figure 98:
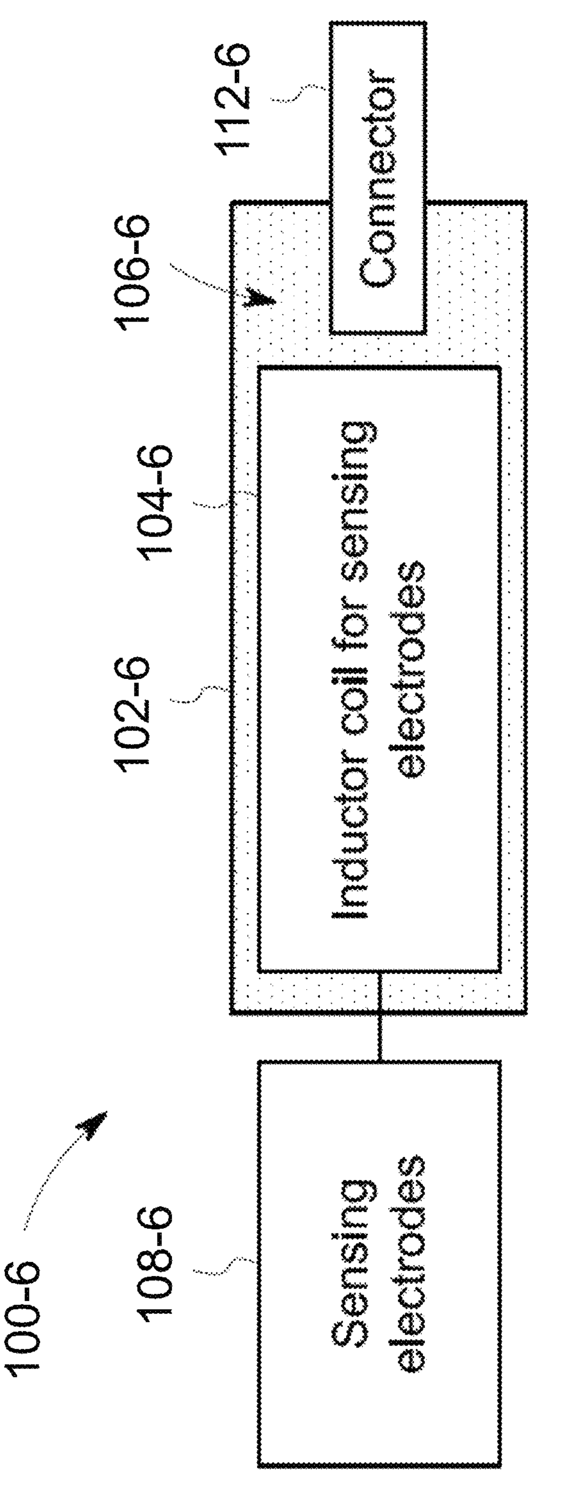
FIG. 98 illustrates a top view of one embodiment of a sensor probe assembly.
Figure 99:
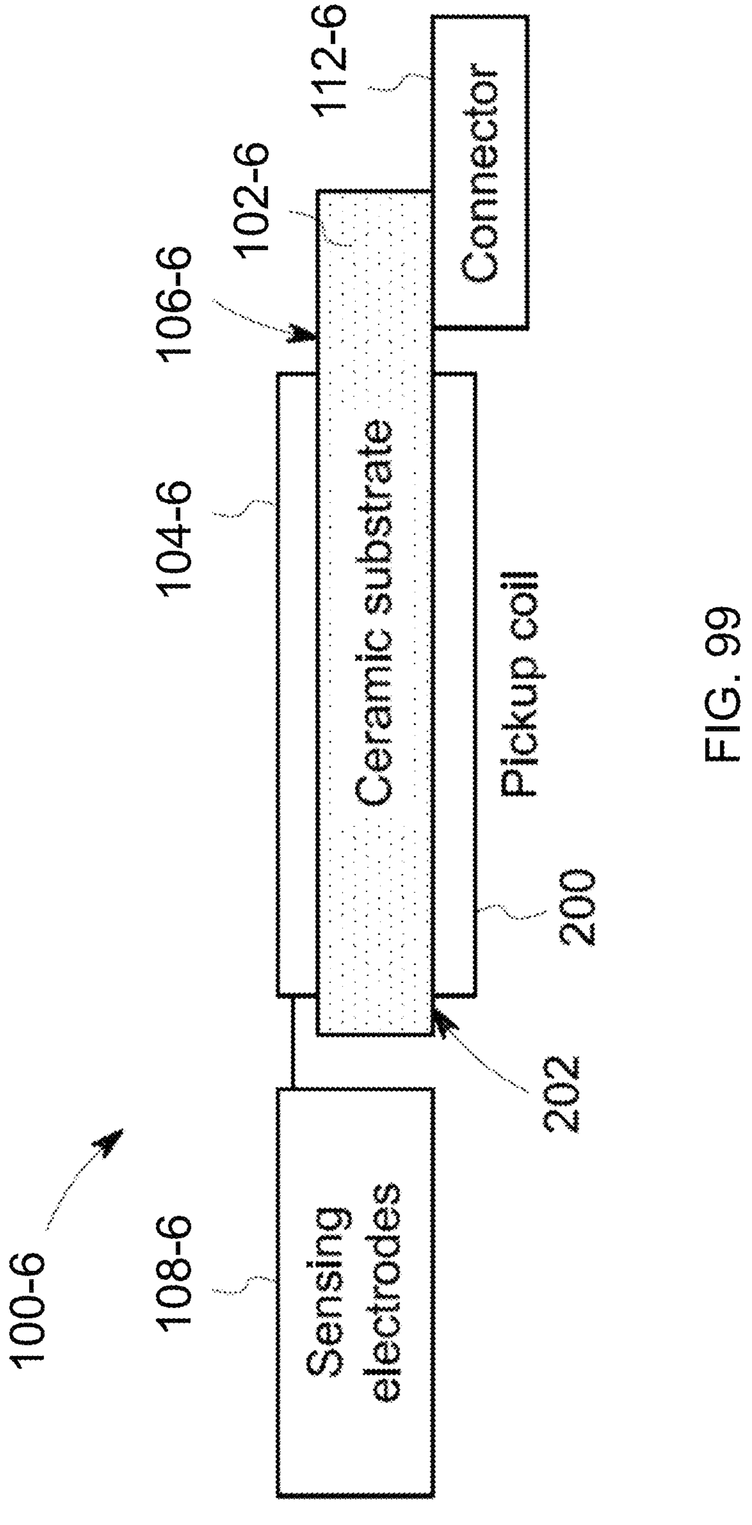
FIG. 99 illustrates a side view of the sensor probe assembly shown in FIG. 1.

FIG. 98 illustrates a top view of one embodiment of a sensor probe assembly 100-6. FIG. 99 illustrates a side view of the sensor probe assembly 100-6 shown in FIG. 98. The sensor probe assembly 100-6 can be included in a measurement system that measures the presence and/or amounts of one or more impurities or other compounds in a fluid of interest, such as oil or another lubricant. The sensor probe assembly 100-6 includes a substrate 102-6 formed from a non-conductive material, such as one or more ceramic materials. The substrate 102-6 can have a planar shape as shown in FIG. 99. A conductive inductor coil 104-6 is mounted on one side 106-6 of the substrate 102-6 and is conductively coupled with one or more free-standing conductive electrodes 108-6. As shown in FIGS. 98 and 99, the electrodes 108-6 are not mounted on the substrate 102-6 in that the electrodes 108-6 are not directly coupled with, do not directly engage, and do not abut any part or surface of the substrate 102-6. Moreover, the electrodes 108-6 are not above or below a footprint of the substrate 102-6, which is defined by the surface area of the side 106-6 of the substrate 102-6 that extends upward and downward in the view of FIG. 99. A conductive pickup coil 200-6 is coupled with the substrate 102-6 on a side 202-6 of the substrate 102-6 that is opposite of the side 106-6 to which the inductor coil 104-6 is mounted. The inductor coil 104-6 is conductively coupled with one or more electronic connectors 112-6.

In operation, the sensor probe assembly 100-6 examines a fluid sample in contact with the electrodes 108-6 for detection of one or more analytes of interest. The sensor probe assembly 100-6 may detect characteristics or properties of the fluid via a resonant or non-resonant impedance spectral response of the material on the electrodes 108-6 (not shown). One or more of the inductor-capacitor-resistor resonant circuits (LCR resonators) that are at least partially formed by the electrodes 108-6 and the inductor coil 104-6 may measure the resonant impedance spectral response of a fluid under inspection. A non-resonant impedance spectral response is measured when the circuit does not contain an inductor. The resonant or non-resonant impedance spectrum of the electrodes 108-6 in proximity to a fluid sample varies based on sample composition and/or components. The measured resonant or non-resonant impedance values Z' (which may be the real part of resonant or non-resonant impedance, Zre) and Z" (which may be the imaginary part of resonant or non-resonant impedance, Zim) reflect the response of the electrodes 108-6 to the fluid. Optionally, an electrical field may be applied to a sensing material or film of the sensor probe assembly 100-6 via the electrodes 108-6. The distance between the electrodes 108-6, may define the magnitude of the electric field. The electrodes 108-6 may be in direct contact with the measured fluid. Alternatively, the electrodes 108-6 may be in direct contact with the sensing material. For example, the sensing element may be a combination of a sensing region and associated circuits and/or the sensing region may be coated with the sensing material. The sensing material may be semiconductor material or metal oxide semiconductor material. The impedance values measured by the electrodes 108-6 and/or coil 104-6 can be inductively communicated through or across the substrate 102-6 to the pickup coil 200-6, and can then be conducted to the connector 112-6 to another system (e.g., data acquisition circuitry).

Data from the sensor probe assembly 100-6 may be acquired via the data acquisition circuitry which is connected with the assembly 100-6 via the connector 112-6. The data acquisition circuitry can be connected with a controller or computer workstation where additional processing and analysis of the sensor data may be performed. The data can be indicative of the health of the fluid, the presence of contaminants within the fluid, and/or the age of the fluid.

Figure 100:
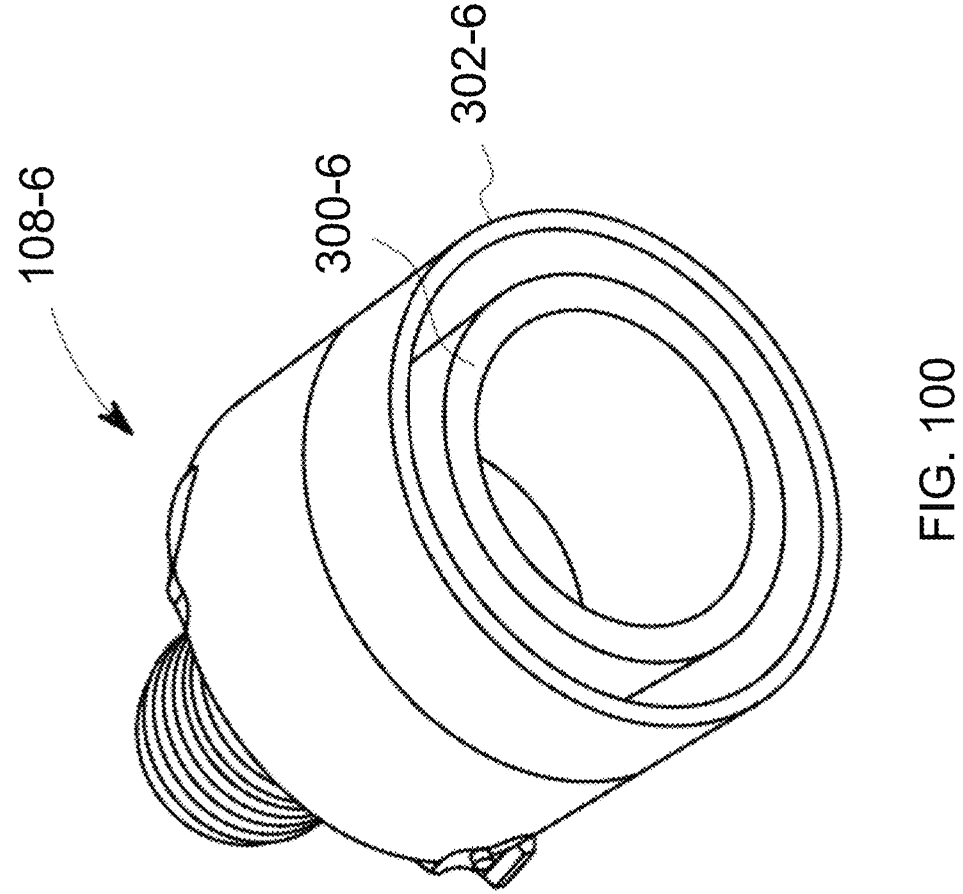
FIG. 100 illustrates a perspective view of an alternative embodiment of electrodes of the sensor probe assembly shown in FIGS. 98 and 99.
Figure 101:
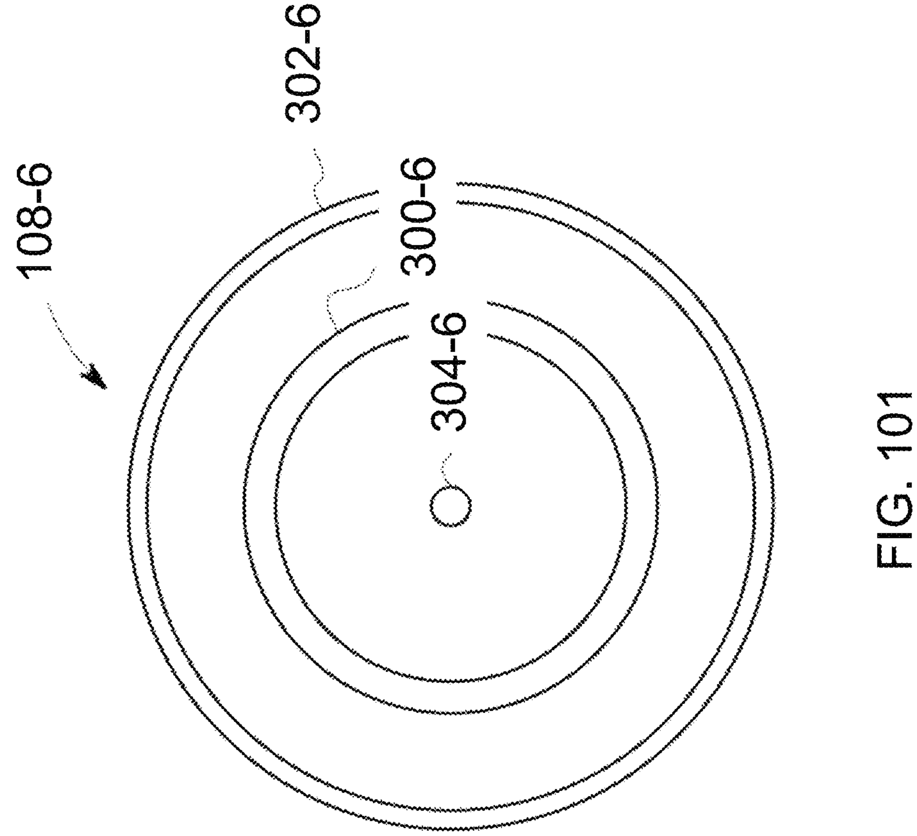
FIG. 101 illustrates an end view of the electrodes shown in FIG. 100.

FIG. 100 illustrates a perspective view of an alternative embodiment of the electrodes 108-6 of the sensor probe assembly 100-6. FIG. 101 illustrates an end view of the electrodes 108-6. In the illustrated embodiment, the electrodes 108-6 are arranged as coaxial tubes or circles 300-6, 302-6 that extend around and share a common center axis 304-6. The electrodes 108-6 are shaped as opposing plates that receive the fluid between the plates in other Figures, but are shown as tubes or circles. The electrode tubes or circles 300-6, 302-6 can be separated from each other by a radial gap so that the electrode tubes or circles 300-6, 302-6 are not conductively coupled with each other off of or outside of the substrate 102-6. The electrode tubes or circles 300-6, 302-6 can be placed into the fluid under examination so that at least some of the fluid enters into the gap between the electrode tubes or circles 300-6, 302-6. The electrodes can have sensing material (e.g., a metal oxide semiconductor) deposited thereon that responds to the presence of one or more impurities of interest and an electric field generated by the electrodes.

Figure 102:
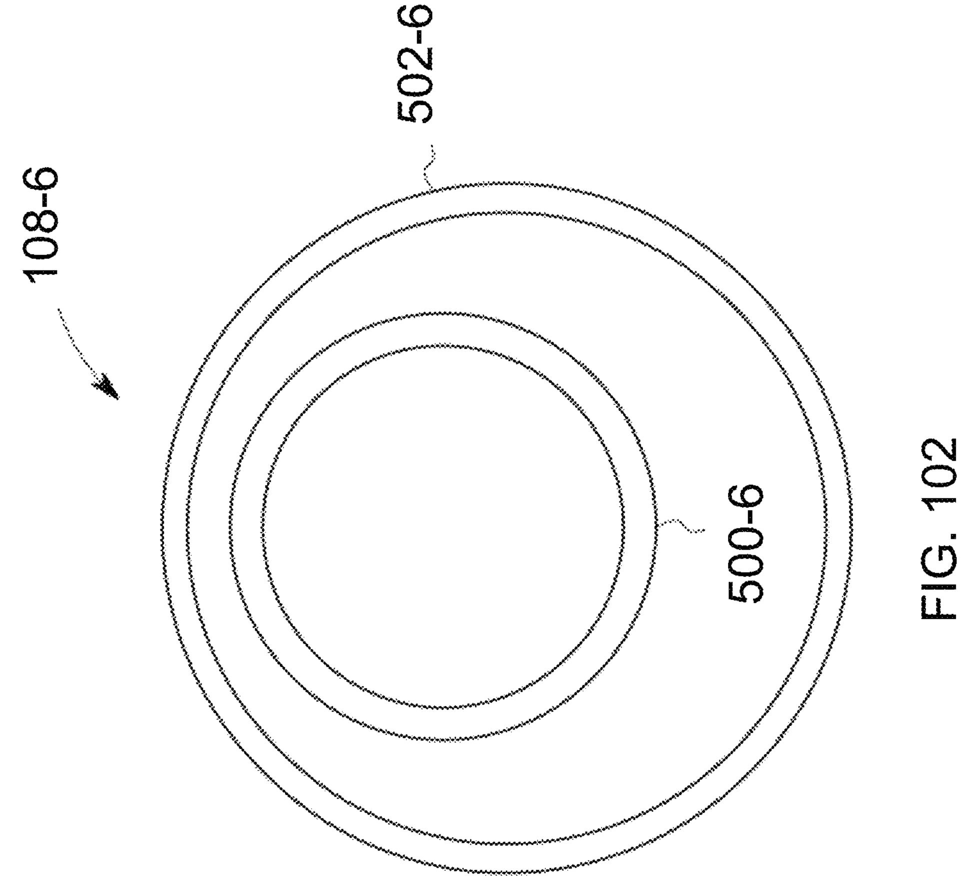
FIG. 102 illustrates an end view of an alternative embodiment of the electrodes of the sensor probe assembly shown in FIGS. 98 and 99.

FIG. 102 illustrates an end view of an alternative embodiment of the electrodes 108-6 of the sensor probe assembly 100-6. In the illustrated embodiment, the electrodes 108-6 are arranged as non-coaxial tubes or circles 500-6, 502-6. The tube or circle 502-6 can extend around the tube or circle 500-6 without the tubes or circles 500-6, 502-6 having the same center axis. The electrode tubes or circles 500-6, 502-6 can be separated from each other by a gap so that the electrode tubes or circles 500-6, 502-6 are not conductively coupled with each other off of or outside of the substrate 102-6. The electrode tubes or circles 500-6, 502-6 can be placed into the fluid under examination so that at least some of the fluid enters into the gap between the electrode tubes or circles 500-6, 502-6. The electrodes can have sensing material (e.g., a metal oxide semiconductor) deposited thereon that responds to the presence of one or more impurities of interest and an electric field generated by the electrodes.

Figure 103:
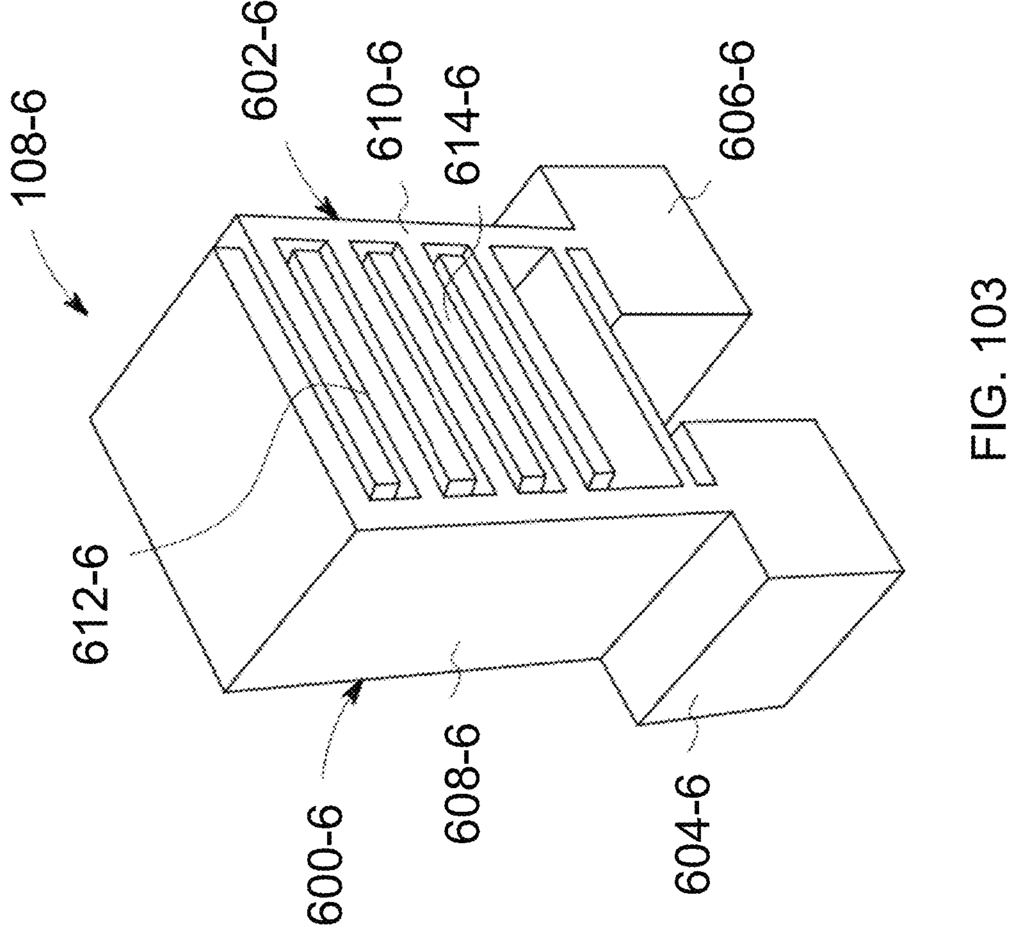
FIG. 103 illustrates a perspective view of another alternative embodiment of the electrodes of the sensor probe assembly shown in FIGS. 98 and 99.
Figure 104:
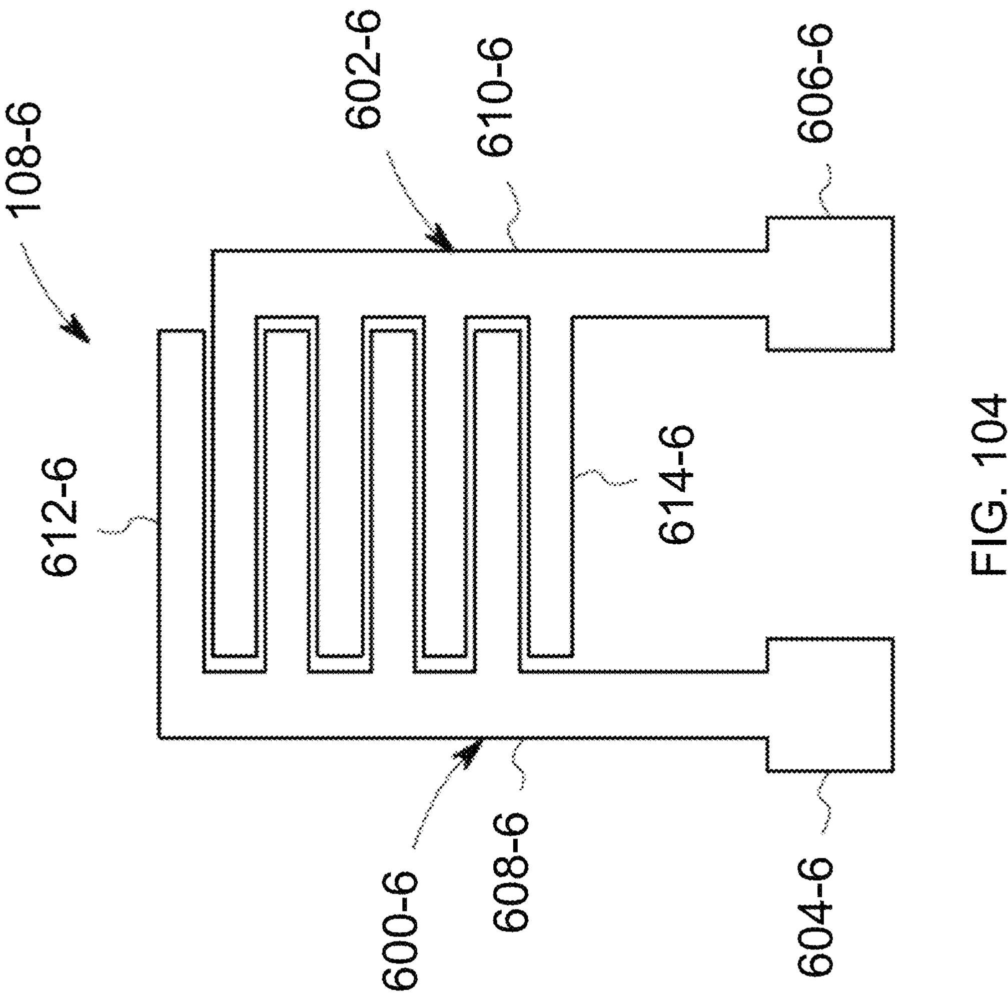
FIG. 104 illustrates a side view of embodiment of the electrodes shown in FIG. 103.
Figure 105:
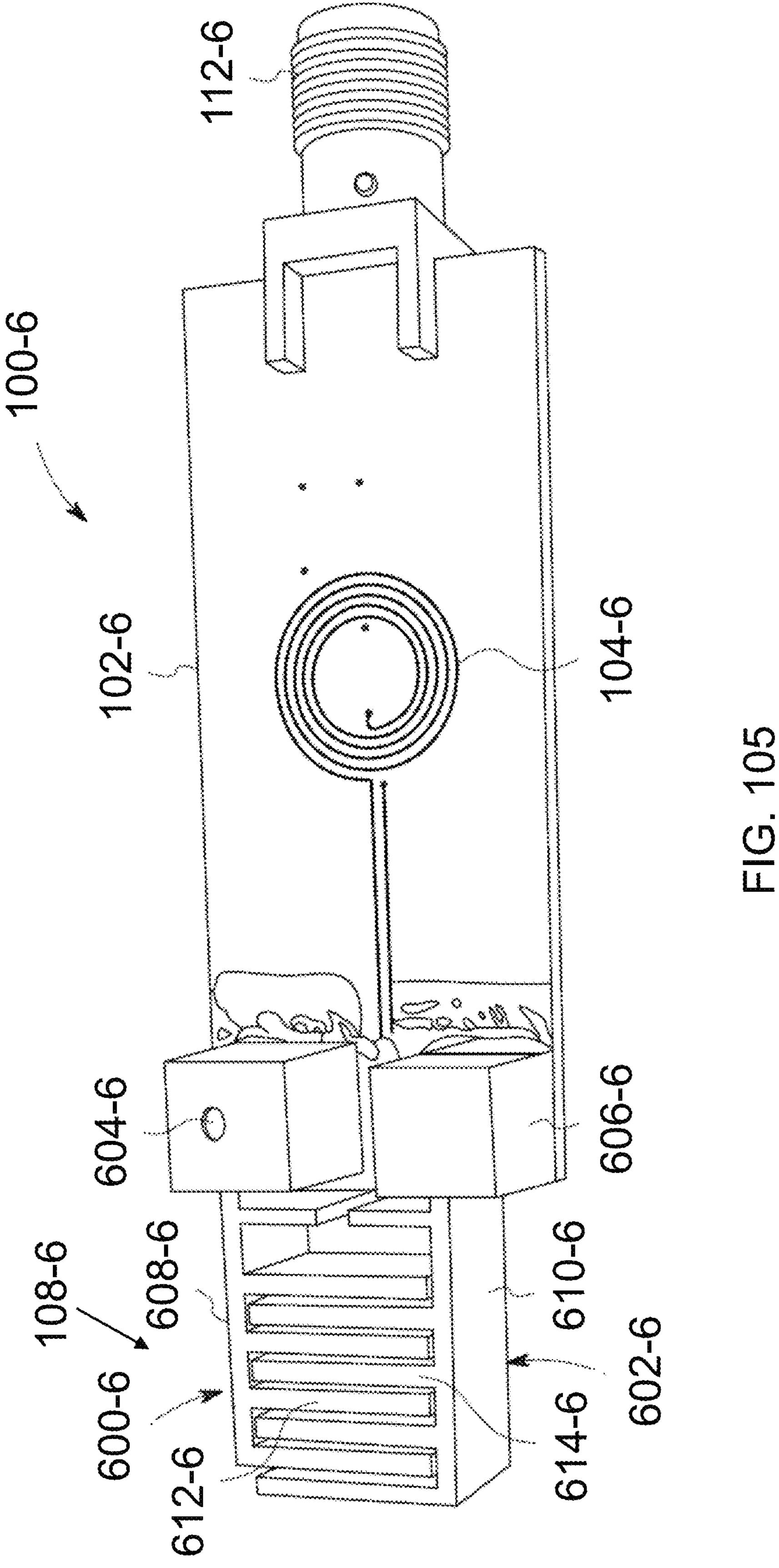
FIG. 105 illustrates the sensor probe assembly shown in FIG. 98 with the embodiment of the electrodes shown in FIGS. 103 and 104.

FIG. 103 illustrates a perspective view of another alternative embodiment of the electrodes 108-6 of the sensor probe assembly 100-6. FIG. 104 illustrates a side view of embodiment of the electrodes 108-6. FIG. 105 illustrates the sensor probe assembly 100-6. In the illustrated embodiment, the electrodes 108-6 are arranged as interdigital electrodes 600-6, 602-6. The interdigital electrodes 600-6, 602-6 extend from different connecting ends 604-6, 606-6 that are separately coupled with the inductor coil 104-6. The connecting ends 604-6, 606-6 are part of elongated connecting bars 608-6, 610-6 of the electrodes 600-6, 602-6. The connecting bars 608-6, 610-6 are oriented parallel to each other. Although not shown, the electrodes can have sensing material (e.g., a metal oxide semiconductor, porous alumina oxide, porous silicon, polymer, zeolite, metal organic framework, or another material) deposited thereon that responds to the presence of one or more impurities of interest and an electric field generated by the electrodes.

The electrodes 600-6, 602-6 include several elongated fingers 612-6, 614-6 that are coupled with a different one of the connecting bars 608-6, 610-6, and that extend toward, but are not coupled with, the other connecting bar 608-6. For example, the fingers 612-6 are coupled with the connecting bar 608-6 and extend toward, but are not coupled with and do not engage, the other connecting bar 610-6. Similarly, the fingers 614-6 are coupled with the connecting bar 610-6 and extend toward, but are not coupled with and do not engage, the other connecting bar 608-6.

The electrode fingers 612-6, 614-6 are oriented parallel to each other such that the electrode fingers 612-6 are spaced apart from the electrode fingers 614 in directions that are perpendicular to the directions in which the fingers 612-6, 614-6 are elongated and in directions that are parallel to the directions in which the connecting bars 608-6, 610-6 are elongated. The electrode fingers 612-6, 614-6 can be placed into the fluid under examination so that at least some of the fluid enters into the gaps between the electrode fingers 612-6, 614-6.

Figure 106:
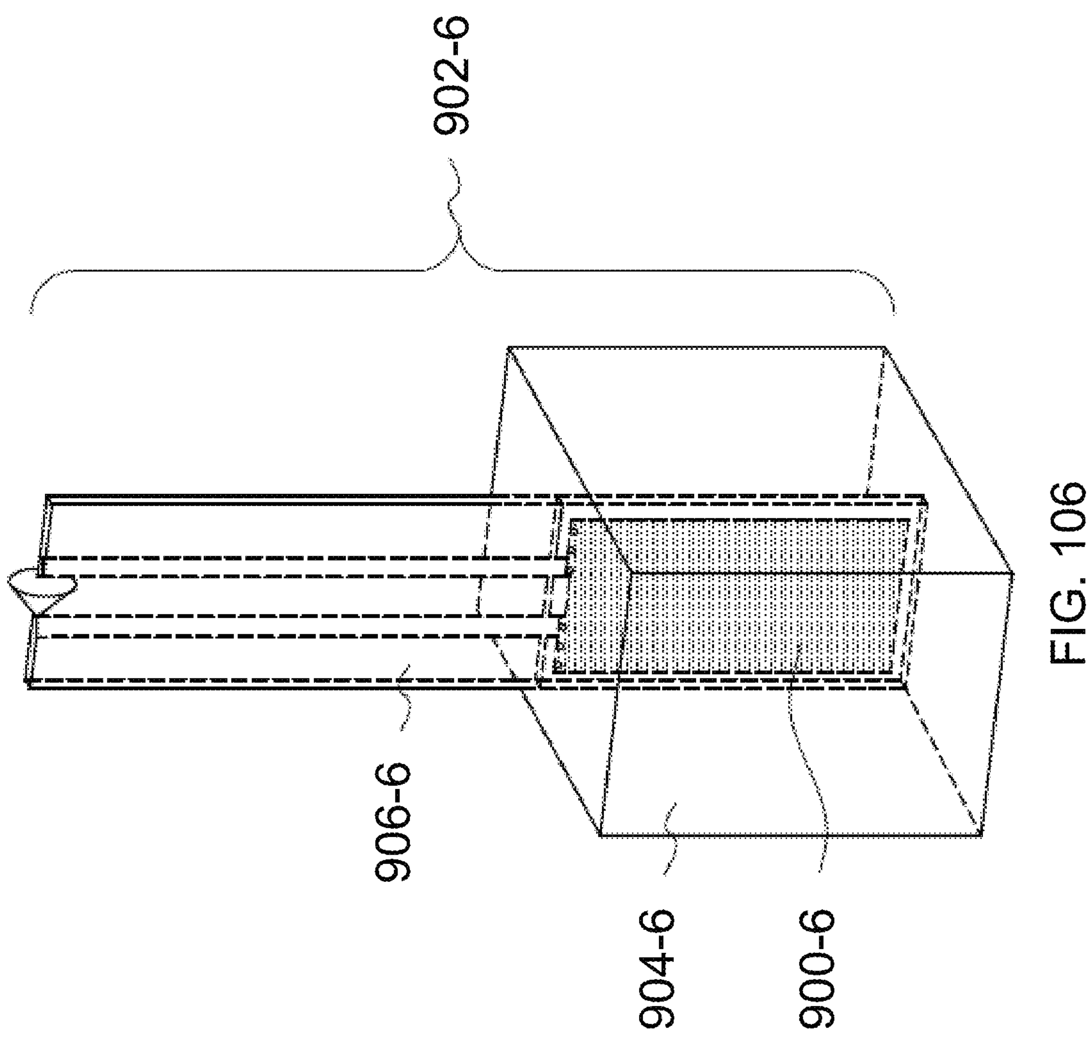
FIG. 106 illustrates partial submersion of electrodes of a known resonant sensor probe assembly into a fluid under examination.
Figure 107:
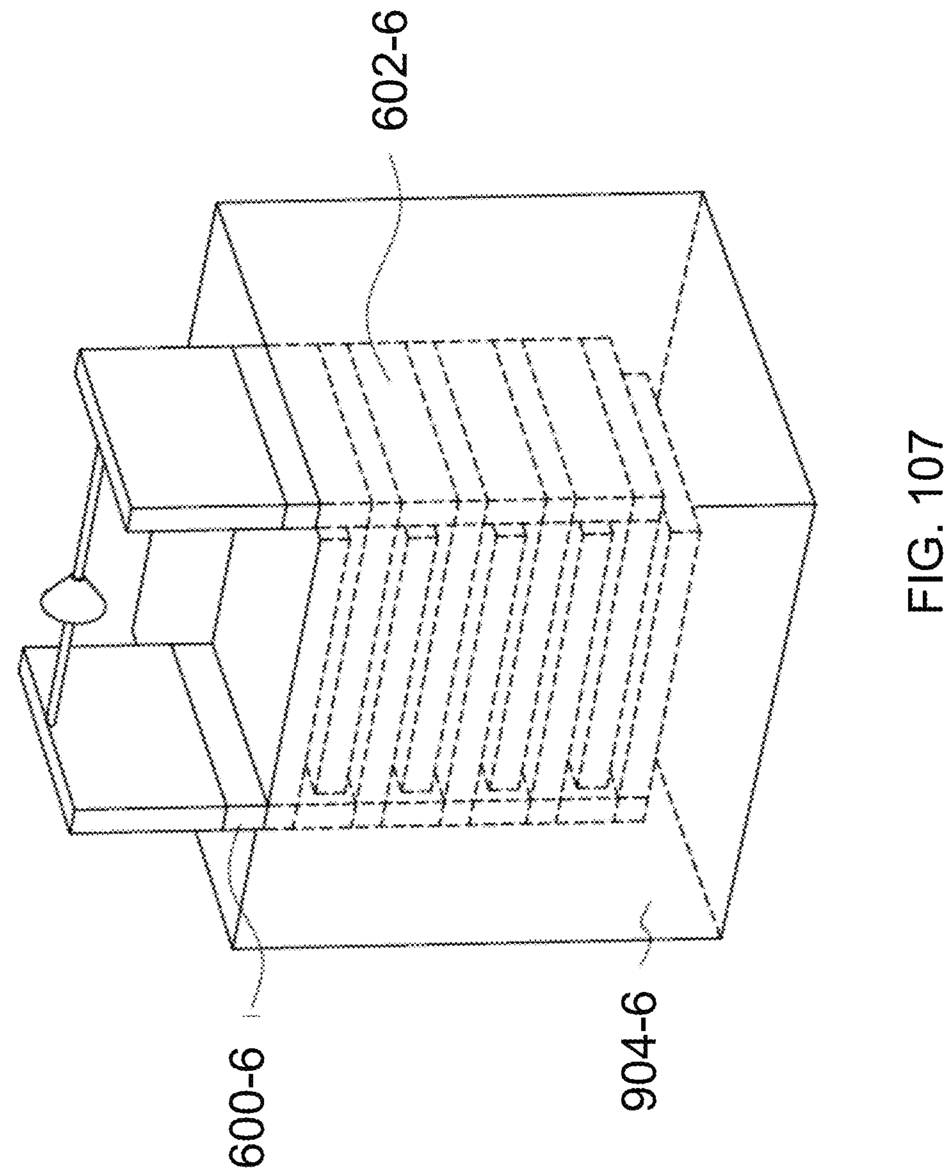
FIG. 107 illustrates partial submersion of the electrodes of the sensor probe assembly shown in FIGS. 103 through 105 into the fluid under examination.

Comparisons of sensitivities was done of a known resonant sensor probe assembly that use electrodes deposited on a substrate and one embodiment of the sensor probe assembly 100-6 having interdigital free-standing electrodes 600-6, 602-6. FIG. 106 illustrates submersion of electrodes 900-6 of a known resonant sensor probe assembly 902-6 into a fluid under examination 904-6 and FIG. 107 illustrates submersion of the electrodes 600-6, 602-6 of the sensor probe assembly 100-6 into the fluid under examination 904-6. The known probe assembly 902-6 includes the electrodes 900-6 being mounted or disposed upon a substrate 906-6. In contrast, the electrodes 600-6, 602-6 of the probe assembly 100-6 are free-standing and are not mounted to any substrate.

As shown in the perspective view of the electrodes 600-6, 602-6, the electrodes 600-6, 602-6 are larger in three orthogonal directions (e.g., the x-, y-, and z-axes of the Cartesian coordinate system) than the electrodes 900-6 that are mounted on the substrate 906-6. The electrodes 900-6 have a more planar shape as these electrodes 900-6 are deposited onto the substrate 906-6 in a thin layer. The electrodes 600-6, 602-6 are larger in three dimensions than the electrodes 900-6.

Three-dimensional electromagnetic modeling was used to determine the effects of the changes of the dielectric properties of the fluid 904-6 surrounding sensing regions of the probe assemblies 902-6, 100-6 that include the electrodes 900-6, 600-6, 602-6 on the spectral responses of the two different types of the resonant sensor probe assemblies 902-6, 100.-6 The sensor probe assembly 100-6 with the free-standing electrodes 600-6, 602-6 is more sensitive to, and therefore more accurate in quantifying, the health and/or contents of the oil than the sensor probe assemblies 902-6 with the substrate-mounted electrodes 900-6.

When the electrodes are fabricated using additive manufacturing methods, auxiliary sensors may be embedded into the structure of the electrodes. For example, an auxiliary temperature sensor may be built together with the electrodes using 3D printing. The temperature sensor may be used for temperature compensation of the measured variables, for example water content in oil and/or oil aging such as total base number (TBN) or total acid number (TAN). The fabrication method of the electrodes may provide control of the fluid-electrode interface contact angle using electrodes with different morphology, surface finishing and materials with the aim of achieving wetting for a wide range of operating conditions and oils that feature different viscosities and compositions.

When electrodes are fabricated using additive manufacturing methods, the electrodes may be fabricated using more than one material to provide more than one functionality for the sensor. Multi-material 3D printing of electrodes may be done where one or more printed materials are magnetic for detection of metal particles while other printed materials are for detection of other properties such as water content and/or TBN, TAN of the fluid media.

In operation, the electrode structure may be protected with a shield. The shield may be designed to have several functions such as to protect electrodes from mechanical damage, to control flow through the sensing element to allow the sensing electrodes to be fully wetted by the measured fluid, and to control air bubble contact with sensing electrodes, where the openings of the shield may be designed to trap and prevent bubbles to reach the sensing electrodes.

In one embodiment, a resonant sensor probe assembly includes a substrate formed from one or more dielectric materials and free-standing electrodes coupled with the substrate. The free-standing electrodes are configured to be placed into a fluid under examination, to generate an electric field between the free-standing electrodes, and to measure an impedance response of the sensor to the fluid between the electrodes.

Optionally, the free-standing electrodes are not directly mounted on the substrate.

Optionally, the free-standing electrodes are not disposed within a footprint of the substrate.

Optionally, the free-standing electrodes are configured to be placed into the fluid and to measure the impedance response of the sensor to the fluid without the substrate being placed into the fluid.

Optionally, the free-standing electrodes include opposing planar plates positioned to receive at least some of the fluid between the plates.

Optionally, the free-standing electrodes include an inner tube electrode disposed within and spaced apart from an outer tube electrode.

Optionally, the inner and outer tube electrodes are concentric tubes.

Optionally, the free-standing electrodes include opposing supporting bars with elongated, interdigital electrode fingers.

Figure 108:
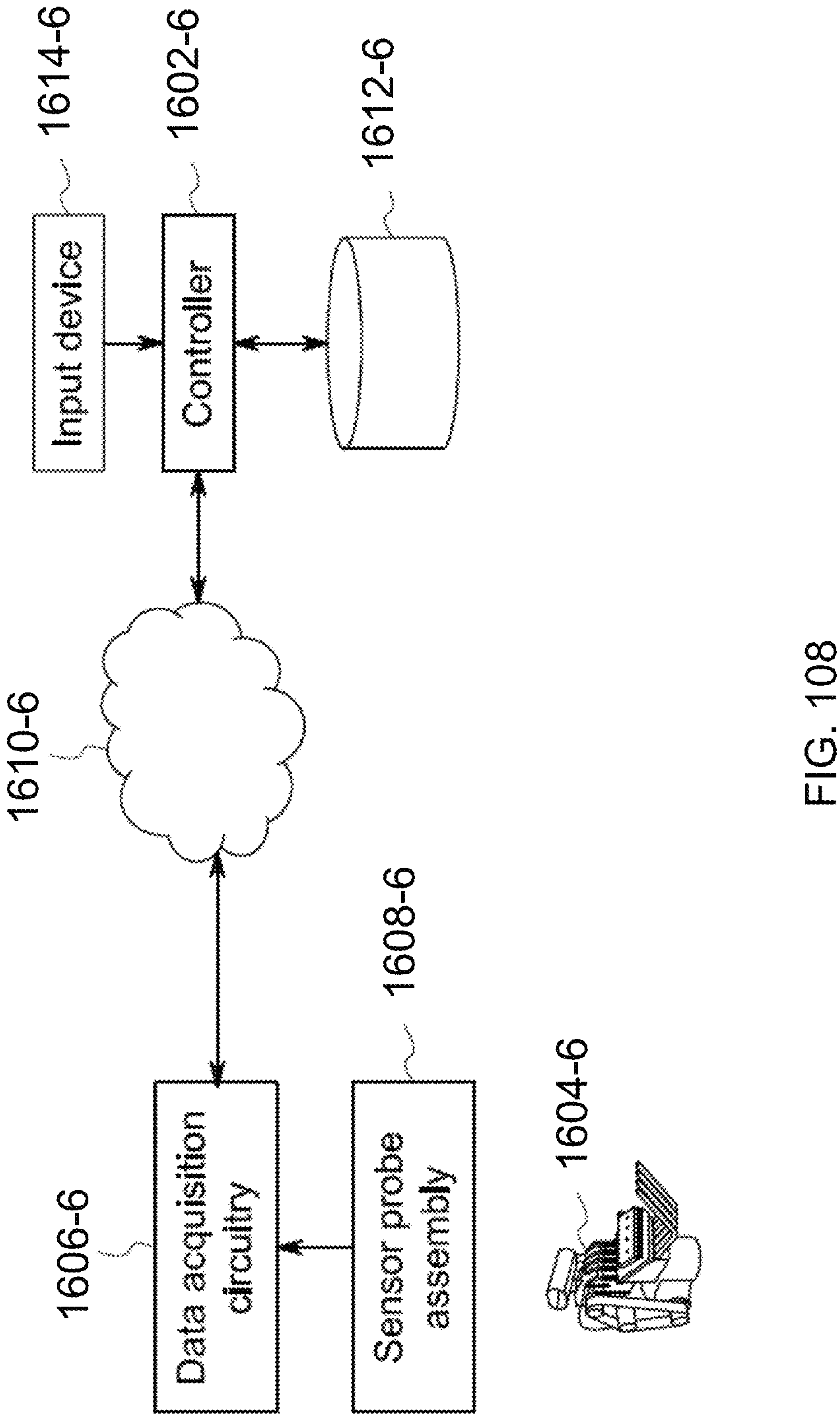
FIG. 108 illustrates one embodiment of a maintenance system.

One example of use of one or more of the sensor probe assemblies described herein (including the assemblies with the free-standing electrodes or the assemblies with the electrodes mounted to substrates) is to measure and quantify the health of engine lubricant, such as oil. FIG. 108 illustrates one embodiment of a maintenance system 1600-6. The maintenance system 1600-6 includes a controller 1602-6 that obtains data from plural different and/or remotely located components and uses the data to create and/or update a model (e.g., digital twin) of equipment 1604-6. The controller 1602-6 optionally can use the model to determine when the equipment 1604-6 (e.g., an engine of a stationary or mobile power-generating machine) needs to have a lubricant (e.g., oil) in the equipment 1604-6 changed or otherwise replaced. The controller 1602-6 represents hardware circuitry that includes and/or is coupled with one or more processors (e.g., one or more microprocessors, field-programmable gate arrays, integrated circuits, or the like) that perform the operations described herein.

The controller 1602-6 obtains measurements of contaminants and other contents of the lubricant from data acquisition circuitry 1606-6 that receives these measurements from one or more sensor probe assemblies 1608-6. The sensor probe assemblies 1608-6 represent one or more of the sensor probe assemblies described herein. The data acquisition circuitry 1606-6 represents one or more computing hardware systems, such as computers, input devices, or the like, that obtain the measurements of the lubricant as created by the sensor probe assemblies 1608-6. Because the data acquisition circuitry 1606-6 and/or sensor probe assemblies 1608-6 may be remotely located from the controller 1602-6 (e.g., not in the same room, building, ZIP code, state, or the like), the data acquisition circuitry 1606-6 can communicate the measurements from the sensor probe assemblies 1608-6 to the controller 1602-6 via one or more computerized communication networks 1610-6, such as one or more public and/or private computer networks.

The controller 1602-6 is communicatively coupled (e.g., by one or more wired and/or wireless connections) with one or more computer memory devices 1612-6, such as one or more servers, computer hard drives, optical drives, or the like. The memory devices 1612-6 can store measurements of the lubricant in the machine 1604-6 from the sensor probe assemblies 1608-6, such as the presence of and/or concentrations of one or more contaminants in the oil of the machine 1604-6 (e.g., water). In one embodiment, the controller 1602-6 obtains the measurements from the sensor probe assemblies 1608-6 via the data acquisition circuitry 1606-6 and stores the measurements in the memory device 1612-6. Optionally, the data acquisition circuitry 1606-6 and/or sensor probe assemblies 1608-6 can send the measurements to the memory device 1612-6 without the measurements first being sent to or otherwise provided to the controller 1602-6.

The controller 1602-6 can examine the measurements provided by the sensor probe assemblies 1608-6 and use the measurements to predict, self-correct (e.g., using a digital twin of the equipment 1604-6), and forecast oil change intervals for the equipment 1604-6. The digital twin of the equipment 1604-6 is a model of the equipment 1604-6 that is updated with actual measured characteristics and operational data of the equipment 1604-6. The digital twin can be used by the controller 1602-6 to determine an oil change interval for the equipment 1604-6, which is a prediction of when the oil of the equipment 1604-6 should be changed based on previous operational data and/or based on hypothetical, planned, or predicted upcoming usage of the equipment 1604-6.

The oil change interval is a time period between changes of the oil in an engine or a remaining time until an oil change is to occur. The time period may be measured as days, weeks, or months of a calendar; hours and/or minutes of a clock; duty cycles of the engine; or the like. The oil change interval is predicted by the controller 1602-6 based on a current operational data (e.g., duty cycle) of the engine, as well as oil sample data obtained from one or more of the sensor probe assemblies described herein. This data can include information on which components or impurities are in the oil, as well as the concentration(s) of the impurities. In addition to operational data and oil sample data, fuel sulfur content and an oil top-up date can be obtained as inputs. The fuel sulfur content is a measurement of how much sulfur is in the fuel supplied to the equipment 1604-6, which can vary widely across different geographical locations. The oil top-up date is the date of the last time that oil was added to the equipment 1604-6 or a time period since the last time that oil was added to the engine. Optionally, one or more equipment characteristics of the equipment 1604-6 may be considered, such as whether the engine is a two- or four-stroke engine. As another example, the type of fuel (e.g., gas versus diesel versus a fuel used in hybrid vehicles) can be received as inputs. These inputs can be provided to the controller 1602-6 by one or more input devices 1614-6 (and optionally stored in the memory device 1612-6), or can be provided to and stored in the memory device 1612-6 from the input device(s) 1614-6 without first being sent to the controller 1602-6.

In operation, the controller 1602-6 obtains information related to the equipment 1604-6 from the memory device 1612-6. This information includes operational data, lubricant sample data, and/or lubricant change data. The operational data can include information indicative of usage of the equipment 1604-6, such as measurements of impurities in oil of the equipment 1604-6, date of or time since the last oil change, operational cycles of the equipment 1604-6, locations where the equipment 1604-6 operated, types of fuel used by the equipment 1604-6, duration of use of the equipment 1604-6, temperatures at which the equipment 1604-6 operated, ambient temperatures in which the equipment 1604-6 operated, geometrical details or measurements of the equipment 1604-6 and/or chamber in the equipment 1604-6 that holds the lubricant, power rating of the equipment 1604-6, lube system parameters of the equipment 1604-6 (e.g., lubricant flow rate, lubricant film temperature, combustion characteristics of the equipment 1604-6, etc.), and the like.

In one embodiment, the operational data obtained by the controller 1602-6 includes a lubricant top-off date and/or an impurity content of fuel used by the equipment 1604-6. The top-off date can be the date of or time since lubricant (e.g., oil) was last added to the equipment 1604-6. The impurity content of the fuel can be the amount of one or more impurities in the fuel consumed by the equipment 1604-6, such as the sulfur content of fuel supplied to the equipment 1604-6. Optionally, the operational data obtained by the controller 1602-6 includes a base oil composition, such as a grade of the lubricant (e.g., different generations of lubricant oils, such as generation 6 or 7).

The lubricant sample data includes measurements of the lubricant in the equipment 1604-6 obtained by the sensor probe assembly or assemblies 1608-6. These measurements can include identification of and/or concentrations of one or more impurities in the lubricant, such as water or non-hydrocarbon components. The lubricant change data can include information on when the lubricant was last changed or replaced, as opposed to when lubricant was last added to the equipment 1604-6. In one embodiment, the measurements obtained from the sensor and/or other systems may be converted from a reference scale (of the sensor or other origin of the measurements) to an absolute scale before providing the measurements to the digital twin. For example, calibration factors used for converting infrared measured soot data may be used. These conversion factors can vary from values of 5 to 60.

Optionally, the measurement of the amount of impurities in the lubricant can include a measurement of one or more additives to the lubricant. For example, base additives can be added to oil to extend the life of the oil. The amount of one or more additives also can be measured and used to determine when a lubricant change is needed. For example, if an impurity measurement trends upward (e.g., soot) and/or an additive measurement trends downward (e.g., a base additive), then a lubricant change may be needed sooner than if the impurity measurement trends downward or remains the same and/or the additive measurement does not decrease.

The controller 1602-6 can perform an analysis of the obtained information to determine a remaining useful life (RUL) of the lubricant in the equipment 1604-6 based on the information. The controller 1602-6 can examine the operational data, lubricant sample data, and/or lubricant change data to determine how much longer the lubricant can be used without being changed or otherwise replaced at a time that is a designated period of time ahead of a scheduled maintenance of the equipment 1604-6. For example, the equipment 1604-6 (or a larger powered system that includes the equipment 1604-6, such as a vehicle) can be scheduled for maintenance or an oil change every three months or three to five thousand miles. At a designated date (e.g., fourteen days ahead of the scheduled oil change or five hundred miles before the next oil change), the controller 1602-6 can automatically obtain the operational data, lubricant sample data, and/or lubricant change data from the memory device 1612-6 and determine the remaining useful life of the lubricant based on this information. Depending on how much longer the remaining useful life is, the controller 1602-6 may direct that the oil change not occur at the next scheduled maintenance, that the next scheduled maintenance be delayed, or that the next scheduled maintenance be performed sooner than the previously scheduled date.

Optionally, the controller 1602-6 can perform the analysis of the operational data, lubricant sample data, and/or lubricant change data to create and/or update a model (e.g., a digital twin) of the equipment 1604-6. This model can be used to determine a remaining useful life of the equipment 1604-6 and/or other systems of the equipment 1604-6 (e.g., the components that hold and/or direct the flow of lubricant in the equipment 1604-6). In one embodiment, the digital twin can be used to predict how much longer the equipment 1604-6 can continue operating with the current lubricant given hypothetical or planned future operating conditions of the equipment 1604-6. For example, a designated number of upcoming operational cycles of the equipment 1604-6, one or more designated locations where the equipment 1604-6 will operate, one or more designated types of fuel that will be used by the equipment 1604-6, a designated upcoming total duration of use of the equipment 1604-6, designated temperatures at which the equipment 1604-6 will operate, designated ambient temperatures in which the equipment 1604-6 will operate, and the like, can be input into the controller 1602-6 (e.g., by the input device(s) 1614-6). Based on the current state or condition of the lubricant (based on the operational data, lubricant sample data, and/or lubricant change data, as described herein), different hypothetical or planned future operating conditions may result in the controller 1602-6 determining that the lubricant needs to be changed sooner (e.g., than a scheduled maintenance), later (than the scheduled maintenance), that the equipment 1604-6 cannot safely operate under the designated conditions, or the like. For example, if the operational data, lubricant sample data, and/or lubricant change data indicate a poor state of health of the lubricant, then more upcoming operational cycles, poorer quality fuel (e.g., more impurities), longer upcoming durations of use, hotter operating temperatures, hotter ambient temperatures, and the like, will result in the controller 1602-6 determining that the equipment 1604-6 cannot safely operate under the designated upcoming operating conditions without an oil change when compared to fewer upcoming operational cycles, higher quality fuel, shorter upcoming durations of use, cooler operating temperatures, cooler ambient temperatures, and the like.

As the equipment 1604-6 operates under the planned or other operational conditions, the operating conditions under which the equipment 1604-6 actually operated can be reported to the controller 1602-6 and/or stored in the memory device 1612-6. This information can be used to update the digital twin of the equipment 1604-6. For example, the total number of operational cycles since a lubricant change, the different types of fuel, the total duration of use since a lubricant change, the operating temperatures and/or ambient temperatures, and the like, can be tracked over time. As the total number of operational cycles since a lubricant change increases, poorer quality fuels are used, the total duration of use since a lubricant change increases, the operating temperatures increase, and/or ambient temperatures increase, the shorter of a time span that the equipment 1604-6 can operate without an oil change.

Once a lubricant change occurs, however, the controller 1602-6 can re-set one or more aspects of the digital twin of the equipment 1604-6. For example, the occurrence of a lubricant change can be input to the controller 1602-6 via the input device(s) 1614-6, and the controller 1602-6 can adjust the digital twin such that data values indicative of previous operating cycles, temperatures, and the like, can be re-set to zero or otherwise changed to indicate that new lubricant is being used in the equipment 1604-6.

In addition to the operational data, the controller 1602-6 also uses the sample data to determine whether a change of the lubricant is needed, when a change in the lubricant is needed, and/or whether the equipment 1604-6 can safely operate under hypothetical or planned upcoming operating conditions without a lubricant change. The sample data can be provided by the sensor probe assemblies 1608-6 and the controller 1602-6 can shorten the time span before the next lubricant change and/or determine that the equipment 1604-6 cannot safely operate without a lubricant change for sample data indicating larger amounts of impurities in the lubricant when compared with sample data indicating smaller or no amounts of impurities in the lubricant.

In one embodiment, the controller 1602-6 also considers the amount of sulfur in the fuel consumed by the equipment 1604-6 in determining the remaining useful life of the lubricant in the equipment 1604-6. For example, one of the inputs considered by the controller 1602-6 in determining how much longer an engine can continue operating before an oil change is needed can be the amount (e.g., concentration or absolute amount) of sulfur in the fuel supplied to the engine. The controller 1602-6 can shorten the amount of time or reduce the number of duty cycles that the equipment 1604-6 can continue operating before a lubricant change is needed for greater amounts of sulfur in the fuel and can lengthen the amount of time or increase the number of duty cycles that the equipment 1604-6 can continue operating before the lubricant change is needed for lesser amounts of sulfur in the fuel.

The controller 1602-6 optionally also considers the time or number of duty cycles since a lubricant top-off of the equipment 1604-6 occurred in determining the remaining useful life of the lubricant in the equipment 1604-6. For example, one of the inputs considered by the controller 1602-6 in determining how much longer an engine can continue operating before an oil change is needed can be when the last time oil was added to the engine. The controller 1602-6 can shorten the amount of time or reduce the number of duty cycles that the equipment 1604-6 can continue operating before a lubricant change is needed for longer periods of time since lubricant was last added to the equipment 1604-6 and can lengthen the amount of time or increase the number of duty cycles that the equipment 1604-6 can continue operating before the lubricant change is needed for shorter time periods since lubricant was last added to the equipment 1604-6.

Figure 109:
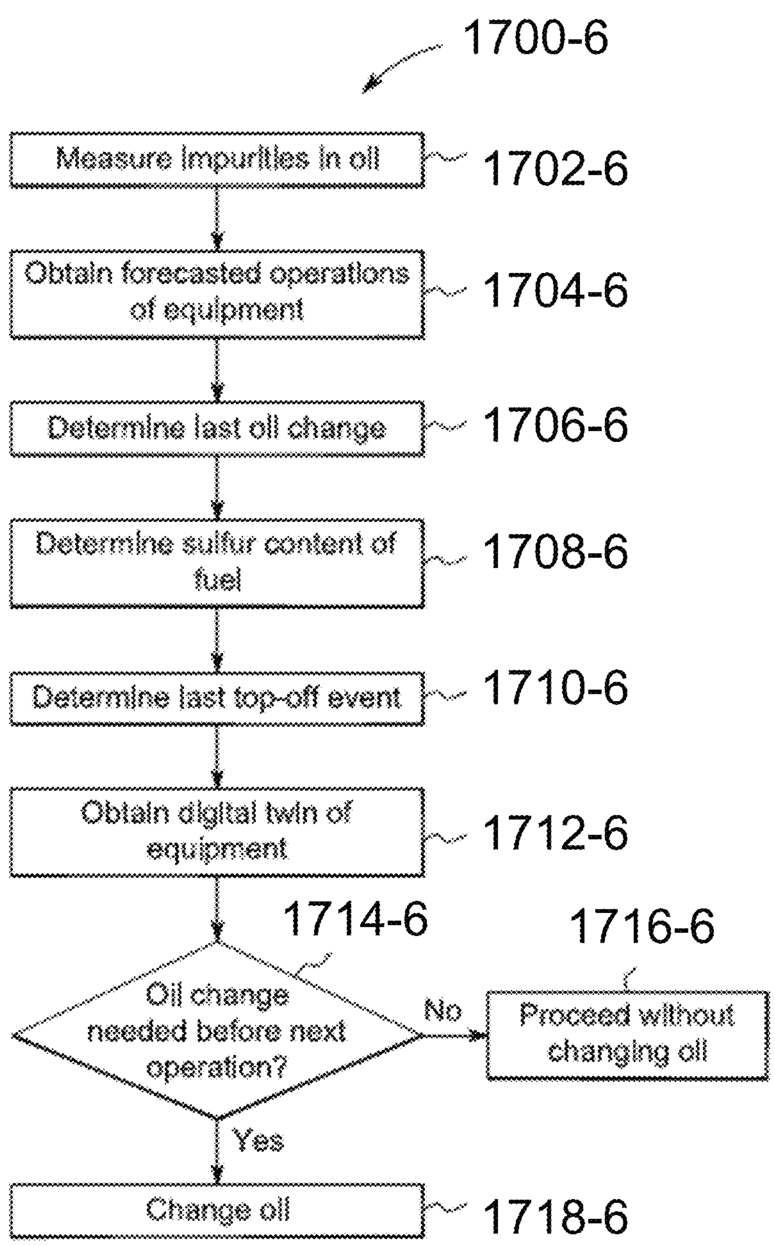
FIG. 109 illustrates a flowchart of one embodiment of a method for determining a maintenance event for equipment.

FIG. 109 illustrates another embodiment of the maintenance system 1600-6 used in connection with a locomotive system 5700-6. The locomotive system 5700-6 represents a rail vehicle 5704-6, such as a locomotive, that includes a vehicle controller 5702-6 and the equipment 1604-6 described above. The vehicle controller 5702-6 can represent hardware circuitry that includes and/or is connected with one or more processors (e.g., one or more microprocessors, field-programmable gate arrays, integrated circuits, or the like) that control operation of the rail vehicle. For example, the equipment 1604-6 can represent an engine under control of the vehicle controller 5702-6 to propel the rail vehicle 5704-6 along one or more tracks. The rail vehicle 5704-6 includes a platform 5706-6, which also can be referred to as a vehicle chassis or body, that supports the maintenance system 1600-6, the equipment 1604-6, and other components. The platform 5706-6 is coupled with multiple wheel-axle sets 5708-6 that each includes two or more wheels 5710-6 coupled with an axle 5712-6. The equipment 1604-6 can operate to rotate the axles 5712-6 and wheels 5710-6 to propel the rail vehicle 5704-6. Optionally, the rail vehicle 5704-6 represents another type of vehicle, such as an automobile, a truck, an aircraft (manned or unmanned), marine vessel, mining vehicle, or the like.

The vehicle controller 5702-6 can be in communication with the data acquisition circuitry 1606-6 (or the controller 1602-6, not shown) to determine when the equipment 1604-6 needs to have a lubricant (e.g., oil) in the equipment 1604-6 changed or otherwise replaced. The equipment 1604-6 includes a reservoir that holds the lubricant. The equipment 1604-6 optionally can represent another reservoir that holds lubricant. The equipment 1604-6 can be directly or indirectly coupled to the platform 5706-6.

The controller 5702-6 obtains measurements of contaminants and other contents of the lubricant from data acquisition circuitry 1606-6 that receives these measurements from one or more sensor probe assemblies 1608-6. The controller 5702-6 can store measurements of the lubricant from the sensor probe assemblies 1608-6, such as the presence of and/or concentrations of one or more contaminants in the oil of the equipment 1604-6 (e.g., water). In one embodiment, the controller 5702-6 obtains the measurements from the sensor probe assemblies 1608-6 via the data acquisition circuitry 1606-6 and stores the measurements in a memory device, such as the memory device 1612-6.

The controller 5702-6 can examine the measurements provided by the sensor probe assemblies 1608-6 and use the measurements to predict, self-correct, and forecast oil change intervals for the equipment 1604-6. The oil change interval can be predicted by the controller 5702-6 based on a current operational data (e.g., duty cycle) of the equipment 1604-6, as well as oil sample data obtained from one or more of the sensor probe assemblies 1608-6 described herein. This data can include information on which components or impurities are in the oil, as well as the concentration(s) of the impurities. In addition to operational data and oil sample data, fuel sulfur content and an oil top-up date can be obtained as inputs. The fuel sulfur content is a measurement of how much sulfur is in the fuel supplied to the equipment 1604-6, which can vary widely across different geographical locations. The oil top-up date is the date of the last time that oil was added to the equipment 1604-6 or a time period since the last time that oil was added to the engine. Optionally, one or more equipment characteristics of the equipment 1604-6 may be considered, such as whether the engine is a two- or four-stroke engine. As another example, the type of fuel (e.g., gas versus diesel versus a fuel used in hybrid vehicles) can be received as inputs.

The controller 5702-6 can obtain information related to the equipment 1604-6 such as operational data, lubricant sample data, and/or lubricant change data. The operational data can include information indicative of usage of the equipment 1604-6, such as measurements of impurities in oil of the equipment 1604-6, date of or time since the last oil change, operational cycles of the equipment 1604-6, locations where the equipment 1604-6 operated, types of fuel used by the equipment 1604-6, duration of use of the equipment 1604-6, temperatures at which the equipment 1604-6 operated, ambient temperatures in which the equipment 1604-6 operated, geometrical details or measurements of the equipment 1604-6 and/or chamber in the equipment 1604-6 that holds the lubricant, power rating of the equipment 1604-6, lube system parameters of the equipment 1604-6 (e.g., lubricant flow rate, lubricant film temperature, combustion characteristics of the equipment 1604-6, etc.), and the like.

In one embodiment, the operational data obtained by the controller 5702-6 includes a lubricant top-off date and/or an impurity content of fuel used by the equipment 1604-6. The top-off date can be the date of or time since lubricant (e.g., oil) was last added to the equipment 1604-6. The impurity content of the fuel can be the amount of one or more impurities in the fuel consumed by the equipment 1604-6, such as the sulfur content of fuel supplied to the equipment 1604-6. Optionally, the operational data obtained by the controller 5702-6 includes a base oil composition, such as a grade of the lubricant.

The lubricant sample data includes measurements of the lubricant in the equipment 1604-6 obtained by the sensor probe assembly or assemblies 1608-6. These measurements can include identification of and/or concentrations of one or more impurities in the lubricant, such as water or non-hydrocarbon components. The lubricant change data can include information on when the lubricant was last changed or replaced, as opposed to when lubricant was last added to the equipment 1604-6.

Optionally, the measurement of the amount of impurities in the lubricant can include a measurement of one or more additives to the lubricant. For example, base additives can be added to oil to extend the life of the oil. The amount of one or more additives also can be measured and used to determine when a lubricant change is needed. For example, if an impurity measurement trends upward (e.g., soot) and/or an additive measurement trends downward (e.g., a base additive), then a lubricant change may be needed sooner than if the impurity measurement trends downward or remains the same and/or the additive measurement does not decrease.

The controller 5702-6 can perform an analysis of the obtained information to determine a remaining useful life (RUL) of the lubricant in the equipment 1604-6 based on the information. The controller 5702-6 can examine the operational data, lubricant sample data, and/or lubricant change data to determine how much longer the lubricant can be used without being changed or otherwise replaced at a time that is a designated period of time ahead of a scheduled maintenance of the equipment 1604-6. For example, the equipment 1604-6 and/or the rail vehicle 5704-6 can be scheduled for maintenance or an oil change every three months or three to five thousand miles. At a designated date (e.g., fourteen days ahead of the scheduled oil change or five hundred miles before the next oil change), the controller 5702-6 can automatically obtain the operational data, lubricant sample data, and/or lubricant change data from the memory device and determine the remaining useful life of the lubricant based on this information. Depending on how much longer the remaining useful life is, the controller 5702-6 may direct that the oil change not occur at the next scheduled maintenance, that the next scheduled maintenance be delayed, or that the next scheduled maintenance be performed sooner than the previously scheduled date. Optionally, the controller 5702-6 can perform the analysis of the operational data, lubricant sample data, and/or lubricant change data to create and/or update a model (e.g., a digital twin) of the equipment 1604-6, as described above.

Figure 110:
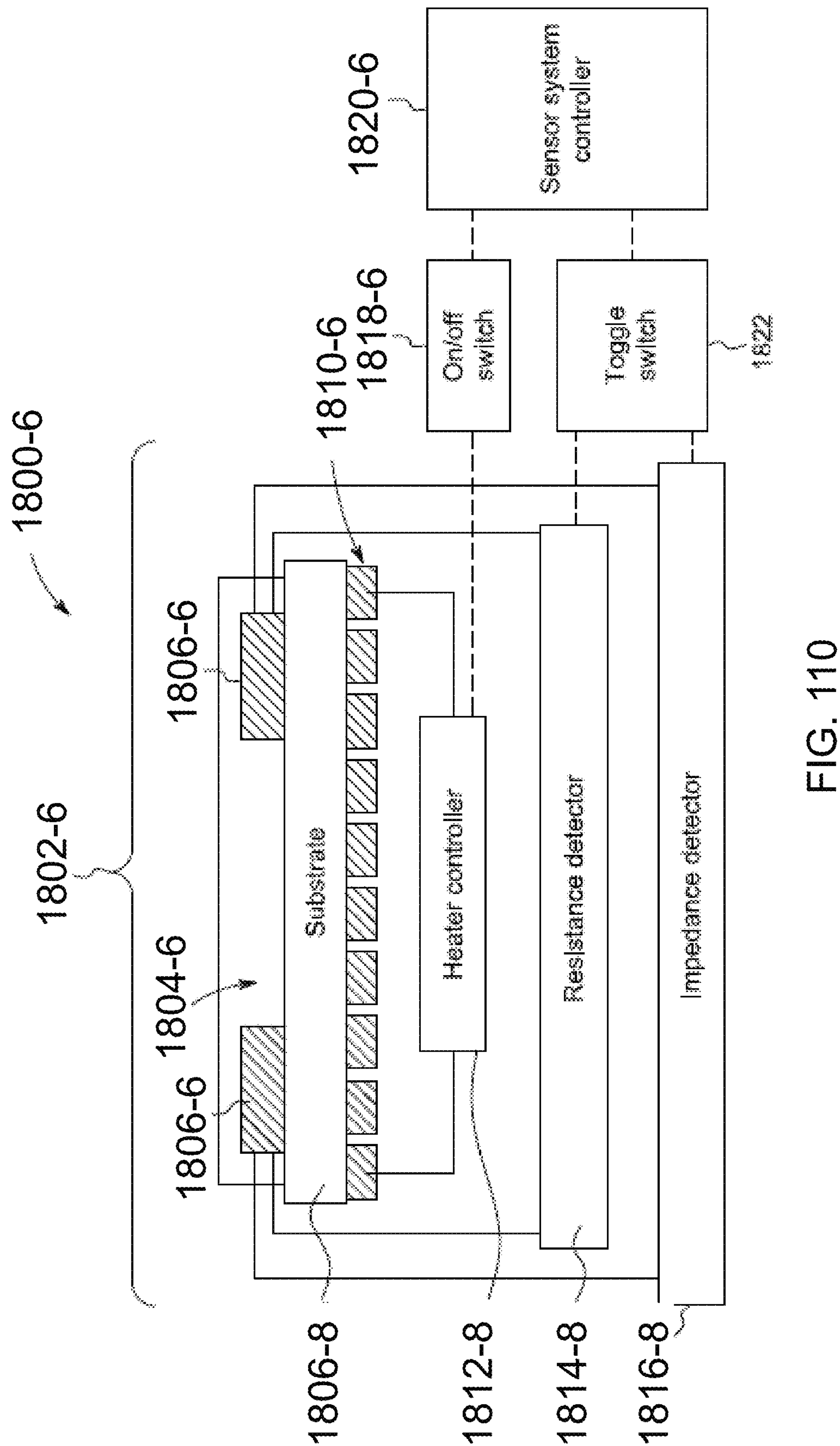
FIG. 110 illustrates one embodiment of a measurement system that corrects for aging in a sensor probe assembly.

FIG. 110 illustrates a flowchart of one embodiment of a method 1700-6 for determining a maintenance event for equipment. The method 1700-6 can be used to determine when a lubricant change for the equipment 1604-6 is needed based on a variety of input data, which can include the sulfur content of fuel supplied to the equipment 1604-6 and/or the last time that lubricant was added to the equipment 1604-6. The flowchart of the method 1700-6 can represent operations performed by the controller 1602-6.

At 1702-6, the amount of one or more impurities in oil in an engine is determined. The impurity amount(s) can be measured by one or more of the sensor probe assemblies described herein. Alternatively, another type of sensor can be used. Optionally, the method 1700-6 does not include 1702-6. At 1704-6, forecasted operational conditions of the engine are obtained. For example, the ambient temperatures, engine speeds, engine temperatures, durations of operation, and the like, can be determined from operator inputs and/or from a scheduled or planned operation or mission of the engine. Optionally, the method 1700-6 does not include 1704-6. At 1706-6, the last time the oil of the engine was changed is determined. The date and/or time of this event can be stored in the memory device, and the time and/or number of duty cycles since the last time the oil was removed from the engine and then replenished is determined. Optionally, the method 1700-6 does not include 1706-6.

At 1708-6, the sulfur content of the fuel that is or will be supplied to the engine is determined. Different geographic areas may have different amounts of fuel impurities (e.g., sulfur) in the fuel that is available in those areas. Greater amounts of sulfur in fuel that is supplied to the equipment 1604-6 can result in the equipment 1604-6 operating at hotter temperatures, which can cause faster deterioration of the lubricant in the equipment 1604-6. One embodiment of the inventive subject matter described herein takes the amount of sulfur in fuel used to power the equipment 1604-6 into consideration when determining whether the existing lubricant in the equipment 1604-6 needs to be changed or whether the equipment 1604-6 can continue operating with the existing lubricant. The amount of sulfur in the fuel can be input by an operator of the system 1600-6, can be obtained from one or more remotely located memory devices (e.g., servers) via the network(s) 1610-6, or the like.

At 1710-6, a determination is made as to when lubricant was last added to the equipment 1604-6. At various times, one or more operators may add lubricant to the equipment 1604-6, such as when the operator(s) discover that the volume of lubricant in the equipment 1604-6 or a reservoir of the equipment 1604-6 is below a designated lower limit. Some volume of the lubricant can be added to the equipment 1604-6 and/or the reservoir of the equipment 1604-6 at a top-off event. The top-off event differs from the changing of the lubricant in that lubricant is added to, but not predominantly removed from, the equipment 1604-6 during a top-off event. Lubricant is predominantly removed (e.g., at least 90% by volume and/or weight) from the equipment 1604-6 and/or an associated reservoir, and then replaced during a changing of the lubricant. The time or date since the last top-off event can be input by an operator of the system 1600-6, can be obtained from one or more remotely located memory devices (e.g., servers) via the network(s) 1610-6, or the like.

At 1712-6, a digital twin of the equipment 1604-6 is obtained. The digital twin of the equipment 1604-6 can be created from the data and information obtained and/or determined at 1702-6, 1704-6, 1706-6, 1708-6, and/or 1710-6, and/or an existing digital twin of the equipment 1604-6 can be modified or updated based on some or all of this information. The digital twin can serve as an electronic representation of the equipment 1604-6, including some or all of the prior usage (duration of use, temperatures, sulfur contents of fuel, date/time of last top-off event, etc.).

At 1714-6, a decision is made by the controller 1602-6 as to whether a change of the lubricant is needed. This decision can be based on the controller 1602-6 examining the digital twin of the equipment 1604-6 (which electronically represents usage and/or wear and tear of the equipment 1604-6, deterioration or deteriorating conditions of the lubricant, etc.), determining forecasted operating conditions (e.g., planned, hypothetical, and/or predicted conditions in which the equipment 1604-6 will operate), the sulfur content of fuel previously supplied to the equipment 1604-6 and/or planned to be provided to the equipment 1604-6, and/or the time since the last top-off event. If the prior usage of the equipment 1604-6 and lubricant (as represented by the digital twin) indicates a longer time and/or more harsh operating conditions for the equipment 1604-6 (than a shorter operating time and/or less harsh operating conditions), then the controller 1602-6 may determine that an oil change is needed; if the previous sulfur content of the fuel used by the equipment 1604-6 is higher, then the controller 1602-6 may decide that an oil change is needed (when compared with lower sulfur contents); if it has been a longer period of time since the last top-off event, then the controller 1602-6 may determine that an oil change is needed (when compared with shorter periods of time since the last top-off event; and/or if the impurities measured in the oil by the sensor probe assemblies 1608-6 indicate greater amounts of impurities, then the controller 1602-6 may recommend changing the oil sooner (than if fewer amounts of impurities were measured). The controller 1602-6 can determine which combinations of these conditions indicate that an oil change is needed before operation of the equipment 1604-6 can continue, which combinations of conditions indicate that an oil change can be delayed, etc., based on empirically derived or determined combinations of conditions of other equipment 1604-6 and when oil changes for that other equipment 1604-6 occurred.

If the controller 1602-6 determines that a change in the lubricant is needed, then flow of the method 1700-6 can proceed toward 1718-6. At 1718-6, the lubricant of the equipment 1604-6 is changed. For example, the controller 1602-6 can prevent continued operation of the equipment 1604-6 by communicating one or more control signals to the equipment 1604-6 to shut down or prevent continued operation of the equipment 1604-6. As another example, the controller 1602-6 can send a warning signal to an operator that an oil change is needed. The controller 1602-6 can change or modify planned operational settings of the equipment 1604-6 to allow the equipment 1604-6 to continue operating without the oil change. For example, the equipment 1604-6 may be scheduled to propel a vehicle along a mountainous route in harsh conditions (e.g., elevated temperatures) carrying a heavy load before the next oil change. The controller 1602-6 can prevent this from occurring by either automatically directing the oil be changed or by changing the scheduled operational settings of the equipment 1604-6.

If the controller 1602-6 determines (at 1714-6) that a change in the lubricant is not needed, then flow of the method 1700-6 can proceed toward 1716-6. For example, the controller 1602-6 can determine that the equipment 1604-6 can continue operating (e.g., with the forecasted operating conditions) before an oil change is needed. As another example, the controller 1602-6 can determine that an oil change is needed, but that the previous and/or planned operating conditions of the equipment 1604-6 and/or lubricant allow for the equipment 1604-6 to continue operating longer without needed a change in lubricant. This can allow for maintenance of the equipment 1604-6 to be delayed without significant risk of damage to the equipment 1604-6.

Determining when or whether to change lubricant of the equipment 1604-6 as described herein provides for a condition-based performance of maintenance without significant changes in current operation of the equipment 1604-6. The useful life of lubricant can be extended beyond a designated oil-change schedule due to usage of the equipment 1604-6 in conditions that do not cause the lubricant to deteriorate as quickly, due to recent top-offs of the lubricant, due to low levels of impurities in the lubricant, etc. Additionally, the frequency at which the lubricant is sampled can be decreased in situations where usage of the equipment 1604-6 is in conditions that do not cause the lubricant to deteriorate as quickly, where the lubricant has been recently added, where there are low levels of impurities in the lubricant, etc. This can reduce the sampling cost involved in maintaining the equipment 1604-6. Additionally, the controller 1602-6 can determine when data outliers (e.g., measurements of abnormally elevated levels of impurities in oil) are false positive detections of impurities, versus when significant and real issues exist, due to examination of the digital twin and previous usage of the equipment 1604-6. For example, if the equipment 1604-6 has been used in less harsh conditions, lubricant has recently been added to the equipment 1604-6, other measurements of impurities were low or within acceptable limits, etc., then an abnormally high measurement of impurities in the lubricant can be identified by the controller 1602-6 as a data outlier, and not an actual problem with the lubricant.

In one embodiment, a method includes monitoring previous operational conditions of an engine that operates using fuel and a lubricant, identifying one or more of an impurity content of the fuel supplied to the engine or an elapsed time since a previous addition of additional lubricant to the lubricant in the engine, and determining whether a change of the lubricant is required prior to continued operation of the engine based on the previous operational conditions and the one or more of the impurity content of the fuel or the elapsed time since the previous addition of the additional lubricant to the lubricant in the engine.

Optionally, the method includes identifying the impurity content of the fuel and the impurity content is an amount of sulfur in the fuel.

Optionally, the method includes both identifying the impurity content of the fuel and the elapsed time since the previous addition of the additional lubricant. Determining whether the change of the lubricant is required can be based on the previous operational conditions, the impurity content of the fuel, and the elapsed time since the previous addition of the additional lubricant.

Optionally, the previous operational conditions include one or more of an elapsed operating time of the engine, an operating temperature of the engine, or an ambient temperature in which the engine operated.

Optionally, the method also can include creating or updating a digital twin of the engine based on the previous operational conditions of the engine, and forecasting upcoming operational conditions of the engine. Determining whether the change of the lubricant is required prior to the continued operation of the engine is based on the previous operational conditions, the one or more of the impurity content of the fuel or the elapsed time since the previous addition of the additional lubricant to the lubricant in the engine, the digital twin of the engine, and the upcoming operational conditions of the engine that are forecasted.

Optionally, the method also includes automatically changing the lubricant in the engine based on determining that the change in the lubricant is required. For example, one or more of the controllers described herein can generate and communicate control signals to a scheduling system that schedules the change or addition of lubricant to the engine.

Optionally, determining whether the change of the lubricant is required involves delaying the change of the lubricant beyond a previously scheduled maintenance of the engine that involves changing the lubricant.

Aging of chemical gas sensor systems such as the sensor probe assemblies described herein can pose a significant limitation in broad industrial application of the assemblies where long term stability of installed sensors is needed. To address this challenging problem, different approaches have been implemented. In particular, sensors are periodically recalibrated by removing the sensors from a measurement system, by bringing a carrier gas to the sensor without removing the sensors from the measurement system, and/or by simultaneously re-charging and calibrating the sensors on a regular basis (e.g., daily). Sensor aging is defined here as any detectable change in sensor sensitivity or sensor selectivity or sensor offset or sensor drift or sensor response time or sensor recovery time upon normal operation conditions of the sensor over time or upon exposure of the sensor to any undesired conditions. Nonlimiting examples of the undesired conditions may include poisoning, mechanical degradation, and any other undesired conditions.

These and other known calibration methods have significant limitations. For example, the methods can require calibrations with an analyte gas that occur more frequently than the maintenance cycle of the system itself (e.g., a transformer). As another example, the methods can require a calibration gas to be presented to the sensor.

One or more embodiments of the inventive subject matter described herein provide systems and methods that correct for the aging of one or more sensor probe assemblies without removal of the sensor probe assemblies from a measurement system and without the need for user interaction or recalibration with analyte. The systems and methods use the condition of the sensor probe assembly when the assembly is not responding to a gas or fluid of interest, but is quantitatively affected by aging of the sensor probe assembly. For example, when a sensor probe assembly is in the OFF state (i.e., not powered), this sensor condition or sensor state is quantitatively affected by the aging of the sensor probe assembly and can be detected by resistance and/or impedance spectroscopy readouts of the assembly at a specific range of frequencies. When the same sensor probe assembly is in the ON state (i.e., powered), the drift in the sensor response due to aging is correlated with the OFF state of the sensor probe assembly.

The response of the sensor probe assembly when in the OFF state (also referred to as the OFF sensor response) can be used to correct for drift in the response of the sensor probe assembly in the ON state (also referred to as the ON sensor response) due to aging. This technique of sensor correction is applied to one or more embodiments of the sensor probe assemblies having metal oxide semiconductor elements on the electrodes. The metal oxide semiconductor sensors can detect numerous gases by the selection of the base semiconductor material and the doping of the material. Impedance measurements of metal oxide semiconductor sensors are used to allow more selective sensor responses. When the sensor is in OFF state (not powered), the sensor output is measured and then utilized to correct for aging effects when the sensor is in the ON state.

This correction can reduce or eliminate the need for frequent sensor calibration using an analyte gas. Instead, when the sensor is aging, the aging condition of the sensor is quantified using the sensor response in the OFF state. The aging condition measured in the OFF state is then used to correct for effect of aging when the sensor is in the ON state and responding to the analyte gas, or gases of interest, and to known interferences. This aging condition of the sensor can be detected by resistance and/or impedance spectroscopy readouts at a specific range of frequencies.

Figure 111:
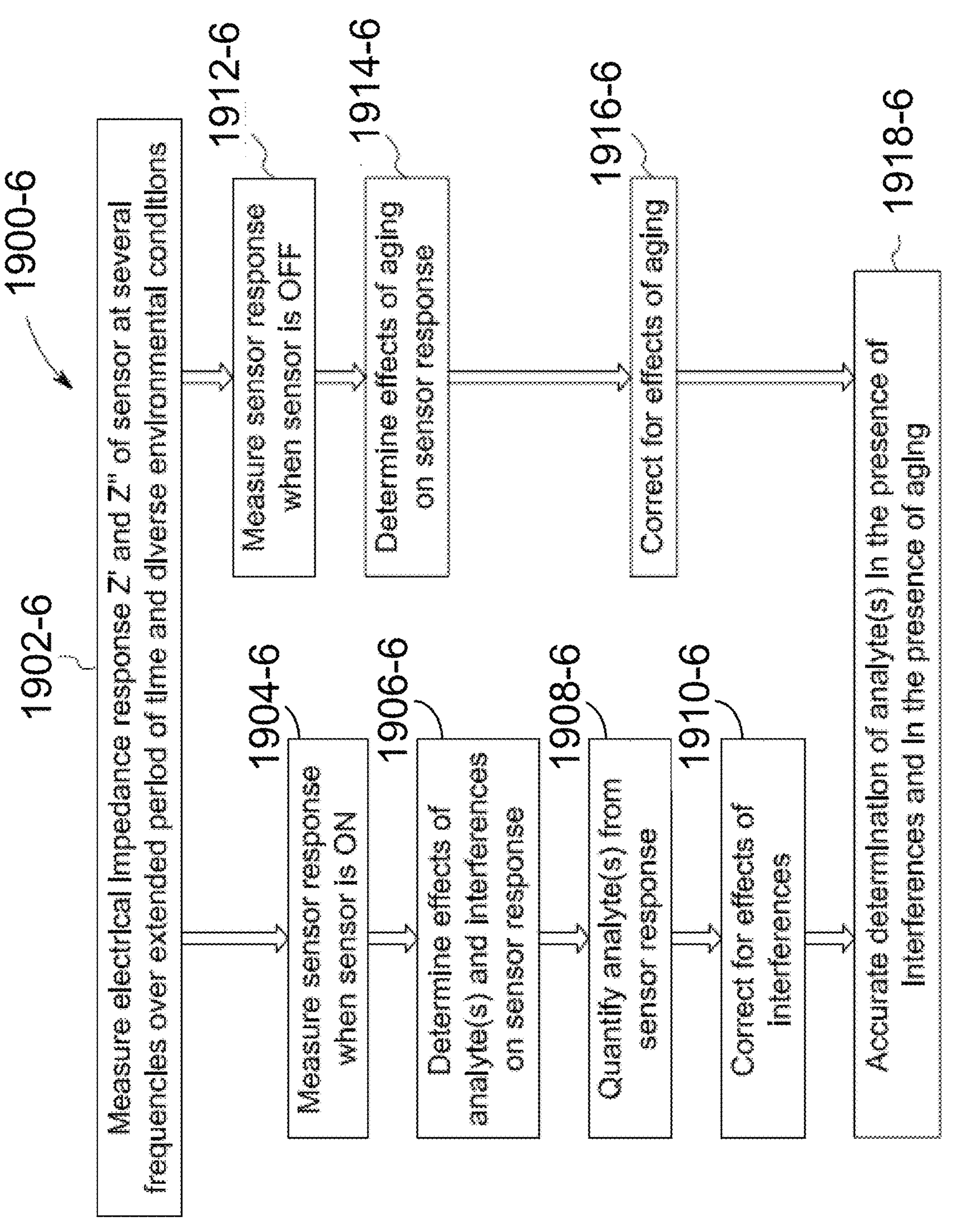
FIG. 111 illustrates a flowchart of one embodiment of a method for correcting measurements of a sensor probe assembly for aging.

FIG. 111 illustrates one embodiment of a measurement system 1800-6 that corrects for aging in a sensor probe assembly 1802-6. The sensor probe assembly 1802-6 can represent one or more of the sensor probe assemblies described herein. Optionally, the sensor probe assembly 1802-6 can be another type of sensor probe assembly that measures concentrations of one or more analytes of interest in a fluid under examination using impedance spectral responses of a semiconductor material to the analytes and an electric field generated by electrodes. The fluid under examination can be gas.

The sensor probe assembly 1802-6 includes sensing material 1804-6 on and/or in contact with conductive electrodes 1806-6 that generate an electric field between the electrodes 1806-6. The sensing material 1804-6 can be a metal oxide semiconductor material, such as SnO2. The electrodes 1806-6 are shown as being deposited on a dielectric substrate 1808-6 (e.g., the substrate 102-6, 906-6), but alternatively may be the free-standing electrodes with the sensing material 1804-6 deposed thereon, as described above. One or more heating elements 1810-6 are formed from conductive bars, plates, or other resistive bodies that receive electric current to heat the substrate 1808-6, the sensing material 1804, and/or the electrodes 1806-6.

A heater controller 1812-6 represents hardware circuitry that is conductively coupled with and conducts electric current to or through the heating elements 1810-6 to generate heat. A resistance detector 1814-6 represents hardware circuitry that is conductively coupled with the electrodes 1806-6 to measure electric resistance between the electrodes 1806-6 (e.g., through the sensing material 1804-6, which can have a resistance and/or impedance that varies based on the presence and/or amount of impurities or analytes of interest in the fluid under examination). The resistance detector 1814-6 performs measurements of resistance of the sensing material 1804 while the sensor probe assembly 1802-6 is in the ON state (e.g., power is being supplied to the heating elements 1810-6 from the heater controller 1812-6).

The system 1800-6 also includes additional sensor components such as an impedance detector 1816-6, which represents hardware circuitry that is conductively coupled with the electrodes 1806-6 and that measures the impedance of the sensing material 1804-6 between the electrodes 1806-6 while the sensor probe assembly 1802-6 is in the ON state and/or the OFF state. The ON state of the sensor is when a nominal required power is supplied to the heating elements 1810-6 from the heater controller 1812-6 to achieve a desired response of the sensor to the analyte of interest. Such desired sensor response is achieved when the sensing material 1804-6 operates at needed temperature in the range from about 100 degrees Celsius to about 800 degrees Celsius and more particularly in the range from about 200 degrees Celsius to about 500 degrees Celsius. The OFF state of the sensor is when a nominal required power is not supplied to the heating elements 1810-6 from the heater controller 1812-6 so the sensor does not have a detectable response to the analyte of interest. Two examples of "no nominal required power" include (1) zero applied power when the heating elements 1810-6 have zero power from the heater controller 1812-6 and allows the sensing material 1804-6 to be at ambient temperature or (2) minimal applied power when the heating elements 1810-6 have minimal power from the heater controller 1812-6 that does not produce a desired response of the sensor to the analyte of interest but allows the sensing material 1804-6 to be slightly above ambient temperature. For example, if ambient temperature is below zero degrees Celsius, the sensing material 1804-6 can be slightly above zero degrees Celsius (for example at 5-20 degrees Celsius) to avoid freezing of condensed water from ambient air onto the sensing material 1804-6. A first switch 1818-6 ("ON/OFF switch") operates under the control of a sensor system controller 1820-6 to switch between activating the heater controller 1812-6 (to supply current to the heating elements 1810-6) and deactivating the heater controller 1812-6 (to stop supplying current to the heating elements 1810-6). A second switch 1822-6 ("Toggle switch") is controlled by the controller 1820-6 to alternate between activating the resistance detector or sensor 1814-6 (to measure the resistance in the sensing material 1804-6) or activating the impedance detector or sensor 1816 (to measure the impedance in the sensing material 1804-6). The controller 1820-6 represents hardware circuitry that includes and/or is connected with one or more processors to control whether the resistance detector 1814-6 or impedance detector 1816-6 is activated, and whether the heater controller 1812-6 is activated using the switches 1818-6, 1822-6. The controller 1820-6 can operate based off on input received from an operator and/or may automatically control the switches 1818-6, 1822-6 (e.g., based on a clock and/or schedule).

One example of a transfer function for predicting a gas concentration from a response of the sensor material 1804 of the sensor probe assembly described herein is:

$$[\text{gas}] = A * [\text{sensor response}]^B$$

where [gas] is the predicted gas concentration (or concentration of an analyte of interest in a fluid such as a gas, [sensor response] is the measured response of the sensor probe assembly, and A and B are coefficients of the transfer function. These coefficients of the transfer function may be used for temperature correction and other factors, such as correction for humidity and other gases. The values of the coefficients can be set based on known concentrations of the analyte of interest in a gas sample during calibration of the sensor probe assembly.

Inventors of the inventive subject matter described herein have discovered that the values of the coefficients A and B of this transfer function are dependent on the aging status of the sensor probe assembly. To get the dependence of these coefficients on sensor aging, but not on the possible analyte gas concentration, the response of the sensor probe assembly can be measured when the sensor probe assembly is unpowered. Stated differently, when the sensor probe assembly is OFF, the sensor probe assembly does not respond to the gas of interest, and measurements of the response of the assembly may be indicative of or represent changes to the values of A and/or B due to aging.

The controller 1820-6 can direct the sensor probe assembly 1802-6 to operate in an impedance mode where the impedance of the sensing material 1804-6 is measured. The switch 1822-6 is actuated to activate the impedance detector 1816-6 and to measure the [sensor response] as $Z_{ON}$ (which is impedance of the sensor probe assembly 1802-6 at a designated frequency) while the sensor probe assembly 1802-6 is ON. The coefficients A and B can be related to the sensor probe assembly in the ON state and OFF state as follows:

$$[\text{gas}] = A_{ON,OFF} * Z_{ON}^{B_{ON,OFF}}$$

where the changes in coefficients $A_{ON,\ OFF}$ and $B_{ON,\ OFF}$ are due to the response of the sensor probe assembly 1802-6 to an analyte of interest (e.g., H2) while the sensor probe assembly 1802-6 is in the ON state as correlated to sensor aging (as determined from measurements obtained while the sensor probe assembly 1802-6 is in the OFF state).

FIG. 19 illustrates a flowchart of one embodiment of a method 1900-6 for correcting measurements of a sensor probe assembly for aging. The method 1900-6 can be performed by the system 1800 and/or the controller 1820 of the system 1800 to correct measurements obtained by one or more of the sensor probe assemblies described herein.

At 1902-6 and 1904-6, real (Z') and imaginary (Z") parts of the electrical impedance response of the sensing material of the sensor probe assembly are measured at several different frequencies while the sensor is in the ON state over an extended period of time and/or under diverse environmental conditions (e.g., exposure to different fluids of interest, different ambient temperatures, etc.). These responses of the sensor probe assembly can be measured by the controller 1802 based on output from the impedance detector 1816. At 1906-6, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 1908-6, the analyte(s) in the fluid under examination can be identified based on the sensor response, such as by identifying peaks in one or more impedance spectra of the sensor probe assembly that are associated with the analyte(s) of interest. At 1910-6, the effects of interferences can be corrected for, such as the impact of aging on the sensor probe assembly, as described in connection with 1912-6, 1914-6, 1916-6. At 1918-6, the accuracy of quantitation of analytes is achieved from the correction of sensor response based on the effects of the interferences (e.g., aging of the sensor probe assembly).

The method 1900-6 also includes, at 1902-6 and 1912-6, measuring the intrinsic impedance of the sensor probe assembly while the sensor probe assembly is OFF (not powered). These measurements can be performed at designated frequencies that allow the use of conventional measurement systems with detection of 1 GOhm, 100 MOhm, 10 MOhm, or 1 MOhm. At 1914-6, the values of the sensor impedance at one or more designated frequencies while the sensor probe assembly is in the OFF state are determined. These frequencies can be empirically determined from the same or other similar sensor probe assemblies. These values indicate the effects of aging on the sensor probe assembly.

At 1916-6, the values determined at 1914-6 are used for correction of the instabilities of the sensor response due to sensor aging. Also, the values of the sensor impedance at certain frequencies are used for correction of the instabilities of the sensor response to an analyte gas of interest when the sensor is powered. For example, these values may be subtracted or otherwise removed from the values determined at 1904-6 and/or 1908-6.

Figure 112:
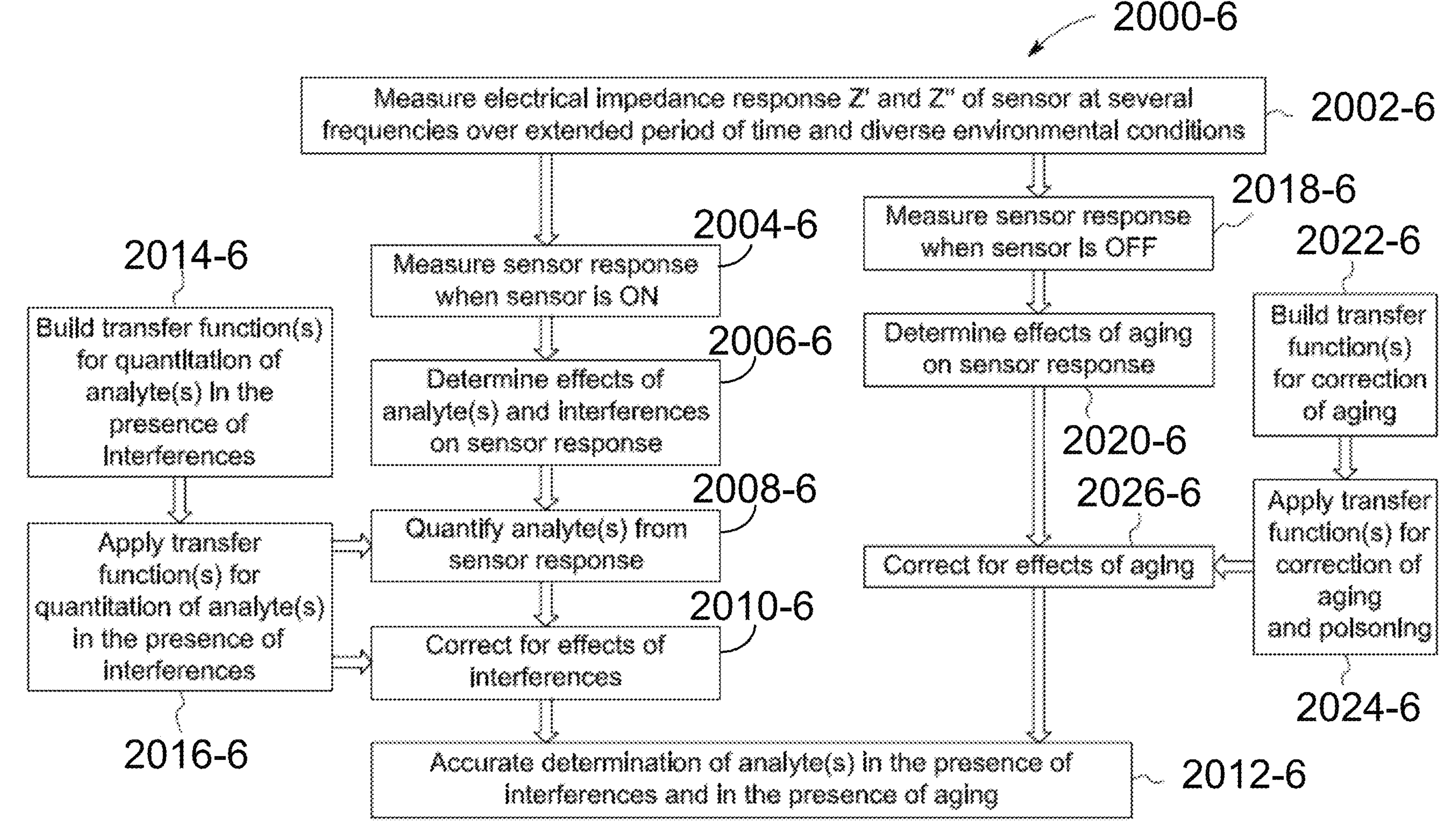
FIG. 112 illustrates another flowchart of one embodiment of a method for correcting measurements of a sensor probe assembly for aging.

FIG. 112 illustrates another flowchart of one embodiment of a method 2000-6 for correcting measurements of a sensor probe assembly for aging. The method 2000-6 can be performed by the system 1800 and/or the controller 1820 of the system 1800 to correct measurements obtained by one or more of the sensor probe assemblies described herein. At 2200-62-6 and 2004-6, the real part (Z') and imaginary part (Z") of the electrical impedance response of the sensor probe assembly are measured at several designated frequencies while the sensor probe assembly is in the ON state over extended period of time and while exposed to diverse environmental conditions.

At 2006-6, the values of the sensor impedance at designated frequencies are used to determine the effects of interferences and analytes on the sensor probe assembly. For example, the presence of some impurities in a fluid under examination can impact the real part (Z') and/or the imaginary part (Z") of the electrical impedance response of the sensor probe assembly, which also can be impacted by one or more analytes of interest in the fluid. At 2008-6, the analyte(s) in the fluid under examination can be identified based on the sensor response, such as by identifying peaks in one or more impedance spectra of the sensor probe assembly that are associated with the analyte(s) of interest.

At 2010-6, the accuracy of quantitation of analytes is achieved from the correction of sensor response based on the effects of the interferences. For example, the impact of sensor aging on the sensor response measured at 2004-6 can be removed from the measured sensor response. The analytes of interest in the fluid under examination can then be identified at 2012-6.

In one embodiment, one or more transfer functions are built or otherwise created for quantitation of one or more analytes of interest in the presence of interferences, such as impurities or manufacturing errors, at 2014-6. These transfer functions can be built during sensor fabrication and calibration. These transfer functions are applied to quantify one or more analytes in the presence of interferences. For example, at 2008-6 and/or 2010-6, one or more of the transfer functions (determined at 2014-6) can be applied to the sensor response to eliminate or reduce the impact of the sensor response on the interferences.

The method 2000-6 also includes, at 2200-62-6 and 2018, measuring the intrinsic impedance of the sensor probe assembly while the sensor probe assembly is OFF (not powered). These measurements can be performed at designated frequencies that allow the use of conventional measurement systems with detection of 1 GOhm, 100 MOhm, 10 MOhm, or 1 MOhm. At 2020-6, the values of the sensor impedance at one or more designated frequencies while the sensor probe assembly is in the OFF state are determined. These frequencies can be empirically determined from the same or other similar sensor probe assemblies. These values indicate the effects of aging on the sensor probe assembly.

One or more transfer functions are built or otherwise created for quantitation of the impact of sensor aging at 2022-6. These transfer functions can be created based on the sensor responses measured when the sensor probe assembly is OFF, as described above. These transfer functions are applied to quantify one or more analytes in the presence of interferences. For example, at 2024-6, one or more of the transfer functions (determined at 2022-6) can be applied to the sensor response to eliminate or reduce the impact of the sensor response due to aging (at 2026-6).

Figure 113:
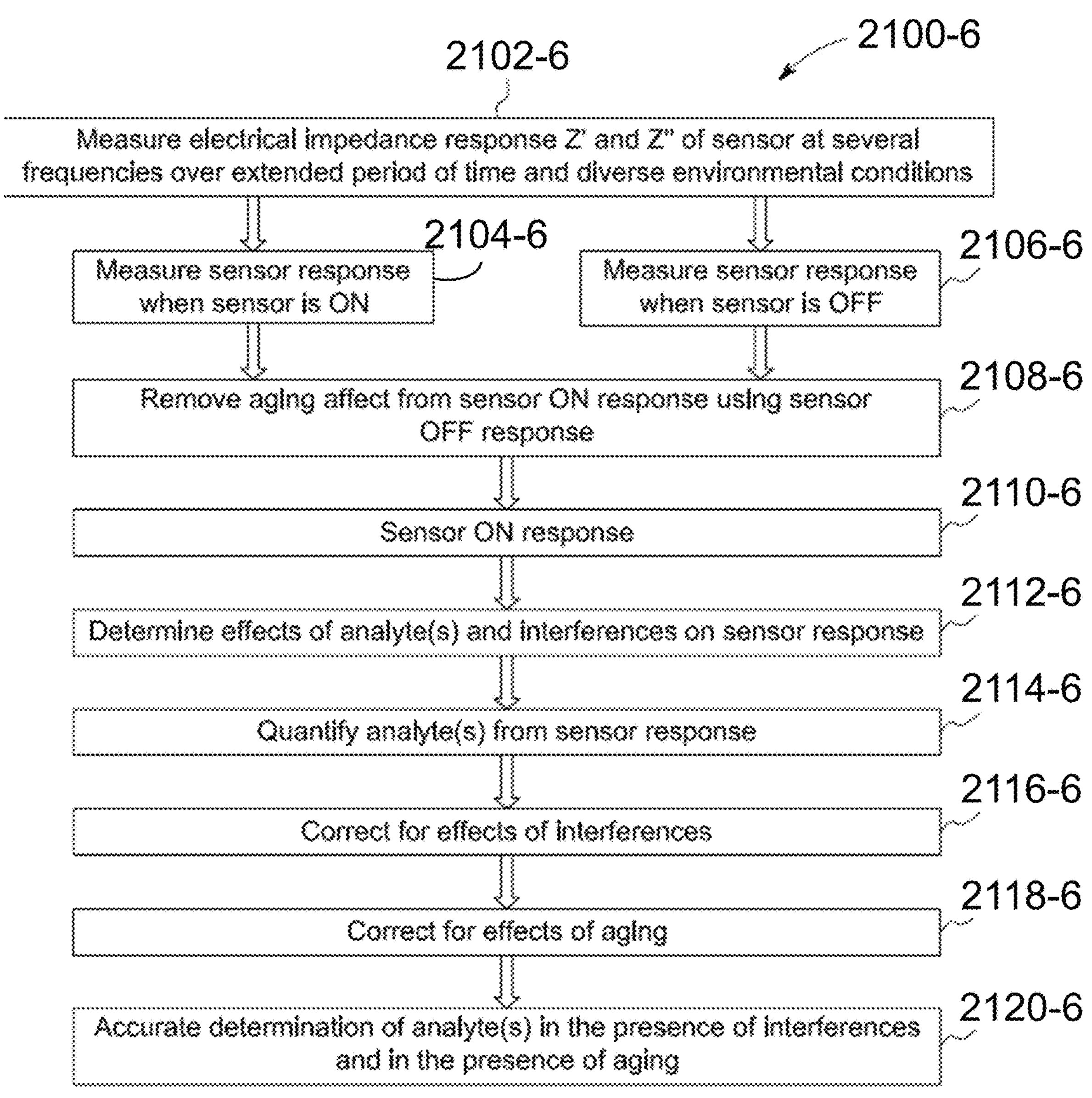
FIG. 113 illustrates a flowchart of one embodiment of a method for correcting measurements of a sensor probe assembly for aging.

FIG. 113 illustrates a flowchart of one embodiment of a method 2100-6 for correcting measurements of a sensor probe assembly for aging. At 2210-62-6, real (Z') and imaginary (Z") parts of the electrical impedance response of the sensing material of the sensor probe assembly are measured at several different frequencies over an extended period of time and/or under diverse environmental conditions (e.g., exposure to different fluids of interest, different ambient temperatures, etc.). These responses can be measured while the sensor probe assembly is ON (at 2104-6) and while the sensor probe assembly is OFF (at 2106-6).

The effects of the sensor responses due to aging of the sensor probe assembly are removed from the sensor responses measured while the sensor probe assembly is ON at 2108-6. For example, the real (Z') and imaginary (Z") parts of the electrical impedance response of the sensing material of the sensor probe assembly may be measured while the sensor probe assembly is OFF (at 2106-6). The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

After removing the effects of sensor aging (or at least determining the impact of aging so that the impact can later be removed), the real (Z') and imaginary (Z") parts of the electrical impedance response of the sensing material of the sensor probe assembly can be measured for a fluid under examination at 2110-6. At 2112-6, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 2114-6, one or more analytes of interest in the fluid under examination are quantified or identified using the sensor response measured at 2110-6. At 2116-6, the effect of these interferences can be corrected for, such as by removing the effect of the interferences from the sensor response determined at 2112-6.

At 2118-6, the effects of the sensor responses due to aging of the sensor probe assembly optionally are removed from the sensor responses measured while the sensor probe assembly is ON (at 2110-6). For example, the real (Z') and imaginary (Z") parts of the electrical impedance response of the sensing material of the sensor probe assembly may be measured while the sensor probe assembly is OFF. The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

At 2120-6, one or more analytes of interest are identified in the fluid under examination with the effects of interferences and the effects of sensor aging removed or reduced from the sensor response. As described herein, different analytes of interest can be associated with different peaks in the real (Z') and/or imaginary (Z") parts of the impedance responses of the sensor probe assembly. After removing the effects of interferences and sensor aging from the sensor response to the fluid under examination, the sensor response may more accurately reflect the presence and/or amount of the analyte(s) of interest in the fluid under examination.

Figure 114:
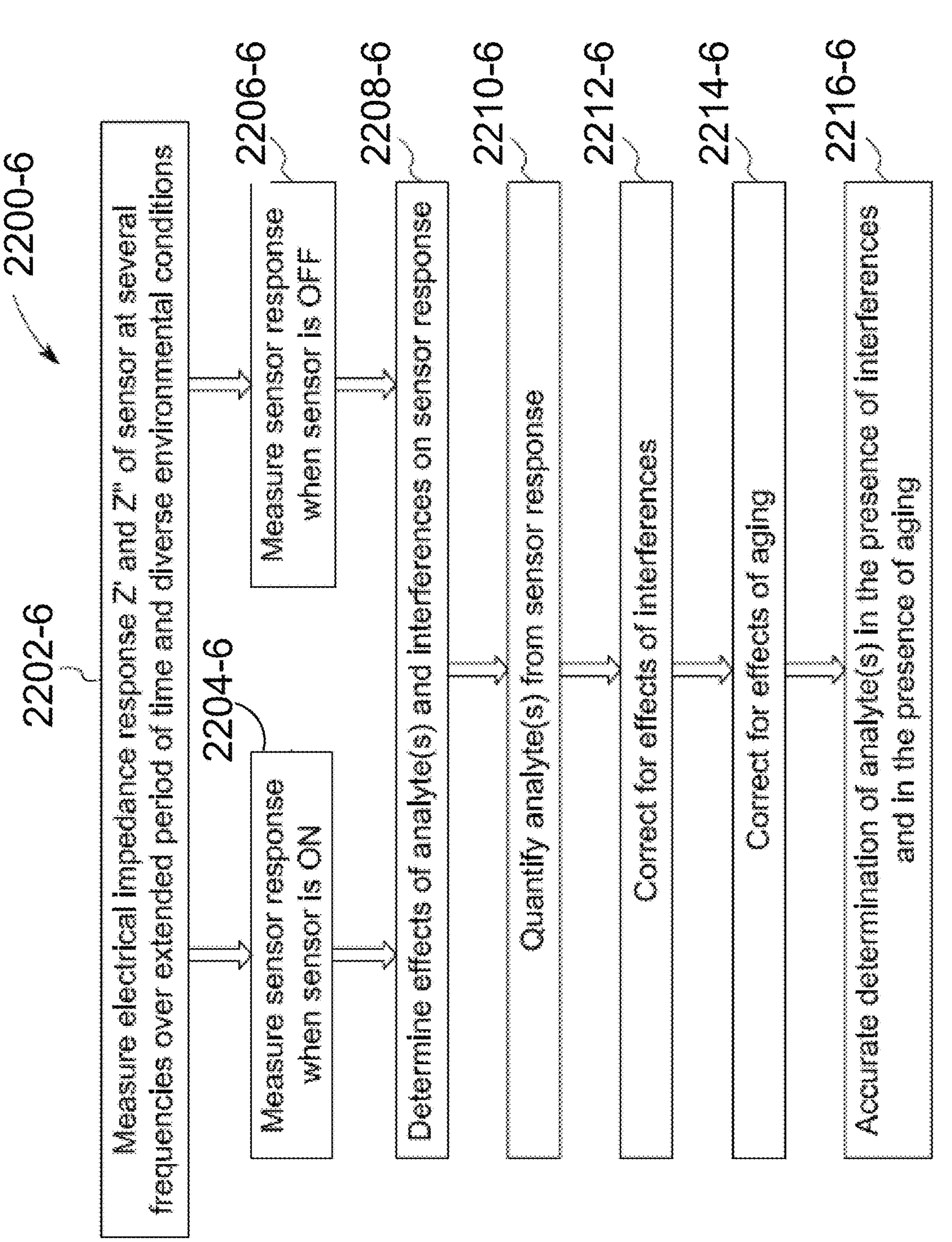
FIG. 114 illustrates a flowchart of one embodiment of a method for correcting measurements of a sensor probe assembly for aging.
Figure 115:
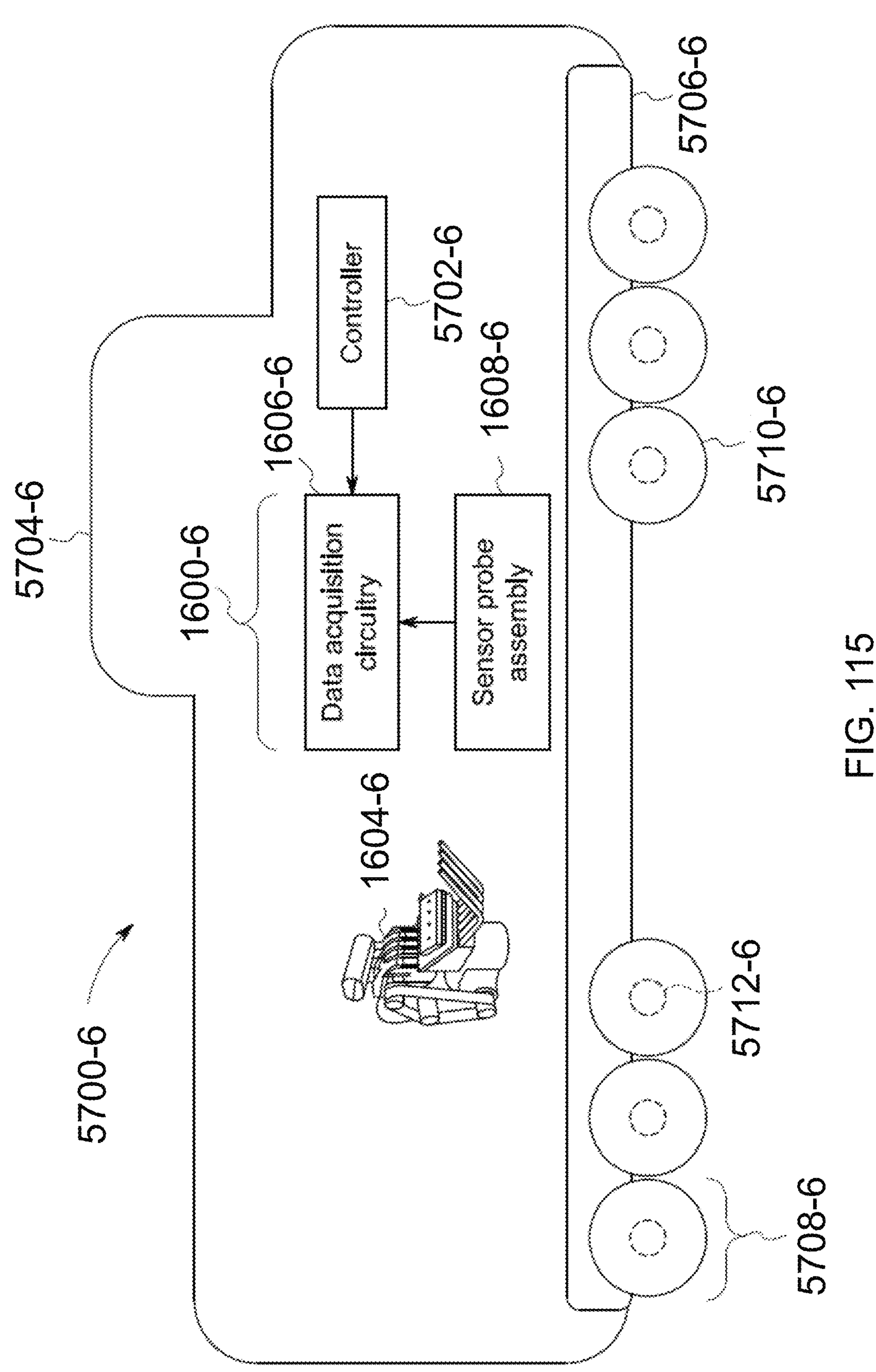
FIG. 115 illustrates another embodiment of the maintenance system used in connection with a locomotive system.

FIG. 114 illustrates a flowchart of one embodiment of a method 2200-6 for correcting measurements of a sensor probe assembly for aging.

At 2202-6, real (Z') and imaginary (Z") parts of the electrical impedance response of the sensing material of the sensor probe assembly are measured at several different frequencies over an extended period of time and/or under diverse environmental conditions (e.g., exposure to different fluids of interest, different ambient temperatures, etc.). These responses can be measured while the sensor probe assembly is ON (at 2204-6) and while the sensor probe assembly is OFF (at 2206-6).

At 2208-6, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 2210-6, one or more analytes of interest in the fluid under examination are quantified or identified using the measured sensor responses.

At 2212-6, the effect of these interferences can be corrected for, such as by removing the effect of the interferences from the sensor response that was determined. At 2214-6, the effects of the sensor responses due to aging of the sensor probe assembly optionally are removed from the sensor responses measured while the sensor probe assembly is ON. For example, the real (Z') and imaginary (Z") parts of the electrical impedance response of the sensing material of the sensor probe assembly may be measured while the sensor probe assembly is OFF. The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

At 2216-6, one or more analytes of interest are identified in the fluid under examination with the effects of interferences and the effects of sensor aging removed or reduced from the sensor response. As described herein, different analytes of interest can be associated with different peaks in the real (Z') and/or imaginary (Z") parts of the impedance responses of the sensor probe assembly. After removing the effects of interferences and sensor aging from the sensor response to the fluid under examination, the sensor response may more accurately reflect the presence and/or amount of the analyte(s) of interest in the fluid under examination.

The sensor probe assemblies described herein can be used to quantify at least one analyte gas that is dissolved in insulating oil of an electrical transformer. The sensor probe assemblies can be used to quantify at least one analyte gas dissolved in insulating oil of an electrical transformer when the sensor probe assemblies are turned off for extended periods of time (e.g., time periods that are at least 10 times longer that the measurement time of the analyte gas dissolved in insulating oil of an electrical transformer). The sensor probe assembly can be used to quantify analytes of interest such as hydrogen, CO, or a hydrocarbon gas.

The measurement systems described herein can be used to measure a gas extracted from oil (e.g., transformer dissolved gas analysis). The measurement system can include a sensing element or material connected to an impedance detector or analyzer circuit, where the impedance detector or analyzer circuit measures the response of the sensing element when exposed to a gas that has been extracted from oil and corrects for sensor aging. The sensing element can be connected to a resistance detector or measurement circuit (or equivalent), where the resistance circuit measures the response of the sensing element when exposed to a gas that has been extracted from oil and corrects for sensor aging.

In one embodiment, the measurement system operates with a sensing element (e.g., the sensing material) in a gas sample which has been extracted from transformer oil. The sensing element is connected to an impedance analyzer and scanned as a function of frequency, where the impedance analyzer circuit provides data output enabling improved sensor selectivity across multiple gases and improved sensor stability based on the correction of the sensor response performed when the sensor is in the OFF state. Aging of the sensor probe assembly can induce significant error in predicted gas concentrations and when the use of sensor readings in a "sensor OFF" state corrects for sensor aging and when incorporation of the "sensor OFF" response into a transfer function reduces prediction error of gas concentrations.

A method also is provided herein where sensor aging induces significant error in predicted gas concentrations. The use of sensor readings in a "sensor OFF" state corrects for sensor aging and incorporation of the "sensor OFF" response into a transfer function reduces prediction error of gas concentrations. The sensor response in the OFF state can be quantified using a resistance measurement of the sensing material (i.e., instead of the impedance response), and the sensor response in the ON state can be quantified using the impedance response. Optionally, the sensor response in the OFF state can be quantified using a resistance measurement of the sensing material (i.e. instead of the impedance response), and the sensor response in the ON state is also quantified using the resistance response.

In one embodiment, the sensor response in the OFF state is quantified using the resistance measurement (i.e. instead of the impedance response), and the sensor response in the ON state is also quantified using the resistance response. Optionally, the sensor response in the OFF state is quantified using the resistance measurement (i.e. instead of the impedance response), and the sensor response in the ON state is also quantified using the resistance response.

The frequencies, or frequency ranges, used to measure the impedance response of the sensor probe assembly to quantify the sensor OFF and ON states are different. The sensor response in the OFF state can be used to correct the sensor response in the ON state prior to applying transfer functions that quantify the analyte gas, or gases of interest. The sensor response in the OFF state can be used simultaneously with the sensor response in the ON state to quantify the analyte gas, or gases of interest. The sensitivity of the transfer functions to the sensor OFF or ON responses can be increased by preprocessing the sensor OFF or ON responses.

In one embodiment, recalibration, realignment or correction for sensor aging using sensor response in the resistance or impedance domain is performed on a periodic basis, as opposed to being part of a standard measurement cycle. Sensor analysis can be performed on a cyclical basis (such as every 24 hours, weekly, monthly, etc.) and changes in measurement performance (drift, aging etc.) can be corrected based on a cyclic correction. The sensor resistance response in the sensor OFF state can be used as a diagnostic indicator for sensor performance. The information extracted from the resistive method will indicate whether the sensor performance is within an acceptable range or whether the sensor performance has drifted outside the acceptable range.

Several measurements were performed using a sensor probe assembly described herein with a $SnO_2$ metal oxide semiconducting sensing material. The readout was performed using an impedance measurement over the relaxation region of the sensing material or classic resistance measurement. A $SnO_2$ sensor probe assembly was aged by exposing the sensor probe assembly to D3 silicone vapor. Such aging reduces the magnitude of the response of the sensor probe assembly to analytes of interest. The sensor probe assembly was exposed to several concentrations of hydrogen gas before and after aging. Concentrations of $H_2$ were 50, 100, 150, and 200 ppm. Exposure to silicone vapor was performed when the sensor probe assembly was in the OFF state to mimic the realistic conditions of the operation of the sensor. Exposures were performed for different durations of 15, 60, and 90 min by keeping the sensor probe assembly in the headspace above the silicone material.

In one embodiment, a method includes measuring an electrical response of a sensing material in a gas sensor probe assembly while the gas sensor probe assembly is in an OFF state, determining an aging effect of the gas sensor probe assembly based on the electrical response of the sensing material in the gas sensor probe assembly while the gas sensor probe assembly is in the OFF state, measuring an electrical response of the sensing material in the gas sensor probe assembly while the sensing material is exposed to a fluid under examination and while the gas sensor probe assembly is in an ON state, and correcting the electrical response of the sensing material in the gas sensor probe assembly that is measured while the gas sensor probe assembly is in the ON state using the aging effect of the gas sensor probe assembly.

Optionally, the electrical response that is measured while the gas sensor probe assembly is in the ON state represents an amount of at least one analyte gas that is dissolved in an insulating oil of an electrical transformer.

Optionally, measuring the electrical response of the sensing material in the gas sensor probe assembly while the gas sensor probe assembly is in the OFF state occurs for a time period that is at least ten times longer than measuring the electrical response of the sensing material in the gas sensor probe assembly while the sensing material is exposed to the insulating oil and while the gas sensor probe assembly is in the ON state.

Optionally, the electrical response that is measured while the gas sensor probe assembly is in the ON state and that is corrected using the aging effect quantifies an amount of one or more of hydrogen, carbon monoxide, or a hydrocarbon gas in the fluid under examination.

Optionally, the gas sensor probe assembly measures the electrical response in the ON state by heating the sensing material and the gas sensor probe assembly measures the electrical response in the OFF state by not heating the sensing material.

Optionally, the electrical response that is measured while the gas sensor probe assembly is in the OFF state is an impedance response and the electrical response that is measured while the gas sensor probe assembly is in the ON state is a resistance response.

Optionally, the electrical response that is measured while the gas sensor probe assembly is in the OFF state is a resistance response and the electrical response that is measured while the gas sensor probe assembly is in the ON state is an impedance response.

Optionally, the electrical response that is measured while the gas sensor probe assembly is in the OFF state and the electrical response that is measured while the gas sensor probe assembly is in the ON state is an impedance response.

Optionally, the electrical response that is measured while the gas sensor probe assembly is in the OFF state and the electrical response that is measured while the gas sensor probe assembly is in the ON state is a resistance response.

Optionally, the electrical response of the gas probe sensor assembly is measured while in the OFF state and the electrical response of the gas probe sensor assembly is measured while in the ON state at different frequencies.

Optionally, correcting the electrical response that is measured while the gas sensor probe assembly is in the ON state uses the aging effect of the gas sensor probe assembly and one or more transfer functions associated with one or more analytes of interest.

In one embodiment, a locomotive system is provided that includes a platform, plural wheel-axle sets operably coupled to the platform, a reservoir attached to the platform and configured to hold a fluid, and a resonant sensor probe assembly coupled to the reservoir. The sensor probe assembly includes a substrate formed from one or more dielectric materials and free-standing electrodes coupled with the substrate. The free-standing electrodes are configured to be placed into the fluid, to generate an electric field between the free-standing electrodes, and to measure an impedance response of the sensor to the fluid between the electrodes.

Optionally, the free-standing electrodes are not directly mounted on the substrate. The free-standing electrodes may not be disposed within a footprint of the substrate. The free-standing electrodes may be configured to be placed into the fluid and to measure the impedance response of the sensor to the fluid without the substrate being placed into the fluid. The free-standing electrodes may include opposing planar plates positioned to receive at least some of the fluid between the plates. The free-standing electrodes can include an inner tube electrode disposed within and spaced apart from an outer tube electrode.

In one embodiment, a method for monitoring a health of equipment lubricant of a locomotive system is provided. The method includes monitoring previous operational conditions of a locomotive engine of the locomotive system that operates using fuel and a lubricant, identifying one or more of an impurity content of the fuel supplied to the locomotive engine or an elapsed time since a previous addition of additional lubricant to the lubricant in the locomotive engine, and determining whether a change of the lubricant is required prior to continued operation of the locomotive engine based on the previous operational conditions and the one or more of the impurity content of the fuel or the elapsed time since the previous addition of the additional lubricant to the lubricant in the locomotive engine.

Optionally, the method includes identifying the impurity content of the fuel and the impurity content is an amount of sulfur in the fuel. The method may include both identifying the impurity content of the fuel and the elapsed time since the previous addition of the additional lubricant and determining whether the change of the lubricant is required is based on the previous operational conditions, the impurity content of the fuel, and the elapsed time since the previous addition of the additional lubricant. The previous operational conditions can include one or more of an elapsed operating time of the locomotive engine, an operating temperature of the locomotive engine, or an ambient temperature in which the locomotive engine operated.

The method also can include creating or updating a digital twin of the locomotive engine based on the previous operational conditions of the locomotive engine and forecasting upcoming operational conditions of the locomotive engine. Determining whether the change of the lubricant is required prior to the continued operation of the locomotive engine can be based on the previous operational conditions, the one or more of the impurity content of the fuel or the elapsed time since the previous addition of the additional lubricant to the lubricant in the locomotive engine, the digital twin of the locomotive engine, and the upcoming operational conditions of the locomotive engine that are forecasted.

The method optionally can include changing the lubricant in the locomotive engine based on determining that the change in the lubricant is required. Determining whether the change of the lubricant is required can involve delaying the change of the lubricant beyond a previously scheduled maintenance of the locomotive engine that involves changing the lubricant.

In one embodiment, a locomotive system includes a platform, plural wheel-axle sets operably coupled to the platform, and a reservoir attached to the platform. The reservoir is configured to hold a fluid. The locomotive system also can include a sensor probe assembly having a substrate formed from one or more dielectric materials and free-standing electrodes coupled with the substrate and configured to be placed into the fluid, to generate an electric field between the electrodes, and to measure an electric response of the sensor to the fluid between the electrodes. The locomotive system also includes a controller configured to determine the electric response of the sensor while the sensor is not generating the electric field between the electrodes and to determine the electric response of the sensor while the sensor is generating the electric field between the electrodes. The controller also is configured to determine an aging effect of the sensor based on the electric response that is measured while the sensor is not generating the electric field between the electrodes. The controller is configured to correct the electric response of the sensor that is measured while the sensor is generating the electric field between the electrodes using the aging effect that is determined.

Optionally, the electric response that is measured while the sensor is generating the electric field between the electrodes represents an amount of at least one analyte gas that is dissolved in an insulating oil of an electrical transformer onboard the platform. The sensor can be configured to measure the electric response of the sensor while the sensor is not generating the electric field occurs for a time period that is longer than the sensor measures the electric response while the sensor is not generating the electric field between the electrodes. The sensor can be configured to measure the electric response while the sensor is generating the electric field between the electrodes and that is corrected using the aging effect quantifies an amount of one or more of hydrogen, carbon monoxide, or a hydrocarbon gas in the fluid.

The controller can be configured to direct one or more heating elements to heat the sensor while the sensor measures the electric response. The sensor can be configured to measure an impedance response of the sensor while the sensor is not generating the electric field between the electrodes, and wherein the electrical response that is measured while the gas sensor probe assembly is in the ON state is a resistance response. The sensor can be configured to measure the electric response while the sensor is not generating the electric field between the electrodes as a resistance response of the sensor, and the sensor can be configured to measure the electric response while the sensor is generating the electric field between the electrodes as an impedance response.

The term "multivariable sensor" is referred to herein as a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

The term "multivariate analysis" refers to a mathematical procedure that is used to analyze more than one variable from the sensor response and to provide the information about the type of at least one environmental parameter from the measured sensor parameters and/or to quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the LCR sensor. In addition to measuring the impedance spectrum in the form of Z-parameters, S-parameters, and other parameters, the impedance spectrum (for example, both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra may also be called "features" or "descriptors." The appropriate selection of features is performed from all potential features that can be calculated from spectra.

As used herein the term "sensing materials and sensing films" includes, but is not limited to, materials deposited onto a transducer's electronics circuit components, such as LCR circuit components to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:

a sensor configured to be in contact with lubricant within an engine, the sensor including a sensing region circuit that is configured to generate stimuli responsive to a change in at least one of an acidic content or a basic content of the lubricant at different times during operation of the engine; and one or more processors configured to receive signals from the sensor during operation of the engine, the signals representative of responses of the lubricant to the stimuli, the one or more processors configured to, during operation of the engine, analyze the responses and determine, in real time with receiving the signals from the sensor, one or more of a total base number (TBN) or a total acid number (TAN) of the lubricant, wherein the one or more processors are configured to:

determine, during operation of the engine, one or more of a rate of change in the TBN or a rate of change in the TAN of the lubricant; and determine, during operation of the engine, an unhealthy state of one or more of the engine or the lubricant based on the one or more of the rate of change in the TBN or the rate of change in the TAN of the lubricant that is determined.

2. The system of claim 1, wherein the sensor comprises one or more of an electrical sensor or an optical sensor and the stimuli include one or more of electrical stimuli or optical stimuli.

3. The system of claim 2, wherein the sensor comprises an optical sensor and the stimuli includes optical stimuli.

4. The system of claim 1, wherein the sensor comprises a capacitor sensor, a resistor sensor, a non-resonant impedance sensor, a resonant impedance sensor, an electro-mechanical resonator sensor, a thermal sensor, an optical sensor, an acoustic sensor, a photoacoustic sensor, a near-infrared sensor, an optical sensor, an ultraviolet sensor, an infrared sensor, a visible light sensor, a fiber-optic sensor, a reflection sensor, a multivariable sensor, or a single-output sensor.

5. The system of claim 1, wherein the sensor comprises a sensing electrode structure coated with a dielectric coating.

6. The system of claim 1, wherein the one or more processors are configured to determine one or more of a second derivative of the TBN of the lubricant or a second derivative of the TAN of the lubricant.

7. The system of claim 6, wherein the one or more processors are configured to determine the unhealthy state of the one or more of the engine or the lubricant responsive to one or more of the second derivative of the TBN of the lubricant changing at a rate that is faster than a designated second derivative or the second derivative of the TAN of the lubricant changing at a rate that is faster than the designated second derivative.

8. The system of claim 1, wherein the one or more processors are configured to determine the unhealthy state of the one or more of the engine or the lubricant responsive to one or more of the TBN of the lubricant being smaller than a designated TBN or the TAN of the lubricant being larger than a designated TAN.

9. The system of claim 1, wherein the one or more processors are configured to deactivate or otherwise control the engine or a vehicle in which the engine is disposed responsive to determining the unhealthy state of the one or more of the engine or the lubricant based on one or more of the TBN or the TAN of the lubricant that is determined.

10. The system of claim 1, wherein the sensor includes a resonant circuit coupled with electrodes that are configured to generate an electric field between the electrodes as the stimuli with at least part of the lubricant disposed between the electrodes and within the electric field, wherein the resonant circuit is configured to resonate at different frequencies responsive to generation of the electric field based on a concentration of one or more basic compounds or acidic compounds in the lubricant between the electrodes, wherein the signals that are output from the sensor to the one or more processors represents one or more of the frequencies at which the resonant circuit resonates, wherein the one or more processors are configured to compare the one or more frequencies at which the resonant circuit resonates with one or more designated frequencies associated with different TBN or TAN of the lubricant to determine the one or more of the TBN or the TAN of the lubricant.

11. The system of claim 10, wherein the resonant circuit comprises a plurality of resonant circuits that are each configured to resonate at different frequencies.

12. The system of claim 11, wherein the plurality of resonant circuits are configured to be in contact with the lubricant at different depths of the lubricant.

13. The system of claim 1, wherein the one or more processors are configured to determine a concentration of potassium hydroxide in the lubricant to determine the TBN of the lubricant.

14. The system of claim 1, wherein the one or more processors are configured to determine a concentration of acids in the lubricant to determine the TAN of the lubricant.

15. The system of claim 14, wherein the one or more processors are configured to determine a concentration of one or more naphthenic acids in the lubricant.

16. A system comprising:

a sensor configured to be in contact with lubricant within an engine, the sensor including a sensing region circuit that is configured to generate stimuli at different times during operation of the engine; and one or more processors configured to receive signals from the sensor during operation of the engine, the signals representative of responses of the lubricant to the stimuli, the one or more processors configured to, during operation of the engine, analyze the responses signals and determine, in real time with receiving the signals from the sensor, one or more of a total base number (TBN) or a total acid number (TAN) of the lubricant, wherein the one or more processors are configured to:

determine, during the operation of the engine, one or more of a rate of change in the TBN or a rate of change in the TAN of the lubricant between a first time and a second time; and determine, during operation of the engine, an unhealthy state of the one or more of the engine or the lubricant responsive to one or more of the rate of change in the TBN of the lubricant decreasing at a rate that is faster than a designated rate of change or the rate of change in the TAN increasing at a rate that is faster than the designated rate of change.

17. A system comprising:

a sensor configured to be in contact with a lubricant within a rotating equipment of a system, wherein the sensor is configured to generate detectable stimuli responsive to a change in at least one of an acidic content or a basic content of the lubricant at different times during operation of the rotating equipment; and one or more processors configured to receive signals from the sensor during operation of the rotating equipment, the signals representative of responses of the lubricant to the stimuli, the one or more processors configured to, during operation of the rotating equipment, analyze the signals and determine one or more of a total base number (TBN) or a total acid number (TAN) of the lubricant, wherein the one or more processors are configured to:

determine, during operation of the rotating equipment, one or more of a rate of change in the TBN or a rate of change in the TAN of the lubricant; and determine, during operation of the rotating equipment, an unhealthy state of one or more of the rotating equipment or the lubricant based on the one or more of the rate of change in the TBN or the rate of change in the TAN of the lubricant that is determined.

18. The system of claim 17, wherein the sensor comprises one or more of an electrical, resonant, non-resonant, optical, or mechanical sensor.

* * * * *